US011872279B2

(12) United States Patent
Love et al.

(10) Patent No.: US 11,872,279 B2
(45) Date of Patent: Jan. 16, 2024

(54) SARS-COV-2 ANTIGENS AND USES THEREOF

(71) Applicant: MASSACHUSETTS INSTITUTE OF TECHNOLOGY, Cambridge, MA (US)

(72) Inventors: J. Christopher Love, Somerville, MA (US); Sergio Andre Rodriguez Aponte, Cambridge, MA (US); Neil Chandra Dalvie, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 192 days.

(21) Appl. No.: 17/512,902

(22) Filed: Oct. 28, 2021

(65) Prior Publication Data

US 2022/0133880 A1    May 5, 2022

Related U.S. Application Data

(60) Provisional application No. 63/108,171, filed on Oct. 30, 2020.

(51) Int. Cl.
*A61K 39/215* (2006.01)
*A61P 31/14* (2006.01)
*C07K 14/165* (2006.01)
*C12N 7/00* (2006.01)
*C12N 7/01* (2006.01)

(52) U.S. Cl.
CPC .......... *A61K 39/215* (2013.01); *A61P 31/14* (2018.01); *C07K 14/165* (2013.01); *C12N 7/00* (2013.01)

(58) Field of Classification Search
CPC .... A61K 2039/55505; A61K 2039/575; A61K 39/12; A61K 39/215; A61P 31/14
See application file for complete search history.

(56) References Cited

U.S. PATENT DOCUMENTS

| 10,787,501 B1 | 9/2020 | Babb et al. |
| 2014/0348820 A1 | 11/2014 | Chennamsetty et al. |
| 2022/0002699 A1* | 1/2022 | Wycoff .................. C12N 9/485 |

FOREIGN PATENT DOCUMENTS

CN     111592602 A    8/2020

OTHER PUBLICATIONS

Chennamsetty, et al. (Jul. 2009) "Design of therapeutic proteins with enhanced stability." PNAS, 106(29): 11937-11942.
Yi, et al. (May 2020) "Key residues of the receptor binding motif in the spike protein of SARS-COV-2 that interact with ACE2 and neutralizing antibodies." Cellular & Molecular Immunology, 17:621-630.
Abe, et al. (2020) JCI Insight 5:e142362.
Belouzard, et al.(2012) Viruses 4:557.
Bolles (2011) Curr Opin Virol. 1:624.
Brouwer, P.J. et al., (2020) bioRxiv 2020.05.12.088716.
Chandrashekar, et al.(2020) Science 369:812.
Chen et al., World J Gastroenterol., 11(39):6159-6164 (2005).
Chen, et al.(2017) J Pharm Sci 106:1961-1970.
Chen, W.h. et al. (2014) Hum. Vaccin. Immunother. 10, 648-658.
Chuck, C.P. et al. (2009) Virus Genes 38, 1-9.
Crooks, et al.(2004) Genome Res 14:1188.
Dalvie, N.C. et al., (2019) doi:10.1021/acssynbio. 9b00372.
Du et al., Viral Immuno., 23(2): 211-219 (2012).
Du et al., Virology., 393(1): 144-150 (2009).
Folegatti, et al (2020) Safety and immunogenicity of the ChAdOx1 nCoV-19 vaccine against SARS-CoV-2: a preliminary report of a phase 1/2, single-blind, randomised controlled trial, Lancet 396: 467-78.
Gates Foundation Teams Up With Vaccine Maker to Produce $3 Covid-19 Shots—WSJ. https://www.wsj.com/articles/gates-foundation-teams-up-with-vaccine-maker-to-produce-3-covid-19-shots-11596804573.
Gates, (2020) NEJM doi:10.1056/nejmp2003762.
Gates, B. (2015) NEJM 372:1381-1384.
Ge, et al (2013) Nature 503:535.
GISAID Accession No. EPI_ISL_402127 (WIV02).
GISAID Accession No. EPI_ISL_402128 (WIV05).
GISAID Accession No. EPI_ISL_402129 (WIV06).
GISAID Accession No. EPI_ISL_402130 (WIV07).
GISAID Accession Nos. EPI_ISL_402124 (WIV04).
GISAID Euro Surveill. 2017 03 30;22(13):30494.
Hu et al (2017) PLoS Pathogens 13:e1006698.
Irvine, et al (2015) Chem Rev 115:11109-11146.
Ishida, et al (2007) Nucleic acids research, 35 (suppl_2), pp. W460-W464.
Jackson et al (2020) NEJM doi: 10.1056/NEJMoa2022483.
Lan et al (2020) Nature 581:215.
Lee and Nathans, J. Biol. Chem. 263:3521, 1988.
Letko, et al (2020) Nat. Microbiol. 5:562.
Li (2015) J. Virol. 89:1954.
Li et al (2003) Nature 426: 450-454.
Li et al (2005) Science 310:676.
Li, et al (2005) Science 309:1864-1868.
Love, et al (2014) Genome Biol 15:1-21.
Matthews, C.B. et al. (2018) Biotechnol. Bioeng. 115, 103-113.
McCarthy, et al.(2012) Nucleic Acids Res 40:4288.

(Continued)

*Primary Examiner* — Barry A Chestnut
(74) *Attorney, Agent, or Firm* — MCDONNELL BOEHNEN HULBERT & BERGHOFF LLP

(57) ABSTRACT

The present disclosure relates to, inter alia, variants of the receptor binding domain of a coronavirus (e.g., SARS-CoV-2) having increased immunogenicity and reduced aggregation, and the use of the RBD variants in methods for preventing infection of the coronavirus.

20 Claims, 13 Drawing Sheets

Specification includes a Sequence Listing.

(56) References Cited

OTHER PUBLICATIONS

Munira, et al.(2019) Vaccine 37:1245.
Pettit, et al. (2016) "CHO cell production and sequence improvement in the 13C6FR1 anti-Ebola antibody." MAbs. vol. 8. No. 2. Taylor & Francis.
Robinson, et al.(2009) Bioinformactics 26:139.
Sankar, et al. (2018) Proteins 86:1147.
Shekhar, (2008) Chem. Biol. 15:201.
Soneson, et al (2016) F1000Research 4.
Starr, et al (2020) bioRxiv https://doi.org/10.1101/2020.06.17.157982.
Subramanian, et al (2005) PNAS 102:15545.
Tian, et al (2020 bioRxiv 2020.06.29.178509.
Timmick, S.M. et al. (2018) Biotechnol. Bioeng. 115, 2048-2060.

\* cited by examiner

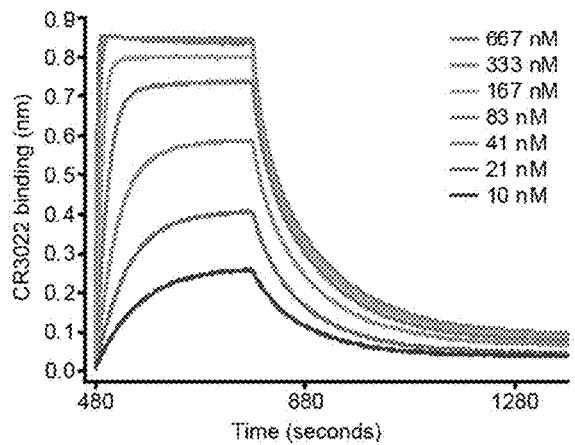
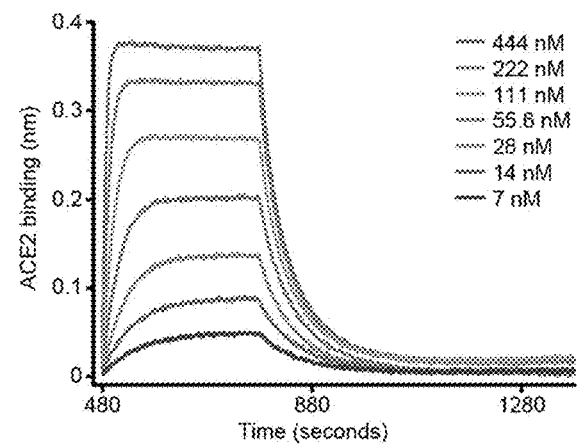
FIG. 1C        FIG. 1D
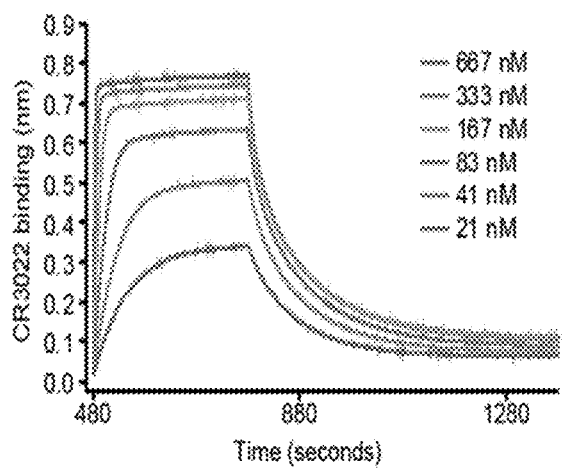
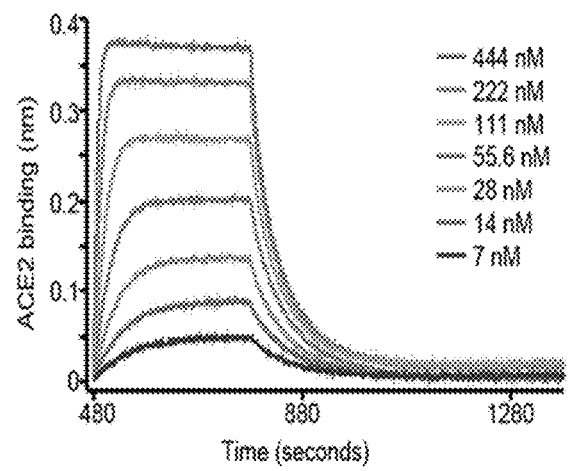
FIG. 1E        FIG. 1F ACE2 binding motif

FIG. 2A

|  | 121 | 122 | 123 | 124 | 125 | 126 |  | 158 | 159 | 160 |
|---|---|---|---|---|---|---|---|---|---|---|
| SARS-Cov-1 | Y | K | Y | R | Y | L | . . | C | Y | W |
| Civet SARS 2002 | Y | K | Y | R | Y | L | . . | C | Y | W |
| Bat SARS 2013 | Y | K | Y | R | S | L | . . | C | Y | W |
| SARS-Cov-2 | Y | L | Y | R | L | F | . . | C | Y | F |
| Variants for expression in K. phaffii | Y | K | Y | R | Y | L | . . | C | Y | W |
|  | Y | K | Y | R | L | F | . . | C | Y | W |

FIG. 2B

SARS-COV-2 ANTIGENS AND USES THEREOF

CROSS REFERENCE

This application claims priority to U.S. Provisional Application Ser. No. 63/108,171 filed Oct. 30, 2020, incorporated by reference herein in its entirety.

SEQUENCE LISTING STATEMENT

A computer readable form of the Sequence Listing is filed with this application by electronic submission and is incorporated into this application by reference in its entirety. The Sequence Listing is contained in the file created on Oct. 12, 2021 having the file name "21-0884-US-SeqList_ST25.txt" and is 185 kb in size.

BACKGROUND

The COVID19 outbreak caused by the severe acute respiratory syndrome coronavirus 2 (SARS-CoV-2) is a widespread public health threat. SARS-CoV-2 belongs to the family of coronaviridae, a family of viruses (e.g., MERS-CoV and Severe Acute Respiratory Syndrome (SARS-CoV)) that primarily infect the upper respiratory and gastrointestinal tracts of mammals and birds, and that are responsible for acute and chronic diseases of the respiratory, hepatic, gastrointestinal and neurological systems. Coronaviruses are enveloped positive-sense, single-stranded RNA viruses with a nucleocapsid of helical symmetry and virions with a crown-like appearance. The crown-like appearance is due to the club-shaped spike (S) proteins projecting from the surface of the envelope.

The S proteins are responsible for virus binding, fusion and entry, and are inducers of neutralizing antibodies. These proteins play critical roles in viral pathogenesis and virulence. The S protein of SARS-CoV-2 is a type I transmembrane glycoprotein consisting of two domains, S1 and S2. S1 is responsible for virus binding to the receptor on the target cell. It has been demonstrated that angiotensin-converting enzyme 2 (ACE2) is a functional receptor for SARS-CoV-2. A fragment located in the middle region of S1 is the receptor-binding domain (RBD). S2 domain, which contains a putative fusion peptide and two heptad repeat (HR1 and HR2) regions, is responsible for fusion between viral and target cell membranes.

A receptor-binding domain (RBD) of the S protein, containing residues 318-510 (RBD193), was identified in the related SARS-CoV and found to bind to ACE2 in vitro (Wong et al., *JBC.*, 279: 3197-3201 (2004)). In addition, recombinant proteins RBD193 and a related construct, RBD219 (residues 318-536), expressed in the culture supernatant of mammalian cells 293T and Chinese hamster ovary (CHO)-K1, respectively, were demonstrated to elicit neutralizing antibodies and protective immunity in vaccinated mice (Du et al., *Virology.*, 393(1): 144-150 (2009); Du et al., *Viral Immuno.*, 23(2): 211-219 (2012). Moreover, RBD can also absorb and remove the majority of neutralizing antibodies in the antisera of mice, monkeys, and rabbits immunized with whole SARS-CoV or vaccinia virus expressing S protein constructs (Chen et al., *World J Gastroenterol.*, 11(39):6159-6164 (2005)).

Containment of COVID-19 will require a coordinated response at a global scale, including the development and distribution of vaccines that are accessible in low-income and remote areas.

SUMMARY OF THE DISCLOSURE

The present disclosure is based, at least in part, on the discovery of novel SARS-CoV-2 Spike (S) glycoprotein variants having reduced aggregation, increased thermostability and/or reduced hydrophobicity, thereby resulting in improved expression and/or production in host cells of interest (e.g., *Komagataella phaffii*). Surprisingly, SARS-CoV-2 S glycoprotein variants were discovered having increased immunogenicity where the variant comprises a mutation of one or more amino acid residues in an ACE2 receptor binding motif (RBM) in the RBD, wherein the residue is (i) hydrophobic; and (ii) within an aggregation-prone region of about 3-15 amino acid residues, and wherein the mutation is a substitution of the hydrophobic residue with a different amino acid residue, e.g., a less hydrophobic residue found in another coronavirus species.

It was also surprisingly discovered that mutating a hydrophobic amino acid residue within an aggregation-prone region in a SARS-CoV-2 RBD to an amino acid residue conserved in at least one coronavirus species (e.g., β-genus coronavirus, e.g., SARS-CoV strains isolated from different hosts and/or in different years), results in improved expression and production. As described herein, aggregation-prone regions and hydrophobic amino acid residues were identified in the RBD of SARS-CoV-2 based on an aggregation score, with the highest scores identified in the ACE2 RBM. The sequences of the aggregation-prone regions in the SARS-CoV-2 RBD was were then compared with RBD sequences of previously known SARS-related coronavirus strains (e.g., isolated from human, civet, or bat) to identify conserved, and/or less hydrophobic amino acid residues at the same position as the one or more the identified hydrophobic amino acid residues in the aggregation-prone regions in the SARS-CoV-2 RBD. SARS-CoV-2 S glycoprotein RBD variants were generated by mutating at least one hydrophobic amino acid residue to an amino acid residue conserved amongst other SARS-CoV virus species.

Without being bound by theory, it is believed that because the SARS-CoV-2 spike protein shares substantial sequence identity with the SARS-CoV spike protein, substitution of a hydrophobic residue in the SARS-CoV-2 S glycoprotein with a conserved residue provides a SARS-CoV-2 S glycoprotein variant that maintains ACE2 receptor binding, while resulting in one or more desired properties in the variant (e.g., reduced aggregation, increased thermostability, reduced hydrophobicity) to improve expression and/or production in host cells of interest (e.g., *K. phaffii*). Moreover, without being bound by theory, it is believed mutating (e.g., substituting) a hydrophobic amino acid residue to a conserved amino acid residue would minimally alter or not alter the overall structure of the protein such that an immune system response directed against the SARS-CoV-2 S glycoprotein variant (e.g., neutralizing antibodies against the SARS-CoV-2 S glycoprotein variant) will likewise recognize the wild-type SARS-CoV-2 S glycoprotein.

As described herein, expression of SARS-CoV-2 S glycoprotein variants having a substitution of at least one hydrophobic amino acid residue within an aggregation-prone region resulted in reduced aggregation of the SARS-CoV-2 S glycoprotein variant, and improved expression in a host cell of interest, e.g., *K. phaffii*. Without wishing to be bound by theory, reduced aggregation during expression is expected to improve the scalability and ease of manufacture of vaccines by recombinant methods in host cells of interest, e.g., *K. phaffii*, and reduced overall cost of manufacture. Surprisingly, the SARS-CoV-2 S glycoprotein variants described herein not only had higher expression levels, but also induced higher levels of IgG neutralizing antibodies in vivo.

Accordingly, in some aspects, the present disclosure provides a SARS-CoV-2 S glycoprotein variant, wherein the S glycoprotein variant comprises a receptor binding domain (RBD) having a mutation of at least one amino acid residue in an ACE2 receptor binding motif (RBM) relative to a wild-type RBD, wherein the residue is (i) hydrophobic; and (ii) within an aggregation-prone region of about 3-15 amino acid residues, wherein the mutation is a substitution of the hydrophobic residue with a different amino acid residue. In some aspects, the S glycoprotein variant comprises a mutation of at least one additional hydrophobic amino acid in the aggregation-prone region, wherein the mutation is a substitution of the at least one additional hydrophobic residue with a different amino acid residue. In some aspects, the S glycoprotein variant comprises a mutation of at least one hydrophobic amino acid in a second aggregation-prone region of about 3-15 amino acid residues, and wherein the mutation is a substitution of the at least one additional hydrophobic residue with a different amino acid residue. In some aspects, the second aggregation-prone region is outside of the ACE2 RBM. In any of the foregoing or related aspects, the RBD comprises at least one mutation to at an asparagine-linked glycosylation site relative to the wild-type RBD.

In any of the foregoing ore related aspects, the different amino acid residue is less hydrophobic. In some aspects, the different amino acid residue is an amino acid residue that is found at the same position in a genetic background of at least one species of SARS-CoV. In some aspects, the different amino acid residue is an amino acid residue that is found at the same position in a genetic background of at least one species of SARS-CoV and is less hydrophobic.

In any of the foregoing or related aspects, the hydrophobic residue has a positive AggScore. In some aspects, the hydrophobic residue has an AggScore of at least 2, or of about 2-10, 5-10, 10-15, or 15-20. In some aspects, the substitution of the hydrophobic residue reduces the AggScore of the hydrophobic residue by about 10-100%. In some aspects, the substitution of the hydrophobic residue reduces the overall aggregation score of the aggregation prone region by about 5-50% relative to the aggregation prone region without the substitution. In some aspects, the substitution of the hydrophobic residue reduces the overall aggregation score of the S glycoprotein variant by about 5-50% relative to the S glycoprotein variant without the substitution.

In any of the foregoing or related aspects, the substitution of the hydrophobic residue reduces the propensity of the SARS-CoV-2 S glycoprotein to aggregate compared to the SARS-CoV-2 S glycoprotein without the substitution. In some aspects, the substitution of the hydrophobic residue increases the thermostability of the S glycoprotein compared to the SARS-CoV-2 S glycoprotein without the substitution.

In some aspects, the disclosure provides a SARS-CoV-2 S glycoprotein variant, wherein the S glycoprotein variant comprises an RBD having a mutation of at least one amino acid residue in a first and/or second aggregation-prone region relative to a wild-type RBD comprising the amino acid sequence of SEQ ID NO: 1, wherein the first aggregation-prone region comprises amino acid residues 122-126 of SEQ ID NO: 1, and the second aggregation-prone region comprises amino acid residues 158-162 of SEQ ID NO: 1, and wherein the mutation is a substitution with a different amino acid residue. In some aspects, the S glycoprotein variant comprises an RBD having a mutation of at least one amino acid residue in the first aggregation-prone region relative to the wild-type RBD comprising the amino acid sequence of SEQ ID NO: 1, wherein the first aggregation-prone region comprises amino acid residues 122-126 of SEQ ID NO: 1, and wherein the mutation is a substitution with a different amino acid residue. In some aspects, the S glycoprotein variant comprises an RBD having a mutation of at least one amino acid residue in the second aggregation-prone region relative to the wild-type RBD comprising the amino acid sequence of SEQ ID NO: 1, wherein the second aggregation-prone region comprises amino acid residues 158-162 of SEQ ID NO: 1, and wherein the mutation is a substitution with a different amino acid residue. In some aspects, the S glycoprotein variant comprises an RBD having a mutation of at least one amino acid residue in the first and the second aggregation-prone region relative to the wild-type RBD comprising the amino acid sequence of SEQ ID NO: 1, wherein the first aggregation-prone region comprises amino acid residues 122-126 of SEQ ID NO: 1, and the second aggregation-prone region comprises amino acid residues 158-162 of SEQ ID NO: 1, and wherein the mutation is a substitution with a different amino acid residue. In some aspects, the at least one amino acid residue is selected from: L122, L125, F126, Y159, F160, and any combination thereof. In some aspects, the S glycoprotein variant comprises an amino acid substitution at L122 with a different amino acid residue. In some aspects, the S glycoprotein variant comprises an amino acid substitution at L122 and F160 with a different amino acid residue. In some aspects, the S glycoprotein variant comprises an amino acid substitution at L122, L125, F126 and F160 with a different amino acid residue. In some aspects, the different amino acid residue is less hydrophobic. In some aspects, the different amino acid residue is an amino acid residue that is found at the same position in a genetic background of at least one species of SARS-CoV. In some aspects, the different amino acid residue is an amino acid residue that is found at the same position in a genetic background of at least one species of SARS-CoV and is less hydrophobic.

In some aspects, the disclosure provides a SARS-CoV-2 S glycoprotein variant, wherein the S glycoprotein variant comprises a RBD comprising a mutation of at least one amino acid residue in an ACE2 RBM relative to a wild-type RBD comprising the amino acid sequence of SEQ ID NO: 1, wherein the amino acid residue is L122 of SEQ ID NO: 1, and optionally F160 of SEQ ID NO: 1, and wherein the mutation is a substitution with a different amino acid residue. In some aspects, the RBD comprises a mutation of at least one amino acid residue in the ACE2 RBM relative to a wild-type RBD comprising the amino acid sequence of SEQ ID NO: 1, wherein the amino acid residue is L122 and F160 of SEQ ID NO: 1, and wherein the mutation is a substitution with a different amino acid residue. In some aspects, the S glycoprotein variant comprises a mutation of at least one additional amino acid residue in a first and/or second aggregation-prone region relative to the wild-type RBD, wherein the first aggregation-prone region comprises amino acid residues 122-126 of SEQ ID NO: 1, and the second aggregation-prone region comprises amino acid residues 158-162 of SEQ ID NO: 1, and wherein the mutation is a substitution with a different amino acid residue. In some aspects, the different amino acid residue is less hydrophobic. In some aspects, the different amino acid residue is an amino acid residue that is found at the same position in a genetic background of at least one species of SARS-CoV. In some aspects, the different amino acid residue is an amino acid residue that is found at the same position in a genetic background of at least one species of SARS-CoV and is less hydrophobic. In some aspects, the mutation of L122 of SEQ ID NO: 1 is a substitution of leucine with lysine (L122K), phenylalanine (L122F), tyrosine (L122Y), or serine (L122S). In some aspects, the mutation of F160 of SEQ ID NO: 1 is a substitution of phenylalanine with tryptophan (F160W), arginine (F160R), tyrosine (F160Y), or asparagine (F160N). In some aspects, the S glycoprotein variant comprises a mutation of at least one additional amino acid residue in a first and/or second aggregation-prone region relative to a wild-type RBD comprising the amino acid sequence of SEQ ID NO: 1, wherein the first aggregation-prone region comprises amino acid residues 122-126 of SEQ ID NO: 1, and the second aggregation-prone region comprises amino acid residues 158-162 of SEQ ID NO: 1, and wherein the mutation is a substitution with a different amino acid residue. In some aspects, the different amino acid residue is less hydrophobic, found at the same position in a genetic background of at least one species of SARS-CoV, or both.

In any of the foregoing or related aspects, the substitution is selected from the group: L122K, L122F, L122Y, L122S, L125Y, L125S, L125W, L125N, F126L, F126H, F126V, F126K, Y159V, Y159A, F160W, F160R, F160Y, F160N, F160M, and any combination thereof. In some aspects, the S glycoprotein variant comprises L122K. In some aspects, the S glycoprotein variant comprises L122K and F160W. In some aspects, the S glycoprotein variant comprises L122K, L125Y, F126L and F160W.

In any of the foregoing or related aspects, the RBD comprises a mutation of at least one asparagine-linked glycosylation site relative to the wild-type RBD. In some aspects, the mutation is selected from: (i) a substitution or deletion of the asparagine-linked glycosylation site at amino acid residue 1 of SEQ ID NO: 1; (ii) a substitution or deletion of the asparagine-linked glycosylation site at amino acid residue 13 of SEQ ID NO: 1; or (iii) a combination of (i)-(ii). In some aspects, the mutation is selected from: (i) a deletion of the asparagine-linked glycosylation site at amino acid residue 1 of SEQ ID NO: 1; and (ii) a substitution of the asparagine-linked glycosylation site at amino acid residue 13 of SEQ ID NO: 1. In some aspects, the RBD comprises a deletion of the asparagine-linked glycosylation site at amino acid residue 1 of SEQ ID NO: 1. In some aspects, the RBD comprises a substitution of the asparagine-linked glycosylation site at amino acid residue 13 of SEQ ID NO: 1. In some aspects, the substitution of the asparagine-linked glycosylation site is N to Q.

In some aspects, the disclosure provides a SARS-CoV-2 S glycoprotein variant, wherein the S glycoprotein variant comprises an amino acid sequence selected from: SEQ ID NO: 8, 9, 11, 15, and 16. In some aspects, the SARS-CoV-2 S glycoprotein variant, wherein the S glycoprotein variant comprises the amino acid sequence of SEQ ID NO: 8. In some aspects, the SARS-CoV-2 S glycoprotein variant, wherein the S glycoprotein variant comprises the amino acid sequence of SEQ ID NO: 9. In some aspects, the SARS-CoV-2 S glycoprotein variant, wherein the S glycoprotein variant comprises the amino acid sequence of SEQ ID NO: 11. In some aspects, the S glycoprotein variant comprises a mutation of at least one additional amino acid residue in a first and/or second aggregation-prone region relative to a wild-type RBD comprising the amino acid sequence of SEQ ID NO: 1, wherein the first aggregation-prone region comprises amino acid residues 122-126 of SEQ ID NO: 1, and the second aggregation-prone region comprises amino acid residues 158-162 of SEQ ID NO: 1, and wherein the mutation is a substitution with a different amino acid residue. In some aspects, the different amino acid residue is less hydrophobic, found at the same position in a genetic background of at least one species of SARS-CoV, or both.

In any of the foregoing or related aspects the SARS-CoV-2 S glycoprotein variant comprises a mutation of at least one additional amino acid residue in a first and/or second aggregation-prone region that is not part of the ACE2 RBM, wherein the first aggregation-prone region comprises amino acid residues 36-40 of SEQ ID NO: 1, and the second aggregation-prone region comprises amino acid residues 185-189 of SEQ ID NO: 1, wherein the mutation is a substitution with a different amino acid residue. In some aspects, the different amino acid residue is less hydrophobic. In some aspects, the different amino acid residue is an amino acid residue that is found at the same position in a genetic background of at least one species of SARS-CoV. In some aspects, the different amino acid residue is an amino acid residue that is found at the same position in a genetic background of at least one species of SARS-CoV and is less hydrophobic. In some aspects, the at least one amino acid residue is selected from: V37, L38, L187, L188, and a combination thereof. In some aspects, the mutation of at least one additional amino acid residue is a substitution selected from: V37F, L38A, L38M, L38F, L187A, L187I, L188A, L188M, L188D, L188T, and a combination thereof.

In some aspects, the disclosure provides a SARS-CoV-2 S glycoprotein variant comprising an amino acid sequence selected from the group consisting of SEQ ID NOs: 6, 7, 12-14, and 18.

In any of the foregoing or related aspects, the SARS-CoV-2 S glycoprotein variant comprises at least one additional amino acid residue substitution selected from: P7D, V11I, A18P, N24E, R27K, Y35W, V37F, K48R, S53D, L60Y, F62W, I72V, R78D, Q84A, K87V, D98N, L111I, L125N, Q168D, Y178H, L188D, V194R, and any combination thereof. In some aspects, the SARS-CoV-2 S glycoprotein variant comprises an amino acid sequence selected from any one of SEQ ID NOs: 26-47.

In some aspects, the disclosure provides a method for reducing aggregation of a SARS-CoV-2 glycoprotein variant comprising a receptor binding domain (RBD), the method comprising introducing a mutation to at least one amino acid residue in an angiostensin-converting enzyme 2 (ACE2) receptor binding motif (RBM) of the RBD relative to a wild-type RBD, wherein the residue is (i) hydrophobic; and (ii) within an aggregation-prone region of about 3-15 amino acid residues, wherein the mutation is a substitution of the hydrophobic residue with a different amino acid residue. In some aspects, the different amino acid residue is less hydrophobic, found at the same position in a genetic background of at least one species of SARS-CoV, or both. In some aspects, the at least one species of SARS-CoV encodes an S glycoprotein comprising an RBD, wherein the RBD has greater than about 50%, 55%, 60%, 65%, 70%, 75%, 80%, 85%, 90%, or 95% sequence homology to the SARS-CoV-2 RBD (e.g., SEQ ID NO: 1). In some aspects, the different amino acid residue is present at a frequency of at least 0.1% in a SARS-CoV genetic background. In some aspects, the different amino acid is less hydrophobic than the hydrophobic residue. In some aspects, the disclosure provides a SARS-CoV-2 S glycoprotein variant produced by a method described herein.

In some aspects, the SARS-CoV-2 S glycoprotein variant described herein has reduced hydrophobicity relative to a SARS-CoV-2 S glycoprotein not having the at least one mutation. In some aspects, the hydrophobicity is reduced by at least 1.1 fold, 1.2 fold, 1.3 fold, 1.4 fold, 1.5 fold, 1.6 fold, 1.7 fold, 1.8 fold, 1.9 fold or 2.0 fold relative to the SARS-CoV-2 S glycoprotein not having the at least one mutation. In some aspects, the SARS-CoV-2 S glycoprotein described herein has reduced aggregation relative to an S glycoprotein not having the at least one mutation. In some aspects, the SARS-CoV-2 S glycoprotein described herein has increased thermostability relative to a SARS-CoV-2 S glycoprotein or fragment not having the at least one mutation. In some aspects, the SARS-CoV-2 S glycoprotein has disorder increased by about 5-30% within the ACE2 RBM relative to an SARS-CoV-2 S glycoprotein variant not having the at least one mutation. In some aspects, the SARS-CoV-2 S glycoprotein variant has increased immunogenicity relative to an SARS-CoV-2 S glycoprotein variant not having the at least one mutation. In some aspects, immunogenicity is measured by the level of IgG neutralizing antibodies produced. In some aspects, the SARS-CoV-2 S glycoprotein variant binds human ACE2 with substantially equivalent binding affinity to a SARS-CoV-2 S glycoprotein comprising the wild-type RBD. In some aspects, the SARS-CoV-2 S glycoprotein variant has increased binding affinity for human ACE2 relative to a SARS-CoV-2 S glycoprotein comprising the wild-type RBD.

In any of the foregoing or related aspects, the SARS-CoV-2 S glycoprotein variant described herein comprises a full-length RBD or portion thereof (e.g., receptor binding portion). In any of the foregoing or related aspects, the SARS-CoV-2 S glycoprotein variant described herein comprises an N-terminal domain or portion thereof. In some aspects, the S glycoprotein variant comprises an S2 subunit or portion thereof.

In some aspects, the disclosure provides a nucleic acid comprising a nucleotide sequence encoding the SARS-CoV-2 S glycoprotein variant described herein. In some aspects, the disclosure provides an expression vector comprising the nucleic acid. In some aspects, the disclosure provides a cell transformed with the expression vector. In some aspects, the cell is a yeast cell. In some aspects, the cell is a fungal cell.

In some aspects, the disclosure provides a method for producing an SARS-CoV-2 S glycoprotein variant, the method comprising maintaining a cell described herein under conditions permitting expression of the SARS-CoV-2 S glycoprotein variant. In some aspects, the expression of the SARS-CoV-2 S glycoprotein variant is increased relative to expression of an SARS-CoV-2 S glycoprotein variant not having the at least one mutation. In some aspects, aggregation of the SARS-CoV-2 S glycoprotein variant is reduced relative to aggregation of an SARS-CoV-2 S glycoprotein variant not having the at least one mutation, and wherein the reduced aggregation results in increased yield of the SARS-CoV-2 S glycoprotein variant.

In some aspects, the disclosure provides a composition comprising the SARS-CoV-2 S glycoprotein variant described herein, and a pharmaceutically acceptable carrier. In some aspects, the composition comprises a monomer of the SARS-CoV-2 S glycoprotein variant. In some aspects, the composition comprises a trimer (e.g., homotrimer) of the SARS-CoV-2 S glycoprotein variant.

In some aspects, the disclosure provides an immunogenic composition comprising the SARS-CoV-2 S glycoprotein variant described herein, or a composition described herein, and an adjuvant. In some aspects, the adjuvant is an immunostimulatory adjuvant. In some aspects, the adjuvant is CpG. In some aspects, the adjuvant is alum. In some aspects, the adjuvant comprises an immunostimulatory adjuvant (e.g., CpG) and alum. In some aspects, the adjuvant comprises a saponin.

In some aspects, the disclosure provides a kit comprising a container comprising the SARS-CoV-2 S glycoprotein variant described herein, the composition described herein, the immunogenic composition described herein, and a package insert comprising instructions for administration of the composition to a subject for inducing an immune response against the S glycoprotein variant, wherein the subject is at risk of being infected with SARS-CoV-2.

In some aspects, the disclosure provides a method of inducing an immune response in a subject comprising, administering to the subject the SARS-CoV-2 S glycoprotein variant described herein, the composition described herein, or the immunogenic composition described herein. In some aspects, the immune response comprises production of antibodies against the S glycoprotein variant. In some aspects, the antibodies are capable of neutralizing SARS-CoV-2. In some aspects, the immune response comprises a T cell response. In some aspects, the subject is at risk for being exposed to and/or infected by SARS-CoV-2. In some aspects, the composition or immunogenic composition is administered prior to the risk of exposure and/or infection. In some aspects, the disclosure provides a method of preventing infection of SARS-CoV-2 in a subject comprising, administering to the subject the SARS-CoV-2 S glycoprotein variant described herein, the composition described herein, or the immunogenic composition described herein.

BRIEF DESCRIPTION OF THE FIGURES

FIGS. 1C-1D are graphs showing binding of SARS-CoV-2 RBD-N1del to CR3022 neutralizing antibody (FIG. 1C) and human ACE2-IgG fusion protein (FIG. 1D) determined by biolayer inferometry.

FIGS. 1E-1F are graphs showing binding of RBD-N1del-N13Q to CR3022 neutralizing antibody (FIG. 1E) and human ACE2-IgG fusion protein (FIG. 1F) determined by biolayer inferometry.

FIG. 2A shows the structure of the RBD-N1del protein, with predicted hydrophobic patches shown in red and the ACE2 receptor binding motif indicated with arrows.

FIGS. 2B-2C provide a sequence logo plot representing conserved residues in the ACE2 receptor binding motif based on the top 96 sequences identified by BLAST for having sequence homology to the SARS-CoV-2 RBD. FIG. 2B provides residues in the ACE2 receptor binding motif identified as belonging to a hydrophobic patches shown in FIG. 2A, and provides alignment with known SARS-CoV2 S glycoprotein sequences and RBD variants of the disclosure (from top to bottom: SEQ ID NOs:120, 120, 121, 122, 123, 124). FIG. 2C provides conserved residues identified across an extended region of the RBD. Residue numbering is according to SEQ ID NO: 1.

FIG. 2D is a graph showing specific productivity of RBD variants tagged with signal peptide alpha (A) or Ost1 (O). Reported values are relative to expression of RBD-N1del with signal peptide A.

DETAILED DESCRIPTION

Figure 1A:
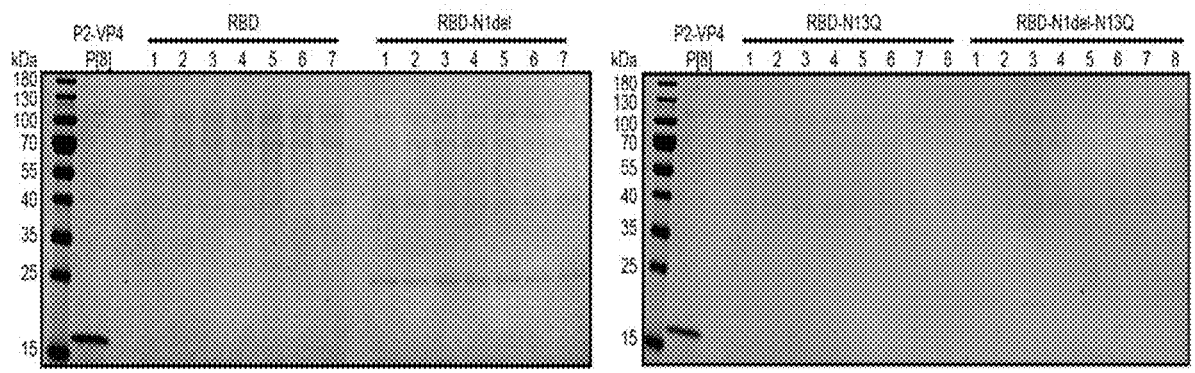
FIG. 1A is a reduced SDS-PAGE of cultivation supernatants of SARS-CoV-2 RBD variants having one (RBD-N1del; RBD-N13Q) or both (RBD-N1del-N13Q) glycosylation sites removed compared to wild-type (RBD), cultured in complex media. Each number represents a unique clone after transformation.

Containment of COVID-19 will require coordinated response at a global scale, including the development and distribution of vaccines that are accessible in low- and middle-income countries (LMICs) (Gates, (2020) *NEJM* doi:10.1056/nejmp2003762). A target product profile (TPP) for a vaccine for LMICs will have stricter requirements for dosing, manufacturing scale, cost of goods (COGs), and cold chain storage than for a vaccine for developed countries. Protection from COVID-19 after a single dose will facilitate broad distribution and reduce the overall dose requirement. Even with single dose administration, 2-4 billion doses are required for global access given the rate of infectivity of SARS-CoV-2. Achieving low COGs (<$1 per dose) will require methods for manufacturing that use low-cost raw materials, including only commercial, commodity adjuvants like alum, currently sold at $0.10 per 50 μg dose (Munira, et al (2019) *Vaccine* 37:1245). Finally, stability of the drug product in non-cryogenic conditions is essential for distribution and access in remote areas.

Vaccines that are currently in clinical development are designed to meet immediate needs in developed countries, but access will likely be limited in LMICs. Several novel vaccines based on nucleic acid technologies show early promise in both animals and humans, but are priced at $10-$40 per dose, and generally require cryogenic temperatures for storage and transport (Jackson et al (2020) *NEJM* doi:10.1056/NEJMoa2022483; Folegatti, et al (2020) *Lancet* 0, 1-13; Zhu, et al (2020) *Lancet* 395:1845). With subsidization, one manufacturer, to date, has promised $3 per dose for ~100 million doses of a vaccine for low- and middle-income countries (LMICs) (Gates Foundation Teams Up With Vaccine Maker to Produce $3 Covid-19 Shots—WSJ. https://www.wsj.com/articles/gates-foundation-teams-up-with-vaccine-maker-to-produce-3-covid-19-shots-11596804573). Prices will need to be lower and the scale of manufacturing larger, however, to achieve the coverage needed to stop the spread of COVID-19 globally (Gates, B. (2015) *NEJM* 372:1381-1384). The first promising protein-based vaccine was also priced >$10/dose, largely due to costly expression in recombinant insect cells (Tian, et al (2020 *bioRxiv* 2020.06.29.178509). Lower cost, high capacity manufacturing can be most practically achieved with a subunit vaccine, which would be compatible with existing facilities for the manufacturing of protein therapeutics at the scale of ~1 billion annual doses, like those used in the production of insulin and Hepatitis B vaccine in *Komagataella phaffii* (*Pichia pastoris*) for global use (Shekhar, (2008) Chem. Biol. 15:201). A vaccine candidate for LMICs which is a protein subunit that is engineered for enhanced manufacturability and immunogenicity, and is compatible with existing platforms for the manufacturing of low-cost vaccine products, is needed.

Accordingly, in some aspects, the present disclosure is provides SARS-CoV-2 S glycoprotein variants with desired properties for vaccine development, e.g., increased expression to enable low-cost manufacture, sufficient thermostability to enable low-cost storage and transport, and/or potent immunogenicity (e.g., to generate neutralizing titers following a single dose). In some aspects, the SARS-CoV-2 S glycoprotein variants comprise a full-length SARS-CoV-2 S glycoprotein (both S1 and S2 subunits) or fragment thereof (e.g., the SARS-CoV-2 RBD), having one or more mutations (e.g., amino acid substitutions) in aggregation-prone regions or hotspots (e.g., within the RBD) that reduce hydrophobicity, reduce aggregation and/or increase expression and/or production in host cells of interest.

SARS-CoV-2 S Glycoprotein Variants of the Disclosure

The present disclosure provides novel S glycoprotein variants derived from SARS-CoV-2. In some embodiments, the SARS-CoV-2 S glycoprotein variants are useful as vaccines to induce an immune response in a subject.

Coronaviruses are enveloped single-stranded, positive-strand RNA viruses of the family Coronaviridae. They divide into four main groups: α, β, γ, and δ. At least seven coronaviruses infect humans: the α-coronaviruses HCoV-229E and HCoV-OC43, and the β-coronaviruses SARS-CoV (SARS-CoV-1), HCoV-NL63, CoV-HKU1, MERS-CoV, and the recently described SARS-CoV-2 (nCoV-19). The severe acute respiratory syndrome-related coronavirus (SARS-CoV) was the source of a SARS outbreak in 2002. A large number of SARS-CoV viral strains have been discovered in bats and palm civets, which provide natural and intermediate host reservoirs (see, e.g., Li et al (2005) *SCIENCE* 310:676; Ge, et al (2013) *NATURE* 503:535; Yang, et al (2013) *EMERG INFECT DIS* 19:989; Hu et al (2017) *PLoS PATHOGENS* 13:e1006698).

The coronavirus genome encodes the structural spike (S) glycoprotein, small envelope (E) protein, membrane (M) glycoprotein, and nucleocapsid (N) protein, in that order from 5'-3'. The genome is packaged into a helical nucleocapsid surrounded by a host-derived lipid bilayer. The virion envelope contains at least three viral proteins, the spike protein (S), the membrane protein (M) and the envelope protein (E). Whereas the M and E proteins are involved in virus assembly, the spike protein is the leading mediator of viral entry. The N protein is the only protein in the nucleocapsid and binds the viral genome. In addition, some coronaviruses also contain a hemagglutinin esterase (HE) which is a viral envelope protein that mediates reversible attachment to O-acetylated sialic acids by acting both as lectins and as receptor-destroying enzymes.

Coronavirus entry into host cells is a necessary requirement for mediating infectivity and pathogenesis. To enter host cells, the coronavirus binds to a cell surface receptor to mediate viral attachment, cellular uptake into endosomes, and eventual fusion with lysosomal membranes to allow entry of the viral genome into the cytosol of the host cell. A virus surface-anchored spike protein found on the surface of the coronavirus mediates viral entry. The surface-anchored spike protein is a homotrimer, composed of monomeric spike (S) glycoproteins that each comprise an S1 subunit and S2 subunit. The S1 subunit comprises a receptor binding domain (RBD) that mediates binding to proteins located on the surface of the host cell.

A critical step for SARS-CoV viral entry into human host cells is the S glycoprotein binding to the human receptor ACE2 (angiotensin 1 converting enzyme 2) through its RBD (see, e.g., Li (2015) *J. VIROL.* 89:1954; Li et al (2003) *NATURE* 426: 450-454; Li, et al (2005) *SCIENCE* 309: 1864-1868). To fuse to membranes, the S protein requires proteolytic activation at the boundary between the S1 and S2 subunit, e.g., by cell-surface proteases and/or lysosomal proteases, whereupon the S1 subunit dissociates and the S2 subunit undergoes a structural rearrangement to facilitate cellular entry (see, e.g., Belouzard, et al (2012) *VIRUSES* 4:557; Bolles (2011) *CURR OPIN VIROL.* 1:624).

Early in the 2019 COVID-19 outbreak, SARS-CoV-2 was isolated from multiple human patients with severe pneumonia, and the genome was sequenced (see, e.g., GISAID Accession Nos. EPI_ISL_402124 (WIV04); EPI_ISL_402127 (WIV02); EPI_ISL_402128 (WIV05); EPI_ISL_402129 (WIV06); and EPI_ISL_402130 (WIV07). The SARS-CoV-2 genome from different patients was found to have high (greater than 99%) sequence identity with one another and substantial sequence identity (approximately 80%) with SARS-CoV (see, e.g., Zhou, et al (2020) *NATURE* 579:7798). Additionally, the SARS-CoV-2 S glycoprotein has been determined to have approximately 75-80% sequence identity with the SARS-CoV S glycoprotein (isolated from human, civet, or bat) (Wan et al (2020) *J VIROL* 94:e00127), and has been shown to likewise bind to human ACE2 (hACE2) to achieve viral entry into human host cells (Wan et al (2020) *J VIROL* 94:e00127; Zhou, et al (2020) *NATURE* 579:270; Letko, et al (2020) *NAT. MICROBIOL.* 5:562).

In some aspects, the disclosure provides a SARS-CoV-2 S glycoprotein variant. As used herein, a "SARS-CoV-2 S glycoprotein variant" refers to a SARS-CoV-2 S glycoprotein comprising at least one mutation in the RBD relative to the amino acid sequence of a wild-type SARS-CoV-2 S glycoprotein. In some embodiments, the amino acid sequence of the wild-type SARS-CoV-2 S glycoprotein has the amino acid sequence set forth by SEQ ID NO: 59. In some embodiments, the amino acid sequence of the wild-type SARS-CoV-2 S glycoprotein without a signal peptide is set forth by SEQ ID NO: 61. As is understood by one of skill in the art, community transmission of the SARS-CoV-2 virus provides naturally-occurring variants of the SARS-CoV-2 S glycoprotein, for example, comprising one or more mutations relative to SEQ ID NO: 59. Such naturally-occurring variants can be identified via public databases such as GISAID (Euro Surveill. 2017 03 30; 22(13):30494), SWISS-PROT, RefSeq, and the PDB. In some embodiments, the wild-type SARS-CoV-2 S glycoprotein is 1273 amino acid residues in length and consists of the following domains linked in order from the N-terminus to C-terminus:

(a) a signal peptide (corresponding to amino acid residues between about 1 and about 13 of SEQ ID NO: 59);

(b) a subunit S1 (corresponding to amino acid residues between about 14 and about 685 of SEQ ID NO: 59) comprising:
  (i) an N-terminal domain (NTD) (corresponding to amino acid residues between about 14 and about 305 of SEQ ID NO: 59);
  (ii) a RBD (corresponding to amino acid residues 319-541 of SEQ ID NO: 59); and (c) a subunit S2 (corresponding to amino acid residues between about 686 and about 1273 of SEQ ID NO: 59) comprising:
  (i) a fusion protein (corresponding to amino acid residues between about 788 and about 806 of SEQ ID NO: 59);
  (ii) a heptapeptide repeat sequence 1 (corresponding to amino acid residues between about 912 and about 984 of SEQ ID NO: 59);
  (iii) a heptapeptide repeat sequence 2 (corresponding to amino acid residues between about 1163 and about 1213 of SEQ ID NO: 59);
  (iv) a transmembrane region (corresponding to amino acid residues between about 1213 and about 1237 of SEQ ID NO: 59); and (v) a cytoplasmic domain (corresponding to amino acid residues between about 1237 and about 1273 of SEQ ID NO: 59).

In some embodiments, the at least one mutation provides (i) reduced aggregation, (ii) reduced hydrophobicity, (iii) increased thermostability, (iv) increased expression, (v) increased immunogenicity, or (vi) any combination of (i)-(v) relative to the SARS-CoV-2 S glycoprotein without the at least one mutation. In some embodiments, the SARS-CoV-2 S glycoprotein variant is sufficient immunogenic to induce an immune response against SARS-CoV-2 (e.g., a neutralizing immune response). In some embodiments, the SARS-CoV-2 S glycoprotein variant comprises one or more mutations relative to the wild-type SARS-CoV-2 S glycoprotein sequence that confer improved expression, production, and/or immunogenicity, as further described herein.

In some embodiments, a SARS-CoV-2 S glycoprotein variant described herein is a trimer (e.g., homotrimer). In some embodiments, the SARS-CoV-2 S glycoprotein variant is a monomer. In some embodiments, the SARS-CoV-2 S glycoprotein variant is a full-length S glycoprotein (S1 subunit+S2 subunit) comprising at least one mutation in the RBD relative to a wild-type SARS-CoV-2 S glycoprotein. In some embodiments, the SARS-CoV-2 S glycoprotein variant comprises a truncated SARS-CoV-2 S glycoprotein, wherein the truncated S glycoprotein comprises at least one mutation in the RBD relative to the wild-type SARS-CoV-2 S glycoprotein. In some embodiments, the SARS-CoV-2 S glycoprotein variant comprises a receptor binding fragment of the SARS-CoV-2 S glycoprotein, wherein the receptor binding fragment comprises a full-length RBD, and wherein the RBD comprises at least one mutation relative to the RBD of a wild-type SARS-CoV-2 S glycoprotein. In some embodiments, the SARS-CoV-2 S glycoprotein variant comprises a receptor binding fragment of the SARS-CoV-2 S glycoprotein, wherein the receptor binding fragment comprises a truncated RBD, and wherein the truncated RBD comprises at least one mutation relative to the RBD of a wild-type SARS-CoV-2 S glycoprotein.

As used herein, the "SARS-CoV-2 RBD" or "RBD" refers to the domain of the SARS-CoV-2 S glycoprotein that binds to a host cell receptor (e.g., hACE2) to mediate viral entry. In some embodiments, the SARS-CoV-2 RBD corresponds to amino acid residues between about 319 and about 541 of the full-length SARS-CoV-2 S glycoprotein (e.g., SEQ ID NO: 59). A wild-type SARS-CoV-2 RBD corresponding to amino acid residues 331-532 of the full-length SARS-CoV-2 S glycoprotein is set forth by SEQ ID NO: 1. Accordingly, amino acid residues 1-202 of the SARS-CoV-2 RBD set forth by SEQ ID NO: 1 correspond to amino acid residues 331-532 of the full-length SARS-CoV-2 S glycoprotein (SEQ ID NO: 59), and such numbering is used interchangeably herein. Specifically, for embodiments described herein wherein an amino acid residue is numbered according to SEQ ID NO: 1, the corresponding position is understood in reference to the full-length SARS-CoV-2 S glycoprotein (SEQ ID NO: 59) based on the interchangeable numbering. For example, the amino acid residue 1 according to SEQ ID NO: 1 corresponds to amino acid residue 331 of the full-length SARS-CoV-2 S glycoprotein (SEQ ID NO: 59), amino acid residue 2 of SEQ ID NO: 1 is to amino acid residue 332 of the full-length SARS-CoV-2 S glycoprotein (SEQ ID NO: 59), and so on.

In some embodiments, the SARS-CoV-2 S glycoprotein variant comprises the SARS-CoV-2 RBD (e.g., amino acid residues 319-541 of SEQ ID NO: 59) or a variant thereof. In some embodiments, the SARS-CoV-2 S glycoprotein variant comprises a truncated SARS-CoV-2 RBD (e.g., amino acid residues 331-532 of SEQ ID NO: 59) or variant thereof. In some embodiments, the SARS-CoV-2 S glycoprotein variant comprises the receptor binding motif of the SARS-CoV-2 RBD. In some embodiments, the SARS-CoV-2 S glycoprotein comprises the receptor binding motif (RBM) that interacts with ACE2 receptor (e.g., hACE2 receptor). Methods to identify the RBM are known in the art.

In some embodiments, a structure (e.g., cryo-electron microscopy structure, X-ray crystal structure) of a SARS-CoV RBD in complex with ACE2 (e.g., hACE2) is used to model the interface between a SARS-CoV-2 RBD and ACE2 to determine regions of the SARS-CoV-2 RBD that reside at the binding interface with ACE2, such as is described by Wan, et al. (2020) J. VIROL. 94:e00127-20). In some embodiments, an amino acid residue of the RBD at the binding interface with ACE2 is any one selected from amino acid residue between about 107 and about 178 and between about 437 and about 508 of the full-length SARS-CoV-2 S glycoprotein (e.g., SEQ ID NO: 59). In some embodiments the SARS-CoV-2 ACE2 RBM comprises one or more amino acid residues selected from 107-178 and 437-508 of the full-length SARS-CoV-2 S glycoprotein (e.g., SEQ ID NO: 59).

In some embodiments, a structure (e.g., cryo-electron microscopy structure, X-ray crystal structure) of the SARS-CoV-2 RBD in complex ACE2 enables identification of contact residues of the RBD that are located at the interface between the RBD and ACE2, such as is described by Lan et al (2020) NATURE 581:215. In some embodiments, an amino acid residue of the RBD that is a contact residue at the RBM-ACE2 binding interface is one that is located within approximately 3 Å, 4 Å, 5 Å, or 6 Å of a residue of ACE2. In some embodiments, the RBM that interacts with the hACE2 receptor comprises all or a portion of the RBD contact residues identified in a structure of the RBD/ACE2 complex (e.g., crystal structure, e.g., crystal structure as deposited in the Protein Databank as 6M0J). In some embodiments, the RBD contact residues comprise one or more amino acid residues selected from Table 1. In some embodiments, the RBD contact residues comprise one or more amino acid residues selected from between about 107 and about 178 and between about 437 and about 508 of the full-length SARS-CoV-2 S glycoprotein (e.g., SEQ ID NO: 59).

TABLE 1

Contact Residues of SARS-CoV-2 RBD when bound to hACE2*

| Contact Residue | Residue number of the full-length S glycoprotein set forth by SEQ ID NO: 59 | Corresponding residue number of the wild-type RBD set forth by SEQ ID NO: 1 |
| --- | --- | --- |
| K | 417 | 87 |
| G | 446 | 116 |
| Y | 449 | 119 |
| Y | 453 | 123 |
| L | 455 | 125 |
| F | 456 | 126 |
| A | 475 | 145 |
| F | 486 | 156 |
| N | 487 | 157 |
| Y | 489 | 159 |
| Q | 493 | 163 |
| G | 496 | 166 |
| Q | 498 | 168 |
| T | 500 | 170 |

TABLE 1-continued

Contact Residues of SARS-CoV-2 RBD when bound to hACE2*

| Contact Residue | Residue number of the full-length S glycoprotein set forth by SEQ ID NO: 59 | Corresponding residue number of the wild-type RBD set forth by SEQ ID NO: 1 |
|---|---|---|
| N | 501 | 171 |
| G | 502 | 172 |
| Y | 505 | 175 |

*Reference: Lan et al (2020) NATURE 581: 215

In some embodiments, the SARS-CoV-2 S glycoprotein variant comprises a fragment of the SARS-CoV-2 S glycoprotein that corresponds to the RBD. In some embodiments, the SARS-CoV-2 S glycoprotein variant comprises a fragment of the SARS-CoV-2 S protein that corresponds to amino acid residues 319-541. In some embodiments, the SARS-CoV-2 S glycoprotein variant comprises a fragment of the SARS-CoV-2 S glycoprotein that corresponds to a truncated RBD. In some embodiments, the SARS-CoV-2 S glycoprotein variant comprises a fragment of the SARS-CoV-2 S glycoprotein that corresponds to amino acid residues 331-532 (e.g., SEQ ID NO: 1). In some embodiments, the SARS-CoV-2 S glycoprotein variant comprises a fragment of the SARS-CoV-2 S glycoprotein comprising the ACE2-receptor RBM. In some embodiments, the RBM comprises the contact residues identified in Table 1. In some aspects, the RBM comprises one or more amino acid residues selected from 107-178 and 437-508 of the full-length SARS-CoV-2 S glycoprotein (e.g., SEQ ID NO: 59).

Generating SARS-CoV-2 S Glycoprotein Variants of the Disclosure

In some embodiments, the mutation is removal of one or more asparagine-linked glycosylation sites. In some embodiments, the mutation removes one or more hydrophobic amino acid residues. In some embodiments, the one or more hydrophobic amino acid residues are located within an aggregation-prone region. In some embodiments, removal of a glycosylation site or hydrophobic amino acid is by deletion or substitution.

In some embodiments, the SARS-CoV-2 S glycoprotein variant has increased expression relative to the corresponding wild-type SARS-CoV-2 S glycoprotein. In some embodiments, the SARS-CoV-2 S glycoprotein variant has reduced aggregation relative to the corresponding wild-type SARS-CoV-2 S glycoprotein. In some embodiments, the SARS-CoV-2 S glycoprotein variant has increased binding affinity or substantially equivalent binding affinity for ACE2 (e.g., hACE2) relative to the corresponding wild-type SARS-CoV-2 S glycoprotein. In some embodiments, the SARS-CoV-2 S glycoprotein variant has increased immunogenicity relative to the corresponding wild-type S glycoprotein or fragment thereof. In some embodiments, the SARS-CoV-2 S glycoprotein variant has:
  (i) increased expression;
  (ii) reduced aggregation;
  (iii) increased or substantially equivalent binding affinity to human ACE2;
  (iv) increased immunogenicity;
  (v) increased thermostability; or
  (vi) any combination of (i)-(v),
  relative to the wild-type SARS-CoV-2 S glycoprotein.

In some embodiments, an SARS-CoV-2 S glycoprotein variant having one or more asparagine-linked glycosylation sites and one or more hydrophobic amino acid residues removed has increased expression relative to the corresponding SARS-CoV-2 S glycoprotein variant without the one or more hydrophobic amino acid residues removed. In some embodiments, an SARS-CoV-2 S glycoprotein variant having one or more asparagine-linked glycosylation sites and one or more hydrophobic amino acid residues removed has reduced aggregation relative to the corresponding SARS-CoV-2 S glycoprotein variant without the one or more hydrophobic amino acid residues removed. In some embodiments, an SARS-CoV-2 S glycoprotein variant having one or more asparagine-linked glycosylation sites and one or more hydrophobic amino acid residues removed has increased binding to human ACE2 relative to the corresponding SARS-CoV-2 S glycoprotein variant without the one or more hydrophobic amino acid residues removed. In some embodiments, an SARS-CoV-2 S glycoprotein variant having one or more asparagine-linked glycosylation sites and one or more hydrophobic amino acid residues removed has increased immunogenicity relative to the corresponding SARS-CoV-2 S glycoprotein variant without the one or more hydrophobic amino acid residues removed. In some embodiments, an SARS-CoV-2 S glycoprotein variant having one or more asparagine-linked glycosylation sites and one or more hydrophobic amino acid residues removed has:
  (i) increased expression;
  (ii) reduced aggregation;
  (iii) increased or substantially equivalent binding affinity to human ACE2;
  (iv) increased immunogenicity;
  (v) increased thermostability; or
  (vi) any combination of (i)-(v),
  relative to the corresponding SARS-CoV-2 S glycoprotein variant without the one or more hydrophobic amino acid residues removed.

A. Removal of Glycosylation Sites

In some embodiments, the SARS-CoV-2 S glycoprotein variant lacks one or more asparagine-linked glycosylation sites relative to the corresponding wild-type SARS-CoV-2 S glycoprotein. In some embodiments, the glycosylation site of the S glycoprotein variant is removed by, for example, substitution or deletion. In some embodiments, one or more asparagine-linked glycosylation site in any domain of the S glycoprotein is removed by substitution or deletion. In some embodiments, one or more asparagine-linked glycosylation site in the RBD is removed by substitution or deletion.

In some embodiments, the SARS-CoV-2 S glycoprotein variant lacks one or more asparagine-linked glycosylation sites within the RBD. In some embodiments, the first glycosylation site of the RBD is deleted. In some embodiments, the first glycosylation site of the RBD is substituted. In some embodiments, the first glycosylation site of the RBD is an asparagine (N) residue. In some embodiments, the asparagine is substituted with glutamine. In some embodiments, the first glycosylation site of the RBD corresponds to amino acid residue N331 in the full-length S glycoprotein or N1 of the wild-type RBD amino acid sequence set forth by SEQ ID NO: 1. In some embodiments, the first glycosylation site is deleted. In some embodiments, the first glycosylation site is substituted, e.g., N331Q in the full-length S glycoprotein or N1Q in the amino acid sequence set forth by SEQ ID NO: 1.

In some embodiments, the SARS-CoV-2 S glycoprotein variant comprising a deletion of the first glycosylation site of the RBD comprises the amino acid sequence set forth in SEQ ID NO: 2. In some embodiments, the SARS-CoV-2 S glycoprotein variant comprises the amino acid sequence set forth by SEQ ID NO: 2. In some embodiments, the SARS-CoV-2 S glycoprotein variant comprises the amino acid sequence set forth by SEQ ID NO: 2, wherein the amino acid sequence comprises at least one additional mutation described herein. In some embodiments, the SARS-CoV-2 S glycoprotein variant consists of the amino acid sequence set forth by SEQ ID NO: 2. In some embodiments, the SARS-CoV-2 S glycoprotein variant consists of the amino acid sequence set forth by SEQ ID NO: 2, wherein the amino acid sequence comprises at least one additional mutation described herein.

In some embodiments, the second glycosylation site of the RBD is deleted or substituted for a different amino acid residue. In some embodiments, the second glycosylation site is an asparagine (N) residue. In some embodiments, the asparagine is substituted with glutamine. In some embodiments, the second glycosylation site of the RBD variant corresponds to amino acid residue N343 of the full-length S glycoprotein or amino acid residue N13 of the wild-type RBD amino acid sequence set forth by SEQ ID NO: 1. In some embodiments, the second glycosylation site of the RBD is deleted or substituted for a different amino acid residue. In some embodiments, the second glycosylation site is substituted, e.g., N343Q in the full-length S glycoprotein or N13Q of the amino acids sequence set forth by SEQ ID NO:1.

In some embodiments, the SARS-CoV-2 S glycoprotein variant comprising a substitution of the second glycosylation site of the RBD comprises the amino acid sequence set forth in SEQ ID NO: 3. In some embodiments, the substitution of the second glycosylation site is the N13Q mutation relative to the amino acids sequence set forth by SEQ ID NO: 1. In some embodiments, the SARS-CoV-2 S glycoprotein variant comprises the amino acid sequence set forth by SEQ ID NO: 3. In some embodiments, the SARS-CoV-2 S glycoprotein variant comprise the amino acid sequence set forth by SEQ ID NO: 3, wherein the amino acid sequence comprises at least one additional mutation described herein. In some embodiments, the SARS-CoV-2 S glycoprotein variant consists of the amino acid sequence set forth by SEQ ID NO: 3. In some embodiments, the SARS-CoV-2 S glycoprotein variant consists of the amino acid sequence set forth by SEQ ID NO: 3, wherein the amino acid sequence comprises at least one additional mutation described herein.

In some embodiments, the first and second glycosylation sites of the RBD are deleted. In some embodiments, the first glycosylation site of the RBD is deleted and the second glycosylation site is substituted for a different amino acid residue (e.g., asparagine to glutamine). In some embodiments, the first and second glycosylation sites are substituted for a different amino acid residue (e.g., asparagine to glutamine). In some embodiments, the first glycosylation site is substituted for a different amino acid residue and the second glycosylation site is deleted. In some embodiments, the first and second glycosylation sites correspond to (i) amino acid residues 1 and 13, respectively, of the wild-type RBD amino acid sequence set forth by SEQ ID NO: 1; and (ii) amino acid residues 331 and 343, respectively, of the wild-type SARS-CoV-2 S glycoprotein (e.g., SEQ ID NO: 59). In some embodiments, an SARS-CoV-2 S glycoprotein variant comprising a deletion of a first glycosylation site in the RBD comprises the amino acid sequence set forth in SEQ ID NO: 2. In some embodiments, an SARS-CoV-2 S glycoprotein variant comprising a substitution of a second glycosylation site in the RBD comprises the amino acid sequence set forth in SEQ ID NO: 3. In some embodiments, an SARS-CoV-2 S glycoprotein variant comprising deletion of a first glycosylation site in the RBD and a substitution of a second glycosylation site in the RBD comprises the amino acid sequence set forth in SEQ ID NO: 4.

In some embodiments, an SARS-CoV-2 S glycoprotein variant comprising a deletion of a first glycosylation site in the RBD comprises the amino acid sequence of any one of SEQ ID NOs: 2, 4-58. In some embodiments, an SARS-CoV-2 S glycoprotein variant comprising a substituted second glycosylation site in the RBD comprises the amino acid sequence of SEQ ID NO: 3 or SEQ ID NO: 4. In some embodiments, the SARS-CoV-2 S glycoprotein variant comprising a deleted first glycosylation site in the RBD and a substituted second glycosylation site in the RBD comprises the amino acid sequence of SEQ ID NO: 4.

In some embodiments, an SARS-CoV-2 S glycoprotein variant comprising removal of one or more glycosylation site in the RBD has one or more optimal features relative to the corresponding S glycoprotein comprising a wild-type RBD. In some embodiments, the removal of one or more glycosylation site increases expression of the SARS-CoV-2 S glycoprotein variant compared to the corresponding S glycoprotein comprising a wild-type RBD (e.g., SEQ ID NO: 1). In some embodiments, the removal of one or more glycosylation site reduces aggregation of the S glycoprotein variant compared to the corresponding S glycoprotein comprising a wild-type RBD (e.g., SEQ ID NO:1). In some embodiments, removal of one or more glycosylation sites increases specific productivity of the SARS-CoV-2 S glycoprotein variant compared to that of the corresponding S glycoprotein comprising a wild-type RBD (e.g., SEQ ID NO: 1).

In some embodiments, any of the SARS-CoV-2 S glycoprotein variants described herein are expressed at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 3-fold, at least 4-fold, at least 5-fold higher, at least 6-fold, at least 7-fold, at least 8-fold, at least 9-fold, or at least 10-fold relative to the corresponding S glycoprotein comprising a wild-type RBD (e.g., SEQ ID NO:1).

In some embodiments, an SARS-CoV-2 S glycoprotein variant having the first glycosylation site of the RBD removed (e.g., an SARS-CoV-2 S glycoprotein variant comprising the amino acid sequence set forth by SEQ ID NO: 2) is expressed at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 3-fold, at least 4-fold, at least 5-fold, at least 6-fold, at least 7-fold, at least 8-fold, at least 9-fold, or at least 10-fold relative to the corresponding S glycoprotein comprising a wild-type RBD (e.g., SEQ ID NO:1).

In some embodiments, an SARS-CoV-2 S glycoprotein variant having the second glycosylation site of the RBD removed (e.g., an SARS-CoV-2 S glycoprotein variant comprising the amino acid sequence set forth by SEQ ID NO: 3) is expressed at least 1.1-fold, at least, 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 3-fold, at least 4-fold, at least 5-fold higher, at least 6-fold, at least 7-fold, at least 8-fold, at least 9-fold, or at least 10-fold relative to the corresponding S glycoprotein comprising a wild-type RBD (e.g., SEQ ID NO: 1).

In some embodiments, an SARS-CoV-2 S glycoprotein variant having the first and second glycosylation sites of the RBD removed (e.g., an SARS-CoV-2 S glycoprotein variant comprising the amino acid sequence set forth by SEQ ID NO: 4) is expressed at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 3-fold, at least 4-fold, at least 5-fold, at least 6-fold, at least 7-fold, at least 8-fold, at least 9-fold, or at least 10-fold relative to the corresponding S glycoprotein comprising a wild-type RBD (e.g., SEQ ID NO: 1).

In some embodiments, an SARS-CoV-2 S glycoprotein variant having the first glycosylation site of the RBD removed (e.g., the SARS-CoV-2 S glycoprotein variant comprising the amino acid sequence set forth by SEQ ID NO: 2) has reduced aggregation relative to the corresponding S glycoprotein comprising a wild-type RBD (e.g., SEQ ID NO: 1). In some embodiments, an SARS-CoV-2 S glycoprotein variant having the second glycosylation site of the RBD removed (e.g., the SARS-CoV-2 S glycoprotein variant comprising the amino acid sequence set forth by SEQ ID NO: 3) has reduced aggregation relative to the corresponding S glycoprotein comprising a wild-type RBD (e.g., SEQ ID NO: 1). In some embodiments, an SARS-CoV-2 S glycoprotein variant having the first and second glycosylation sites of the RBD removed (e.g., an SARS-CoV-2 S glycoprotein variant comprising SEQ ID NO: 4) has reduced aggregation relative to the corresponding S glycoprotein comprising a wild-type RBD (e.g., SEQ ID NO:1).

Methods to detect and quantify the presence of aggregates in a protein sample are known in the art. Non-limiting examples of method suitable for use in the present disclosure include analysis of protein aggregation by size-exclusion chromatography, HPLC, dynamic light scattering, static light scattering, capillary electrophoresis, electron microscopy, and analytical ultracentrifugation. In some embodiments, aggregation of the SARS-CoV-2 S glycoprotein variant is reduced by about 10%, by about 20%, by about 30%, by about 40%, by about 50%, by about 60%, or by about 70% to that of the corresponding S glycoprotein comprising a wild-type RBD (e.g., SEQ ID NO: 1).

In some embodiments, a SARS-CoV-2 S glycoprotein variant comprising the first glycosylation site of the RBD removed (e.g., SARS-CoV-2 S glycoprotein variant comprising the amino acid sequence set forth by SEQ ID NO: 2) has comparable or improved immunogenicity relative to the corresponding SARS-CoV-2 S glycoprotein variant comprising a wild-type RBD (e.g., SEQ ID NO: 1). In some embodiments, a SARS-CoV-2 S glycoprotein variant comprising the second glycosylation site of the RBD removed (e.g., SARS-CoV-2 S glycoprotein variant comprising SEQ ID NO: 3) has comparable or improved immunogenicity relative to the corresponding S glycoprotein comprising a wild-type RBD (e.g., SEQ ID NO: 1). In some embodiments, a SARS-CoV-2 S glycoprotein variant having the first and second glycosylation sites of the RBD removed (e.g., SARS-CoV-2 S glycoprotein variant comprising the amino acid sequence set forth by SEQ ID NO: 4) has comparable or improved immunogenicity relative to the corresponding S glycoprotein comprising a wild-type RBD (e.g., SEQ ID NO: 1).

In some embodiments, the SARS-CoV-2 S glycoprotein variant comprises an amino acid sequence set forth in any one of SEQ ID NOs: 2-4. In some embodiments, the SARS-CoV-2 S glycoprotein variant comprises an amino acid sequence having at least 80%, at least 85%, at least 90%, at least 95%, at least 96%, at least 97%, at least 98%, or at least 99% identity to an amino acid sequence selected from SEQ ID NOs: 2-4.

B. Removal of Hydrophobic Amino Acid Residues

Aggregation is a significant hurdle in the manufacture of proteins for therapeutic use (e.g., subunit vaccines). A significant driving force in the transition of an isolated globular protein in solution to multimeric protein aggregates and/or insoluble protein precipitate are hydrophobic interactions between patches on the protein surface comprising poorly soluble amino acid residues. Methods to reduce hydrophobic interactions that promote aggregation, without jeopardizing proper folding or functional properties of the protein, are desirable for manufacture of therapeutic proteins, including the coronavirus antigens of the disclosure.

Accordingly, in some embodiments, the disclosure provides SARS-CoV-2 S glycoprotein variants comprising a mutation of one or more hydrophobic amino acid residues in the RBD, in order to prevent protein aggregation, promote proper protein folding, increase stability, or a combination thereof. In some embodiments, the activity of the SARS-CoV-2 S glycoprotein variant (e.g., receptor binding properties, immunogenicity) is substantially equivalent or improved relative to the S glycoprotein lacking the mutation of the one or more hydrophobic amino acid residues.

In some embodiments, a method to provide a SARS-CoV-2 S glycoprotein variant of the disclosure comprises (i) identifying one or more candidate hydrophobic amino acid residues within the RBD of the wild-type SARS-CoV-2 S glycoprotein; and (ii) identifying an appropriate mutation of the one or more candidate hydrophobic amino acid residues.

In some embodiments, the mutation of the one or more hydrophobic amino acid residues provides an SARS-CoV-2 S glycoprotein variant with reduced propensity to aggregate, proper folding, increased stability, or a combination thereof, relative to the corresponding SARS-CoV-2 S glycoprotein variant lacking the mutation of the one or more hydrophobic amino acid residues. In some embodiments, the SARS-CoV-2 S glycoprotein variant has substantially equivalent or improved activity (e.g., receptor binding properties, immunogenicity) relative to the S glycoprotein lacking the mutation of the one or more hydrophobic amino acid residues.

(i) Identifying the Hydrophobic Amino Acid Residue

In some embodiments, the one or more candidate hydrophobic amino acid residues is located within an aggregation-prone region of the wild-type S glycoprotein. As used herein, the term "aggregation prone region" or "APR" refers to a linear span of amino acid residues present on the surface of the SARS-CoV-2 S glycoprotein when folded that have a tendency to associate, e.g., due to hydrophobic interactions, to form multimeric protein aggregates, e.g., under certain temperature, concentration, and/or pH conditions. In some embodiments, the APR comprises about 3-15 amino acid residues in length. In some embodiments, the APR is predominantly composed of hydrophobic amino acid residues (e.g., Gly, Ala, Val, Leu, Ile, Pro, Met) or aromatic (e.g., Trp, Phe) amino acid residues. For example, for an APR of 10 linear amino acid residues, the APR would have at least 5, 6, 7, 8, 9, or 10 amino acid residues that are hydrophobic or aromatic amino acid residues. In some embodiments, the APR has either none or few (e.g., 1, 2, 3, 4) charged amino acid residues (e.g., Asp, Glu, Lys, Arg, or His).

Methods to predict regions of the S glycoprotein that are APRs are known in the art and described herein. In some embodiments, a suitable method to predict an APR is based on the algorithm described in Sankar, et al. (2018) PROTEINS 86:1147, wherein each amino acid residue of the S glycoprotein (e.g., RBD) is assigned an aggregation score, referred to herein as an "AggScore". As is understood by one skilled in the art, AggScores are determined based on three-dimensional structure input and uses the distribution of hydrophobic and electrostatic patches on the surface of the protein, factoring in the intensity and relative orientation of the respective surface patches into an aggregation propensity function. In some embodiments, the three-dimensional structure input is generated in silico using a computer program, e.g., SWISS-MODEL. In some embodiments, a region is an APR if at least two amino acid residues have a positive AggScore. In some embodiments, a region is an APR if at least two amino acid residues have an AggScore of about 1 to about 20. In some embodiments, a region is an APR if at least two amino acid residues have an AggScore of about 5 to about 20. In some embodiments, a region is an APR if at least two amino acid residues have an AggScore of about 10 to about 20.

In some embodiments, an overall aggregation score is calculated for the span of amino acid residues that is the APR or for all amino acid residues in the SARS-CoV-2 S glycoprotein variant. As used herein, the term "overall aggregation score" refers to a sum of the AggScores of amino acid residues in either (i) a given region of the SARS-CoV-2 S glycoprotein; or (ii) the SARS-CoV-2 S glycoprotein. In some embodiments, the overall aggregation score is for an APR, wherein the score is equivalent to the sum of the AggScores of each amino acid residues in the APR. In some embodiments, the overall aggregation score if for the SARS-CoV-2 S glycoprotein, wherein the score is equivalent to the sum of the AggScores of each amino acid residue in the SARS-CoV-2 S glycoprotein.

In some embodiments, the APR present on the surface of a SARS-CoV-2 S glycoprotein forms a hydrophobic patch that engages in functional protein-protein interactions, such as receptor binding interactions with the ACE2 receptor. In some embodiments, the hydrophobic patch is either formed from a single APR, or multiple APRs that have close spatial proximity on the surface of the folded protein. In some embodiments, the APR is located within the portion of the SARS-CoV-2 glycoprotein that binds to the ACE2 receptor (e.g., hACE2 receptor). In some embodiments, the APR is within the ACE2 RBM or comprises amino acid residues that are part of the ACE2 RBM. In some embodiments, the APR within the ACE2 RBM comprises amino acid residues 122-126 of SEQ ID NO: 1 (i.e., amino acid residues 452-456 of the full-length SARS-CoV-2 S glycoprotein). In some embodiments, the APR within the ACE2 RBM comprises amino acid residues 158-160 of SEQ ID NO: 1 (i.e., amino acid residues 488-490 of the full-length SARS-CoV-2 S glycoprotein).

In some embodiments, the APR is located within a portion of the SARS-CoV-2 S glycoprotein that does not bind to the ACE2 receptor. In some embodiments, the APR comprises amino acid residues 36-40 of SEQ ID NO: 1 (i.e., amino acid residues 366-370 of the full-length SARS-CoV-2 S glycoprotein). In some embodiments, the APR comprises amino acid residues 185-188 of SEQ ID NO: 1 (i.e., amino acid residues 515-518 of the full-length SARS-CoV-2 S glycoprotein).

(ii) Identifying a Mutation

In some embodiments, the mutation of the hydrophobic amino acid residue is a substitution with any different amino acid residue. In some embodiments, the substitution is with an amino acid residue that is less hydrophobic. For example, the hydrophobic amino acid residue is assigned a hydrophobicity score, such as an octanol/water log P value, and the substitution is with an amino acid residue having a lower hydrophobicity score. In some embodiments, a hydrophobicity parameter known in the art is used to identify a substitution with an amino acid residue that is less hydrophobic, such as one described in: Janin, Nature 277:491-92, 1979; Wolfenden et al, Biochemistry 20:849-855, 1981; Kyte et al J. Mol Biol 157:105-132, 1982; Rose et al, Science 229:834-838, 1985; Cornette et al, J. Mol Biol 195:659-685, 1987; Charton et al., J. Theor. Biol. 99:629-644, 1982.

In some embodiments, the hydrophobic amino acid residue has a positive AggScore, and the substitution is with a different amino acid residue that reduces the AggScore of the residue by 10-100%, or about 10%, 20%, 30%, 40%, 50%, 60%, 70%, 80%, 90%, or 100%. In some embodiments, the hydrophobic amino acid residue is in an aggregation-prone region, and the substitution is with a different amino acid residue that reduces the overall aggregation score of the aggregation prone region by 5-50%, or about 5%, 10%, 15%, 20%, 25%, 30%, 35%, 40%, 45%, or 50%, i.e., relative to the overall aggregation score of the aggregation-prone region without the substitution. In some embodiments, the substitution is with a different amino acid residue that reduces the overall aggregation score of the full-length polypeptide by 5-50%, or about 5%, 10%, 15%, 20%, 25%, 30%, 35%, 40%, 45%, or 50%, i.e., relative to the overall aggregation score of the full-length polypeptide without the substitution.

In some embodiments, the mutation is a substitution with an amino acid residue which is conserved in a SARS-CoV genetic background. As used herein, the term "SARS-CoV genetic background" refers to genome sequences of SARS-related coronaviruses that are optimally aligned against a SARS-CoV-2 reference sequence (e.g., SEQ ID NO: 59) to enable identification of conserved amino acid residues, e.g., in the S glycoprotein. Sources available for identifying annotated SARS-related coronavirus genome sequences are known in the art, and include databanks such as the Global Initiative on Sharing All Influenza Data (https://www.gisaid.org/), GenBank (https//www.ncbi.nlm.nih.gov/genbank), and NMDC (http://nmdc.cn/#/nCoV). Upon identification of suitable genome sequences, a sequence alignment algorithm is applied to provide optimal alignment of coding sequences for the SARS-related coronavirus genome sequences relative to the SARS-CoV-2 reference sequence. Methods for optimal alignment of related genomic sequences are known in the art, and include those based on the Clustal Omega algorithm as described in Sievers, et al (2011) *MOL. SYST. BIOL* 7:539, the MUSCLE algorithm as described in Edgar, et al (2004) *NUCLEIC ACIDS RES* 32:1792, and BLAST.

In some embodiments, the mutation is a substitution with an amino acid residue identified at the same position in the S glycoprotein expressed by at least one strain of SARS-CoV (e.g., a SARS CoV strain identified in a human, bat, or civet host), a coronavirus of the β-genus (e.g., MERS-CoV or strain thereof identified in a human, bat, or civet host), or any coronavirus. In some embodiments, the amino acid residue is identified in a coronavirus expressing an S glycoprotein with at least 50%, 55%, 60%, 65%, 70%, 75%, 80%, 85%, 90% or higher sequence identity to the SARS-CoV-2 S glycoprotein. In some embodiments, the amino acid residue is identified in a coronavirus expressing an S glycoprotein RBD with at least 50%, 55%, 60%, 65%, 70%, 75%, 80%, 85%, 90% or higher sequence identity to the SARS-CoV-2 RBD. In some embodiments, the SARS-CoV strain is any one previously identified in human or other species, including bat or civet.

In some embodiments, identification of the amino acid residue is performed by (i) generating an optimal alignment of the wild-type SARS-CoV-2 S glycoprotein (e.g., SEQ ID NO: 59) with one or more S glycoproteins expressed by an alternate coronavirus (e.g., SARS-CoV, MERS-CoV); (ii) identifying an amino acid residue occurring at the same position in at least one additional S glycoprotein; and (iii) replacing the one or more identified hydrophobic residues with the amino acid residues identified in the at least one additional S glycoprotein.

(iii) Mutations of Hydrophobic Amino Acid Residues of the Disclosure

In some embodiments, an SARS-CoV-2 S glycoprotein variant described herein has one or more hydrophobic amino acid residues removed. In some embodiments, the SARS-CoV-2 S glycoprotein variant has one or more hydrophobic amino acid residues located with an aggregation-prone region removed. In some embodiments, the SARS-CoV-2 S glycoprotein variant has one or more amino acid residues located in an aggregation-prone region removed. Hydrophobic amino acid residues or amino acid residues are removed, for example, by substitution or deletion.

In some embodiments, an aggregation-prone region comprises about 2-15 proximal amino acids. In some embodiments, an aggregation-prone region comprises about 2-15 proximal hydrophobic amino acids. In some embodiments, an aggregation-prone region comprises about 2-15 proximal amino acids, wherein at least one amino acid is hydrophobic.

In some embodiments, an aggregation-prone region comprises 3-7 proximal amino acids. In some embodiments, an aggregation-prone region comprises 3-7 proximal hydrophobic amino acids. In some embodiments, an aggregation-prone region comprises 3-7 proximal amino acids, wherein at least one amino acid is hydrophobic.

In some embodiments, the proximal amino acids form a three-dimensional hydrophobic pocket. In some embodiments, the three-dimensional hydrophobic pocket comprises one or more residues of the S glycoprotein that contacts the human ACE2 receptor.

In some embodiments, a hydrophobic amino acid residue and/or amino acid residue within an aggregation prone region is substituted for an amino acid residue conserved in at least one species of coronaviridae, e.g., SARS-CoV. In some embodiments, a hydrophobic amino acid residue and/or amino acid residue within an aggregation prone region is substituted for an amino acid residue conserved among at least two, at least three, at least four, or at least five species of coronaviridae, e.g., SARS-CoV.

In some embodiments, the aggregation-prone region is located within a portion of the S glycoprotein that binds the ACE2 receptor. In some embodiments, the aggregation-prone region is in an ACE2 RBM or comprises amino acid residues that belong to the ACE2 receptor binding motif. In some embodiments, the aggregation-prone region in an ACE2 RBM comprises amino acid residues 122-126 of SEQ ID NO: 1 (i.e., amino acid residues 452-456 of SEQ ID NO: 59). In some embodiments, the aggregation-prone region comprises amino acid residue 122 of SEQ ID NO: 1 (i.e., amino acid residue 452 of SEQ ID NO: 59). In some embodiments, the aggregation-prone region comprises amino acid residue 123 of SEQ ID NO: 1 (i.e., amino acid residue 453 of SEQ ID NO: 59). In some embodiments, the aggregation-prone region comprises amino acid residue 124 of SEQ ID NO: 1 (i.e., amino acid residue 454 of SEQ ID NO: 59). In some embodiments, the aggregation-prone region comprises amino acid residue 125 of SEQ ID NO: 1 (i.e., amino acid residue 455 of SEQ ID NO: 59). In some embodiments, the aggregation-prone region comprises amino acid residue 126 of SEQ ID NO: 1 (i.e., amino acid residue 456 of SEQ ID NO: 59).

In some embodiments, the aggregation-prone region in an ACE2 RBM comprises amino acid residues 157-162 of SEQ ID NO: 1 (i.e., amino acid residues 487-492 of SEQ ID NO: 59). In some embodiments, the aggregation-prone region comprises amino acid residues 157-160 of SEQ ID NO: 1 (i.e., amino acid residues 487-490 of SEQ ID NO: 59). In some embodiments, the aggregation-prone region comprises amino acid residues 157 of SEQ ID NO: 1 (i.e., amino acid residues 487 of SEQ ID NO: 59). In some embodiments, the aggregation-prone region comprises amino acid residues 158 of SEQ ID NO: 1 (i.e., amino acid residues 488 of SEQ ID NO: 59). In some embodiments, the aggregation-prone region comprises amino acid residues 159 of SEQ ID NO: 1 (i.e., amino acid residues 489 of SEQ ID NO: 59). In some embodiments, the aggregation-prone region comprises amino acid residues 160 of SEQ ID NO: 1 (i.e., amino acid residues 490 of SEQ ID NO: 59). In some embodiments, the aggregation-prone region comprises amino acid residues 161 of SEQ ID NO: 1 (i.e., amino acid residues 491 of SEQ ID NO: 59). In some embodiments, the aggregation-prone region comprises amino acid residues 162 of SEQ ID NO: 1 (i.e., amino acid residue 492 of SEQ ID NO: 59).

In some embodiments, the aggregation-prone region is located within a portion of the S glycoprotein that does not bind the ACE2 receptor. In some embodiments, the aggregation-prone region that does not bind the ACE2 receptor comprises amino acid residues 36-40 of SEQ ID NO: 1 (i.e., amino acid residues 366-370 of SEQ ID NO: 59). In some embodiments, the aggregation-prone region comprises amino acid residue 36 of SEQ ID NO: 1 (i.e., amino acid residue 366 of SEQ ID NO: 59). In some embodiments, the aggregation-prone region comprises amino acid residue 37 of SEQ ID NO: 1 (i.e., amino acid residue 367 of SEQ ID NO: 59). In some embodiments, the aggregation-prone region comprises amino acid residue 38 of SEQ ID NO: 1 (i.e., amino acid residue 368 of SEQ ID NO: 59). In some embodiments, the aggregation-prone region comprises amino acid residue 39 of SEQ ID NO: 1 (i.e., amino acid residue 369 of SEQ ID NO: 59). In some embodiments, the aggregation-prone region comprises amino acid residue 40 of SEQ ID NO: 1 (i.e., amino acid residue 370 of SEQ ID NO: 59).

In some embodiments, the aggregation-prone region that does not bind the ACE2 receptor comprises amino acid residues 185-189 of SEQ ID NO: 1 (i.e., amino acid residues 515-519 of SEQ ID NO: 59). In some embodiments, the aggregation-prone region comprises amino acid residue 185 of SEQ ID NO: 1 (i.e., amino acid residue 515 of SEQ ID NO: 59). In some embodiments, the aggregation-prone region comprises amino acid residue 186 of SEQ ID NO: 1 (i.e., amino acid residue 516 of SEQ ID NO: 59). In some embodiments, the aggregation-prone region comprises amino acid residue 187 of SEQ ID NO: 1 (i.e., amino acid residue 517 of SEQ ID NO: 59). In some embodiments, the aggregation-prone region comprises amino acid residue 188 of SEQ ID NO: 1 (i.e., amino acid residue 518 of SEQ ID NO: 59). In some embodiments, the aggregation-prone region comprises amino acid residue 189 of SEQ ID NO: 1 (i.e., amino acid residue 519 of SEQ ID NO: 59).

In some embodiments, the SARS-CoV-2 S glycoprotein variant comprises a mutation of at least one hydrophobic amino acids in an aggregation-prone region described herein. In some embodiments, the hydrophobic amino acid is a glycine, alanine, valine, leucine, isoleucine, proline, phenylalanine, methionine, or tryptophan. In some embodiments, the mutation is a substitution with any other amino acid residue, e.g., alanine. In some embodiments, the substitution is with an amino acid residue that is less hydrophobic. In some embodiments, the amino acid residue that is less hydrophobic is a polar or charged amino acid (e.g. serine, threonine, cysteine, asparagine, glutamine, tyrosine, arginine, lysine, aspartic acid, and glutamic acid).

In some embodiments, the mutation is with an amino acid residue found at the same position in a genetic background of at least one species of coronavirus, e.g., SARS-CoV. In some embodiments, the residue is conserved in a SARS-CoV genetic background.

In some embodiments, the mutation is with an amino acid residue that is (i) found at the same position in a genetic background of at least one species of coronavirus, e.g., SARS-CoV; and (ii) is less hydrophobic. In some embodiments, the mutation is with an amino acid residue that is (i) conserved in a SARS-CoV genetic background; and (ii) is less hydrophobic.

In some embodiments, the SARS-CoV-2 S glycoprotein variant comprises a mutation of an amino acid residue in an aggregation-prone region, and
  (i) a mutation of at least one additional amino acid residue in the same aggregation-prone region (e.g., a mutation of one, two, three, four, five, six, seven, eight, nine, or ten additional amino acid residues in the same aggregation-prone region);
  (ii) a mutation of at least one additional amino acid residue in a second aggregation-prone region (e.g., a mutation of one, two, three, four, five, six, seven, eight, nine, or ten additional amino acid residues in the same aggregation-prone region); or
  (iii) a combination of (i) and (ii).

In some embodiments, the mutation of the at least one additional amino acid residue is a substitution with any different amino acid residue, e.g., alanine. In some embodiments, the mutation of the at least one additional amino acid residue is a substitution with a less hydrophobic amino acid residue, e.g., a charged or polar amino acid residue. In some embodiments, the mutation of the at least one additional amino acid residue is a substitution with an amino acid residue found in the same position in a genetic background of at least one other species of coronavirus, e.g., SARS-CoV.

In some embodiments, the SARS-CoV-2 S glycoprotein variant comprises a substitution of an amino acid residue selected from: L122, L125, F126, C158, Y159, F160 and any combination thereof, with amino acid residues as numbered in the amino acid sequence of the wild-type RBD as set forth by SEQ ID NO: 1 (i.e., corresponding to amino residues L452, L455, F456, C488, Y489, and F490 of the full-length SARS-CoV-2 S glycoprotein). In some embodiments, the SARS-CoV-2 S glycoprotein variant comprises an amino acid substitution at L122. In some embodiments, the SARS-CoV-2 S glycoprotein variant comprises an amino acid substitution at (i) L122 and F160; or (ii) L122, L125, F126 and F160. In some embodiments, the SARS-CoV-2 S glycoprotein variant comprises an amino acid substitution at L122 and F160. In some embodiments, the SARS-CoV-2 S glycoprotein variant comprises an amino acid substitution at L122, L125, F126 and F160.

In some embodiments, the amino acid substitution of L122, L125, F126, C158, Y159, and/or F160 is with any different amino acid residue, e.g., alanine. In some embodiments, the SARS-CoV-2 S glycoprotein variant comprises an amino acid substitution selected from: L122A, L125A, F126A, C158A, Y159A, F160A, and any combination thereof.

In some embodiments, the amino acid substitution of L122, L125, F126, C158, Y159, and/or F160 is with a less hydrophobic amino acid residue, e.g., a polar or charged amino acid residue, e.g., serine, threonine, cysteine, asparagine, glutamine, tyrosine, arginine, lysine, aspartic acid, and glutamic acid.

In some embodiments, the amino acid substitution of L122, L125, F126, C158, Y159, and/or F160 is with an amino acid residue that is found in the same position in a genetic background of at least one other species of a coronavirus or SARS-CoV, e.g., an amino acid residue that is conserved in a SARS-CoV genetic background. In some embodiments, the amino acid substitution of L122, L125, F126, C158, Y159, and/or F160 is with a corresponding amino acid substitution identified in Table 2.

In some embodiments, the SARS-CoV-2 S glycoprotein variant comprises an amino acid substitution of an amino acid residue selected from: V37, L38, L187, L188, and any combination thereof, with amino acid residues as numbered in the amino acid sequence of the wild-type RBD as set forth by SEQ ID NO: 1 (i.e., corresponding to amino residues V367, L368, L517, and L518 of the full-length SARS-CoV-2 S glycoprotein). In some embodiments, the amino acid substitution of V37, L38, L187, and/or L188 is with any different amino acid residue, e.g., alanine. In some embodiments, the amino acid substitution of V37, L38, L187, and/or L188 is with a less hydrophobic amino acid residue, e.g., a polar or charged amino acid residue, e.g., serine, threonine, cysteine, asparagine, glutamine, tyrosine, arginine, lysine, aspartic acid, and glutamic acid. In some embodiments, the amino acid substitution of V37, L38, L187, and/or L188 is with an amino acid residue that is found in the same position in a genetic background of at least one other species of coronavirus or SARS-CoV, e.g., an amino acid residue that is conserved in a SARS-CoV genetic background. In some embodiments, the amino acid substitution of L38, L187, and/or L188 is with a corresponding amino acid substitution identified in Table 2.

TABLE 2

Conserved Mutations of Amino Acid Residue in Aggregation-Prone Regions of SARS-CoV-2 S Glycoprotein

| Residue of Wild-type SARS-CoV-2 S protein | Position based on SARS-CoV-2 RBD (SEQ ID NO: 1) | Position based on full-length SARS-CoV-2 S protein (SEQ ID NO: 59) | Amino Acid Substitution | SARS-CoV Species Source(s) for Conserved Substitution |
|---|---|---|---|---|
| L | 38 | 368 | F | Bat SARS CoV |
| L | 122 | 452 | K | Bat SARS CoV, Civet SARS CoV, Human SARS CoV, |

TABLE 2-continued

Conserved Mutations of Amino Acid Residue in Aggregation-Prone Regions of SARS-CoV-2 S Glycoprotein

| Residue of Wild-type SARS-CoV-2 S protein | Position based on SARS-CoV-2 RBD (SEQ ID NO: 1) | Position based on full-length SARS-CoV-2 S protein (SEQ ID NO: 59) | Amino Acid Substitution | SARS-CoV Species Source(s) for Conserved Substitution |
|---|---|---|---|---|
| L | 122 | 452 | F | Bat SARS CoV |
| L | 122 | 452 | Y | Bat SARS CoV |
| L | 122 | 452 | S | MERS CoV |
| L | 125 | 455 | S | Bat SARS CoV |
| L | 125 | 455 | Y | Civet SARS CoV, Human SARS CoV |
| L | 125 | 455 | W | Bat SARS CoV |
| L | 125 | 455 | N | MERS CoV |
| F | 126 | 456 | L | Bat SARS CoV, Civet SARS CoV, Human SARS CoV |
| F | 126 | 456 | H | Bat SARS CoV |
| F | 126 | 456 | V | Bat SARS CoV |
| F | 126 | 456 | K | MERS CoV |
| C | 158 | 488 | G | Bat SARS CoV |
| C | 158 | 488 | T | MERS CoV |
| Y | 159 | 489 | V | Bat SARS CoV, MERS CoV |
| Y | 159 | 489 | A | Bat SARS CoV |
| F | 160 | 490 | W | Bat SARS 2013, Civet SARS CoV, Human SARS CoV |
| F | 160 | 490 | R | Bat SARS CoV |
| F | 160 | 490 | Y | Bat SARS CoV |
| F | 160 | 490 | N | Bat SARS CoV |
| L | 187 | 517 | I | MERS CoV |
| L | 188 | 518 | T | MERS CoV |

In some embodiments, amino acid 122 of SEQ ID NO: 1 is mutated from a leucine to a lysine (i.e. L122K), phenylalanine (i.e., L122F), tyrosine (i.e., L122Y), or serine (i.e., L122S). In some embodiments, amino acid 125 of SEQ ID NO: 1 is mutated from a leucine to a tyrosine (i.e. L125Y), serine (i.e., L125S), tryptophan (i.e., L125W), or asparagine (i.e., L125N). In some embodiments, amino acid 126 of SEQ ID NO: 1 is mutated from a phenylalanine to a leucine (i.e. F126L), histidine (i.e., F126H), valine (i.e., F126V), or lysine (i.e., F126K). In some embodiments, amino acid 158 of SEQ ID NO: 1 is mutation from a cysteine to a glycine (i.e., C158G) or threonine (i.e., C158T). In some embodiments, amino acid 159 of SEQ ID NO: 1 is mutated from a tyrosine to an arginine (i.e. Y159R), valine (i.e., Y159V), or alanine (i.e., Y159A). In some embodiments, amino acid 160 of SEQ ID NO: 1 is mutated from a phenylalanine to a tryptophan (i.e. F160W), arginine (i.e., F160R), tyrosine (i.e., F160Y), or asparagine (i.e., F160N). In some embodiments, amino acid 160 of SEQ ID NO:1 is mutated from a phenylalanine to a methionine (i.e. F160M).

In some embodiments, amino acid 37 of SEQ ID NO: 1 is mutated from valine to phenylalanine (i.e., V37F). In some embodiments, amino acid 38 of SEQ ID NO: 1 is mutated from leucine to alanine (i.e., L38A), methionine (i.e., L38M), or phenylalanine (i.e., L38F). In some embodiments, amino acid 187 of SEQ ID NO:1 is mutated from a leucine to an alanine (i.e. L187A) or isoleucine (i.e., L187I). In some embodiments, amino acid 188 of SEQ ID NO: 1 is mutated from a leucine to an alanine (i.e. L188A) or threonine (i.e., L188T). In some embodiments, amino acid 188 of SEQ ID NO: 1 is mutated from a leucine to a methionine (i.e. L188M).

In some embodiments, the SARS-CoV-2 S glycoprotein variant comprises a mutation of at least one amino acid residue in an aggregation-prone region and removal of at least one glycosylation site by mutation or substitution. In some embodiments, the glycosylation site corresponds to residue 1 of SEQ ID NO: 1 (i.e., residue 331 of the full-length SARS-CoV-2 S glycoprotein). In some embodiments, the glycosylation site corresponds to residue 13 SEQ ID NO: 1 (i.e., residue 343 of the full-length SARS-CoV-2 S glycoprotein).

In some embodiments, the SARS-CoV-2 S glycoprotein variant comprises a deletion of residue 1 and an amino acid substitution of residue 122 from leucine to lysine (L122K), each according to SEQ ID NO: 1. In some embodiments, the SARS-CoV-2 S glycoprotein variant comprises the amino acid sequence set forth by SEQ ID NO: 11.

In some embodiments, the SARS-CoV-2 S glycoprotein variant comprises at least one additional amino acid substitution selected from: L38A, L125Y, L125S, F126L, Y159V, F160W, F160N, F160R, L187A, L188A, and a combination thereof. In some embodiments, the SARS-CoV-2 S glycoprotein variant comprises the amino acid sequence set forth by any one of SEQ ID NOs: 6-9, 14, 18, 20, 22, 24-25.

In some embodiments, the SARS-CoV-2 S glycoprotein variant comprises a deletion of residue 1, an amino acid substitution of residue 38 from leucine to alanine (L38A), an amino acid substitution of residue 122 from leucine to lysine (L122K), an amino acid substitution of residue 125 from leucine to tyrosine (L125Y), an amino acid substitution of residue 160 from phenylalanine to tryptophan (F160W), an amino acid substitution of residue 187 from leucine to alanine (L187A), and an amino acid substitution of residue 188 from leucine to alanine (L188A), each according to SEQ ID NO: 1. In some embodiments, the SARS-CoV-2 S glycoprotein variant comprises the amino acid sequence set forth by SEQ ID NO: 6.

In some embodiments, the SARS-CoV-2 S glycoprotein variant comprises a deletion of residue 1, an amino acid substitution of residue 38 from leucine to alanine (L38A), an amino acid substitution of residue 122 from leucine to lysine (L122K), an amino acid substitution of residue 160 from phenylalanine to tryptophan (F160W), an amino acid substitution of residue 187 from leucine to alanine (L187A), and an amino acid substitution of residue 188 from leucine to alanine (L188A), each according to SEQ ID NO: 1. In some embodiments, the SARS-CoV-2 S glycoprotein variant comprises the amino acid sequence set forth by SEQ ID NO: 7.

In some embodiments, the SARS-CoV-2 S glycoprotein variant comprises a deletion of residue 1, an amino acid substitution of residue 122 from leucine to lysine (L122K), an amino acid substitution of residue 125 from a leucine to tyrosine (L125Y), and an amino acid substitution of residue 126 from phenylalanine to leucine (F126L), an amino acid substitution of residue 160 from phenylalanine to tryptophan (F160W), each according to SEQ ID NO: 1. In some embodiments, the SARS-CoV-2 S glycoprotein variant comprises the amino acid sequences set forth by SEQ ID NO: 8.

In some embodiments, the SARS-CoV-2 S glycoprotein variant comprises a deletion of residue 1, an amino acid substitution of residue 122 from leucine to lysine (L122K), and an amino acid substitution of residue 160 from phenylalanine to tryptophan (F160W, each according to SEQ ID NO: 1. In some embodiments, the SARS-CoV-2 S glycoprotein variant comprises the amino acid sequence set forth by SEQ ID NO: 9.

In some embodiments, the SARS-CoV-2 S glycoprotein variant comprises the amino acid sequence set forth by any one of SEQ ID NOs: 6-25.

In some embodiments, the S glycoprotein comprises at least one additional amino acid substitution selected from any one identified by Starr, et al (2020) bioRxiv https://doi.org/10.1101/2020.06.17.157982. In some embodiments, the at least one additional amino acid residue is selected from: P7D, V11I, A18P, N24E, R27K, Y35W, V37F, K48R, S53D, L60Y, F62W, I72V, R78D, Q84A, K87V, D98N, L111I, L125N, Q168D, Y178H, L188D, and V194R, each according to SEQ ID NO: 1. In some embodiments, the SARS-CoV-2 S glycoprotein variant comprises a deletion of residue 1, an amino acid substitution of residue 122 from leucine to lysine (L122K), and a substitution of at least one additional amino acid residue selected from: P7D, V11I, A18P, N24E, R27K, Y35W, V37F, K48R, S53D, L60Y, F62W, I72V, R78D, Q84A, K87V, D98N, L111I, L125N, Q168D, Y178H, L188D, and V194R, each according to SEQ ID NO: 1. In some embodiments, the SARS-CoV-2 S glycoprotein variant comprises the amino acid sequence set forth by any one of SEQ ID NOs: 26-47.

Properties of SARS-CoV-2 S Glycoprotein Variants of the Disclosure

A. Reduced Aggregation and Expression

In some embodiments, the one or more amino acid mutation(s) described herein increases expression and/or reduces aggregation of the SARS-CoV-2 S glycoprotein variant relative to a corresponding SARS-CoV-2 S glycoprotein not having the one or more mutation(s). In some embodiments, the SARS-CoV-2 S glycoprotein variant is expressed at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 3-fold, at least 4-fold or at least 5-fold higher relative to the corresponding wild-type S glycoprotein (e.g., S glycoprotein comprising SEQ ID NO: 1). In some embodiments, the SARS-CoV-2 S glycoprotein variant is expressed at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 3-fold, at least 4-fold or at least 5-fold higher relative to the corresponding S glycoprotein variant having a first glycosylation site mutated (e.g., S glycoprotein comprising SEQ ID NO: 2).

In some embodiments, the SARS-CoV-2 S glycoprotein variant having the first glycosylation site mutated and comprising an amino acid substitution at residues L122 and F160 (e.g., S glycoprotein variant comprising SEQ ID NO: 9) is expressed at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 3-fold, at least 4-fold or at least 5-fold higher relative to the corresponding S glycoprotein comprising a wild-type RBD (e.g., SEQ ID NO: 1). In some embodiments, the SARS-CoV-2 S glycoprotein variant having the first glycosylation site mutated and comprising an amino acid substitution at residues L122 and F160 (e.g., S glycoprotein comprising SEQ ID NO: 9) is expressed at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 3-fold, at least 4-fold or at least 5-fold higher relative to the corresponding S glycoprotein having a first glycosylation site mutated (e.g., S glycoprotein comprising SEQ ID NO: 2).

In some embodiments, the SARS-CoV-2 S glycoprotein variant has reduced aggregation relative to the corresponding S glycoprotein comprising a wild-type RBD (e.g., SEQ ID NO: 1). In some embodiments, the SARS-CoV-2 S glycoprotein variant described herein has reduced aggregation compared to the corresponding S glycoprotein variant having only the first glycosylation site mutated (e.g., S glycoprotein comprising SEQ ID NO: 2). In some embodiment, the at least one amino acid mutation in an SARS-CoV-2 S glycoprotein variant reduces the overall aggregation score by 5-50%, or by about 5%, 10%, 15%, 20%, 25%, 30%, 35%, 40%, 45%, or 50% relative to the corresponding SARS-CoV-2 S glycoprotein variant without the mutation. In some embodiments, the overall aggregation score of the SARS-CoV-2 S glycoprotein variant is reduced by 10%, by 20%, by 30%, by 40%, by 50%, by 60%, or by 70% to that of the corresponding S glycoprotein comprising a wild-type RBD (e.g., S glycoprotein comprising SEQ ID NO: 1). In some embodiments, the overall aggregation score of the SARS-CoV-2 S glycoprotein variant is reduced by 10%, by 20%, by 30%, by 40%, by 50%, by 60%, or by 70% relative to the overall aggregation score of the corresponding S glycoprotein variant having only the first glycosylation site mutated (e.g., S glycoprotein comprising SEQ ID NO: 2).

In some embodiments, an S glycoprotein variant having the first glycosylation site mutated and comprising an amino acid substitution at residues L122 and F160 (e.g., S glycoprotein comprising SEQ ID NO: 9) has reduced aggregation compared to the corresponding wild-type S glycoprotein (e.g., S glycoprotein comprising SEQ ID NO: 1). In some embodiments, an S glycoprotein variant having the first glycosylation site mutated and comprising an amino acid substitution at residues L122 and F160 (e.g., S glycoprotein comprising SEQ ID NO: 9) has reduced aggregation compared to the corresponding S glycoprotein variant only having the first glycosylation site mutated (e.g., S glycoprotein variant comprising SEQ ID NO: 2). In some embodiments, an S glycoprotein variant having the first glycosylation site mutated and comprising an amino acid substitution at residues L122 and F160 (e.g., S glycoprotein comprising SEQ ID NO: 9) has an overall aggregation score that is reduced by 5-50% relative to a corresponding S glycoprotein variant having only the first glycosylation site mutatec (e.g., S glycoprotein variant comprising SEQ ID NO: 2). In some embodiments, aggregation of an S glycoprotein variant having the first glycosylation site mutated and comprising an amino acid substitution at residues L122 and F160 (e.g., S glycoprotein comprising SEQ ID NO: 9) is reduced by 10%, 20%, 30%, 40%, 50%, 60%, or 70% relative to a corresponding wild-type S glycoprotein (e.g., S glycoprotein variant comprising SEQ ID NO: 1). In some embodiments, aggregation of an S glycoprotein variant having the first glycosylation site mutated and comprising an amino acid substitution at residues L122 and F160 (e.g., S glycoprotein variant comprising SEQ ID NO: 9) is reduced by 10%, 20%, 30%, 40%, 50%, 60%, or 70% relative to a corresponding S glycoprotein variant only having the first glycosylation site mutated (e.g., S glycoprotein variant comprising SEQ ID NO: 2).

In some embodiments, the expression of the SARS-CoV-2 S glycoprotein variant is measured as specific productivity or final titer. Methods of measuring expression of a protein from a cell are known to those of skill in the art. Methods measuring the amount of recombinant protein of interest produced includes but is not limited to "specific productivity," which is the amount of protein of interest produced per cell per day, or by measuring the amount of protein of interest produced per amount of cell protein. In some embodiments, expression of the SARS-CoV-2 S glycoprotein variant is measured as specific productivity.

Methods of measuring protein characteristics are known to those of skill in the art. Methods for measuring include, but are not limited to size-exclusion chromatography, static light scater, chromatographic techniques, e.g., high-performance liquid chromatography (HPLC), immunoassays, electrophoresis, ultra-violet/visible/infrared spectroscopy, raman spectroscopy, surface enhanced raman spectroscopy, mass spectrometry, gas chromatography, static light scattering (SLS), Fourier Transform Infrared Spectroscopy (FTIR), circular dichroism (CD), urea-induced protein unfolding techniques, intrinsic tryptophan fluorescence, differential scanning calorimetry, and/or ANS protein binding.

In some embodiments, aggregation is measured using size-exclusion chromatography. In some embodiments, an SARS-CoV-2 S glycoprotein variant described herein has reduced aggregation propensity compared to the corresponding wild-type S glycoprotein (e.g., S glycoprotein comprising SEQ ID NO: 1) when measured by size-exclusion chromatography. In some embodiments, an SARS-CoV-2 S glycoprotein variant described herein has reduced aggregation propensity compared to an S glycoprotein variant having the first glycosylation site mutated (e.g., S glycoprotein variant comprising SEQ ID NO: 2) when measured by size-exclusion chromatography.

In some embodiments, aggregation is determined by static light scatter (Wyatt DynaPro NanoStar™). In some embodiments, an SARS-CoV-2 S glycoprotein variant described herein has reduced aggregation propensity compared to the corresponding wild-type S glycoprotein (e.g., S glycoprotein comprising SEQ ID NO: 1) when measured by static light scattering. In some embodiments, an SARS-CoV-2 S glycoprotein variant described herein has reduced aggregation compared to an S glycoprotein variant only having the first glycosylation site mutated (e.g., S glycoprotein variant comprising SEQ ID NO: 2) when measured by static light scattering.

In some embodiments, methods for characterizing protein-containing compositions and assessing protein aggregation involves continuous quantitative monitoring of test compositions using static light scattering. For instance, the ARGEN platform from Fluence Analytics, New Orleans, LA USA, uses this technique. To determine colloidal stability, compositions are stored in a sample holder and stressed at a predetermined temperature for a defined period of time. The static light scattering signal is measured continuously through the time period. When the sample begins to aggregate, the light scattering signal increases. One of the ways to assess colloidal stability is to measure the 'lag time' which is the time taken for the light scattering signal to increase (or the time taken for the samples to aggregate). The greater the lag time for a given composition, the more stable is the composition.

In some embodiments, an SARS-CoV-2 S glycoprotein variant described herein has improved thermostability compared to a corresponding wild-type S glycoprotein (e.g., S glycoprotein comprising SEQ ID NO: 1). In some embodiments, an SARS-CoV-2 S glycoprotein variant described herein has improved thermostability compared to an S glycoprotein variant only having the first glycosylation site mutated (e.g., S glycoprotein variant comprising SEQ ID NO: 2). In some embodiments, an S glycoprotein variant having the first glycosylation site mutated and comprising an amino acid substitution at residues L122 and F160 (e.g., S glycoprotein variant comprising SEQ ID NO: 9) has improved thermostability compared to a wild-type S glycoprotein (e.g., S glycoprotein comprising SEQ ID NO: 1). In some embodiments, an S glycoprotein variant having the first glycosylation site mutated and comprising an amino acid substitution at residues L122 and F160 (e.g., S glycoprotein comprising SEQ ID NO: 9) has improved thermostability compared to an S glycoprotein variant only having the first glycosylation site mutated (e.g., S glycoprotein variant comprising SEQ ID NO: 2).

Methods of measuring thermostability are known to those of skill in the art. Methods for measuring include, but are not limited to differential scanning calorimetry (DSC). DSC is a thermodynamic tool for direct assessment of the heat energy uptake, which occurs in a sample within a regulated increase or decrease in temperature. Calorimetry is applied to monitor phase transitions. DSC measures heat capacity as a function of temperature using a thermal analysis instrument that determines the temperature and heat flow associated with material transitions as a function of time and temperature.

B. Improved Immunogenicity and Neutralization Activity

In some embodiments, the one or more amino acid mutation(s) within at least one hydrophobic region increases immunogenicity of the S glycoprotein variant compared to a wild-type S glycoprotein (e.g., SEQ ID NO:1). In some embodiments, the one or more amino acid mutation(s) within at least one hydrophobic region increases immunogenicity of the S glycoprotein variant compared to an S glycoprotein variant only having the first glycosylation site mutated (e.g., SEQ ID NO: 2). In some embodiments, an S glycoprotein variant having the first glycosylation site mutated and comprising an amino acid substitution at residues L122 and F160 (e.g., SEQ ID NO: 9) has increased immunogenicity compared to a wild-type S glycoprotein (e.g., SEQ ID NO:1). In some embodiments, an S glycoprotein variant having the first glycosylation site mutated and comprising an amino acid substitution at residues L122 and F160 (e.g., SEQ ID NO: 9) has increased immunogenicity compared to an S glycoprotein variant only having the first glycosylation sited mutated (e.g. SEQ ID NO:2).

In some embodiments, the SARS-CoV-2 S glycoprotein has a higher neutralizing titer (NT50) compared to a wild-type S glycoprotein (e.g., SEQ ID NO:1). In some embodiments, the SARS-CoV-2 S glycoprotein has a higher neutralizing titer (NT50) compared to an S glycoprotein variant only having the first glycosylation site mutated (e.g., SEQ ID NO: 2). In some embodiments, an S glycoprotein variant having the first glycosylation site mutated and comprising an amino acid substitution at residues L122 and F160 (e.g., SEQ ID NO: 9) has a higher neutralizing titer (NT50) compared to a wild-type S glycoprotein (e.g., SEQ ID NO: 1). In some embodiments, an S glycoprotein variant having the first glycosylation site mutated and comprising an amino acid substitution at residues L122 and F160 (e.g., SEQ ID NO: 9) has a higher neutralizing titer (NT50) compared to an S glycoprotein variant only having the first glycosylation sited mutated (e.g. SEQ ID NO: 2).

In some embodiments, immunogenicity is determined based on the induction of IgG antibodies specific to the S glycoprotein variant. In some embodiments, increased immunogenicity is measured by the level of neutralizing IgG antibodies generated.

Methods assessing immunogenicity and neutralization are known to those of skill in the art. Methods for measuring immunogenicity and neutralization includes, but is not limited to, antibody binding via ELISA, bio-layer inferometry, or neutralization assays incubating a variant or antibody with a virus producing reporter cell line to measure neutralization.

C. Improved Binding Capacity

In some embodiments, the one or more amino acid mutation(s) within at least one aggregation-prone region increases binding of the S glycoprotein variant to human ACE2 compared to a wild-type S glycoprotein (e.g., SEQ ID NO:1). In some embodiments, the one or more amino acid mutation(s) within at least one aggregation-prone region increases binding of the S glycoprotein variant to human ACE2 compared to an S glycoprotein variant only having the first glycosylation site mutated (e.g., SEQ ID NO: 2).

In some embodiments, the one or more amino acid mutation(s) within at least one aggregation-prone region increases binding of the S glycoprotein variant to a SARS neutralizing antibody (e.g., CR3022) compared to a wild-type S glycoprotein (e.g., SEQ ID NO:1). In some embodiments, the one or more amino acid mutation(s) within at least one aggregation-prone region increases binding of the S glycoprotein variant to a SARS neutralizing antibody (e.g., CR3022) compared to an S glycoprotein variant only having the first glycosylation site mutated (e.g., SEQ ID NO: 2).

In some embodiments, binding of the S glycoprotein variant to human ACE2-Fc is measured by bio-layer inferometry. In some embodiments, binding of the S glycoprotein variant to CR3022 is measured by bio-layer inferometry. In some embodiments, binding of S glycoprotein variant is measured using ELISA. In some embodiments, an S glycoprotein variant having the first glycosylation site mutated and comprising an amino acid substitution at residues L122 and F160 (e.g., SEQ ID NO: 9) has a reduced dissociation constant ($K_D$) compared to wild-type S glycoprotein (e.g., SEQ ID NO:1) for binding to human ACE2-IgG fusion protein. In some embodiments, R an S glycoprotein variant having the first glycosylation site mutated and comprising an amino acid substitution at residues L122 and F160 (e.g., SEQ ID NO: 9) has a reduced dissociation constant (Kb) compared to an S glycoprotein variant only having the first glycosylation site mutated (e.g., SEQ ID NO: 2) for binding to human ACE2-IgG fusion protein.

Exemplary S Glycoprotein Variants

In some embodiments, a SARS-CoV-2 S glycoprotein variant of the disclosure comprises an RBD comprising one or more mutations relative to a wild-type RBD (e.g., SEQ ID NO: 1), wherein the mutation is any one described herein. In some embodiments, the SARS-CoV-2 S glycoprotein variant has increased expression and/or reduced aggregation, and increased immunogenicity, relative to a wild-type S glycoprotein (e.g., SEQ ID NO:1). In some embodiments, the SARS-CoV-2 S glycoprotein has increased expression and/or reduced aggregation, and increased immunogenicity, relative to an S glycoprotein variant only having the first glycosylation site mutated (e.g., SEQ ID NO: 2). In some embodiments, an S glycoprotein variant having an amino acid sequence selected from the group of SEQ ID NOs: 5-25 has increased expression and/or reduced aggregation, and increased immunogenicity, relative to a wild-type S glycoprotein (e.g., SEQ ID NO: 1). In some embodiments, an S glycoprotein variant having an amino acid sequence selected from the group of SEQ ID NOs: 5-25 has increased expression and/or reduced aggregation, and increased immunogenicity, relative to an S glycoprotein variant only having the first glycosylation site mutated (e.g., SEQ ID NO: 2). In some embodiments, an S glycoprotein variant comprising the amino acid sequence set forth in SEQ ID NO: 9 has increased expression and/or reduced aggregation, and increased immunogenicity, relative to a wild-type S glycoprotein (e.g., SEQ ID NO:1). In some embodiments, an S glycoprotein variant comprising the amino acid sequence set forth in SEQ ID NO: 9 has increased expression and/or reduced aggregation, and increased immunogenicity, relative to an S glycoprotein variant only having the first glycosylation site mutated (e.g., SEQ ID NO: 2).

In some embodiments, the SARS-CoV-2 S glycoprotein variant comprises an amino acid sequence encoded by the nucleic acid sequence selected from the group set forth in SEQ ID NOs: 62-119. In some embodiments, the SARS-CoV-2 S glycoprotein variant comprises a amino acid sequence encoded by a nucleic acid sequence with at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of any one nucleic acid sequence selected from: SEQ ID NOs: 62-119.

In some embodiments, nucleic acid sequence encodes an S glycoprotein having a signal peptide. In some embodiments, the signal peptide is an alpha signal peptide. In some embodiments, the signal peptide is an Ost1 signal peptide.

Compositions of Vectors Expressing SARS-CoV-2 S Glycoprotein Variants of the Disclosure In some embodiments, the disclosure provides compositions comprising a viral particle comprising a nucleic acid molecule comprising a nucleotide sequence encoding an SARS-CoV-2 S glycoprotein variant described herein.

In some embodiments, the composition is generated from one or more viral vectors that include a nucleic acid encoding an SARS-CoV-2 S glycoprotein variant. In some embodiments, the one or more viral vectors is capable of expressing the variant. In some embodiments, the viral vector comprises a nucleic acid sequence containing an origin of replication. In some embodiments, the viral vector is a plasmid. In some embodiments, the viral vector is an expression construct, which is generally a plasmid that is used to introduce a specific gene into a target cell. Once the expression vector is inside the cell, the protein that is encoded by the gene is produced by the cellular transcription and translation machinery ribosomal complexes. In some embodiments, the plasmid is engineered to contain regulatory sequences that act as enhancer and promoter regions and lead to efficient transcription of the gene carried on the expression vector. The viral vectors of the present disclosure express large amounts of stable messenger RNA, and therefore proteins.

In some embodiments, the viral vectors have expression signals such as a strong promoter, a strong termination codon, adjustment of the distance between the promoter and the cloned gene, and the insertion of a transcription termination sequence and a PTIS (portable translation initiation sequence).

In some embodiments, the viral vector is a circular plasmid or a linear nucleic acid. The circular plasmid and linear nucleic acid are capable of directing expression of a particular nucleotide sequence in an appropriate subject cell. In some embodiments, the viral vector comprises a promoter operably linked to the antigen encoding nucleotide sequence, which may be operably linked to termination signals. In some embodiments, the viral vector comprising the nucleotide sequence of interest may be chimeric, meaning that at least one of its components is heterologous with respect to at least one of its other components. In some embodiments, the expression of the nucleotide sequence in the expression cassette is under the control of a constitutive promoter or of an inducible promoter, which initiates transcription only when the host cell is exposed to some particular external stimulus.

Methods of Making SARS-CoV-2 S Glycoprotein Variants of the Disclosure

In some embodiments, the SARS-CoV-2 S glycoprotein variants described herein are made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The methods of making SARS-CoV-2 S glycoprotein variants also include a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be suitable for use in the methods disclosed herein. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as $E.\ coli$ sp.), yeast (such as $Saccharomyces$ sp.) and other fungi, insects, plants, diatoms, parasites, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The SARS-CoV-2 S glycoprotein variants may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

The nucleic acid molecules described herein can be contained within a vector that is capable of directing their expression in, for example, a cell that has been transduced with the vector. Accordingly, in addition to polypeptide mutants, expression vectors containing a nucleic acid molecule encoding a mutant and cells transfected with these vectors are among the certain embodiments.

Vectors suitable for use include T7-based vectors for use in bacteria (see, for example, Rosenberg et al., Gene 56: 125, 1987), the pMSXND expression vector for use in mammalian cells (Lee and Nathans, J. Biol. Chem. 263:3521, 1988), and baculovirus-derived vectors (for example the expression vector pBacPAKS from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance ($neo^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that are suitable for use include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes an SARS-CoV-2 S glycoprotein variant are also suitable for use. A cell is a transfected cell, i.e., a cell into which a nucleic acid molecule, for example a nucleic acid molecule encoding an SARS-CoV-2 S glycoprotein variant, has been introduced by means of recombinant DNA techniques. The progeny of such a cell are also considered suitable for use in the methods disclosed herein.

An SARS-CoV-2 S glycoprotein variant can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). If guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., conjugated to a lipid, as described herein.

In some embodiments, a recombinant protein described herein, e.g., an SARS-CoV-2 S glycoprotein variant, is generated using yeast. In some embodiments, production of an SARS-CoV-2 S glycoprotein variant is performed in *Komagataella phaffi* (strain NRRL Y-11430). In some embodiments, production of an SARS-CoV-2 S glycoprotein variant is performed using a *K. phaffi* host variant described in Brady, et al (2020) *Biotechnol Bioeng* 117:543 (e.g., GS115, X-33). In some embodiments, production of an SARS-CoV-2 S glycoprotein variant is performed using a yeast host variant derived from *Hansenula polymorpha, Saccramychese cerevisiae, Kluyveromyces lactis*, and *Arxula adeninivorans*. In some embodiments, production of an SARS-CoV-2 S glycoprotein variant is performed in a fungal host according to methods known in the art. Non-limiting exemplary fungal hosts for expression of an SARS-CoV-2 S glycoprotein variant described herein include *Aspergillus niger, Trichoderma reesei*, and *Myceliophthora thermophila*.

In some embodiments, Integrated Scalable Cyto-Technology (InSCyT) is used for a manufacturing platform (Crowell, L. E. et al. (2018) *Nature Biotechnology* vol. 36 988) to produce any of the SARS-CoV-2 S glycoprotein variants described herein. In some embodiments, the volumetric productivity of any SARS-CoV-2 S glycoprotein variant described herein manufactured using, e.g., InSCyT, is about 27 to about 96 mg/L/day, about 50 to about 100 mg/l/day, about 50 to about 200 mg/L/day, about 50 to about 300 mg/L/day, about 100 to about 400 mg/L/day, about 100 to about 500 mg/L/day, about 100 to about 600 mg/L/day, about 500 to about 1000 mg/L/day, or about 500 to about 2000 mg/L/day. In some embodiments, the volumetric productivity is up to about 0.1 g/L/day, 0.5 g/L/day, 1 g/L/day, or 2 g/L/day.

Immunogenic Compositions and Vaccines

In some embodiments, the disclosure provides immunogenic compositions, such as vaccines, comprising a SARS-CoV-2 S glycoprotein variant or composition described herein.

In some embodiments, the immunogenic composition comprises an SARS-CoV-2 S glycoprotein variant described herein, wherein the SARS-CoV-2 S glycoprotein variant is present in the immunogenic composition as a monomer. In some embodiments, the SARS-CoV-2 S glycoprotein variant is present in the immunogenic composition as a homotrimer. In some embodiments, an SARS-CoV-2 S glycoprotein variant present as a trimer (e.g., homotrimer), comprises an S2 subunit or a portion thereof.

In some embodiments, the immunogenic composition comprises an SARS-CoV-2 S glycoprotein variant formulated as a lipid particle (e.g., liposome, lipid nanoparticle), synthetic nanoparticle (e.g., polymeric nanoparticle), protein-based nanoparticle, or a metal nanoparticle (e.g., aluminum nanoparticle). In some embodiments, the formulation enables delivery of the S glycoprotein variant to a particular target tissue and/or target cell population, protects the SARS-CoV-2 S glycoprotein variant from degradation, and/or promotes cellular uptake.

In some embodiments, the immunogenic composition comprises an SARS-CoV-2 S glycoprotein variant formulated as a lipid nanoparticle (LNPs). LNPs include, but are not limited to, liposomes and micelles. Methods for preparation of LNPs comprising polypeptides are known in the art. Any number of lipids may be present, alone or in combination, including cationic and/or ionizable lipids, anionic lipids, neutral lipids, amphipathic lipids, conjugated lipids (e.g., PEGylated lipids), and/or structural lipids. In some embodiments, the immunogenic composition comprises liposome having a lipid bilayer with a diameter of 500 nm or less. In some embodiments, the immunogenic composition comprises vesicles that include one or more lipid bilayers. In some embodiments, the immunogenic composition comprises two or more concentric bilayers separated by aqueous compartments, optionally wherein the lipid bilayers are functionalized and/or crosslinked to one another.

In some embodiments, the immunogenic composition comprises an SARS-CoV-2 S glycoprotein variant formulated with an adjuvant particle, e.g., a metal hydroxide particle, e.g., aluminum hydroxide particle. In some embodiments, the SARS-CoV-2 S glycoprotein variant is adsorbed to the adjuvant particle. In some embodiments, the adjuvant particle comprises a metal hydroxide that is one selected to be biocompatible with a human or mammalian species. In some embodiments, the metal hydroxide is an aluminum-containing metal hydroxide (e.g. aluminum hydroxide, e.g., aluminum phosphate). A person skilled in the relevant field will appreciate that the term "aluminum hydroxide" is used in this field to identify a crystalline aluminum oxyhydroxide compound. Aluminum hydroxide has only hydroxyl groups at the surface, covalently bonded to aluminum. The term "aluminum phosphate" is used in this field to identify amorphous aluminum hydroxyphosphate. Aluminum phosphate has phosphate groups and hydroxyl groups at the surface, covalently bonded to aluminum.

In some embodiments, the immunogenic composition is useful for treating a subject infected by any number of strains of coronavirus. In some embodiments, the immunogenic composition is useful for preventing a subject against infection by any number of strains of coronavirus. In some embodiments, the immunogenic composition induces an immune response of a subject administered the immunogenic composition, thereby preventing against and treating coronavirus infection.

In some embodiments, the immunogenic composition is suitable for treating a subject infected by any number of strains of SARS-CoV-2. In some embodiments, the immunogenic composition is suitable for preventing a subject against infection by any number of strains of SARS-CoV-2. In some embodiments, the immunogenic composition induces an immune response of a subject administered the immunogenic composition, thereby preventing against and treating SARS-CoV-2 infection.

In some embodiments, the immunogenic compositions of the present disclosure comprise other components such as adjuvants, buffers and the like. In some embodiments, the immunogenic compositions and vaccine compositions of the disclosure are administered with one or more adjuvants.

In some embodiments, the immunogenic composition may comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

In some embodiments, the transfection facilitating agent is a polyanion, polycation, including poly-L glutamate (LGS), or lipid. The transfection facilitating agent is poly-L-glutamate, and the poly-L-glutamate may be present in the immunogenic composition at a concentration less than 6 mg/ml. The transfection facilitating agent may also include surface active agents such as immune stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct.

In some embodiments, the pharmaceutically acceptable excipient is an adjuvant. The adjuvant may be other genes that are expressed in an alternative plasmid or are delivered as proteins in combination with the plasmids of the disclosure. In some embodiments, the adjuvant is Alum. In some embodiments, the adjuvant is selected from the group consisting of: a-interferon (IFN-a), p-interferon (IFN-p), 7-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

In some embodiments, the adjuvant is an immunostimulatory oligonucleotide. In certain embodiments, the immunostimulatory oligonucleotide can serve as a ligand for pattern recognition receptors (PRRs). Examples of PRRs include the Toll-like family of signaling molecules that play a role in the initiation of innate immune responses and also influence the later and more antigen specific adaptive immune responses. Therefore, the oligonucleotide can serve as a ligand for a Toll-like family signaling molecule, such as Toll-Like Receptor 9 (TLR9). For example, unmethylated CpG sites can be detected by TLR9 on plasmacytoid dendritic cells and B cells in humans (Zaida, et al., *Infection and Immunity*, 76(5):2123-2129, (2008)). Therefore, the sequence of oligonucleotide can include one or more unmethylated cytosine-guanine (CG or CpG, used interchangeably) dinucleotide motifs. The 'p' refers to the phosphodiester backbone of DNA, as discussed in more detail below, some oligonucleotides including CG can have a modified backbone, for example a phosphorothioate (PS) backbone.

In certain embodiments, an immunostimulatory oligonucleotide can contain more than one CG dinucleotide, arranged either contiguously or separated by intervening nucleotide(s). The CpG motif(s) can be in the interior of the oligonucleotide sequence. Numerous nucleotide sequences stimulate TLR9 with variations in the number and location of CG dinucleotide(s), as well as the precise base sequences flanking the CG dimers.

Typically, CG ODNs are classified based on their sequence, secondary structures, and effect on human peripheral blood mononuclear cells (PBMCs). The five classes are Class A (Type D), Class B (Type K), Class C, Class P, and Class S (Vollmer, J & Krieg, A M, *Advanced drug delivery reviews* 61(3): 195-204 (2009), incorporated herein by reference). CG ODNs can stimulate the production of Type I interferons (e.g., IFNα) and induce the maturation of dendritic cells (DCs). Some classes of ODNs are also strong activators of natural killer (NK) cells through indirect cytokine signaling. Some classes are strong stimulators of human B cell and monocyte maturation (Weiner, G L, PNAS USA 94(20): 10833-7 (1997); Dalpke, A H, Immunology 106(1): 102-12 (2002); Hartmann, G, J of Immun. 164(3): 1617-2 (2000), each of which is incorporated herein by reference).

Other PRR Toll-like receptors include TLR3, and TLR7 which may recognize double-stranded RNA, single-stranded and short double-stranded RNAs, respectively, and retinoic acid-inducible gene I (RIG-I)-like receptors, namely RIG-I and melanoma differentiation-associated gene 5 (MDA5), which are best known as RNA-sensing receptors in the cytosol. Therefore, in certain embodiments, the oligonucleotide contains a functional ligand for TLR3, TLR7, or RIG-I-like receptors, or combinations thereof.

Examples of immunostimulatory oligonucleotides, and methods of making them are known in the art, see for example, Bodera, P. *Recent Pat Inflamm Allergy Drug Discov.* 5(1):87-93 (2011), incorporated herein by reference.

In some embodiments, the adjuvant may comprise those encoding: MCP-1, MIP 1α, MIP-1β, IL-8, RANTES, L-selectin, P-selectin, E-selectin, CD34, GlyCAM-I, MadCAM 1, LFA-1, VLA-1, Mac-1, p150.95, PECAM, ICAM-1, ICAM-2, ICAM-3, CD2, LFA-3, M CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, TAP2 and functional fragments thereof.

In some embodiments, the immunogenic composition is formulated according to the mode of administration to be used. An injectable immunogenic composition pharmaceutical composition may be sterile, pyrogen free and particulate free. An isotonic formulation or solution can be used. Additives for isotonicity can include sodium chloride, dextrose, mannitol, sorbitol, and lactose. The immunogenic composition may comprise a vasoconstriction agent. The isotonic solutions may include phosphate buffered saline. In some embodiments, the immunogenic composition further comprises stabilizers including gelatin and albumin. The stabilizers can allow the formulation to be stable at room or ambient temperature for extended periods of time, including LGS or polycations or polyanions.

In some embodiments, the adjuvant is a mineral-containing composition. Mineral-containing compositions suitable for use as adjuvants in the disclosure include mineral salts, such as calcium salts and aluminum salts (or mixtures thereof). The disclosure includes mineral salts such as hydroxides (e.g. ox hydroxides), phosphates (e.g. hydroxyphosphates, orthophosphates), sulphates, etc., or mixtures of different mineral compounds, with the compounds taking any suitable form (e.g. gel, crystalline, amorphous, etc.), and some embodiments with adsorption. Calcium salts include calcium phosphate. Aluminum salts include hydroxides, phosphates, sulfates, and the like. The mineral containing compositions may also be formulated as a particle of metal salt (see WO/2000/023105, incorporated herein by reference). Aluminum salt adjuvants are described in US2011/0305727, incorporated herein by reference).

In some embodiments, the adjuvant is an oil emulsion composition (described in US2011/0305727). Oil emulsion compositions suitable for use as adjuvants in the disclosure include squalene-water emulsions, such as MF59 (5% Squalene, 0.5% Tween 80 and 0.5% Span, formulated into submicron particles using a microfluidizer).

In some embodiments, the adjuvant is a lipid-based adjuvant (described in US2011/0305727), including oil-in-water emulsions, modified natural lipid as derived from enterobacterial lipopolysaccharides, phospholipid compounds (such as the synthetic phospholipid dimer, E6020) and the like.

In some embodiments, the adjuvant is a saponin-based adjuvant. Saponins are steroid or triterpenoid glycosides found in wild or cultivated plants, lower marine animals and some bacteria (Riguera, 1997; Yoshiki et al., 1998). In some embodiments, the saponin and SARS-CoV-2 S glycoprotein variant are formulated as an ISCOM. In some embodiments, the saponin is Matrix-M™. In some embodiments, the adjuvant is a saponin MPLA nanoparticles (SMNP).

In some embodiments, the adjuvant is a microparticle (i.e., a particle of ~100 nm to ~150 μm in diameter, or ~200 nm to ~30 μm in diameter, or ~500 nm to ~10 μm in diameter) formed from materials that are biodegradable and non-toxic (e.g., a poly(α-hydroxy acid), a polyhydroxybutyric acid, a polyorthoester, a polyanhydride, a polycaprolactone, and the like), or poly(lactide-co-glycolide), optionally treated to have a negatively-charged surface (e.g., with SDS) or a positively-charged surface (e.g., with a cationic detergent, such as CTAB).

In some embodiments, the adjuvant is a liposome (Chapters 13 & 14 of Vaccine Design: the Subunit and Adjuvant Approach (eds. Powell & Newman) Plenum Press 1995 (ISBN 0-306-44867-X), each of which is incorporated herein by reference)). Examples of liposome formulations suitable for use as adjuvants are described in U.S. Pat. Nos. 6,090,406, 5,916,588, and EP-A-0626169, each of which is incorporated herein by reference).

In some embodiments, the adjuvant is a polyoxyethylene ethers or polyoxvethylene ester. Such formulations further include polyoxyethylene sorbitan ester surfactants in combination with an octoxynol as well as polyoxyethylene alkyl ethers or ester surfactants in combination with at least one additional non-ionic surfactant such as an octoxynol.

In some embodiments, the adjuvant is a muramyl peptide, such as N-acetylmuramyl-L-threonyl-D-isoglutamine ("thr-MDP"), N-acetyl-normuramyl-L-alanyl-D-isoglutamine (nor-MDP), N-acetyiglucsaminyl-N-acetylmuramyl-L-A1-D-isoglu-L-Ala-dipalmitoxy propylamide ("DTP-DPP", or "Theramide™), N-acetylmuramyl-L-alanyl-D-isoglutami-nyl-L-alanine-2-(1'-2' dipalmitoyl-sn-glyeero-3-hydroxy-phosphoryloxy)-ethylamine ("MTP-PE").

In some embodiments, the adjuvant is an outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "TVX-908", a complex comprised of *Neisseria meningitidis* outer membrane and lipopolysaccharides.

In some embodiments, the adjuvant is a polyoxidonium polymer (Dyakonova et al., *Int Immunopharmacol.,* 4:1615-23 (2004); FR-2859633) or other N-oxidized polyethylene-pi erazine derivative. In some embodiments, the adjuvant is methyl inosine 5'-monophosphate ("MIMP") (Signorelli& Hadden, *Int Immunopharmacol.,* 3: 1177-86(2003)).

In some embodiments, the adjuvant is a CD1d ligand, such as an α-glycosylceramide (De Libera et al., *Nature Reviews Immunology* 2005:485-96 (2005); U.S. Pat. No. 5,936,076; Old et al., J Clin Invest., 113: 1631-40 (2004)); US2005/0192248; Yang et al., *Angew Chem Int Ed.,* 43:3818-22 (2004); WO2005/102049; Goffet et al., *Am Chem Soc.,* 126: 13602-3(2004); WO2003/105769) (e.g., α-galactosylceramide), phytosphingosine-containing α-glycosylceramides, OCH, KRN7000 [(2S,3 S,4R)-1-O-(α-D-galactopyranosyl)-2-(N-hexacosanoylamino)-1,3,4-octadecanetriol], CRONY-101, 3"-O-sulfo-galactosylceramide, etc.

In some embodiments, the adjuvant is a gamma inulin (Cooper et al., *Pharm Biotechnol.,* 6:559-80(1995)) or derivative thereof, such as algammulin.

In some embodiments, adjuvant combinations include combinations of Th1 and Th2 adjuvants such as CpG and alum, or resiquimod and alum. A combination of aluminum phosphate and 3dMPL may be used. Other combinations that may be used include: alum and a benzonapthridine compound or a SMIP, a squalene-in-water emulsion (such as MF59) and a benzonapthridine compound or a S IP, and E6020 and a squalene-in-water emulsion, such as MF59) or alum.

In some embodiments, adjuvants include: genetic adjuvants such as IL-2 gene or fragments thereof, the granulocyte macrophage colony-stimulating factor (GM-CSF) gene or fragments thereof, the IL-18 gene or fragments thereof, the chemokine (C—C motif) ligand 21 (CCL21) gene or fragments thereof, the IL-6 gene or fragments thereof; and other immune stimulatory genes; protein adjuvants such IL-2 or fragments thereof, the granulocyte macrophage colony-stimulating factor (GM-CSF) or fragments thereof, IL-18 or fragments thereof, the chemokine (C—C motif) ligand 21 (CCL21) or fragments thereof, IL-6 or fragments thereof, lipid adjuvants such as cationic liposomes, N3

(cationic lipid), monophosphoryl lipid A (MPL1); other adjuvants including Fms-like tyrosine kinase-3 ligand (FK-3L), bupivacaine, marcaine, and levamisole.

In some embodiments, any of the immunogenic compositions of the present disclosure are formulated with at least one adjuvant disclosed herein which may increase immunogenicity of the immunogenic compositions of the present disclosure. It is within the purview of the skilled artisan to utilize available adjuvants which may increase the immune response of the immunogenic compositions of the present disclosure in comparison to administration of a non-adjuvanted immunogenic composition.

Methods of Treatment and Prophylaxis

In some embodiments, the immunogenic compositions and vaccines described herein induce a cellular immune response in a subject. In some embodiments, the induced cellular immune response is specific for any coronavirus protein described herein. In some embodiments, the induced cellular immune response is reactive to any coronavirus protein described herein. In some embodiments, the induced cellular immune response is specific for SARS-CoV-2 S glycoprotein variant. In some embodiments, the induced cellular immune response is reactive to the SARS-CoV-2 S protein variant.

In some embodiments, a humoral immune response is induced by any of the viral particles, immunogenic compositions or vaccines described herein. In some embodiments, the humoral immune response comprises an increased level of neutralizing antibodies compared to the level of neutralizing antibodies in a subject not administered the viral particle, immunogenic composition, or vaccine. In some embodiments, the neutralizing antibodies are specific for the antigen expressed by the viral particle, e.g., a SARS-CoV-2 S glycoprotein variant. In some embodiments, the neutralizing antibodies are reactive with the antigen expressed by the infectious disease agent, e.g., a SARS-CoV-2 S glycoprotein. In some embodiments, the neutralizing antibodies provide protection against and/or treatment of COVID-19 infection and its associated pathologies in the subject administered the immunogenic composition.

In some embodiments, the humoral immune response comprises an increased level of IgG antibodies compared to the level of IgG antibodies in a subject not administered the viral particle, immunogenic composition, or vaccine. In some embodiments, the IgG antibodies are specific for the antigen expressed by the viral particle, e.g., a SARS-CoV-2 S glycoprotein. In some embodiments, the IgG antibodies are reactive with the antigen, e.g., a SARS-CoV-2 S glycoprotein.

In some embodiments, the induced cellular immune response comprises a CD8+ T cell response. In some embodiments, the CD8+ T cells are reactive to the antigen, e.g., a SARS-CoV-2 S glycoprotein. In some embodiments, the CD8+ T cells are polyfunctional making them able to perform multiple functions such as degranulation of cytotoxic proteins and production of multiple cytokines simultaneously. In some embodiments, the CD8+ T cells produce interferon gamma (IFN-γ), tumor necrosis factor alpha (TNF-α), interleukin-2 (IL-2), or a combination of IFN-γ and TNF-α.

In some embodiments, the humoral immune response is induced by about 1.5-fold to about 16-fold, about 2-fold to about 12-fold, or about 3-fold to about 10-fold. In some embodiments, the humoral immune response is induced by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0 fold, at least about 13.5-fold, at least about 14.0-fold, at least about 14.5-fold, at least about 15.0-fold, at least about 15.5-fold, or at least about 16.0-fold.

In some embodiments, the humoral immune response comprises an increased level of IgG antibodies compared to a subject not administered the immunogenic composition. In some embodiments, these IgG antibodies are specific for the coronavirus antigen described herein. In some embodiments, these IgG antibodies are specific for the SARS-CoV-2 S glycoprotein. In some embodiments, these IgG antibodies are reactive with the SARS-CoV-2 S glycoprotein. In some embodiments, the level of IgG antibody is increased by about 1.5-fold to about 16-fold, about 2-fold to about 12-fold, or about 3-fold to about 10-fold as compared to a subject not administered the immunogenic composition. In some embodiments, the level of IgG antibody increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0 fold, at least about 13.5-fold, at least about 14.0-fold, at least about 14.5-fold, at least about 15.0-fold, at least about 15.5-fold, or at least about 16.0-fold as compared to a subject not administered the immunogenic composition.

In some embodiments, the induced cellular immune response includes an increased CD8+ T cell response as compared to a subject not administered the immunogenic composition. In some embodiments, the CD8+ T cell response is increased by about 2-fold to about 30-fold, about 3-fold to about 25-fold, or about 4-fold to about 20-fold as compared to a subject not administered the immunogenic composition. In some embodiments, the CD8+ T cell response is increased by at least about 1.5-fold, at least about 2.0-fold, at least about 3.0-fold, at least about 4.0 fold, at least about 5.0-fold, at least about 6.0-fold, at least about 6.5-fold, at least about 7.0 fold, at least about 7.5-fold, at least about 8.0-fold, at least about 8.5-fold, at least about 9.0 fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0 fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition.

In some embodiments, the cellular immune response includes eliciting a CD4+ T cell response. In some embodiments, the elicited CD4+ T cell response is reactive with any coronavirus antigen described herein. In some embodiments, the elicited CD4+ T cell response is reactive with the SARS-CoV-2 spike protein. In some embodiments, the elicited CD4+ T cell response is polyfunctional. In some embodiments, the induced cellular immune response includes eliciting a CD4+ T cell response, in which the CD4+ T cells produce IFN-7, TNF-α, IL-2, or a combination of IFN-7 and TNF-α.

In some embodiments, the immunogenic compositions of the present disclosure have features required of effective immunogenic compositions such as being safe so the immunogenic composition itself does not cause illness or death; is protective against illness resulting from exposure to live pathogens such as viruses or bacteria; induces neutralizing antibody to prevent disclosure of cells; induces protective T cells against intracellular pathogens; and provides ease of administration, few side effects, and biological stability.

In some embodiments, the immunogenic composition further induces an immune response when administered to different tissues such as the muscle or skin. In some embodiments, the immunogenic composition induces an immune response when administered via electroporation, or injection, or subcutaneously, or intramuscularly.

The compositions of the disclosure may elicit both a cell mediated immune response as well as a humoral immune response. A TH1 immune response may be elicited using a TH1 adjuvant. In some embodiments, a TH1 adjuvant elicits increased levels of IgG2a production relative to immunization of any coronavirus antigen described herein without adjuvant. In some embodiments, a TH1 adjuvant elicits increased levels of IgG2a production relative to immunization of the SARS-CoV-2 S protein without adjuvant. TH1 adjuvants suitable for use in the disclosure may include for example saponin formulations, virosomes and virus like particles, non-toxic derivatives of enterobacterial lipopolysaccharide (LPS), immunostimulatory oligonucleotides. In some embodiments, the TH1 adjuvant is an immunostimulatory oligonucleotide, such as oligonucleotides containing a CpG motif. A TH2 immune response may be elicited using a TH2 adjuvant. In some embodiments, a TH2 adjuvant elicits increased levels of IgG1 production relative to immunization of any coronavirus antigen described herein without a TH2 adjuvant. In some embodiments, a TH2 adjuvant elicits increased levels of IgG1 production relative to immunization of the SARS-CoV-2 S protein without a TH2 adjuvant. TH2 adjuvants suitable for use in the disclosure include, for example, mineral containing compositions, oil-emulsions, and ADP-ribosylating toxins and detoxified derivatives thereof. In some embodiments, the TH2 adjuvant is a mineral containing composition, such as aluminum salts.

In some embodiments, the composition includes a combination of a TH1 adjuvant and a TH2 adjuvant. In some embodiments, such a composition elicits an enhanced TH1 and an enhanced TH2 response, i.e., an increase in the production of both IgG1 and IgG2a production relative to immunization without an adjuvant. Furthermore, in some embodiments, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

Methods of preparing and administering immunogenic compositions to a subject in need thereof are well known in the art or readily determined by those skilled in the art. The dosage and frequency of administration may depend on whether the treatment is prophylactic or therapeutic.

In some embodiments, the induced humoral immune response includes IgG antibodies and/or neutralizing antibodies that are reactive to any coronavirus antigen described herein. In some embodiments, the induced humoral immune response includes IgG antibodies and/or neutralizing antibodies that are reactive to the SARS-CoV-2 S protein. In some embodiments, the induced cellular immune response includes a CD8+ T cell response, which is induced by about 2-fold to about 30-fold, about 3-fold to about 25-fold, or about 4-fold to about 20-fold.

In some embodiments, wherein a subject is administered an immunogenic composition or vaccine described herein comprising an SARS-CoV-2 S glycoprotein variant is sufficient prevent the onset of a SARS-CoV-2 infection. In some embodiments, a single dose induces neutralizing antibodies that are reactive to the SARS-CoV-2 S protein. In some embodiments, a single dose induces a humoral immune response that prevents infection with SARS-CoV-2. In some embodiments, a single dose is sufficient to reduce severity of symptoms caused by SARS-CoV-2 in a subject administered the immunogenic composition or vaccine relative to an untreated subject.

In some embodiments, wherein a subject was administered any of the vaccines or recombinant proteins described herein, SARS-CoV-2 reinfection is prevented after re-challenge.

In some embodiments, serum anti-coronavirus antibody titers are measured after each injection with any of the immunogenic compositions described herein and control serum titers are measured prior to immunization. In some embodiments, serum anti-coronavirus antibody titers are measure prior to immunization. In some embodiments, serum anti-coronavirus antibody titers are measure two or three weeks after each injection with any of the immunogenic compositions described herein and two or three weeks after the second injection with any of the immunogenic compositions described herein. In other embodiments, serum anti-SARS-CoV-2 antibody titers are measured two or three weeks after the second, third and/or fourth injection with any of the immunogenic compositions described herein.

In some embodiments, the serum anti-SARS-CoV-2 antibody titers are measured after each injection with any of the immunogenic compositions described herein and control serum titers are measured prior to immunization. In some embodiments, serum anti-SARS-CoV-2 antibody titers are measured two or three weeks after each injection with any of the immunogenic compositions described herein and two or three weeks after the second injection with any of the immunogenic compositions described herein. In other embodiments, serum anti-SARS-CoV-2 antibody titers are measured two or three weeks after the second, third and/or fourth injection with any of the immunogenic compositions described herein. Antibody titers may be determined by methods known in the art. For example, antibody titers may be assayed by ELISA, Immunoblot assays or indirect immunofluorescence. The antigen used in these assays may be an SARS-CoV-2 protein.

In some embodiments, the subject administered an immunogenic composition described herein is challenged intranasally with SARS-CoV-2 after the final immunization to determine whether neutralizing antibodies were generated in the vaccinated subject. For example, the subjects may be challenged with SARS-CoV-2 three, four or five weeks after the final immunization. In some embodiments, control unvaccinated subjects are challenged with SARS-COV-2 concurrently with the vaccinated subjects.

Serum samples from vaccinated subjects may be tested for the presence of neutralizing antibodies by microneutralization assay. Microneutralization assays may be performed by methods known in the art. The number of infectious virus particles may be determined by detection of syncytia formation by immunostaining. The neutralization titer may be defined as the reciprocal of the serum dilution producing at least a 60% reduction in number of synctia per well, relative to controls (no serum).

Viral load in the lung of the subjects may be determined by plaque assay. The lungs of the subjects may be harvested post SARS-COV-2 infection and a plaque assay may be used to test for infectious virus. Plaques may be counted to determine the viral load.

An alternative method for determining viral load is quantitative real-time PCR (qRT-PCR). Viral load can be determined by qRT-PCR using oligonucleotide primers specific for the SARS-CoV-2 gene as described; the oligonucleotide primers may comprise some modifications. Methods for performing qRT-PCR are known in the art.

Methods for assessing antibody generation and immune response after vaccination are well known in the art. Methods for measuring immune response in a subject include, but is not limited to, isolating blood sample from a subject immunized with any of the immunogenic compositions described herein. Blood samples are incubated with fluorescently tagged anti-bodies against any of the immune markers described herein and analyzed using flow-cytometry methods. The immune markers are then compared to an unimmunized subject to measure immune response.

Methods of Administration

Any of the compositions described herein may be formulated in accordance with standard techniques well known to those skilled in the pharmaceutical art. In some embodiments, such compositions are administered in dosages and by techniques well known to those skilled in the medical arts taking into consideration such factors as the age, sex, weight, and condition of the particular subject, and the route of administration. In some embodiments the subject is a mammal, such as a human, a horse, a cow, a pig, a sheep, a cat, a dog, a rat, or a mouse.

In some embodiments, the subject is a "patient", i.e., a warm-blooded animal, a human, who which is awaiting the receipt of, or is receiving medical care or was/is/will be the object of a medical procedure, or is monitored for the development of a disease. In some embodiments, the subject is an adult (for example a subject above the age of 18). In some embodiments, the subject is a child (for example a subject below the age of 18). In some embodiments, the subject is a male. In some embodiments, the subject is a female.

In some embodiments, the immunogenic composition is administered prophylactically or therapeutically. In some embodiments for prophylactic administration, the immunogenic composition is administered in an amount sufficient to induce an immune response. In some embodiments, the immunogenic compositions are administered to a subject in need thereof in an amount sufficient to elicit a therapeutic effect. An amount adequate to accomplish this is defined as "therapeutically effective dose." Amounts effective for this use will depend on, e.g., the particular composition of the immunogenic composition regimen administered, the manner of administration, the stage and severity of the disease, the general state of health of the patient, and the judgment of the prescribing physician.

In some embodiments, the delivery route of the immunogenic composition is parenteral administration, e.g., intradermal, intramuscular or subcutaneous delivery. In some embodiments, routes include oral administration, intranasal, and intravaginal routes. In some embodiments, epidermal administration of the immunogenic composition is employed. Epidermal administration involves mechanically or chemically irritating the outermost layer of epidermis to stimulate an immune response to the irritant In some embodiments, the immunogenic composition is formulated for administration via the nasal passages. In some embodiments, formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. In some embodiments, the formulation is a nasal spray, nasal drops, or by aerosol administration by nebulizer. In some embodiments, the formulation includes aqueous or oily solutions of the immunogenic composition.

In some embodiments, the immunogenic composition is a liquid preparation such as a suspension, syrup or elixir. In some embodiments, the immunogenic composition is a preparation for parenteral, subcutaneous, intradermal, intramuscular or intravenous administration (e.g., injectable administration), such as a sterile suspension or emulsion.

In some embodiments, the dose of the immunogenic composition varies according to factors such as the disease state, age, sex, and weight of the individual, and the ability of antibody to elicit a desired response in the individual. In some embodiments, the dosage regime is adjusted to provide the optimum therapeutic response. In some embodiments, the dose of the immunogenic composition is varied to provide optimum preventative dose response depending upon the circumstances.

In some embodiments, the disclosure provides methods of preventing or delaying the onset of any coronavirus described herein, or of reducing at least one symptom of any coronavirus described herein in an individual, comprising the step of providing an effective amount of any of the compositions of the disclosure to the individual. In some embodiments, a composition is provided to the individual once or more than once. The composition may be provided subsequently to the individual within weeks, months, or years of the first providing step. In some embodiments, an individual displays one or more symptoms of any coronavirus described herein, lacks any symptoms of any coronavirus described herein, or has been exposed to any coronavirus described herein. In some embodiments, the individual has come into contact with an individual that has any coronavirus described herein. In some embodiments, the individual is a child, an elderly person, exposed to a bioweapon or at risk thereof, or is a health care worker.

In some embodiments, the disclosure provides methods of preventing or delaying the onset of SARS-CoV-2 or of reducing at least one symptom of SARS-CoV-2 in an individual, comprising the step of providing an effective amount of any of the compositions of the disclosure to the individual. In some embodiments, a composition is provided to the individual once or more than once. The composition may be provided subsequently to the individual within weeks, months, or years of the first providing step. In some embodiments, an individual displays one or more symptoms of SARS-CoV-2, lacks any symptoms of SARS-CoV-2, or has been exposed to SARS-CoV-2. In some embodiments, the individual has come into contact with an individual that has SARS-CoV-2. In some embodiments, the individual is a child, an elderly person, exposed to a bioweapon or at risk thereof, or is a health care worker.

In some embodiments, the immunogenic composition of the disclosure is a prophylactic vaccine. By "prophylactic vaccine" is meant that the immunogenic composition is administered before definitive clinical signs, diagnosis or identification of the disease. In some embodiments, the immunogenic composition is administered to prevent the disease.

If the immunogenic composition appears to induce an effective, but short-lived immune response, prophylactic immunogenic compositions may also be designed to be used as booster immunogenic compositions. Such booster immunogenic compositions are given to individuals who have previously received a vaccination, with the intention of prolonging the period of protection.

In some embodiments, the immunogenic composition is a therapeutic vaccine, i.e., is administered after first clinical signs, diagnosis or identification of the disease. In some embodiments, the immunogenic composition is administered to treat the disease.

Severely affected people with SARS-CoV-2 develop a potentially fatal form of respiratory failure, referred to as adult respiratory distress syndrome (ARD or ARDS). In such cases the virus attacks organs in the body other than the lungs, causing kidney failure, inflammation of the heart sac (pericarditis), severe systemic bleeding from disruption of clotting system (disseminated intravascular coagulation), reduced white blood cell counts (lymphopenia), inflammation of the arteries (vasculitis), or inflammation of the gut with diarrhea, for example.

In some embodiments, the immunogenic compositions of the present disclosure include two, three, four or more adjuvants.

In some embodiments, compositions of the disclosure are administered in a number of suitable ways, such as intramuscular injection (e.g., into the arm or leg), subcutaneous injection, intranasal administration, oral administration, intradermal administration, transcutaneous administration, transdermal administration, intramedullary injections, intrathecal, direct intraventricular, intravenous, intraperitoneal, intranasal, or intraocular injections and the like. In some embodiments, the immunogenic compositions may be administered by means including, but not limited to, traditional syringes, needleless injection devices, or microprojectile bombardment gene guns. In some embodiments, the compositions are formulated for injection in aqueous solutions, in physiologically compatible buffers such as Hanks' solution, Ringer's solution, or physiological saline buffer.

The appropriate route of administration will be dependent upon the age, health and other characteristics of the mammal A clinician will be able to determine an appropriate route of administration based on these and other factors.

In some embodiments, the treatment is a single dose schedule or a multiple dose schedule. Multiple doses may be used in a primary immunization schedule and/or in a booster immunization schedule. In some embodiments, in a multiple dose schedule, the various doses are given by the same or different routes, e.g., a parenteral prime and mucosal boost, a mucosal prime and parenteral boost, etc. Administration of more than one dose (typically two doses) is particularly useful in immunologically naive patients. In some embodiments, multiple doses are administered at least 1 week apart (e.g., about 2 weeks, about 3 weeks, about 4 weeks, about 6 weeks, about 8 weeks, about 10 weeks, about 12 weeks, about 16 weeks, and the like.)

In some embodiments, the immunogenic composition formulations produced using a composition of the disclosure are administered to patients at substantially the same time as (e.g., during the same medical consultation or visit to a healthcare professional or vaccination center) other immunogenic compositions.

In some embodiments, the immunogenic compositions of the present disclosure are used to vaccinate individuals using a prime/boost protocol (described in U.S. Patent Publication No. 2011/0177122, incorporated herein by reference). In some embodiments, a first immunogenic composition is administered to the individual (prime) and then after a period of time, a second immunogenic composition is administered to the individual (boost). In some embodiments, administration of the boosting composition is generally weeks or months after administration of the priming composition, about 2-3 weeks or 4 weeks, or 8 weeks, or 16 weeks, or 20 weeks, or 24 weeks, or 28 weeks, or 32 weeks. In some embodiments, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition In some embodiments, the first and second immunogenic compositions are the same composition. In some embodiments, the first and second immunogenic compositions are different compositions. In some embodiments, the step of administering the immunogenic composition comprises administering a first immunogenic composition, and then at a later time, administering a second immunogenic composition.

In some embodiments, the individual is at risk for infection with any coronavirus described herein. In some embodiments, the individual has been exposed to any coronavirus described herein. For example, the individual may be an elderly individual, a child, an infant or an immunocompromised individual. As used herein, the terms exposed, exposure, and the like, indicate the subject has come in contact with a person or animal that is known to be infected with any coronavirus described herein. In some embodiments, the individual is at risk for infection with SARS-COV-2. In some embodiments, the individual has been exposed to SARS-COV-2. For example, the individual may be an elderly individual, a child, an infant or an immunocompromised individual. As used herein, the terms exposed, exposure, and the like, indicate the subject has come in contact with a person or animal that is known to be infected with SARS-COV-2.

In some embodiments, the immunogenic composition dose is between 1 pg to 10 mg active component/kg body weight/time, and is 20 pg to 10 mg component/kg body weight/time. In some embodiments, the immunogenic composition is administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments, the number of immunogenic composition doses for effective treatment is 1, 2, 3, 4, 5, 6, 7, 8, 9, or 10.

Kits

In some embodiments, any of the immunogenic compositions described herein are provided in a kit. In some embodiments, the kit includes (a) a container that contains a composition that includes one or more unit doses of the immunogenic composition, and optionally (b) instructions. In some embodiments, the unit doses of the immunogenic composition are sufficient to cause an immunogenic response (e.g., antibody production) in a subject. In some embodiments, the kit also includes reagents and instructions useful in the testing (assaying) for an immunogenic response. Such methods of assaying for an immunogenic response include, but are not limited to, any of the testing methods described herein. In some embodiments, the kit includes one or more additional agents for treating any coronavirus described herein. In some embodiments, the kit includes one or more additional agents for treating SARS-COV-2. For example, in some embodiments the kit includes a first container that contains a composition that includes the immunogenic composition, and a second container that includes the one or more additional agents.

In some embodiments, the instructions relate to methods of administering the immunogenic composition, e.g., in a suitable dose, dosage form, or mode of administration (e.g., a dose, dosage form, or mode of administration described herein), to treat a subject who is infected with SARS-CoV-2, or who is at risk of being infected with SARS-CoV-2.

In some embodiments, in addition to the agent (e.g., SARS-CoV-2 immunogenic composition), the composition in the kit includes other ingredients, such as a solvent or buffer, a stabilizer, or a preservative. In some embodiments, the agent is provided in any form, e.g., liquid, dried or lyophilized form, is substantially pure and/or sterile. In some embodiments, the liquid solution is an aqueous solution. In some embodiments, when the agents are provided as a dried form, reconstitution generally is by the addition of a suitable solvent. In some embodiments, the solvent, e.g., sterile water or buffer, is optionally provided in the kit.

The kit may include one or more containers for the composition or compositions containing the agents. In some embodiments, the kit contains separate containers, dividers or compartments for the composition and informational material. In some embodiments, the composition is contained in a bottle, vial, or syringe, and the informational material is contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. In some embodiments, the containers include a combination unit dosage, e.g., a unit that includes both the SARS-CoV-2 immunogenic composition and the second agent, e.g., in a desired ratio. In some embodiments, the kit includes a plurality of syringes, ampules, foil packets, blister packs, or medical devices, e.g., each containing a single combination unit dose. The containers of the kits may be air-tight, waterproof (e.g., impermeable to changes in moisture or evaporation), and/or light-tight.

The kit optionally includes a device suitable for administration of the composition, e.g., a syringe or other suitable delivery device. In some embodiments, the device is provided pre-loaded with one or both of the agents or is empty, but suitable for loading.

In some embodiments, instructions are provided for administration of the composition for enhancing an immune response in an individual. In some embodiments, instructions are provided for administration of the compositions for producing antibodies in an individual. In some embodiments, instructions are provided for administration of the composition for activating T cells in an individual. In some embodiments, instructions are provided for administration of the composition for preventing infection in an individual.

In some embodiments, the kit comprises a container comprising any of the immunogenic compositions described herein, and an optional pharmaceutically acceptable carrier, and a package insert comprising instructions for administration of the composition for enhancing an immune response in an individual, wherein the individual is at risk of being infected with any coronavirus described herein.

All publications, patents, and patent applications cited herein, whether supra or infra, are hereby incorporated by reference in their entirety.

Definitions

Terms used in the claims and specification are defined as set forth below unless otherwise specified.

As used herein, the term "adjuvant" refers to a compound that, when used in combination with a specific immunogen (e.g., an SARS-CoV-2 S glycoprotein variant described herein) in a formulation, will augment or otherwise alter or modify the resultant immune response. Modification of the immune response includes intensification or broadening the specificity of either or both antibody and cellular immune responses.

As used herein, the term "aggregation-prone region" refers to a three-dimensional area comprising hydrophobic amino residues that can cause aggregation of a protein. In some embodiments, an aggregation-prone region is identified by measuring the AggScore of a region.

The term "AggScore" or "aggregation score" refers to measurement determined by analyzing the distribution of hydrophobic and electrostatic patches on the surface of a protein, factoring in the intensity and relative orientation of the respective surface patches into an aggregation propensity function that has been trained on a benchmark set of 31 adnectin proteins. AggScore can accurately identify aggregation-prone regions in several well-studied proteins and also reliably predict changes in aggregation behavior upon residue mutation.

The term "effective amount" as used herein is defined as the amount of a compound required to prevent a SARS or SARS-related infection or delay the onset of or improve at least one symptom of a SARS or a SARS-related disease. For example, in the treatment or prevention of a SARS or a SARS-related disease, a compound that improves inhibits development of at least one symptom or delays the onset or reduces the severity of at least one symptom would be effective. In embodiments, an effective amount of a compound is not required to cure a disease but will provide a treatment or prevention for a disease.

The term "hydrophobe" or "hydrophobic" as used herein refers to a molecule or part of a molecule which is not attracted by water or does not interact with water. Hydrophobic molecules tend to be non-polar and, thus, prefer other neutral molecules and non-polar solvents, and often cluster together in water, forming micelles.

As used herein the term "neutralizing antibody" refers to an antibody that binds to a virus and interferes with its ability to infect a cell. Neutralizing antibodies are antibodies that prevent the virus from completing one round of replication. Such antibodies can interfere with any step in the virus life cycle including, but not limited to, the steps of attaching to a cell, entering a cell, cleavage of the polyprotein, fusion of the viral membrane with endosomal membrane, release of viral proteins into the cytoplasm, formation of new viral particles and budding of viral particles from the host cell membrane.

The term "neutralizing titer" or "NT50" refers to the reciprocal of the highest dilution of serum or antibody at which infectivity is reduced by 50%.

The term "nucleic acid molecule," as used herein, is intended to include DNA molecules and RNA molecules. A nucleic acid molecule may be single-stranded or double-stranded, but preferably is double-stranded DNA.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable excipient" refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

"Subject" as used herein can mean a mammal that wants to or is in need of being immunized with a composition described herein. The mammal can be a human, chimpanzee, dog, cat, horse, cow, mouse, or rat.

As used herein, the term "preventing" refers to partially or completely inhibiting the onset of one or more symptoms or features of a particular infection, disease, disorder, and/or condition.

As used herein, the term "receptor binding domain" or "S glycoprotein" refers to a polypeptide of a coronavirus spike protein capable of binding to a receptor on a host cell. In some embodiments, the S glycoprotein is from the spike protein of a SARS-CoV-2. In some embodiments, the S glycoprotein comprises the amino acid sequence set forth in SEQ ID NO: 1.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleic acid sequence and a second nucleic acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence.

Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

As used herein, the term "therapeutically effective amount" refers to is an amount that is effective to ameliorate a symptom of a disease. A therapeutically effective amount can be a "prophylactically effective amount" as prophylaxis can be considered therapy. "Treatment" or "treating," as used herein can mean protecting of an animal from a disease through means of preventing, suppressing, repressing, or completely eliminating the disease. Preventing the disease involves administering a immunogenic composition of the present disclosure to an animal prior to onset of the disease. Suppressing the disease involves administering a immunogenic composition of the present disclosure to an animal after induction of the disease but before its clinical appearance. Repressing the disease involves administering a immunogenic composition of the present disclosure to an animal after clinical appearance of the disease.

The terms "Titer" or "transduction efficiency" is used as a means to characterize and compare vector particles with regard to their ability to transduce their target cells. Thus, vector particles having an "increased titer" or an "increased transduction efficiency" are able to transduce a higher number of cells at a given vector particle volume than other vector particles with the same volume.

As used herein, the term "vaccine" refers to a formulation which contains an SARS-CoV-2 S glycoprotein variant of the present disclosure, which is in a form that is capable of being administered to a vertebrate and which induces a protective immune response sufficient to induce immunity to prevent and/or ameliorate an infection or disease, and/or to reduce at least one symptom of an infection or disease, and/or to enhance the efficacy of another dose of a fusion protein or nanoparticle. Typically, the vaccine comprises a conventional saline or buffered aqueous solution medium in which the composition of the present disclosure is suspended or dissolved. In this form, the composition of the present disclosure can be used conveniently to prevent, ameliorate, or otherwise treat an infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

"Variant" used herein is a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. A variant may be an amino acid sequence that is substantially identical over the full length of the amino acid sequence. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The term "volumetric productivity" refers to amount of protein i.e. titer, obtained per unit volume of the culture media. The per unit culture media can range from per ml to per reactor volume.

Referring to the well-recognized nomenclature for amino acids, the three letter code, or one letter code, is used, including the codes "Xaa" or "X" to indicate any amino acid residue. Thus, Xaa or X may typically represent any of the 20 naturally occurring amino acids.

EQUIVALENTS AND SCOPE

Those skilled in the art will recognize, or be able to ascertain using no more than routine experimentation, many equivalents to the specific embodiments, in accordance with the disclosure described herein. The scope of the present disclosure is not intended to be limited to the Description below, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments, in which exactly one member of the group is present in, employed in, or otherwise relevant to a given product or process. The disclosure includes embodiments, in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

Example 1: Generation of a SARS-CoV-2 Antigen for Low Cost Vaccine

To identify an appropriate vaccine subunit for expression in yeast, previous efforts to express subunits of the homologous spike proteins from SARS-CoV-1 and MERS-CoV were investigated. Large protein subunits may include multiple epitopes for neutralization and high immunogenicity, exemplified by the 140 kDa MERS-CoV spike glycoprotein that elicits a potent, broadly neutralizing response in several animal models (Wang, L. et al. (2015) *Nat. Commun.* 6, 1-11). Heavily modified proteins, however, can present manufacturing challenges, exemplified by the inverse scaling of subunit size and expressibility of the SARS-CoV-1 spike protein in microbial hosts (Chuck, C. P. et al. (2009) *Virus Genes* 38, 1-9). The SARS-CoV-1 RBD alone has been demonstrated to express well in *K. phaffii*, and is sufficient to raise a neutralizing response in animals after removal of one or more N-linked glycosylation sites (Chen, W. h. et al. (2014) *Hum. Vaccin. Immunother.* 10, 648-658). As the SARS-CoV-2 receptor binding domain (RBD) of the spike protein contains only two of the three N-linked glycosylation sites found in SARS-CoV-1 RBD, four SARS-CoV-2 RBD variants were generated that removed both, each, or none of the glycosylation sites (SEQ ID NOs: 1-4). Specifically, strains were derived from wild-type *Komagataella phaffii* (NRRL Y-11430). Genes containing RBD variants were codon optimized, synthesized (Integrated DNA Technologies), and cloned into a custom vector. *K. phaffii* strains were transformed as described previously (Dalvie, N. C. et al., (2019) doi:10.1021/acssynbio. 9b00372).

Strains for initial characterization and titer measurement were grown in 3 mL culture in 24-well deep well plates (25° C., 600 rpm), and strains for protein purification were grown in 200 mL culture in 1 L shake flasks (25° C., 250 rpm). Two media compositions were used: complex media (potassium phosphate buffer pH 6.5, 1.34% nitrogen base w/o amino acids, 1% yeast extract, 2% peptone), and rich defined media described previously (Matthews, C. B. et al. (2018) *Biotechnol. Bioeng.* 115, 103-113). Cells were inoculated at 0.1 OD600, outgrown for 24 hours with 4% glycerol feed, pelleted, and resuspended in fresh media with a combination of 40 g/L sorbitol and 1-5% methanol feed. Supernatant samples were collected after 24 hours of production, filtered, and analyzed. InSCyT bioreactors were operated as described previously (Crowell, L. E. et al. (2018) *Nature Biotechnology* vol. 36 988). Removal of the first glycosylation site N1 was necessary for expression in *K. phaffii*, as observed previously for SARS-CoV-1 RBD (FIG. 1A).

To characterize the two expressed variants, strains producing RBD-N1del (SEQ ID NO: 2) and RBD-N1del-N13Q (SEQ ID NO: 4) were cultivated in a 200 mL shake flask. A purification method based on biophysical characteristics of the RBD and prior experience with purifying heterologous proteins with similar molecular weight, isoelectric point, and hydrophobicity was developed (Timmick, S. M. et al. (2018) *Biotechnol. Bioeng.* 115, 2048-2060). Specifically, protein purification was carried out on the purification module of the InSCyT system as described previously (Crowell, L. E. et al., (2018) *Nature Biotechnology* vol. 36, 988). All columns were equilibrated in the appropriate buffer prior to each run. Product-containing supernatant was adjusted to pH 4.5 using 100 mM citric acid. The adjusted supernatant was loaded into a pre-packed CMM HyperCel column (1-mL or 5-mL) (Pall Corporation, Port Washington, N.Y.), re-equilibrated with 20 mM sodium citrate pH 4.5, washed with 20 mM sodium phosphate pH 6.0, and eluted with 20 mM sodium phosphate pH 7.0, 100 mM NaCl. Eluate from column 1 above 15 mAU was flowed through a 1-mL pre-packed HyperCel STAR AX column (Pall Corporation, Port Washington, NY). Flow-through from column 2 above 15 mAU was collected. Purified protein was then visualized on SDS PAGE (FIG. 1B).

The material generated in small-scale batch cultivation was sufficient for characterization of the bioactivity and immunogenicity of the RBD. Biolayer inferometry was performed using the Octet Red96 with Protein A (ProA) biosensors (Sartorius ForteBio, Fremont, CA), which were hydrated for 15 minutes in kinetics buffer prior to each run. Kinetics buffer consisting of 1×PBS pH 7.2, 0.5% BSA, and 0.05% Tween 20 was used for all dilutions, baseline, and disassociation steps. Variants were tested for binding to human ACE2-Fc, the cognate human receptor for SARS-CoV-2, and CR3022, a neutralizing antibody to SARS-CoV-1 and SARS-CoV-2. CR3022 and ACE2-Fc were used in the assay at concentrations of 2 and 10 μg/mL, respectively. Samples were loaded in a 96-well black microplate (Greiner Bio-One, Monroe, NC) at starting concentrations of 15 and 10 μg/mL, respectively. Seven 1:1 serial dilutions and a reference well of kinetics buffer were analyzed for each sample. Association and dissociation were measured at 1000 rpm for 300 and 600 sec, respectively. Binding affinity was calculated using the Octet Data Analysis software v10.0 (Pall ForteBio), using reference subtraction, baseline alignment, inter-step correction, Savitzky-Golay filtering, and a global 1:1 binding model. Both variants displayed binding with nM affinity to human ACE2-Fc and CR3022 (FIGS. 1C-1F).

Purified proteins were also characterized by mass spectrometry. Specifically, Intact mass analysis was performed on a 6230B time of flight (TOF) LC-MS with a 1220 series HPLC (Agilent Technologies, Santa Clara, CA). Mobile phase A consisted of water with 0.1% formic acid, and mobile phase B was acetonitrile with 0.1% formic acid.

About 20 pmol of each sample was injected, bound to a ZORBAX 300SB C3 column (Agilent Technologies), desalted, and subjected to electrospray ionization. The LC gradient consisted of 20-70% B over 1 minute at a flow rate of 1.5 mL/min. Elution of proteins was monitored using the absorbance signal at 214 nm. 50 μL of isopropanol was injected after each sample to control sample carry-over. The typical electrospray ionization parameters consisted of: 290° C. gas temperature, 4000 V Vcap, 2000 V nozzle, and 275 V fragmentor voltage. Mass spectra were collected from 700-2800 m/z at a scan rate of 1 spectra/sec. MS spectra were processed using MassHunter Qualitative Analysis software (v B.07.00, Agilent Technologies) with deconvolution range of 10-50 kDa, using 1 Da mass step. Analysis revealed that the RBD-N1del protein displayed a typical profile of $Man_{12-14}$N-linked glycans, while the RBD-N1del-N13Q protein had no modifications (data not shown). Aggregation was observed in purified samples of both variants, particularly RBD-N1del (FIGS. 1B & 1G).

Example 2: Identification of Amino Acid Motifs that Drive Aggregation

Figure 1B:
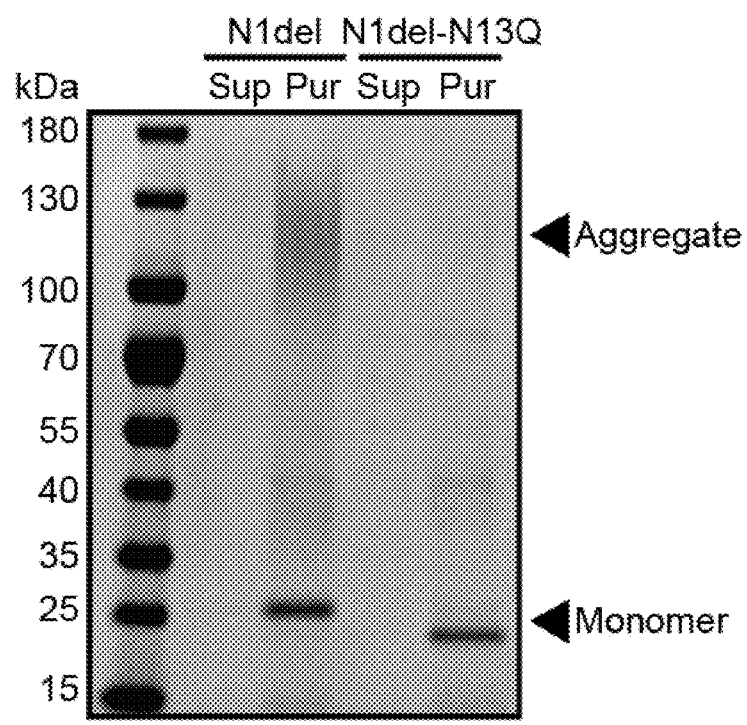
FIG. 1B is a reduced SDS-PAGE of purified SARS-CoV-2 RBD variants having one (RBD-N1del) or both (RBD-N1del-N13Q) glycosylation sites removed from cultures of rich defined media. Sup=cultivation supernatants; Pur=purified protein.
Figure 1G:
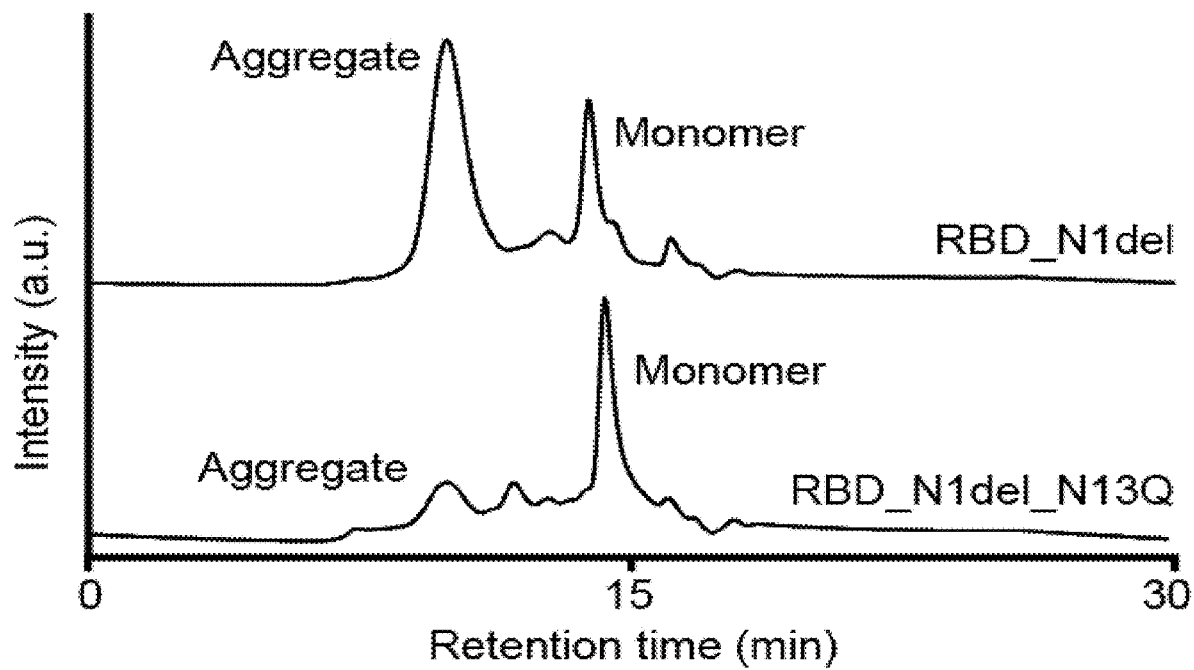
FIG. 1G is a graph showing results of size exclusion chromatography of purified RBD variants RBD-N1del and RBD-N1del-N13Q demonstrating aggregation in variants.

As shown in FIGS. 1B & 1G, aggregation was observed in purified samples of both RBD variants described in Example 1, particularly for RBD-N1del, which is a concern for yield and consistency in a commercial process. Initial expression of RBD-N1del in 3 mL cultures yielded a titer of 12 mg/L. Based on understanding in the art for the manufacture of subunit vaccines in *K. phaffii*, this titer would be insufficient to consistently reach 1 g/L in optimized fed-batch fermentation (Velez-Suberbie, et al (2020) *Biotechnol. Prog.* 36). Thus, the titer would not meet the manufacturing requirements set forth in the target product profile thought to be suitable for a vaccine in LMICs, and of what has been observed for the SARS-CoV-1 RBD when manufactured in *K. phaffii* (Chen, et al (2017) *J Pharm Sci* 106:1961-1970). Specific productivity and titer are key process parameters that impact COGs, thus improvement of secretion of the RBD in yeast is desirable.

Figure 1H:
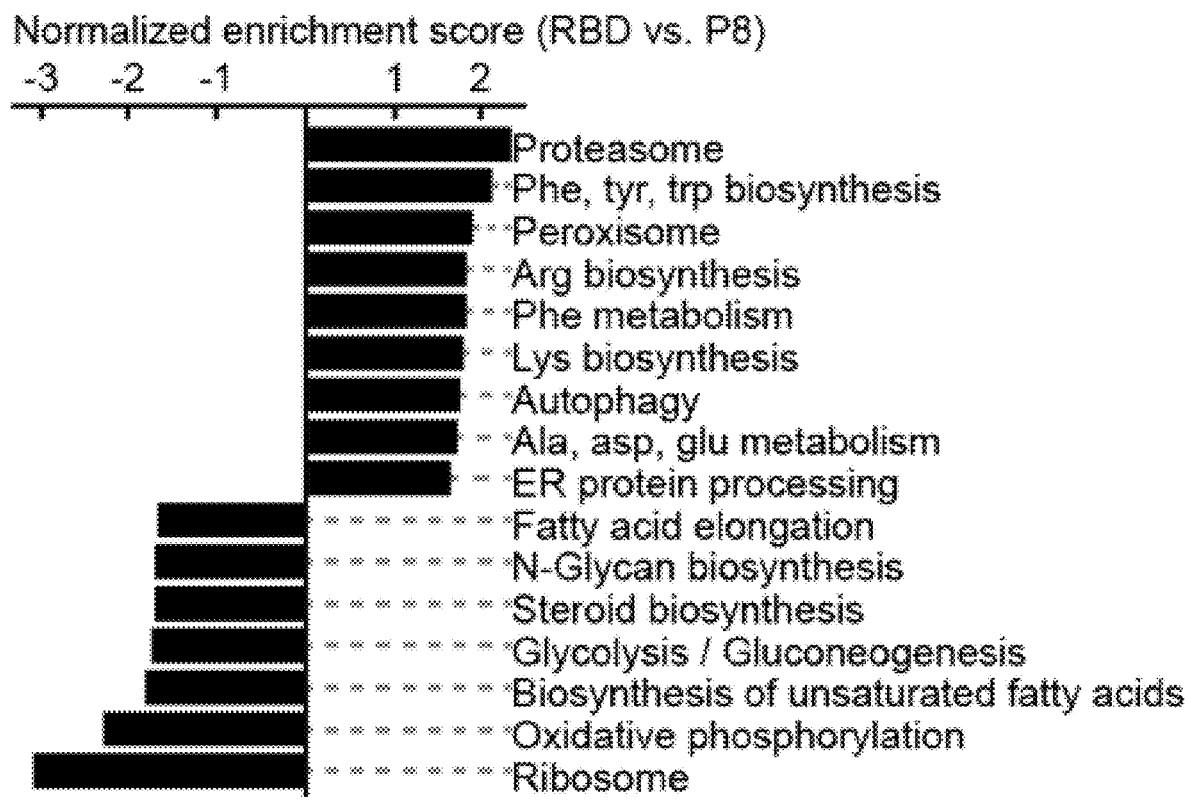
FIG. 1H provides a bar graph showing gene set enrichment analysis between a yeast strain expressing RBD-N1del and a strain expressing a subunit vaccine for a rotavirus VP8 fragment. Gene sets shown have an adjusted p-value<0.05, among all available sets for P. pastoris in the KEGG GENOME database.
Figure 1I:
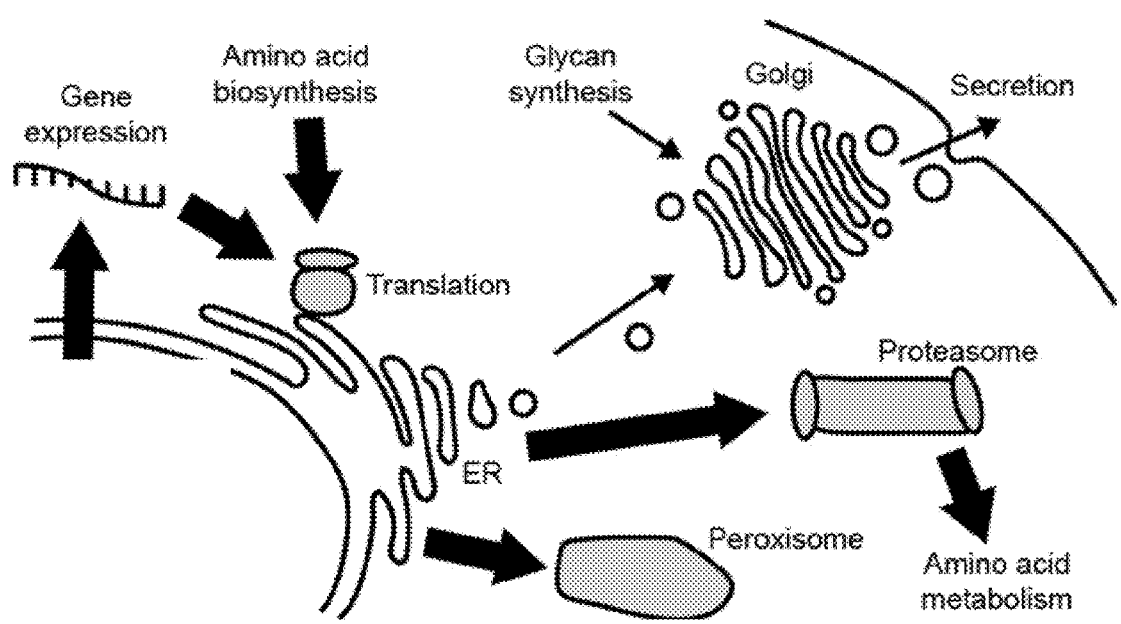
FIG. 1I provides a schematic showing a model of degradation of the RBD in the proteasome and peroxisome suggested by the gene set enrichment analysis in FIG. 1H, with higher flux of recombinant protein based on the analysis corresponding to the width of the arrows.

It was evaluated if the specific productivity of RBD-N1del is inhibited by the intrinsic tendency of this subunit to aggregate. Efficient secretion of recombinant protein requires successful folding and modification of the nascent peptide in the endoplasmic reticulum (ER). Insoluble or misfolded protein inside the host cells could lead to an unfolded protein response and subsequent degradation of the recombinant product. To evaluate if this phenotype might occur in host cells, RNA sequencing on the strain secreting RBD-N1del was performed. Gene sets that were differentially expressed relative to a strain that capably secretes P2-VP4-P[8], a subunit vaccine for rotavirus that is produced with high specific productivity, were determined. Specifically, cells were harvested after 18 h of production at 3 mL plate scale. RNA was extracted and purified according to the Qiagen RNeasy kit (cat #74104) and RNA quality was analyzed to ensure RNA Quality Number >6.5. RNA libraries were prepared using the 3'DGE method and sequenced on an Illumina Nextseq to generate paired reads of 20 (read 1) and 72 bp (read 2). Sequenced mRNA transcripts were demultiplexed using sample barcodes and PCR duplicates were removed by selecting one sequence read per Unique Molecular Identifier (UMI) using a custom python script. Transcripts were quantified with Salmon version 1.1.0[30] and selective alignment using a target consisting of the *K. phaffii* transcripts, the RBD-N1del, P[8] and selectable marker transgene sequences and the *K. Phaffii* genome as a selective alignment decoy. Expression values were summarized with tximport version 1.12.3 (Soneson, et al (2016) F1000Research 4) and edgeR version 3.26.8 (Robinson, et al (2009) *Bioinformactics* 26:139; McCarthy, et al (2012) *Nucleic Acids Res* 40:4288). Expression was visualized using $\log_2$ (Transcripts per Million+1) values. Gene set enrichment analysis (GSEA) was performed in R using the fgsea package using Wald statistics calculated by DESeq2 (Love, et al (2014) *Genome Biol* 15:1-21) and all available KEGG pathways for *K. phaffii* (Subramanian, et al (2005) PNAS 102:15545). Based on this analysis, gene sets related to proteolysis and ER-associated protein degradation were upregulated, suggesting the recombinant RBD is routed from the ER for degradation instead of secretion (FIG. 1H-1I).

Figures 2C, 2D:
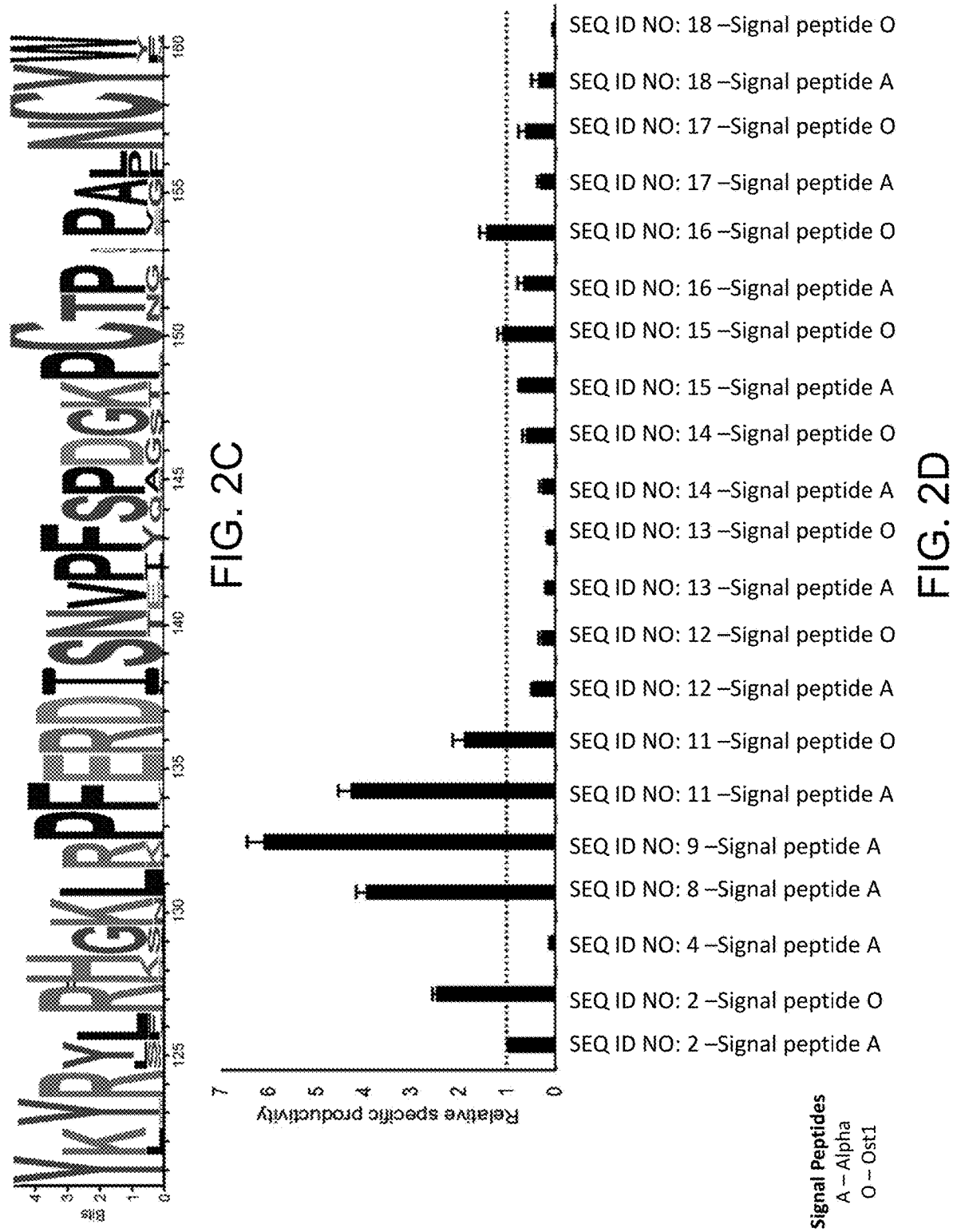

Small, conservative changes to a protein sequence can have dramatic impact on host cell biology and subsequent manufacturing metrics like aggregation and fermentation titer (see, e.g., Pettit, et al. (2016) "CHO cell production and sequence improvement in the 13C6FR1 anti-Ebola antibody." MAbs. Vol. 8. No. 2. Taylor & Francis). Accordingly, molecular engineering of the RBD was performed to assess if the intrinsic propensity of the RBD to aggregate contributed to protein folding stress in the manufacturing cell line. To identify specific amino acid motifs that could drive aggregation, the folded structure of the RBD as predicted by SWISS-Model was inspected for highly hydrophobic patches on the surface of the molecule using BioLuminate® (FIG. 2A). The region that was predicted to have the highest hydrophobicity included amino acids 122-126 and 158-160 in the predicted ACE2 binding motif (Starr, T. N. et al. (2020) *bioRxiv* 2020.06.17.157982). Variants of the RBD were generated (outlined in Table 3) to exhibit less hydrophobicity and propensity for aggregation by replacing hydrophobic residues with residues that are highly conserved across previous SARS coronaviruses that bind ACE2, as shown in FIGS. 2B-2C (Wan, Y. et al., (2020) *J. Virol.* 94, 127-147). Both provide a sequence logo of the ACE2 receptor binding motif using the top 96 non-SARS-CoV-2 homologous sequence found with BLAST (Crooks, et al (2004) *Genome Res* 14:1188) using the protein sequence of the SARS-CoV-2 RBD (SEQ ID NO: 1). The top homologous sequences identified had homology between approximately 73% and 100% with the SARS-CoV-2 RBD reference sequence. FIG. 2C providing an extended sequence logo for the ACE2 receptor binding motif. FIG. 2B additionally provides an alignment for RBD variants in Table 1 having L122K-F160W mutations or L122K-L125Y-F128L-F160W mutations in the ACE2 receptor binding motif.

Lysine residues have been shown to mitigate adjacent sequences that are prone to aggregation, as may be the case for K122. AggScores for individual amino acid residues in RBD-N1del (SEQ ID NO: 2) and RBD-N1del-L122K-F160W (SEQ ID NO: 9) are shown in Table 4. Only residues having a positive AggScore in either SEQ ID NO: 2, SEQ ID NO: 9, or both are included in Table 4. AggScores were determined based on the amino acid and its properties, the solvent exposed surface of the amino acid and the spatially close amino acids. As shown in Table 4, the L122K and F160W amino acid substitutions significantly reduced the hydrophobicity within regions 122-126 and 158-160. Additionally, the overall aggregation score was determined for SEQ ID NO: 2 and SEQ ID NO: 9 by obtaining the sum of the AggScores for each residue in the polypeptide. As shown in Table 4, SEQ ID NO: 9 had an overall aggregation score of 158.4, which is 20% decrease relative to the overall aggregation score of SEQ ID NO: 2 (score of 199.6).

TABLE 3

RBD Variants

| SEQ ID NO | Mutations |
|---|---|
| 1 | RBD (Native SARS-CoV-2 Sequence) |
| 2 | RBD-N1del |
| 3 | RBD-N13Q |
| 4 | RBD-N1del -N13Q |
| 6 | RBD-N1del -L38A -L122K -L125Y -F126L -F160W- L187A- L188A |
| 7 | RBD-N1del- L38A -L122K- F160W- L187A- L188A |
| 8 | RBD-N1del- L122K- L125Y -F160W- F126L |
| 9 | RBD-N1del -L122K- F160W |
| 10 | RBD-N1del -L38A- L187A- L188A |
| 11 | RBD-N1del- L122K |
| 12 | RBD-N1del- L38M |
| 13 | RBD-N1del -L38M- L188M |
| 14 | RBD-N1del- L38M- L122K- L188M |
| 15 | RBD-N1del -Y159R |
| 16 | RBD-N1del- F160M |
| 17 | RBD-N1del -Y159R- F160M |
| 18 | RBD-N1del -L38M -L122K -Y159R -F160M- L188M |

TABLE 4

AggScores of Individual Residues and Full-length Polypeptide

| Residue Number of SEQ ID NO: 1 | Residue Number Corresponding to Full Spike Protein (SEQ ID NO: 59) | AggScore in SEQ ID NO: 2 | AggScore in SEQ ID NO: 9 |
|---|---|---|---|
| 21 | 351 | 1.571 | 0.853 |
| 22 | 352 | 2.01 | 1.384 |
| 23 | 353 | 0 | 0.885 |
| 32 | 362 | 0.353 | 0 |
| 36 | 366 | 4.415 | 4.695 |
| 37 | 367 | 7.969 | 8.359 |
| 38 | 368 | 8.117 | 7.833 |
| 39 | 369 | 2.371 | 0.914 |
| 46 | 376 | 0 | 0.225 |
| 50 | 380 | 3.479 | 2.875 |
| 51 | 381 | 3.679 | 2.984 |
| 52 | 382 | 1.375 | 0.175 |
| 54 | 384 | 2.591 | 1.513 |
| 60 | 390 | 0.289 | 2.262 |
| 61 | 391 | 9.307 | 9.891 |
| 62 | 392 | 6.533 | 5.731 |
| 63 | 393 | 0 | 1.845 |
| 64 | 394 | 0.174 | 0 |
| 102 | 432 | 0.594 | 2.879 |
| 103 | 433 | 0 | 3.111 |
| 104 | 434 | 1.834 | 3.203 |
| 106 | 436 | 0 | 0 |
| 107 | 437 | 0.9 | 1.122 |
| 116 | 446 | 3.145 | 0 |
| 122* | 452 | 6.054 | 0 |
| 123 | 453 | 6.682 | 0 |
| 124 | 454 | 8.26 | 3.628 |
| 125 | 455 | 10.07 | 8.149 |
| 126 | 456 | 8.99 | 8.084 |
| 134 | 464 | 1.289 | 0.879 |
| 138 | 468 | 2.128 | 0 |
| 139 | 469 | 0.53 | 0 |
| 143 | 473 | 0.045 | 0 |
| 157 | 487 | 0.826 | 1.199 |
| 158 | 488 | 6.76 | 0 |
| 159 | 489 | 12.431 | 12.754 |
| 160* | 490 | 12.837 | 13.179 |
| 162 | 492 | 1.715 | 0 |
| 174 | 504 | 4.278 | 2.447 |
| 175 | 505 | 6.33 | 4.128 |
| 176 | 506 | 5.263 | 3.636 |
| 183 | 513 | 0.187 | 0.265 |
| 186 | 516 | 2.952 | 0 |
| 187 | 517 | 8.212 | 4.203 |
| 188 | 518 | 10.957 | 10.356 |
| 189 | 519 | 8.366 | 8.426 |
| 190 | 520 | 5.703 | 5.429 |
| 191 | 521 | 4.33 | 4.359 |
| 192 | 522 | 2.545 | 2.815 |
| 193 | 523 | 0 | 0.721 |
| Overall Aggregation Score of full-length polypeptide | | 199.6 | 158.4 |

*= amino acid substitution

Figure 2E:
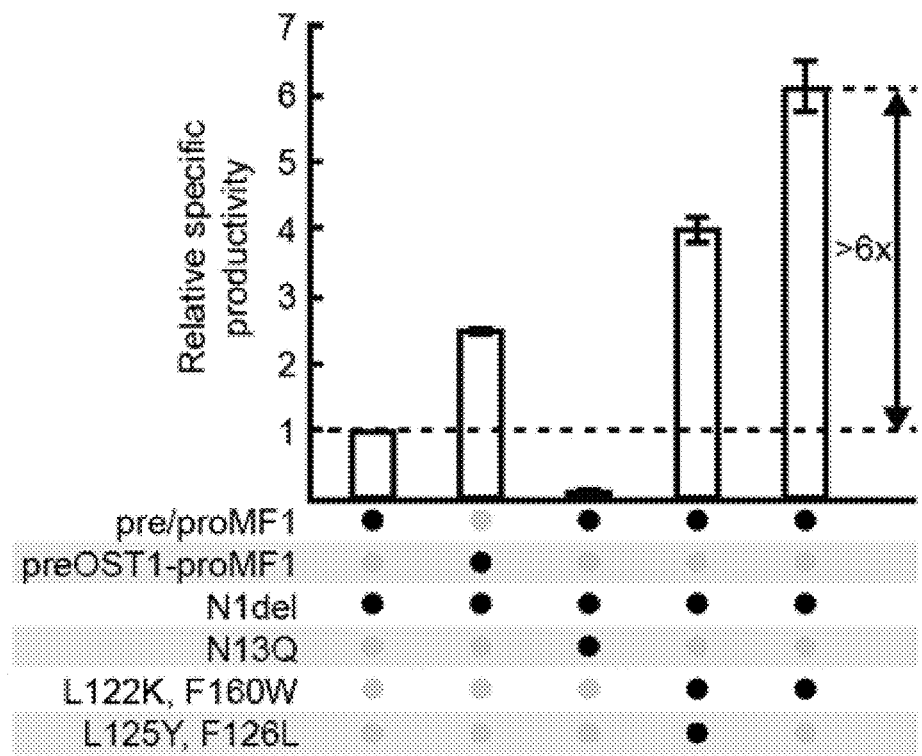
FIG. 2E is a graph showing specific productivity of RBD variants. Titers were measured by reverse phase liquid chromatography, and normalized by cell density, measured by OD600. Reported values are relative to expression of RBD-N1del.
Figure 2F:
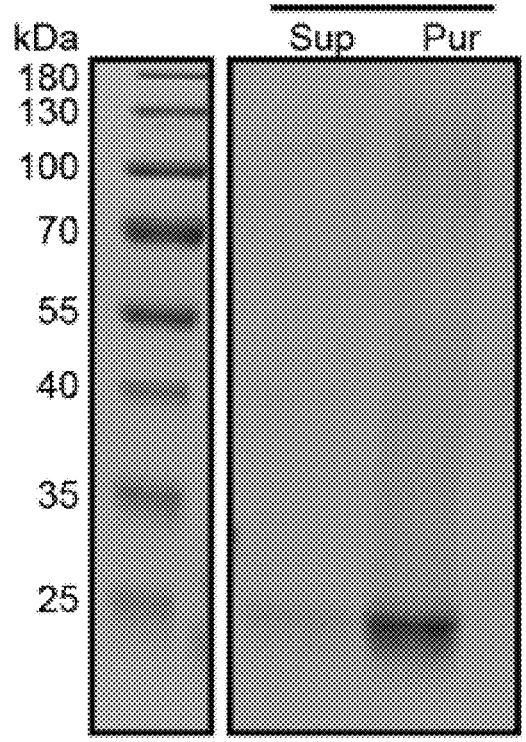
FIG. 2F provides a reduced SDS-PAGE of purified RBD variant RBD-N1del-L122K-F160W derived from 200 mL culture with complex media. Sup=cultivation supernatants; Pur=purified protein.
Figure 2G:
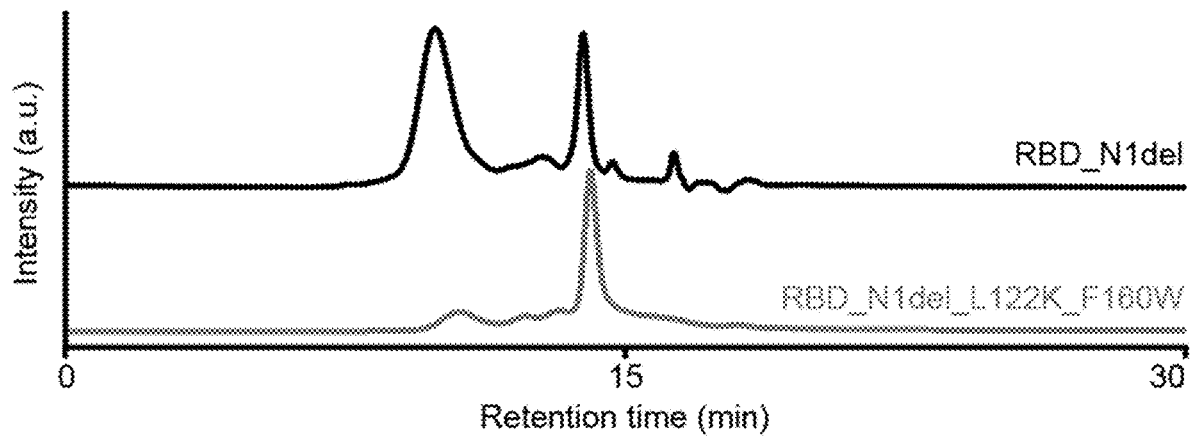
FIG. 2G provides size exclusion chromatographs of purified RBD-N1del and RBD-N1del-L122K-F160W.

The variants from Table 1 were measured for their specific productivity. Specifically, RBD variants were expressed in *K. phaffii* using two different signal peptides: alpha factor (A) and Ost1 (O). Results are shown in FIG. 2D, which indicate the highest producing variants had higher productivity with the A signal peptide. The RBD variants which demonstrated the highest relative specific productivity were further tested for expression in *K. phaffii* and demonstrated a several fold increase in specific productivity in the base strain (FIG. 2E). The RBD-N1del-L122K-F160W-L125Y-F126L variant (SEQ ID NO: 8) demonstrated an increase in specific productivity compared to native RBD (SEQ ID NO:1). However, as the RBD-N1del-L122K-F160W variant (SEQ ID NO: 9) exhibited the highest increase in specific productivity with only two mutated residues, reaching a titer in 3 mL plate cultivations that is predicted to scale to >1 g/L in fed-batch. Material was generated at 200 mL batch scale and the same purification method developed for RBD-N1del (Example 1) was successfully used for purification. Subsequent analysis by SDS-PAGE and size exclusion chromatography indicated that the purified RBD-N1del-L122K-F160W has less aggregation than the original RBD-N1del protein (FIGS. 2F-2G). Accordingly, this variant was selected for further characterization.

Figure 2H:
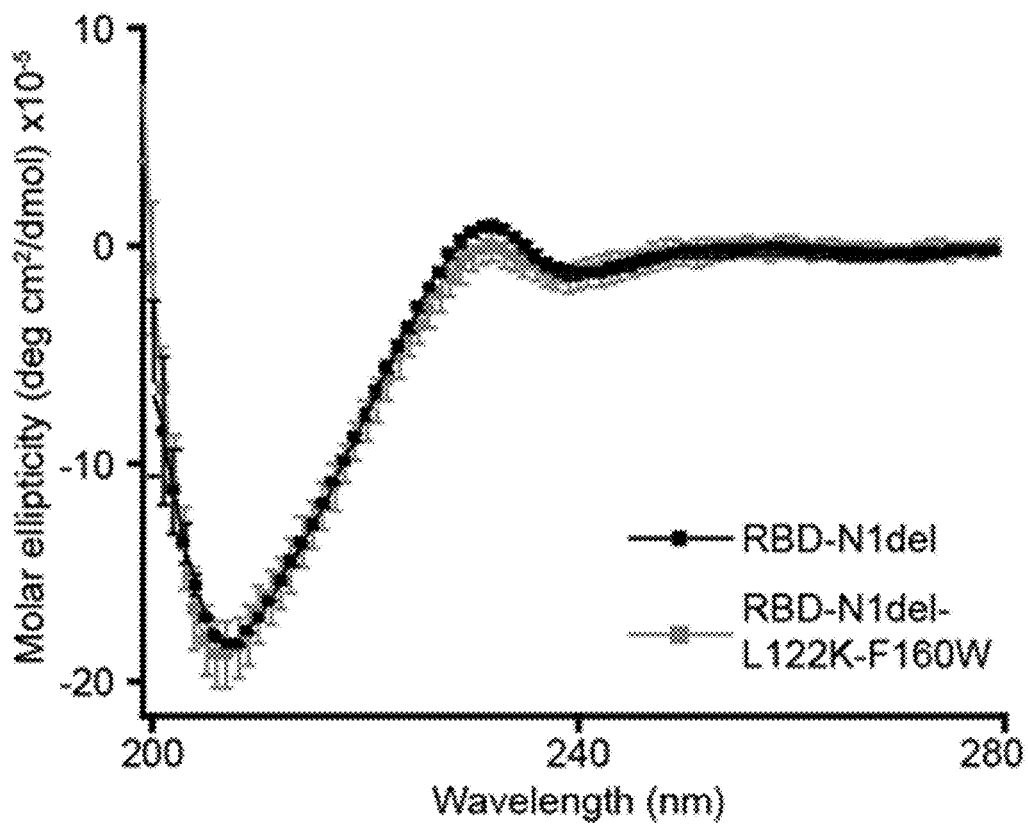
FIG. 2H provides a comparison of protein secondary structure for purified RBD-N1del and RBD-N1del-L122K-F160W as measured by far-UV circular dichroism.

Characterization by far-UV circular dichroism suggests that the secondary structure of RBD-N1del-L122K-F160W is similar to RBD-N1del (FIG. 2H). CD spectroscopy was carried out using a Chirascan-plus CD spectrometer (Applied Photophysics Ltd., Leatherhead, UK) equipped with a 6-cuvette position Peltier temperature controller (Quantum Northwest, Liberty Lake, WA) and a high-performance solid-state detector. The lamp (150 W air-cooled Xe arc) housing, monochromator and sample compartment were continuously purged with N2 gas. The 10° C. CD spectra of RBD samples at 0.2 mg/mL were collected in triplicate in the range of 280-200 nm using quartz cuvettes (1 mm path length) sealed with a Teflon stopper (Starna Cells Inc., Atascadero, CA). Data were subjected to a 3-point Savitzky-Golay smoothing filter using the Chirascan software (Applied Photophysics) and buffer reading was subtracted from all sample measurements.

Figure 2I:
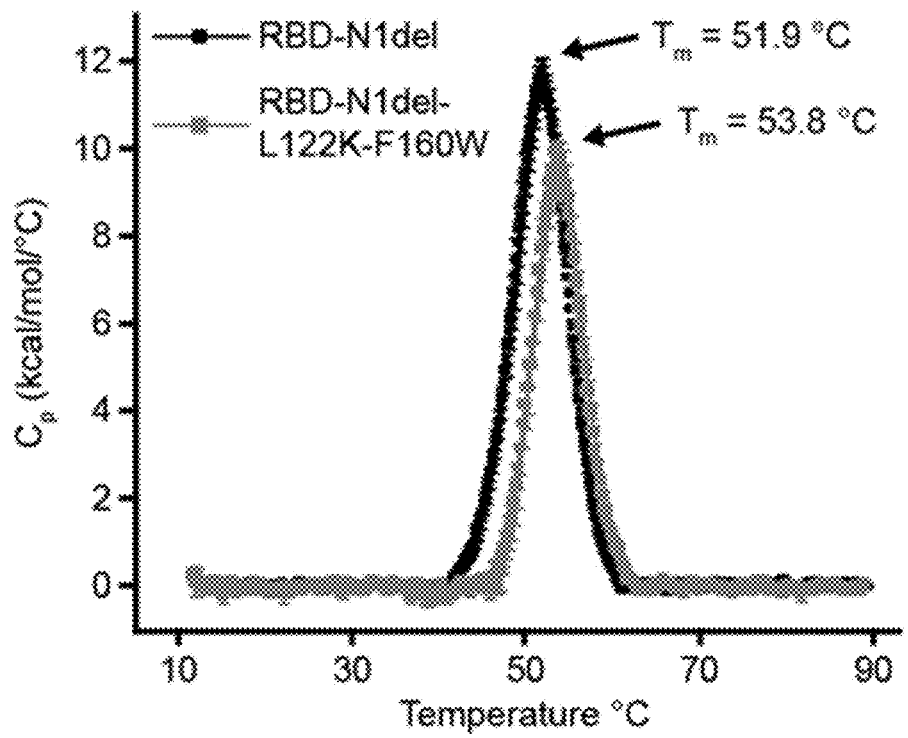
FIG. 2I is a graph showing differential scanning calorimetry demonstrating increased thermostability of RBD-N1del-L122K-F160W compared to RBD-N1del.

Characterization of the purified RBD-N1del-L122K-F160W by differential scanning calorimetry revealed a higher melting temperature than RBD-N1del, indicating that the engineered molecule may be more thermostable (FIG. 2I). DSC was performed in triplicate using an auto-VP capillary differential scanning calorimeter (MicroCal/GE Health Sciences, Pittsburgh, PA) equipped with Tantalum sample and reference cells. RBD samples at 0.2 mg/mL were loaded in the autosampler tray held at 4° C. and scans were completed from 10° C. to 90° C. using a scanning rate of 60° C./h. Buffer subtraction and concentration normalization were performed using Origin (OriginLab, Northampton, MA). Data analysis was performed using the MicroCal LLC DSC plug-in for the Origin 7.0 software package.

Figure 2J:
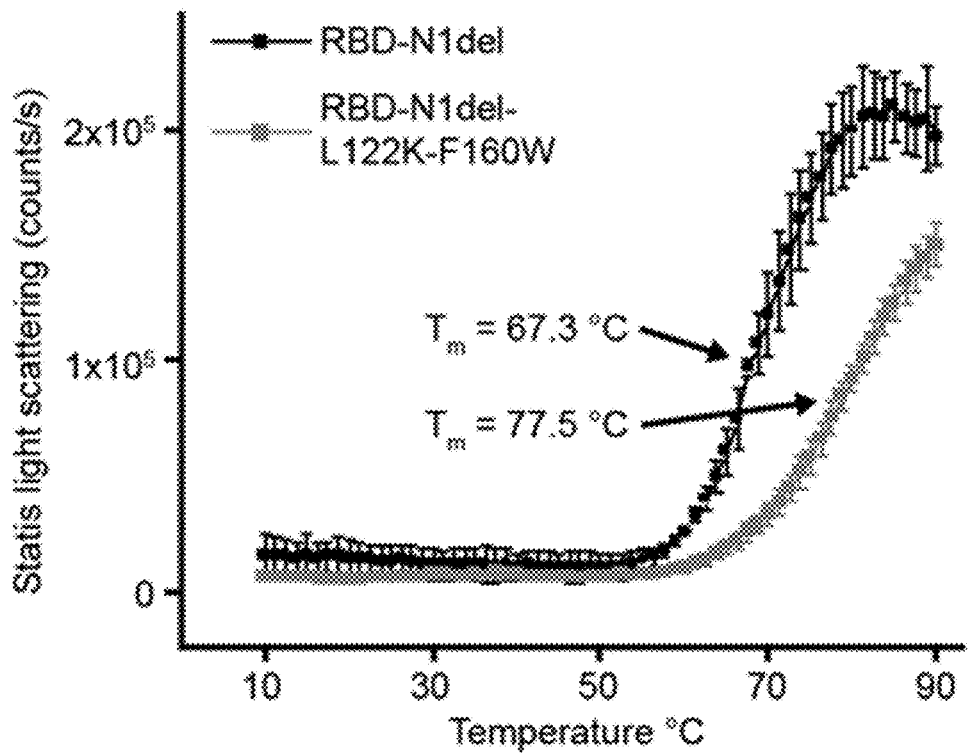
FIG. 2J is a graph showing static light scattering demonstrating reduced aggregation of RBD-N1del-L122K-F160W compared to RBD-N1del.

Static light scattering revealed that the RBD-N1del-L122K-F160W aggregated nearly 10° C. higher than RBD-N1del, confirming that the mutations reduced the tendency of the molecule to aggregate (FIG. 2J). To do so, the intrinsic tryptophan fluorescence spectra were measured in triplicate using a dual emission PTI QM-40 Spectrofluorometer (Photon Technology International, Inc., Birmingham, NJ) equipped with a 4-position cell holder Peltier temperature control device, a high-power continuous 75 W short-arc Xe lamp (Ushio), and a Hamamatsu R1527 photomultiplier tube. Data were collected using FelixGX software (Photon Technology International, Inc.) in 10 mm path length quartz cuvettes. Fluorescence emission spectra of 0.2 mg/mL protein samples were collected as a function of temperature (10° C.-90° C.) using an excitation wavelength of 295 nm. Emission spectra were collected from 305 nm to 405 nm with a step size of 1 nm and an integration time of 1 s. Static light scattering data were acquired concurrently with the fluorescence spectra by using a second detector (90° to the incident light and 180° to the fluorescence detector) that collected light scattered signal at the excitation wavelength as a function of increasing temperature. The spectra were collected at 1.25° C. intervals with a 2 min equilibration time at each temperature. The position of the emission wavelength maximum was determined using a mean spectral center of mass method executed using in-house software (MiddaughSuite) following buffer subtraction. The analysis algorithm increases net signal-to-noise ratio, but the peak positions are generally red shifted by 5-10 nm from their experimental positions. Based on the analysis, the intrinsic stability conferred by these mutations may be responsible for the increased specific productivity and product quality observed for RBD-N1del-L122K-F160W.

While the L122K and F160W mutations improved the manufacturability of the RBD, these changes to the ACE2 binding pocket risked altering the immunogenicity and antigenicity of the molecule. The ACE2 binding motif serves as an epitope for several known neutralizing antibodies, many of which bind near RBD-L122 (Brouwer, P. J. et al., (2020) bioRxiv 2020.05.12.088716).

Example 3: RBD Variants Demonstrate Higher Binding Affinity and Immunogenicity

Figure 3A:
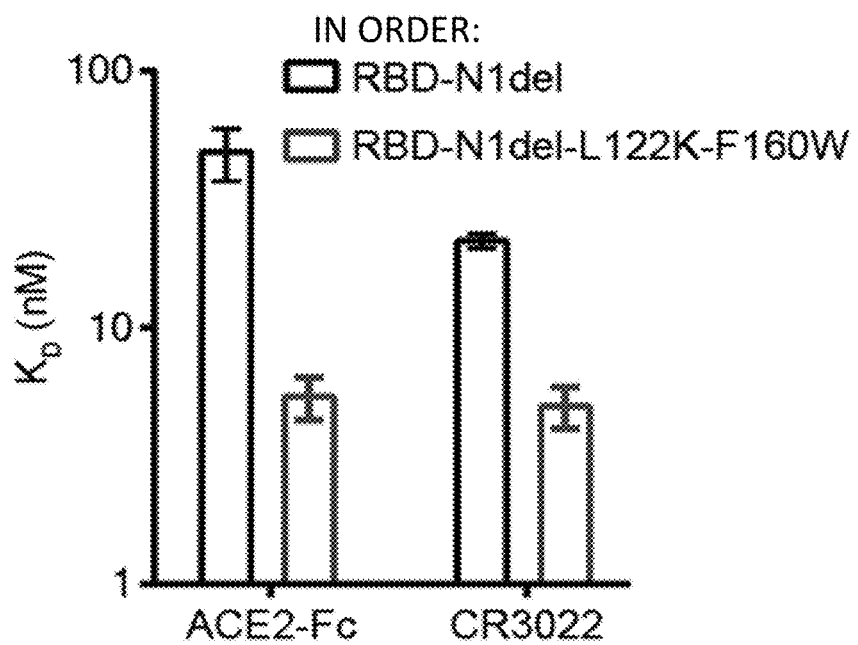
FIG. 3A is a graph showing binding of RBD-N1del and RBD-N1del-L22K-F160W to human ACE2-IgG fusion protein and CR3022 neutralizing antibody determined by biolayer inferometry.

To confirm the overall structure and ACE2 binding had not been disrupted, the binding of each RBD variant to human ACE2-Fc and CR3022 antibody was evaluated. Surprisingly, the RBD-N1del-L122K-F160W exhibited higher binding affinity to both molecules (FIG. 3A). Based on the observation that RBD-N1del-L122K-F160W as a lower tendency to aggregate than RBD-N1del (FIG. 2G), it is thought this contributes to higher bioactivity and antigenicity.

The immunogenicity and antigenicity of both the RBD-N1del and RBD-N1del-L122K-F160W was evaluated in mice by subcutaneous injection of 5 µg of RBD-N1del or RBD-N1del-L122K-F160W at day 0 and day 21 and monitoring of neutralizing antibody responses. Specifically, age-matched 6-8 week old Balb/cJ female mice (The Jackson Laboratory) were immunized on day 0 and day 21 with 5 µg RBD plus adjuvant: 50 µg alum Alhydrogel (Invivogen), 30 µg CpG1826 (Invivogen), or 5 µg saponin MPLA nanoparticles (SMNP) synthesized in-house (see Irvine, et al (2015) CHEM REV 115:11109-11146). Immunizations were administered via subcutaneous injection in 100 ul PBS at the tail base (2×50 ul injections, one on each side of the tail base). Blood was collected by cheek or retro-orbital bleed for ELISA antibody analysis on wk 2, 3, 4, and then every 2 weeks thereafter. Serum was isolated from blood using serum separator tubes, centrifuged at 10,000×g for 5 min at 4 C, then stored at −80 C. Anti-RBD IgG was measured in mouse serum by ELISA. To capture serum antibodies from mice immunized with histagged antigen, Nunc Immuno MaxiSorp 96-well plates (Thermo Scientific) were coated with rabbit anti-histag antibody (Genscript) at 1 ug/ml in PBS for 4 hr at 25 C, blocked with PBS+2% BSA overnight at 4 C, then incubated with histagged-RBD at 2 ug/ml in block buffer for 2 hr at 25 C. To capture serum antibodies from mice immunized with non-histagged antigen, Costar Polystyrene High Binding 96-well plates (Corning) were coated directly with RBD antigen at 2 ug/ml in PBS overnight at 4 C, then blocked with PBS+2% BSA for 2 hr at 25 C. Mouse sera were diluted in block buffer starting at 1:100 followed by 4× serial dilutions and incubated in plates for 2 hr at 25 C, followed by detection with 1:5000 goat anti-mouse IgG-HRP (BioRad) in block buffer for 1 hr. Plates were developed using TMB substrate for 1-20 min and stopped with 2N sulfuric acid. For all titer analyses, samples directly compared across groups were developed for the same amount of time. Cut-off titers are reported as inverse dilutions giving a 0.2 HRP absorbance (A450-A540).

Figure 3B:
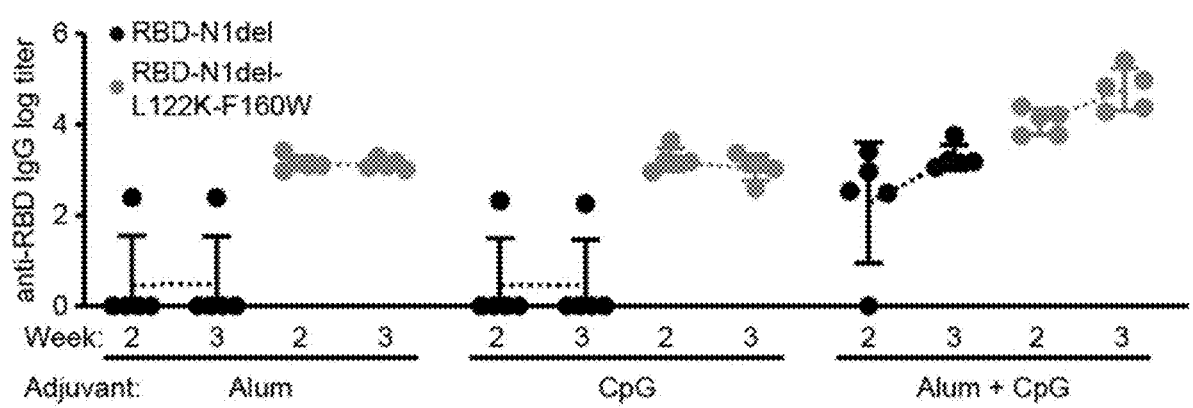
FIG. 3B is a graph showing anti-RBD IgG titer in sera from mice inoculated with RBD variant and adjuvant at 0 and 21 days as measured by ELISA, where the RBD variant was RBD-N1del or RBD-N1del-L122K-F160W and the adjuvant was alum, CpG, or a combination of alum and CpG.

Mice administered the RBD variants with alum, CpG, or both adjuvants in combination were compared for IgG responses. Sera from all groups of mice exhibited high titers of IgG antibodies that bound the administered antigen when analyzed by ELISA (FIG. 3B). Mice that received RBD-N1del-L122K-F160W exhibited 100% seroconversion after a single dose with either alum or CpG adjuvants, and an exceedingly strong response with both adjuvants in combination.

Figure 3C:
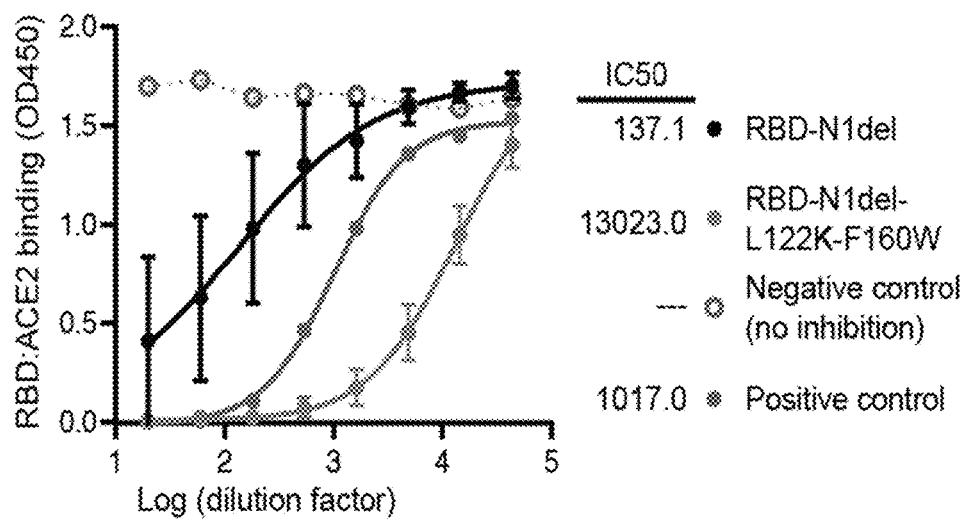
FIG. 3C is a graph showing blocking of SARS-CoV-2 RBD binding to hACE2 by day 42 sera obtained from mice vaccinated on day 0 and 21 with RBD-N1del or RBD-N1del-L122K-F160W and saponin MPLA nanoparticles (SMNP) as determined by a plate-based assay.

The activity of serum from vaccinated mice was evaluated for blocking SARS-Cov-2 RBD binding to ACE2. Specifically, serum were obtained on day 42 from mice that were inoculated on day 0 and 21 with RBD-N1del or RBD-N1del-L122K-F160W and SMNP at doses described above. The serum was evaluated using a plate-based assay for detection of antibodies that block the interaction of the SARS-CoV-2 RBD with ACE2 (see, e.g., Abe, et al (2020) JCI Insight 5:e142362). The sera from both the RBD-N1del and RBD-N1del-L122K-F160W vaccinated mice obstructed binding of the RBD to human ACE2 (FIG. 3C). Interestingly, sera from RBD-N1del-L122K-F160W exhibited 2 orders of magnitude higher blocking of ACE2 binding.

The neutralizing activity of the antibodies raised against RBD-N1del and RBD-N1del-L122K-F160W was evaluated with a luciferase-based lentivirus assay using pseudovirus displaying the wild type SARS-Cov-2 spike protein. Serum were obtained on day 21 and 42 from mice that were inoculated on day 0 and 21 with RBD-N1del or RBD-N1del-L122K-F160W and SMNP at doses described above. The SARS-CoV-2 pseudoviruses expressing a luciferase reporter gene were generated in an approach similar to as described previously (Yang, et al (2004) Nature 428:561; Yu, et al (2020) Science 369:806; Chandrashekar, et al (2020) Science 369:812). Briefly, the packaging plasmid psPAX2 (AIDS Resource and Reagent Program), luciferase reporter plasmid pLenti-CMV Puro-Luc (Addgene), and spike protein expressing pcDNA3.1-SARS CoV-2 SACT were co-transfected into HEK293T cells by lipofectamine 2000

Figures 3D, 3E:
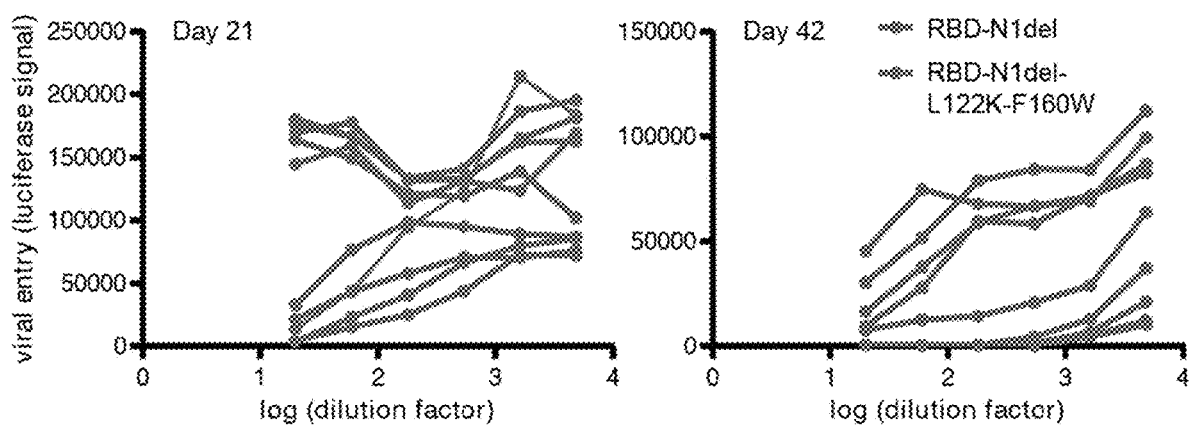
FIGS. 3D-3E is a graph showing neutralization dilutions for individual animals treated with RBD-N1del or RBD-N1del-L122K-F160W using a luciferase-based lentivirus assay. Mice were vaccinated at day 0 and 21 with RBD-N1del or RBD-N1del-L122K-F160W and SMNP. Serum was collected at day 21 (FIG. 3D) and day 42 (FIG. 3E) and dilution were evaluated for inhibiting viral entry of pseudovirus expressing SARS-CoV-2 S glycoprotein into ACE2-expressing cells.
Figure 3F:
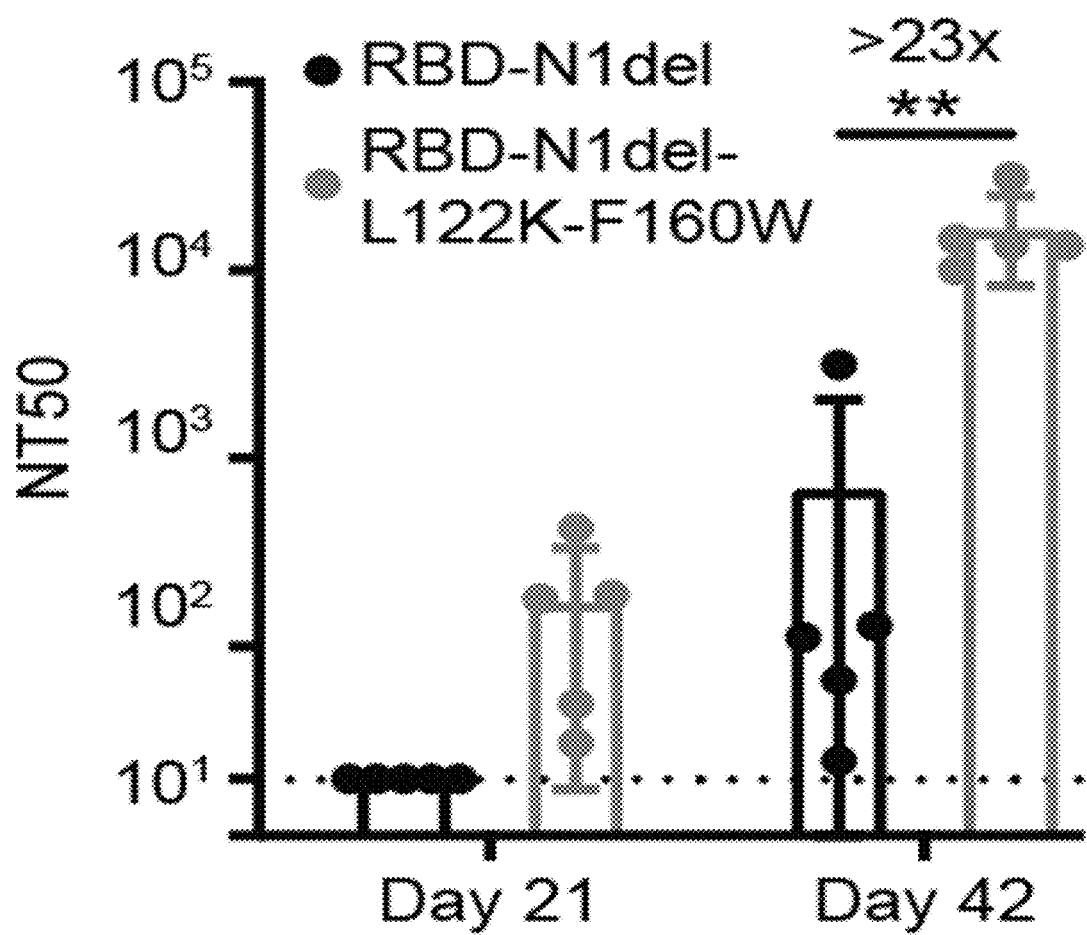
FIG. 3F is a graph showing quantification of pseudovirus neutralizing titer of sera based on dilutions curves shown in FIGS. 3D-3E.

(ThermoFisher). The supernatants containing the pseudotype viruses were collected 48 h post-transfection, which were purified by centrifugation and filtration with 0.45 μm filter. To determine the neutralization activity of the plasma or serum samples from animals, HEK293T-hACE2 cells were seeded in 96-well tissue culture plates at a density of 1.75×10^4 cells/well overnight. Three-fold serial dilutions of heat inactivated plasma samples were prepared and mixed with 50 μL of pseudovirus. The mixture was incubated at 37° C. for 1 hour before adding to HEK293T-hACE2 cells. 48 hours after infection, cells were lysed in Steady-Glo Luciferase Assay (Promega) according to the manufacturer's instructions. SARS-CoV-2 neutralization titers were defined as the sample dilution at which a 50% reduction in relative light unit (RLU) was observed relative to the average of the virus control wells. Neutralization dilutions for individual animals were evaluated with sera obtained from vaccinated animals on day 21 (FIG. 3D) and day 42 (FIG. 3E). Only the RBD-N1del-L122K-F160W antigen raised a complete and overwhelming neutralizing response, including signs of neutralization after a single dose (FIG. 3F). These assays indicate that the L122K and F160W mutations dramatically improve the immunogenicity of the soluble RBD, while maintaining antigenicity and neutralizing activity against SARS-Cov-2 spike protein.

Example 4: Analysis of Local Disorder of RBD Variants with Mutations in the ACE2 Receptor Binding Motif The effect of substitution of one or more amino acids on local disorder of the RBD was determined. The RBD variants evaluated in the analysis and corresponding substitutions are shown in Table 5, including the residue number of the substitution in the full-length S protein.

TABLE 5

RBD Variants Analyzed for Local Disorder

| RBD Construct | SEQ ID NO | SARS-CoV-2 RBD Construct* |
|---|---|---|
| RBD-N1del | 2 | N331del |
| RBD-N1del-L122K-L125Y-F126L-F160W | 8 | N331del-L452K-L455Y-F456L-F490W |
| RBD-N1del-L122K-F160W | 9 | N331del-L452K-F490W |
| RBD-N1del-L122K | 11 | N331del-L452K |

TABLE 5-continued

RBD Variants Analyzed for Local Disorder

| RBD Construct | SEQ ID NO | SARS-CoV-2 RBD Construct* |
|---|---|---|
| RBD-N1del-V37F-L122K | 28 | N331del-V367F-L452K |
| RBD-N1del-L122K-L188D | 32 | N331del-L452K-L518D |

*Corresponding mutations in the RBD of the full-length SARS-CoV-2 glycoprotein (SEQ ID NO: 59)

Briefly, the disorder probabilities and plots were obtained using the PrDOS server (Ishida, et al (2007) *Nucleic acids research*, 35 (suppl_2), pp. W460-W464), set to a 5% false probability prediction rate with template-based prediction enabled. Data visualization was performed using R (R Core Team (2019). R: A language and environment for statistical computing. R Foundation for Statistical Computing, Vienna, Austria. URL https://www.R-project.org/) in conjunction with software packages ggplot2 (Wickham H (2016). ggplot2: Elegant Graphics for Data Analysis. Springer-Verlag New York. ISBN 978-3-319-24277-4), tidyr (Hadley Wickham and Lionel Henry (2020). tidyr: Tidy Messy Data. R package version 1.0.2. https://CRAN.R-project.org/package=tidyr), dplyr (Hadley Wickham, Romain François, Lionel Henry and Kirill Müller (2018). dplyr: A Grammar of Data Manipulation. R package version 0.7.6. https://CRAN.R-project.org/package=dplyr), and ggsci (Nan Xiao (2018). ggsci: Scientific Journal and Sci-Fi Themed Color Palettes for 'ggplot2'. R package version 2.9. https://CRAN.R-project.org/package=ggsci).

Figure 4:
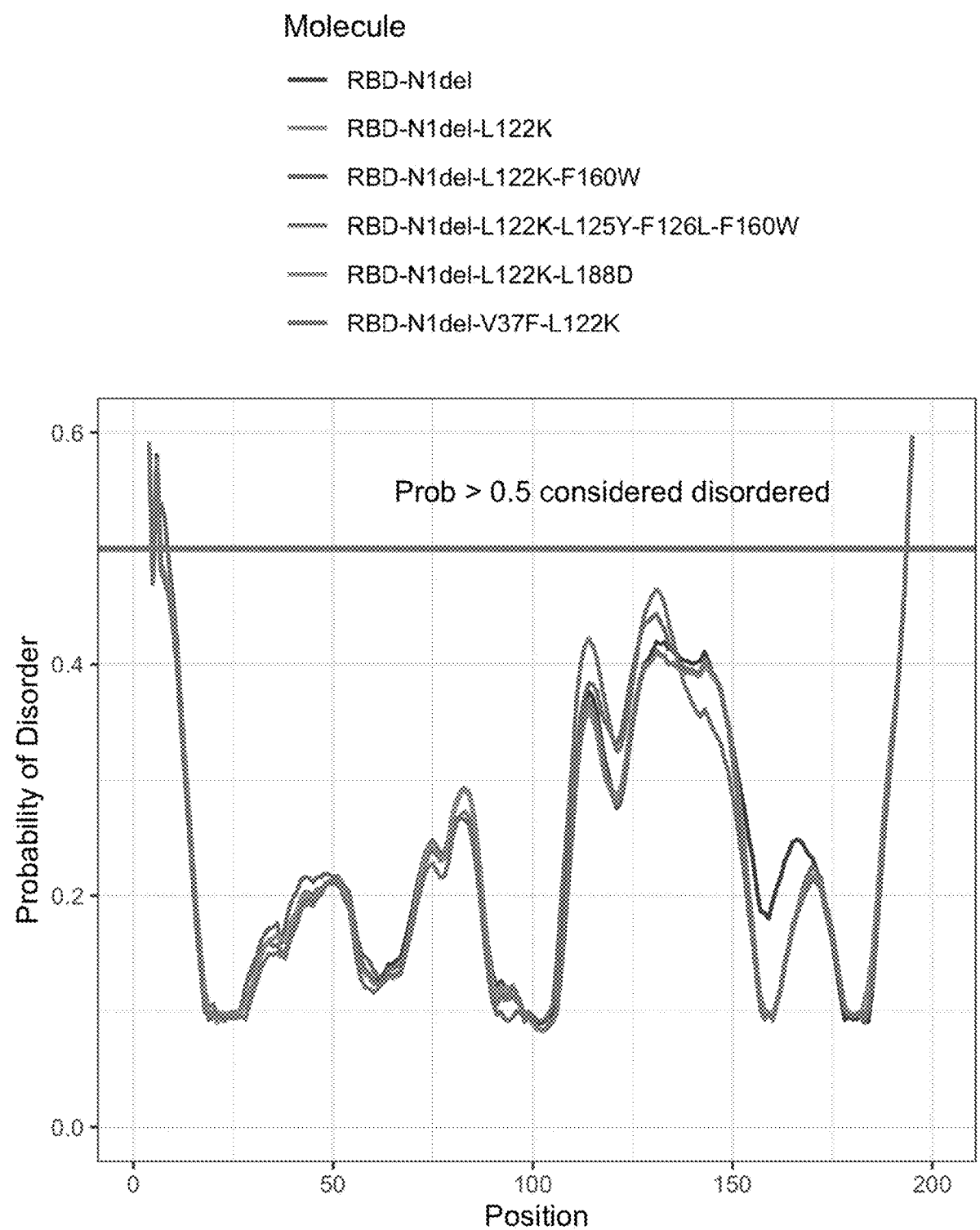
FIG. 4 is a graph quantifying the probability of local disorder for RBD variants listed and further provided in Table 5. Regions of the RBD polypeptide with a probability greater than 0.5 are considered to be disordered.

As shown in FIG. 4, the probability of disorder is provided per each amino acid residue position of the RBD variants evaluated, with a probability greater than 0.5 indicating local disorder (e.g., lacking in defined or rigid secondary structure). Based on the analysis, the N-terminus of each RBD variant is predicted to be disordered. The disorder at the N-terminus is expected given the RBD variants are a segment of the mid-domain of the full-length spike protein (i.e., corresponding to amino acid residues 331-552 of the full-length spike protein). Additionally, the RBD-N1del variant having the amino acid substitutions L122K and F160W (SEQ ID NO: 9) had altered local disorder within the ACE-2 RBM relative to the RBD variant without these substitutions (i.e., RBD-N1del; SEQ ID NO: 2). Specifically, the local disorder surrounding amino acid residue 122 was increased in RBD-N1del-L122K-F160W relative to RBD-N1del. This change in local disorder proximal to the ACE2 RBM are thought to contribute to the increased immunogenicity of this variant, as well as increased binding affinity of the variant.

SEQUENCE LISTING

| SEQ ID NO | Description | Sequence |
|---|---|---|
| 1 | RBD-A (Native SARS-CoV-2 Sequence) | NITNLCPFGEVFNATRFASVYAWNRKRISNCVADYSVLYNSASFSTFKC YGVSPTKLNDLCFTNVYADSFVIRGDEVRQIAPGQTGKIADYNYKLPDD FTGCVIAWNSNNLDSKVGGNYNYLYRLFRKSNLKPFERDISTEIYQAGS TPCNGVEGFNCYFPLQSYGFQPTNGVGYQPYRVVVLSFELLHAPATVCG PKKSTN |
| 2 | RBD-B N1del (Native Sequence minus N1) | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGST PCNGVEGFNCYFPLQSYGFQPTNGVGYQPYRVVVLSFELLHAPATVCGP KKSTN |
| 3 | RBD-C N13Q | NITNLCPFGEVFQATRFASVYAWNRKRISNCVADYSVLYNSASFSTFKC YGVSPTKLNDLCFTNVYADSFVIRGDEVRQIAPGQTGKIADYNYKLPDD FTGCVIAWNSNNLDSKVGGNYNYLYRLFRKSNLKPFERDISTEIYQAGS |

| SEQ ID NO | Description | Sequence |
|---|---|---|
| | | TPCNGVEGFNCYFPLQSYGFQPTNGVGYQPYRVVVLSFELLHAPATVCG PKKSTN |
| 4 | RBD-D N1del N13Q | ITNLCPFGEVFQATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGST PCNGVEGFNCYFPLQSYGFQPTNGVGYQPYRVVVLSFELLHAPATVCGP KKSTN |
| 5 | RBD-E N1del 230 Histag | ITNLCPFGEVFNATKFPSVYAWERKKISNCVADYSVLYNSTFFSTFKCY GVSATKLNDLCFSNVYADSFVVKGDDVRQIAPGQTGVIADYNYKLPDDF MGCVLAWNTRNIDATSTGNYNYKYRYLRHGKLRPFERDISNVPFSPDGK PCTPPALNCYWPLNDYGFYTTTGIGYQPYRVVVLSFELLNAPATVCGPK LSTDLIKNQCVNFNFNGLTGTGGSLEVLFQGPGSHHHHHHHHHH |
| 6 | RBD-G N1del L38A L122K L125Y F126L F160W L187A L188A | ITNLCPFGEVFNATRFASVYAWNRKRISNCVADYSVAYNSASFSTFKCY GVSPTKLNDLCFTNVYADSFVIRGDEVRQIAPGQTGKIADYNYKLPDDF TGCVIAWNSNNLDSKVGGNYNYKYRYLRKSNLKPFERDISTEIYQAGST PCNGVEGFNCYWPLQSYGFQPTNGVGYQPYRVVVLSFEAAHAPATVCGP KKSTN |
| 7 | RBD-H N1del L38A L122K F160W L187A L188A | ITNLCPFGEVFNATRFASVYAWNRKRISNCVADYSVAYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYWPLQSYGFQPTNGVGYQPYRVVVLSFEAAHAPATVCGP KKSTN |
| 8 | RBD-I N1del L122K L125Y F160W F126L | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRYLRKSNLKPFERDISTEIYQAGST PCNGVEGFNCYWPLQSYGFQPTNGVGYQPYRVVVLSFELLHAPATVCGP KKSTN |
| 9 | RBD-J N1del L122K F160W | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYWPLQSYGFQPTNGVGYQPYRVVVLSFELLHAPATVCGP KKSTN |
| 10 | RBD-K N1del L38A L187A L188A | ITNLCPFGEVFNATRFASVYAWNRKRISNCVADYSVAYNSASFSTFKCY GVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGST PCNGVEGFNCYFPLQSYGFQPTNGVGYQPYRVVVLSFEAAHAPATVCGP KKSTN |
| 11 | RBD-L N1del L122K | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |
| 12 | RBD-M N1del L38M | ITNLCPFGEVFNATRFASVYAWNRKRISNCVADYSVMYNSASFSTFKCY GVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGST PCNGVEGFNCYFPLQSYGFQPTNGVGYQPYRVVVLSFELLHAPATVCGP KKSTN |
| 13 | RBD-N N1del L38M L188M | ITNLCPFGEVFNATRFASVYAWNRKRISNCVADYSVMYNSASFSTFKCY GVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGST PCNGVEGFNCYFPLQSYGFQPTNGVGYQPYRVVVLSFELMHAPATVCGP KKSTN |
| 14 | RBD-O N1del L38M L122K L188M | ITNLCPFGEVFNATRFASVYAWNRKRISNCVADYSVMYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELMHAPATVCGP KKSTN |
| 15 | RBD-P N1del Y159R | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGST PCNGVEGFNCRFPLQSYGFQPTNGVGYQPYRVVVLSFELLHAPATVCGP KKSTN |

-continued

SEQUENCE LISTING

| SEQ ID NO | Description | Sequence |
|---|---|---|
| 16 | RBD-Q N1del F160M | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGST PCNGVEGFNCYMPLQSYGFQPTNGVGYQPYRVVVLSFELLHAPATVCGP KKSTN |
| 17 | RBD-R N1del Y159R F160M | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGST PCNGVEGFNCRMPLQSYGFQPINGVGYQPYRVVVLSFELLHAPATVCGP KKSTN |
| 18 | RBD-S N1del L38M L122K Y159R F160M L188M | ITNLCPFGEVFNATRFASVYAWNRKRISNCVADYSVMYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCRMPLQSYGFQPINGVGYQPYRVVVLSFELMHAPATVCGP KKSTN |
| 19 | RBD-T L125Y F126L | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYLYRYLRKSNLKPFERDISTEIYQAGST PCNGVEGFNCYFPLQSYGFQPTNGVGYQPYRVVVLSFELLHAPATVCGP KKSTN |
| 20 | RBD-U L122K L125Y F126L | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRYLRKSNLKPFERDISTEIYQAGST PCNGVEGFNCYFPLQSYGFQPTNGVGYQPYRVVVLSFELLHAPATVCGP KKSTN |
| 21 | RBD-V L125S F126L | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYLYRSLRKSNLKPFERDISTEIYQAGST PCNGVEGFNCYFPLQSYGFQPTNGVGYQPYRVVVLSFELLHAPATVCGP KKSTN |
| 22 | RBD-W L122K L125S F126L | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRSLRKSNLKPFERDISTEIYQAGST PCNGVEGFNCYFPLQSYGFQPTNGVGYQPYRVVVLSFELLHAPATVCGP KKSTN |
| 23 | RBD-X L122A | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYAYRLFRKSNLKPFERDISTEIYQAGST PCNGVEGFNCYFPLQSYGFQPTNGVGYQPYRVVVLSFELLHAPATVCGP KKSTN |
| 24 | RBD-Y L122K Y159V F160R | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCVRPLQSYGFQPTNGVGYQPYRVVVLSFELLHAPATVCGP KKSTN |
| 25 | RBD-Z L122K F160N | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYNPLQSYGFQPTNGVGYQPYRVVVLSFELLHAPATVCGP KKSTN |
| 26 | RBD-Lmut1 N1del L122K N24E | ITNLCPFGEVFNATRFASVYAWERKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |
| 27 | RBD-Lmut2 N1del L122K Y35W | ITNLCPFGEVFNATRFASVYAWNRKRISNCVADWSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |

-continued

SEQUENCE LISTING

| SEQ ID NO | Description | Sequence |
|---|---|---|
| 28 | RBD-Lmut3 N1del L122K V37F | ITNLCPFGEVFNATRFASVYAWNRKRISNCVADYSFLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |
| 29 | RBD-Lmut4 N1del L122K V11I | ITNLCPFGEAFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |
| 30 | RBD-Lmut5 N1del L122K A18P | ITNLCPFGEVFNATRFPSVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |
| 31 | RBD-Lmut6 N1del L122K K87V | ITNLCPFGEVFNATRFASVYAWNRKRISNCVADYSVLYNSASFSTFKCY GVSPTKLNDLCFTNVYADSFVIRGDEVRQIAPGQTGVIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |
| 32 | RBD-Lmut7 N1del L122K L188D | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELDHAPATVCGP KKSTN |
| 33 | RBD-Lmut8 N1del L122K V194R | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATRCGP KKSTN |
| 34 | RBD-Lmut9 N1del L122K P7D | ITNLCDFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |
| 35 | RBD-Lmut10 N1del L122K R27K | ITNLCPFGEVFNATRFASVYAWNRKKISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |
| 36 | RBD-Lmut11 N1del L122K 53D | ITNLCPFGEVFNATRFASVYAWNRKRISNCVADYSVLYNSASFSTFKCY GVDPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |
| 37 | RBD-Lmut12 N1del L122K L60Y | ITNLCPFGEVFNATRFASVYAWNRKRISNCVADYSVLYNSASFSTFKCY GVSPTKLNDYCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |
| 38 | RBD-Lmut13 N1del L122K F62W | ITNLCPFGEVFNATRFASVYAWNRKRISNCVADYSVLYNSASFSTFKCY GVSPTKLNDLCWTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |
| 39 | RBD-Lmut14 N1del L122K R78D | ITNLCPFGEVFNATRFASVYAWNRKRISNCVADYSVLYNSASFSTFKCY GVSPTKLNDLCFTNVYADSFVIRGDEVDQIAPGQTGKIADYNYKLPDDF TGCVIAWNSNNLDSKVGGNYNYKYRLFRKSNLKPFERDISTEIYQAGST PCNGVEGFNCYFPLQSYGFQPTNGVGYQPYRVVVLSFELLHAPATVCGP KKSTN |

-continued

SEQUENCE LISTING

| SEQ ID NO | Description | Sequence |
|---|---|---|
| 40 | RBD-Lmut15<br>N1del L122K<br>Q84A | ITNLCPFGEVFNATRFASVYAWNRKRISNCVADYSVLYNSASFSTFKCY<br>GVSPTKLNDLCFTNVYADSFVIRGDEVRQIAPGATGKIADYNYKLPDDF<br>TGCVIAWNSNNLDSKVGGNYNYKYRLFRKSNLKPFERDISTEIYQAGST<br>PCNGVEGFNCYFPLQSYGFQPTNGVGYQPYRVVVLSFELLHAPATVCGP<br>KKSTN |
| 41 | RBD-Lmut16<br>N1del L122K<br>D98N | ITNLCPFGEVFNATRFASVYAWNRKRISNCVADYSVLYNSASFSTFKCY<br>GVSPTKLNDLCFTNVYADSFVIRGDEVRQIAPGQTGKIADYNYKLPDNF<br>TGCVIAWNSNNLDSKVGGNYNYKYRLFRKSNLKPFERDISTEIYQAGST<br>PCNGVEGFNCYFPLQSYGFQPTNGVGYQPYRVVVLSFELLHAPATVCGP<br>KKSTN |
| 42 | RBD-Lmut17<br>N1del L122K<br>L111I | ITNLCPFGEVFNATRFASVYAWNRKRISNCVADYSVLYNSASFSTFKCY<br>GVSPTKLNDLCFTNVYADSFVIRGDEVRQIAPGQTGKIADYNYKLPDDF<br>TGCVIAWNSNNIDSKVGGNYNYKYRLFRKSNLKPFERDISTEIYQAGST<br>PCNGVEGFNCYFPLQSYGFQPTNGVGYQPYRVVVLSFELLHAPATVCGP<br>KKSTN |
| 43 | RBD-Lmut18<br>N1del L122K<br>Y178H | ITNLCPFGEVFNATRFASVYAWNRKRISNCVADYSVLYNSASFSTFKCY<br>GVSPTKLNDLCFTNVYADSFVIRGDEVRQIAPGQTGKIADYNYKLPDDF<br>TGCVIAWNSNNLDSKVGGNYNYKYRLFRKSNLKPFERDISTEIYQAGST<br>PCNGVEGFNCYFPLQSYGFQPTNGVGYQPHRVVVLSFELLHAPATVCGP<br>KKSTN |
| 44 | RBD-Lmut19<br>N1del L122K<br>K48R | ITNLCPFGEVFNATRFASVYAWNRKRISNCVADYSVLYNSASFSTFRCY<br>GVSPTKLNDLCFTNVYADSFVIRGDEVRQIAPGQTGKIADYNYKLPDDF<br>TGCVIAWNSNNLDSKVGGNYNYKYRLFRKSNLKPFERDISTEIYQAGST<br>PCNGVEGFNCYFPLQSYGFQPTNGVGYQPYRVVVLSFELLHAPATVCGP<br>KKSTN |
| 45 | RBD-Lmut20<br>N1del L122K<br>I72V | ITNLCPFGEVFNATRFASVYAWNRKRISNCVADYSVLYNSASFSTFKCY<br>GVSPTKLNDLCFTNVYADSFVVRGDEVRQIAPGQTGKIADYNYKLPDDF<br>TGCVIAWNSNNLDSKVGGNYNYKYRLFRKSNLKPFERDISTEIYQAGST<br>PCNGVEGFNCYFPLQSYGFQPTNGVGYQPYRVVVLSFELLHAPATVCGP<br>KKSTN |
| 46 | RBD-Lmut21<br>N1del L122K<br>Q168D | ITNLCPFGEVFNATRFASVYAWNRKRISNCVADYSVLYNSASFSTFKCY<br>GVSPTKLNDLCFTNVYADSFVIRGDEVRQIAPGQTGKIADYNYKLPDDF<br>TGCVIAWNSNNLDSKVGGNYNYKYRLFRKSNLKPFERDISTEIYQAGST<br>PCNGVEGFNCYFPLDSYGFQPTNGVGYQPYRVVVLSFELLHAPATVCGP<br>KKSTN |
| 47 | RBD-Lmut22<br>N1del L122K<br>L125N | ITNLCPFGEVFNATRFASVYAWNRKRISNCVADYSVLYNSASFSTFKCY<br>GVSPTKLNDLCFTNVYADSFVIRGDEVRQIAPGQTGKIADYNYKLPDDF<br>TGCVIAWNSNNLDSKVGGNYNYKYRNFRKSNLKPFERDISTEIYQAGST<br>PCNGVEGFNCYFPLQSYGFQPTNGVGYQPYRVVVLSFELLHAPATVCGP<br>KKSTN |
| 48 | RBD-B<br>Histag<br>FreeCys | ITNLCPFGEVFNATRFASVYAWNRKRISNCVADYSVLYNSASFSTFKCY<br>GVSPTKLNDLCFTNVYADSFVIRGDEVRQIAPGQTGKIADYNYKLPDDF<br>TGCVIAWNSNNLDSKVGGNYNYLYRLFRKSNLKPFERDISTEIYQAGST<br>PCNGVEGFNCYFPLQSYGFQPTNGVGYQPYRVVVLSFELLHAPATVCGP<br>KKSTNHHHHHHC |
| 49 | RBD-B N1del<br>Long Linker<br>SpyTag | ITNLCPFGEVFNATRFASVYAWNRKRISNCVADYSVLYNSASFSTFKCY<br>GVSPTKLNDLCFTNVYADSFVIRGDEVRQIAPGQTGKIADYNYKLPDDF<br>TGCVIAWNSNNLDSKVGGNYNYLYRLFRKSNLKPFERDISTEIYQAGST<br>PCNGVEGFNCYFPLQSYGFQPTNGVGYQPYRVVVLSFELLHAPATVCGP<br>KKSTNGGDGGDGGDGGAHIVMVDAYKPTK |
| 50 | RBD-J N1del<br>L122K F160W<br>Long Linker<br>SpyTag | ITNLCPFGEVFNATRFASVYAWNRKRISNCVADYSVLYNSASFSTFKCY<br>GVSPTKLNDLCFTNVYADSFVIRGDEVRQIAPGQTGKIADYNYKLPDDF<br>TGCVIAWNSNNLDSKVGGNYNYKYRLFRKSNLKPFERDISTEIYQAGST<br>PCNGVEGFNCYWPLQSYGFQPTNGVGYQPYRVVVLSFELLHAPATVCGP<br>KKSTNGGDGGDGGDGGAHIVMVDAYKPTK |
| 51 | RBD-B 207C | ITNLCPFGEVFNATRFASVYAWNRKRISNCVADYSVLYNSASFSTFKCY<br>GVSPTKLNDLCFTNVYADSFVIRGDEVRQIAPGQTGKIADYNYKLPDDF<br>TGCVIAWNSNNLDSKVGGNYNYLYRLFRKSNLKPFERDISTEIYQAGST<br>PCNGVEGFNCYWPLQSYGFQPTNGVGYQPYRVVVLSFELLHAPATVCGP<br>KKSTNLVKNKC |

-continued

SEQUENCE LISTING

| SEQ ID NO | Description | Sequence |
|---|---|---|
| 52 | RBD-J 207C | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYWPLQSYGFQPTNGVGYQPYRVVVLSFELLHAPATVCGP KKSTNLVKNKC |
| 53 | RBD-B C207S 259C | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGST PCNGVEGFNCYWPLQSYGFQPTNGVGYQPYRVVVLSFELLHAPATVCGP KKSTNLVKNKSVNFNFNGLTGTGVLTESNKKFLPFQQFGRDIADTTDAV RDPQTLEILDITPC |
| 54 | RBD-B C207S 259CPPC | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGST PCNGVEGFNCYWPLQSYGFQPTNGVGYQPYRVVVLSFELLHAPATVCGP KKSTNLVKNKSVNFNFNGLTGTGVLTESNKKFLPFQQFGRDIADTTDAV RDPQTLEILDITPCPPC |
| 55 | RBD-J C207S 259C | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYWPLQSYGFQPTNGVGYQPYRVVVLSFELLHAPATVCGP KKSTNLVKNKSVNFNFNGLTGTGVLTESNKKFLPFQQFGRDIADTTDAV RDPQTLEILDITPC |
| 56 | RBD-J C207S 259CPPC | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYWPLQSYGFQPTNGVGYQPYRVVVLSFELLHAPATVCGP KKSTNLVKNKSVNFNFNGLTGTGVLTESNKKFLPFQQFGRDIADTTDAV RDPQTLEILDITPCPPC |
| 57 | RBD-B 260 B-Long | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGST PCNGVEGFNCYWPLQSYGFQPTNGVGYQPYRVVVLSFELLHAPATVCGP KKSTNLVKNKCVNFNFNGLTGTGVLTESNKKFLPFQQFGRDIADTTDAV RDPQTLEILDITPCS |
| 58 | RBD-J 260 J-Long | ITNLCPFGEVFNATRFASVYAWNRKRISNCVADYSVLYNSASFSTFKCY GVSPTKLNDLCFTNVYADSFVIRGDEVRQIAPGQTGKIADYNYKLPDDF TGCVIAWNSNNLDSKVGGNYNYKYRLFRKSNLKPFERDISTEIYQAGST PCNGVEGFNCYWPLQSYGFQPTNGVGYQPYRVVVLSFELLHAPATVCGP KKSTNLVKNKCVNFNFNGLTGTGVLTESNKKFLPFQQFGRDIADTTDAV RDPQTLEILDITPCS |
| 59 | SARS-CoV-2 Spike glycoprotein Signal peptide in underline RBD corresponding to SEQ ID NO: 1 in bold | <u>FVFLVLLPLVSS</u>QCVNLTTRTQLPPAYTNSFTRGVYYPDKVFRSSVLHS TQDLFLPFFSNVTWFHAIHVSGTNGTKRFDNPVLPFNDGVYFASTEKSN IIRGWIFGTTLDSKTQSLLIVNNATNVVIKVCEFQFCNDPFLGVYYHKN NKSWMESEFRVYSSANNCTFEYVSQPFLMDLEGKQGNFKNLREFVFKNI DGYFKIYSKHTPINLVRDLPQGFSALEPLVDLPIGINITRFQTLLALHR SYLTPGDSSSGWTAGAAAYYVGYLQPRTFLLKYNENGTITDAVDCALDP LSETKCTLKSFTVEKGIYQTSNFRVQPTESIVRFPNITNLCPFGEVFNA TRFASVYAWNRKRISNCVADYSVLYNSASFSTFKCYGVSPTKLNDLCFT NVYADSFVIRGDEVRQIAPGQTGKIADYNYKLPDDFTGCVIANNSNNLD SKVGGNYNYLYRLFRKSNLKPFERDISTEIYQAGSTPCNGVEGFNCYFP LQSYGFQPTNGVGYQPYRVVVLSFELLHAPATVCGPKKSTNLVKNKCVN FNFNGLTGTGVLTESNKKFLPFQQFGRDIADTTDAVRDPQTLEILDITP CSFGGVSVITPGTNTSNQVAVLYQDVNCTEVPVAIHADQLTPTWRVYST GSNVFQTRAGCLIGAEHVNNSYECDIPIGAGICASYQTQTNSPSGAGSV ASQSIIAYTMSLGAENSVAYSNNSIAIPTNFTISVTTEILPVSMTKTSV DCTMYICGDSTECSNLLLQYGSFCTQLNRALTGIAVEQDKNTQEVFAQV KQIYKTPPIKDFGGFNFSQILPDPSKPSKRSFIEDLLFNKVTLADAGFI KQYGDCLGDIAAARDLICAQKFNGLTVLPPLLTDEMIAQYTSALLAGTIT SGWTFGAGAALQIPFAMQMAYRFNGIGVTQNVLYENQKLIANQFNSAIG KIQDSLSSTASALGKLQDVVNQNAQALNTLVKQLSSNFGAISSVLNDIL SRLDPPEAEVQIDRLITGRLQSLQTYVTQQLIRAAEIRASANLAATKMS ECVLGQSKRVDFCGKGYHLMSFPQSAPHGVVFLHVTYVPAQEKNFTTAP AICHDGKAHFPREGVFVSNGTHWFVTQRNFYEPQIITTDNTFVSGNCDV |

| SEQ ID NO | Description | Sequence |
|---|---|---|
| | | VIGIVNNTVYDPLQPELDSFKEELDKYFKNHTSPDVDLGDISGINASVV NIQKEIDRLNEVAKNLNESLIDLQELGKYEQYIKWPWYIWLGFIAGLIA IVMVTIMLCCMTSCCSCLKGCCSCGSCCKFDEDDSEPVLKGVKLHYT |
| 60 | SARS-CoV-2 S glycoprotein signal peptide | FVFLVLLPLVSS |
| 61 | SARS-CoV-2 S glycoprotein without signal peptide | QCVNLTTRTQLPPAYTNSFTRGVYYPDKVFRSSVLHSTQDLFLPFFSNV TWFHAIHVSGTNGTKRFDNPVLPFNDGVYFASTEKSNIIRGWIFGTTLD SKTQSLLIVNNATNVVIKVCEFQFCNDPFLGVYYHKNNKSWMESEFRVY SSANNCTFEYVSQPFLMDLEGKQGNFKNLREFVFKNIDGYFKIYSKHTP INLVRDLPQGFSALEPLVDLPIGINITRFQTLLALHRSYLTPGDSSSGW TAGAAAYYVGYLQPRTFLLKYNENGTITDAVDCALDPLSETKCTLKSFT VEKGIYQTSNFRVQPIESIVRFPNITNLCPFGEVFNATRFASVYAWNRK RISNCVADYSVLYNSASFSTFKCYGVSPTKLNDLCFTNVYADSFVIRGD EVRQIAPGQTGKIADYNYKLPDDFTGCVIAWNSNNLDSKVGGNYNYLYR LFRKSNLKPFERDISTEIYQAGSTPCNGVEGFNCYFPLQSYGFQPTNGV GYQPYRVVVLSFELLHAPATVCGPKKSTNLVKNKCVNFNFNGLIGTGVL TESNKKFLPFQQFGRDIADTTDAVRDPQTLEILDITPCSFGGVSVITPG TNTSNQVAVLYQDVNCTEVPVAIHADQLTPTWRVYSTGSNVFQTRAGCL IGAEHVNNSYECDIPIGAGICASYQTQTNSPSGAGSVASQSIIAYTMSL GAENSVAYSNNSIAIPTNFTISVTTEILPVSMTKTSVDCTMYICGDSTE CSNLLLQYGSFCTQLNRALTGIAVEQDKNTQEVFAQVKQIYKTPPIKDF GGFNFSQILPDPSKPSKRSFIEDLLFNKVTLADAGFIKQYGDCLGDIAA RDLICAQKFNGLTVLPPLLTDEMIAQYTSALLAGTITSGWTFGAGAALQ IPFAMQMAYRFNGIGVTQNVLYENQKLIANQFNSAIGKIQDSLSSTASA LGKLQDVVNQNAQALNTLVKQLSSNFGAISSVLNDILSRLDPPEAEVQI DRLITGRLQSLQTYVTQQLIRAAEIRASANLAATKMSECVLGQSKRVDF CGKGYHLMSFPQSAPHGVVFLHVTYVPAQEKNFTTAPAICHDGKAHFPR EGVFVSNGTHWFVTQRNFYEPQIITTDNTFVSGNCDVVIGIVNNTVYDP LQPELDSFKEELDKYFKNHTSPDVDLGDISGINASVVNIQKEIDRLNEV AKNLNESLIDLQELGKYEQYIKWPWYIWLGFIAGLIAIVMVTIMLCCMT SCCSCLKGCCSCGSCCKFDEDDSEPVLKGVKLHYT |
| 62 | RBD-A (nucleotide sequence of SEQ ID NO: 1) | AACATCACCAACTTGTGCCCATTCGGTGAGGTTTTCAACGCTACTAGAT TCGCTTCCGTTTACGCCTGGAACAGAAAGAGAATCTCCAACTGCGTTGC TGACTACTCCGTCTTGTACAACTCTGCTTCATTCTCCACCTTCAAGTGC TACGGTGTTTCCCCAACTAAGTTGAACGACCTGTGTTTCACTAACGTCT ACGCCGACTCCTTCGTTATTAGAGGTGACGAGGTTAGACAGATCGCTCC AGGTCAAACTGGTAAGATCGCTGACTACAACTACAAGCTGCCAGACGAC TTCACCGGTTGTGTTATTGCTTGGAACTCCAACAACCTGGACTCCAAGG TTGGTGGTAACTACAATTACCTGTACCGTCTGTTCAGAAAGTCCAACCT GAAGCCATTCGAGAGAGACATCTCCACTGAGATCTACCAAGCTGGTTCC ACTCCATGTAACGGTGTTGAGGGTTTCAACTGTTACTTCCCATTGCAGT CCTACGGTTTCCAGCCAACTAATGGTGTTGGTTACCAGCCATACAGAGT CGTCGTTTTGTCCTTCGAGTTGTTGCATGCTCCAGCTACTGTTTGCGGT CCAAAGAAGTCCACTAAC |
| 63 | RBD-B N1del (nucleotide sequence of SEQ ID NO: 2) | ATCACCAACTTGTGTCCATTCGGTGAGGTTTTCAACGCTACTAGATTCG CTTCCGTTTACGCCTGGAACAGAAAGAGAATCTCCAACTGCGTTG -continued

SEQUENCE LISTING

| SEQ ID NO | Description | Sequence |
|---|---|---|
| | | CTTACGGTTTCCAGCCAACTAACGGTGTCGGTTACCAACCATACAGAGT<br>TGTCGTTTTGTCCTTCGAGTTGTTGCACGCTCCAGCTACTGTTTGTGGT<br>CCAAAGAAGTCCACTAAC |
| 65 | RBD-D N1del N13Q (nucleotide sequence of SEQ ID NO: 4) | ATCACCAACTTGTGTCCATTCGGTGAGGTTTTCCAGGCTACTAGATTCG<br>CTTCTGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACCAACGTTTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACCTGTACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGCTACTTCCCATTGCAGTCTT<br>ACGGTTTCCAGCCAACTAACGGTGTCGGTTACCAACCATACAGAGTTGT<br>CGTTTTGTCCTTCGAGTTGTTGCACGCTCCAGCTACTGTTTGTGGTCCA<br>AAGAAGTCCACTAAC |
| 66 | RBD-E N1del 230 Histag (nucleotide sequence of SEQ ID NO: 5) | ATCACCAACTTGTGTCCATTCGGTGAGGTTTTCAACGCCACTAAGTTCC<br>CATCTGTTTACGCCTGGGAGAGAAAGAAGATCTCCAACTGCGTTGCTGA<br>CTACTCCGTCTTGTACAACTCCACATTCTTCAGCACCTTCAAGTGCTAC<br>GGTGTTTCCGCTACTAAGTTGAACGACCTGTGTTTCTCCAACGTTTACG<br>CCGACTCCTTCGTTGTTAAGGGTGACGACGTTAGACAGATTGCTCCAGG<br>TCAGACTGGTGTTATCGCTGACTACAACTACAAGCTGCCAGACGACTTC<br>ATGGGTTGTGTTTTGGCTTGGAACACCAGAAACATCGACGCTACTTCCA<br>CCGGTAATTACAATTACAAGTACCGTTACCTGAGGCACGGTAAGCTTAG<br>ACCATTCGAGAGAGACATCTCTAACGTCCCATTCTCTCCAGACGGTAAG<br>CCTTGTACTCCTCCTGCTTTGAACTGTTACTGGCCATTGAACGACTACG<br>GTTTCTACACTACTACCGGTATCGGTTACCAGCCATACAGAGTTGTTGT<br>CTTGTCCTTCGAGTTGTTGAACGCTCCAGCTACTGTTTGCGGTCCAAAG<br>TTGTCCACCGACCTGATTAAGAACCAGTGCGTCAACTTTAACTTCAACG<br>GTCTGACTGGTACTGGTGGTTCCTTGGAGGTTTTGTTTCAAGGTCCAGG<br>TTCTCATCACCACCACCATCACCATCATCACCAC |
| 67 | RBD-G N1del L38A L122K L125Y F12 6L F160W L187A L188A (nucleotide sequence of SEQ ID NO: 6) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCGCTTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTTATTTGAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTGGCCATTGCAGTCCT<br>ACGGTTTCCAGCCAACTAATGGTGTTGGTTACCAGCCATACAGAGTCGT<br>CGTTTTGTCCTTCGAGGCTGCTCATGCTCCAGCTACTGTTTGCGGTCCA<br>AAGAAGTCCACTAAC |
| 68 | RBD-H N1del L38A L122K F160W L187A L188A (nucleotide sequence of SEQ ID NO: 7) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCGCTTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTTTGTTTAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTGGCCATTGCAGTCCT<br>ACGGTTTCCAGCCAACTAATGGTGTTGGTTACCAGCCATACAGAGTCGT<br>CGTTTTGTCCTTCGAGGCTGCTCATGCTCCAGCTACTGTTTGCGGTCCA<br>AAGAAGTCCACTAAC |
| 69 | RBD-I N1del L122K L125Y F160W F126L (nucleotide sequence of SEQ ID NO: 8) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTTATTTGAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTGGCCATTGCAGTCCT |

SEQUENCE LISTING

| SEQ ID NO | Description | Sequence |
|---|---|---|
|  |  | ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 70 | RBD-J N1del L122K F160W (nucleotide sequence of SEQ ID NO: 9) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTTTGTTTAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTGGCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 71 | RBD-K N1del L38A L187A L188A (nucleotide sequence of SEQ ID NO: 10) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCGCTTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACTTGTACCGTTTGTTTAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTTCCATTGCAGTCCT<br>ACGGTTTCCAGCCAACTAATGGTGTTGGTTACCAGCCATACAGAGTCGT<br>CGTTTTGTCCTTCGAGGCTGCTCATGCTCCAGCTACTGTTTGCGGTCCA<br>AAGAAGTCCACTAAC |
| 72 | RBD-L N1del L122K (nucleotide sequence of SEQ ID NO: 11) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 73 | RBD-M N1del L38M (nucleotide sequence of SEQ ID NO: 12) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCATGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACCTGTACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 74 | RBD-N N1del L38M L188M (nucleotide sequence of SEQ ID NO: 13) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCATGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACCTGTACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGATGCATGCTCCAGCTACTGTTTGCGGTCCA<br>AAGAAGTCCACTAAC |

-continued

SEQUENCE LISTING

| SEQ ID NO | Description | Sequence |
|---|---|---|
| 75 | RBD-O N1del L38M L122K L188M (nucleotide sequence of SEQ ID NO: 14) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCATGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGATGCATGCTCCAGCTACTGTTTGCGGTCCA AAGAAGTCCACTAAC |
| 76 | RBD-P N1del Y159R (nucleotide sequence of SEQ ID NO: 15) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACCTGTACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTAGATTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 77 | RBD-Q N1del F160M (nucleotide sequence of SEQ ID NO: 16) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACCTGTACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACATGCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 78 | RBD-R N1del Y159R F160M (nucleotide sequence of SEQ ID NO: 17) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACCTGTACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTAGAATGCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 79 | RBD-S N1del L38M L122K Y159R F160M L188M (nucleotide sequence of SEQ ID NO: 18) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCATGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTAGAATGCCATTGCAGTCCT ACGGTTTCCAGCCAACTAATGGTGTTGGTTACCAGCCATACAGAGTCGT CGTTTTGTCCTTCGAGTTGATGCATGCTCCAGCTACTGTTTGCGGTCCA AAGAAGTCCACTAAC |
| 80 | RBD-T L125Y F126L (nucleotide sequence of | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG |

-continued

SEQUENCE LISTING

| SEQ ID NO | Description | Sequence |
|---|---|---|
| | SEQ ID NO: 19) | CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACCTGTACCGTTACCTGAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 81 | RBD-U L122K L125Y F126L (nucleotide sequence of SEQ ID NO: 20) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAATTACAATTACAAGTACCGTTACCTGAGGAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 82 | RBD-V L125S F126L (nucleotide sequence of SEQ ID NO: 21) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACCTGTACAGATCCCTGAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 83 | RBD-W L122K L125S F126L (nucleotide sequence of SEQ ID NO: 22) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAATTACAATTACAAGTACAGGTCCCTGAGGAAGTCCAACTTGAA<br>GCCATTCGAGAGAGACATCTCCACCGAGATCTACCAAGCTGGTTCTACT<br>CCATGTAACGGTGTCGAGGGTTTCAACTGTTACTTCCCATTGCAGTCCT<br>ACGGTTTCCAGCCAACTAACGGTGTTGGTTACCAGCCATACAGAGTTGT<br>CGTTTTGTCCTTCGAGTTGTTGCACGCTCCAGCTACTGTTTGTGGTCCA<br>AAGAAGTCCACTAAC |
| 84 | RBD-X L122A (nucleotide sequence of SEQ ID NO: 23) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACGCCTACAGGCTGTTCAGAAAGTCCAACTTGAA<br>GCCATTCGAGAGAGACATCTCCACCGAGATCTACCAAGCTGGTTCTACT<br>CCATGTAACGGTGTCGAGGGTTTCAACTGTTACTTCCCATTGCAGTCCT<br>ACGGTTTCCAGCCAACTAACGGTGTTGGTTACCAGCCATACAGAGTTGT<br>CGTTTTGTCCTTCGAGTTGTTGCACGCTCCAGCTACTGTTTGTGGTCCA<br>AAGAAGTCCACTAAC |
| 85 | RBD-Y L122K Y159V F160R (nucleotide sequence of SEQ ID NO: 24) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAATTACAATTACAAGTACAGGCTGTTCCGTAAGTCCAACCTGAA |

| SEQ ID NO | Description | Sequence |
|---|---|---|
| | | GCCATTCGAGAGAGACATCTCCACTGAGATCTACCAAGCTGGTTCCACT CCATGTAACGGTGTTGAGGGTTTCAACTGCGTCAGACCATTGCAATCTT ACGGTTTCCAGCCAACTAACGGTGTCGGTTACCAACCATACAGAGTTGT CGTTTTGTCCTTCGAGTTGTTGCACGCTCCAGCTACTGTTTGTGGTCCA AAGAAGTCCACTAAC |
| 86 | RBD-Z L122K F160N (nucleotide sequence of SEQ ID NO: 25) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAATTACAATTACAAGTACAGGCTGTTCCGTAAGTCCAACCTGAA GCCATTCGAGAGAGACATCTCCACTGAGATCTACCAAGCTGGTTCCACT CCATGTAACGGTGTTGAGGGTTTCAACTGTTACAACCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 87 | RBD-Lmut1 N1del L122K N24E (nucleotide sequence of SEQ ID NO: 26) | ATCACCAACTTGTGTCCATTCGGTGAGGTTTTCAACGCTACTAGATTCG CTTCCGTTTACGCCTGGGAAAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 88 | RBD-Lmut2 N1del L122K Y35W (nucleotide sequence of SEQ ID NO: 27) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTGGTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 89 | RBD-Lmut3 N1del L122K V37F (nucleotide sequence of SEQ ID NO: 28) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCTTTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 90 | RBD-Lmut4 N1del L122K V11I (nucleotide sequence of SEQ ID NO: 29 | ATCACCAACTTGTGTCCATTCGGTGAGATTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT |

-continued

SEQUENCE LISTING

| SEQ ID NO | Description | Sequence |
|---|---|---|
| | | ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 91 | RBD-Lmut5 N1del L122K A18P (nucleotide sequence of SEQ ID NO: 30) | ATCACCAACTTGTGTCCATTCGGTGAGGTTTTCAACGCTACTAGATTCC<br>CATCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 92 | RBD-Lmut6 N1del L122K K87V (nucleotide sequence of SEQ ID NO: 31) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTGTTATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 93 | RBD-Lmut7 N1del L122K L188D (nucleotide sequence of SEQ ID NO: 32) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGGATCATGCTCCAGCTACTGTTTGCGGTCCA<br>AAGAAGTCCACTAAC |
| 94 | RBD-Lmut8 N1del L122K V194R (nucleotide sequence of SEQ ID NO: 33) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTAGATGCGGTCCA<br>AAGAAGTCCACTAAC |
| 95 | RBD-Lmut9 N1del L122K P7D (nucleotide sequence of SEQ ID NO: 34) | ATCACCAACTTGTGTGATTTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |

-continued

SEQUENCE LISTING

| SEQ ID NO | Description | Sequence |
|---|---|---|
| 96 | RBD-Lmut10 N1del L122K R27K (nucleotide sequence of SEQ ID NO: 35) | ATCACCAACTTGTGTCCATTCGGTGAGGTTTTCAACGCTACTAGATTCG CTTCCGTTTACGCCTGGAACAGAAAGAAAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 97 | RBD-Lmut11 N1del L122K 53D (nucleotide sequence of SEQ ID NO: 37) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTGATCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 98 | RBD-Lmut12 N1del L122K L60Y (nucleotide sequence of SEQ ID NO: 38) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACTATTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 99 | RBD-Lmut13 N1del L122K F62W (nucleotide sequence of SEQ ID NO: 39) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTGGACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 100 | RBD-Lmut14 N1del L122K R78D (nucleotide sequence of SEQ ID NO: 40) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTGATCAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 101 | RBD-Lmut15 N1del L122K Q84A (nucleotide | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG |

-continued

SEQUENCE LISTING

| SEQ ID NO | Description | Sequence |
|---|---|---|
| | sequence of<br>SEQ ID NO:<br>41) | CCGACTCCTTCGTTATTAGAGGTGACGAGGTTAGACAGATCGCTCCAGG<br>TGCTACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 102 | RBD-Lmut16<br>N1del L122K<br>D98N<br>(nucleotide<br>sequence of<br>SEQ ID NO:<br>42) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACAATTTC<br>ACCGGTTGTGTTATTGCTTGGAACTCCAACAACCTGGACTCCAAGGTTG<br>GTGGTAACTACAATTACAAATACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 103 | RBD-Lmut17<br>N1del L122K<br>L111I<br>(nucleotide<br>sequence of<br>SEQ ID NO:<br>43) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACATTGACTCCAAGGTTG<br>GTGGTAACTACAATTACAAATACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 104 | RBD-Lmut18<br>N1del L122K<br>Y178H<br>(nucleotide<br>sequence of<br>SEQ ID NO:<br>44) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCACATAGAGTCGT<br>CGTTTTGTCCTTCGAGTTGTTGCATGCTCCAGCTACTGTTTGCGGTCCA<br>AAGAAGTCCACTAAC |
| 105 | RBD-Lmut19<br>N1del L122K<br>K48R<br>(nucleotide<br>sequence of<br>SEQ ID NO:<br>45) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAGATGCTAC<br>GGTGTTTCCCCAACTAAGTTGAACGACCTGTGTTTCACTAACGTCTACG<br>CCGACTCCTTCGTTATTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTCTGTTCAGAAAGTCCAACCTGAA<br>GCCATTCGAGAGAGACATCTCCACTGAGATCTACCAAGCTGGTTCCACT<br>CCATGTAACGGTGTTGAGGGTTTCAACTGTTACTTCCCATTGCAGTCCT<br>ACGGTTTCCAGCCAACTAATGGTGTTGGTTACCAGCCATACAGAGTCGT<br>CGTTTTGTCCTTCGAGTTGTTGCATGCTCCAGCTACTGTTTGCGGTCCA<br>AAGAAGTCCACTAAC |
| 106 | RBD-Lmut20<br>N1del L122K<br>I72V<br>(nucleotide<br>sequence of<br>SEQ ID NO:<br>46) | ATCACCAACTTGTGTCCATTCGGTGAGGTTTTCAACGCTACTAGATTCG<br>CTTCCGTTTACGCCTGGAACAGAAAGAGAATCTCCAACTGCGTTGCTGA<br>CTACTCCGTCTTGTACAACTCTGCTTCATTCTCCACCTTCAAGTGCTAC<br>GGTGTTTCCCCAACTAAGTTGAACGACCTGTGTTTCACTAACGTCTACG<br>CCGACTCCTTCGTTGTTAGAGGTGACGAGGTTAGACAGATCGCTCCAGG<br>TCAAACTGGTAAGATCGCTGACTACAACTACAAGCTGCCAGACGACTTC<br>ACCGGTTGTGTTATTGCTTGGAACTCCAACAACCTGGACTCCAAGGTTG<br>GTGGTAACTACAATTACAAATACCGTCTGTTCAGAAAGTCCAACCTGAA |

-continued

SEQUENCE LISTING

| SEQ ID NO | Description | Sequence |
|---|---|---|
| | | GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 107 | RBD-Lmut21 N1del L122K Q168D (nucleotide sequence of SEQ ID NO: 47) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCGATCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 108 | RBD-Lmut22 N1del L122K L125N (nucleotide sequence of SEQ ID NO: 48) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTAATTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAAC |
| 109 | RBD-B N1del Histag FreeCys (nucleotide sequence of SEQ ID NO: 49) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACCTGTACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAACCATCATCATCATCATCATTGT |
| 110 | RBD-B N1del Long Linker SpyTag | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACCTGTACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAATCTACCAATGGTGGTGATGGTGGCGACGGCGGAGATGGTGGTG CTCATATAGTTATGGTTGACGCCTACAAGCCTACTAAG |
| 111 | RBD-J N1del L122K F160W Long Linker SpyTag (nucleotide sequence of SEQ ID NO: 50) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAATTACAATTACAAGTACAGGCTGTTCCGTAAGTCCAACCTGAA GCCATTCGAGAGAGACATCTCCACTGAGATCTACCAAGCTGGTTCCACT CCATGTAACGGTGTTGAGGGTTTCAACTGTTACTGGCCATTGCAGTCTT ACGGTTTCCAGCCAACTAACGGTGTCGGTTACCAACCATACAGAGTTGT |

SEQUENCE LISTING

| SEQ ID NO | Description | Sequence |
|---|---|---|
| | | CGTTTTGTCCTTCGAGTTGTTGCACGCTCCAGCTACTGTTTGTGGTCCA AAGAAATCCACCAATGGTGGTGATGGTGGCGACGGCGGAGATGGTGGTG CTCATATAGTTATGGTTGACGCCTACAAGCCTACTAAG |
| 112 | RBD-B 207C (nucleotide sequence of SEQ ID NO: 51) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACCTGTACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAACTTGGTCAAGAACAAATGT |
| 113 | RBD-J 207C (nucleotide sequence of SEQ ID NO: 52) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACAAATACCGTTTGTTTAGAAAGTCCAACCTGAA GCCATTCGAGAGAGACATCTCCACTGAGATCTACCAAGCTGGTTCCACT CCATGTAACGGTGTTGAGGGTTTCAACTGTTACTGGCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAACTTGGTCAAGAACAAATGT |
| 114 | RBD-B C207S 259C (nucleotide sequence of SEQ ID NO: 53) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACCTGTACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAACTTGGTCAAGAACAAATCTGTCAACTTTAACTTCA ACGGCCTGACCGGTACTGGTGTTTTGACTGAATCCAACAAGAAGTTCCT GCCATTCCAGCAGTTCGGTAGAGACATTGCTGACACTACTGACGCCGTT AGAGATCCACAGACTTTGGAGATCTTGGACATCACCCCATGT |
| 115 | RBD-B C207S 259CPPC (nucleotide sequence of SEQ ID NO: 54) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG GTGGTAACTACAATTACCTGTACCGTCTGTTCAGAAAGTCCAACCTGAA GCCATTCGAGAGAGACATCTCCACTGAGATCTACCAAGCTGGTTCCACT CCATGTAACGGTGTTGAGGGTTTCAACTGTTACTTCCCATTGCAGTCCT ACGGTTTCCAGCCAACTAATGGTGTTGGTTACCAGCCATACAGAGTCGT CGTTTTGTCCTTCGAGTTGTTGCATGCTCCAGCTACTGTTTGCGGTCCA AAGAAGTCCACTAACTTGGTCAAGAACAAATCTGTCAACTTTAACTTCA ACGGCCTGACCGGTACTGGTGTTTTGACTGAATCCAACAAGAAGTTCCT GCCATTCCAGCAGTTCGGTAGAGACATTGCTGACACTACTGACGCCGTT AGAGATCCACAGACTTTGGAGATCTTGGACATCACCCCATGTCCACCAT GT |
| 116 | RBD-J C207S 259C (nucleotide sequence of SEQ ID NO: 55) | ATCACCAACTTGTGTCCATTCGGTGAGGTTTTCAACGCTACTAGATTCG CTTCCGTTTACGCCTGGAACAGAAAGAGAATCTCCAACTGCGTTGCTGA CTACTCCGTCTTGTACAACTCTGCTTCATTCTCCACCTTCAAGTGCTAC GGTGTTTCCCCAACTAAGTTGAACGACCTGTGTTTCACTAACGTCTACG CCGACTCCTTCGTTATTAGAGGTGACGAGGTTAGACAGATCGCTCCAGG TCAAACTGGTAAGATCGCTGACTACAACTACAAGCTGCCAGACGACTTC ACCGGTTGTGTTATTGCTTGGAACTCCAACAACCTGGACTCCAAGGTTG |

| SEQ ID NO | Description | Sequence |
|---|---|---|
| | | GTGGTAACTACAATTACAAATACCGTTTGTTTAGAAAGTCCAACCTGAA
GCCATTCGAGAGAGACATCTCCACTGAGATCTACCAAGCTGGTTCCACT
CCATGTAACGGTGTTGAGGGTTTCAACTGTTACTGGCCATTGCAGTCCT
ACGGTTTCCAGCCAACTAATGGTGTTGGTTACCAGCCATACAGAGTCGT
CGTTTTGTCCTTCGAGTTGTTGCATGCTCCAGCTACTGTTTGCGGTCCA
AAGAAGTCCACTAACTTGGTCAAGAACAAATCTGTCAACTTTAACTTCA
ACGGCCTGACCGGTACTGGTGTTTTGACTGAATCCAACAAGAAGTTCCT
GCCATTCCAGCAGTTCGGTAGAGACATTGCTGACACTACTGACGCCGTT
AGAGATCCACAGACTTTGGAGATCTTGGACATCACCCCATGT |
| 117 | RBD-J C207S 259CPPC | ATCACCAACTTGTGTCCATTCGGTGAGGTTTTCAACGCTACTAGATTCG
CTTCCGTTTACGCCTGGAACAGAAAGAGAATCTCCAACTGCGTTGCTGA
CTACTCCGTCTTGTACAACTCTGCTTCATTCTCCACCTTCAAGTGCTAC
GGTGTTTCCCCAACTAAGTTGAACGACCTGTGTTTCACTAACGTCTACG
CCGACTCCTTCGTTATTAGAGGTGACGAGGTTAGACAGATCGCTCCAGG
TCAAACTGGTAAGATCGCTGACTACAACTACAAGCTGCCAGACGACTTC
ACCGGTTGTGTTATTGCTTGGAACTCCAACAACCTGGACTCCAAGGTTG
GTGGTAACTACAATTACAAATACCGTTTGTTTAGAAAGTCCAACCTGAA
GCCATTCGAGAGAGACATCTCCACTGAGATCTACCAAGCTGGTTCCACT
CCATGTAACGGTGTTGAGGGTTTCAACTGTTACTGGCCATTGCAGTCCT
ACGGTTTCCAGCCAACTAATGGTGTTGGTTACCAGCCATACAGAGTCGT
CGTTTTGTCCTTCGAGTTGTTGCATGCTCCAGCTACTGTTTGCGGTCCA
AAGAAGTCCACTAACTTGGTCAAGAACAAATCTGTCAACTTTAACTTCA
ACGGCCTGACCGGTACTGGTGTTTTGACTGAATCCAACAAGAAGTTCCT
GCCATTCCAGCAGTTCGGTAGAGACATTGCTGACACTACTGACGCCGTT
AGAGATCCACAGACTTTGGAGATCTTGGACATCACCCCATGTCCACCAT
GT |
| 118 | RBD-B 260 B-Long (nucleotide sequence of SEQ ID NO: 56) | ATCACCAACTTGTGTCCATTCGGTGAGGTTTTCAACGCTACTAGATTCG
CTTCCGTTTACGCCTGGAACAGAAAGAGAATCTCCAACTGCGTTGCTGA
CTACTCCGTCTTGTACAACTCTGCTTCATTCTCCACCTTCAAGTGCTAC
GGTGTTTCCCCAACTAAGTTGAACGACCTGTGTTTCACTAACGTCTACG
CCGACTCCTTCGTTATTAGAGGTGACGAGGTTAGACAGATCGCTCCAGG
TCAAACTGGTAAGATCGCTGACTACAACTACAAGCTGCCAGACGACTTC
ACCGGTTGTGTTATTGCTTGGAACTCCAACAACCTGGACTCCAAGGTTG
GTGGTAACTACAATTACCTGTACCGTCTGTTCAGAAAGTCCAACCTGAA
GCCATTCGAGAGAGACATCTCCACTGAGATCTACCAAGCTGGTTCCACT
CCATGTAACGGTGTTGAGGGTTTCAACTGTTACTTCCCATTGCAGTCCT
ACGGTTTCCAGCCAACTAATGGTGTTGGTTACCAGCCATACAGAGTCGT
CGTTTTGTCCTTCGAGTTGTTGCATGCTCCAGCTACTGTTTGCGGTCCA
AAGAAGTCCACTAACCTGGTCAAGAACAAGTGCGTCAACTTTAACTTCA
ACGGTCTGACCGGTACTGGTGTTTTTGACTGAGTCCAACAAGAAGTTCCT
GCCATTCCAGCAATTCGGTAGAGACATTGCTGACACTACTGACGCCGTT
AGAGATCCACAGACTTTGGAGATCTTGGACATCACCCCATGTTCT |
| 119 | RBD-J 260 J-Long (nucleotide sequence of SEQ ID NO: 57) | ATCACCAACTTGTGTCCATTCGGTGAGGTTTTCAACGCTACTAGATTCG
CTTCCGTTTACGCCTGGAACAGAAAGAGAATCTCCAACTGCGTTGCTGA
CTACTCCGTCTTGTACAACTCTGCTTCATTCTCCACCTTCAAGTGCTAC
GGTGTTTCCCCAACTAAGTTGAACGACCTGTGTTTCACTAACGTCTACG
CCGACTCCTTCGTTATTAGAGGTGACGAGGTTAGACAGATCGCTCCAGG
TCAAACTGGTAAGATCGCTGACTACAACTACAAGCTGCCAGACGACTTC
ACCGGTTGTGTTATTGCTTGGAACTCCAACAACCTGGACTCCAAGGTTG
GTGGTAACTACAATTACCTGTACCGTCTGTTCAGAAAGTCCAACCTGAA
GCCATTCGAGAGAGACATCTCCACTGAGATCTACCAAGCTGGTTCCACT
CCATGTAACGGTGTTGAGGGTTTCAACTGTTACTTCCCATTGCAGTCCT
ACGGTTTCCAGCCAACTAATGGTGTTGGTTACCAGCCATACAGAGTCGT
CGTTTTGTCCTTCGAGTTGTTGCATGCTCCAGCTACTGTTTGCGGTCCA
AAGAAGTCCACTAACCTGGTCAAGAACAAGTGCGTCAACTTTAACTTCA
ACGGTCTGACCGGTACTGGTGTTTTGACTGAGTCCAACAAGAAGTTCCT
GCCATTCCAGCAATTCGGTAGAGACATTGCTGACACTACTGACGCCGTT
AGAGATCCACAGACTTTGGAGATCTTGGACATCACCCCATGTTCT |

What is claimed is:

1. A SARS-CoV-2 Spike (S) glycoprotein variant, wherein the S glycoprotein variant comprises a receptor binding domain (RBD) having a mutation of at least one amino acid residue in an angiostensin-converting enzyme 2 (ACE2) receptor binding motif (RBM) relative to a wild-type RBD, wherein the residue is (i) hydrophobic; and (ii) within an aggregation-prone region of about 3-15 amino acid residues, wherein the mutation is a substitution of the hydrophobic residue with a different amino acid residue.

2. The SARS-CoV-2 S glycoprotein variant of claim 1, wherein (a) the hydrophobic residue has a positive AggScore, (b) the substitution of the hydrophobic residue reduces the overall aggregation score of the aggregation prone region by about 5-50% relative to the aggregation prone region without the substitution, and/or (c) the substitution of the hydrophobic residue reduces the overall aggregation score of the S glycoprotein variant by about 5-50% relative to the S glycoprotein variant without the substitution.

3. A SARS-CoV-2 Spike (S) glycoprotein variant, wherein the S glycoprotein variant comprises an RBD having a mutation of at least one amino acid residue in a first and/or second aggregation-prone region relative to a wild-type RBD comprising the amino acid sequence of SEQ ID NO: 1, wherein the first aggregation-prone region comprises amino acid residues 122-126 of SEQ ID NO: 1, and the second aggregation-prone region comprises amino acid residues 158-162 of SEQ ID NO: 1, and wherein the mutation is a substitution with a different amino acid residue.

4. The SARS-CoV-2 S glycoprotein variant of claim 3, wherein
(a) the at least one amino acid residue is selected from: L122, L125, F126, Y159, F160, and any combination thereof;
(b) the S glycoprotein variant comprises an amino acid substitution at L122 with a different amino acid residue;
(c) the S glycoprotein variant comprises an amino acid substitution at L122 and F160 with a different amino acid residue; or
(d) the S glycoprotein variant comprises an amino acid substitution at L122, L125, F126 and F160 with a different amino acid residue.

5. The SARS-CoV-2 S glycoprotein variant of claim 3, wherein the substitution is selected from the group: L122K, L122F, L122Y, L122S, L125Y, L125S, L125W, L125N, F126L, F126H, F126V, F126K, Y159V, Y159A, F160W, F160M, F160R, F160N, F160Y, and any combination thereof.

6. The SARS-CoV-2 S glycoprotein variant of claim 5, wherein
(a) the S glycoprotein variant comprises L122K;
(b) the S glycoprotein variant comprises L122K and F160W; or
(c) the S glycoprotein variant comprises L122K, L125Y, F126L and F160W.

7. The SARS-CoV-2 S glycoprotein variant of claim 3, wherein the RBD comprises a mutation of at least one asparagine-linked glycosylation site relative to the wild-type RBD.

8. The SARS-CoV-2 S glycoprotein variant of claim 7, wherein the mutation is selected from:
(i) a substitution or deletion of the asparagine-linked glycosylation site at amino acid residue 1 of SEQ ID NO: 1;
(ii) a substitution or deletion of the asparagine-linked glycosylation site at amino acid residue 13 of SEQ ID NO: 1; or
(iii) a combination of (i)-(ii).

9. The SARS-CoV-2 S glycoprotein variant of claim 3, comprising an amino acid sequence selected from: SEQ ID NO: 8, 9, 11, 15, and 16.

10. The SARS-CoV-2 S glycoprotein variant of claim 3, wherein the S glycoprotein variant comprises a mutation of at least one amino acid residue in a first and/or second aggregation-prone region of 3-15 amino acid residues that is not part of the ACE2 RBM, wherein the mutation is a substitution with a different amino acid residue, optionally wherein the different amino acid residue is less hydrophobic, found at the same position in a genetic background of at least one species of SARS-CoV, or both.

11. The SARS-CoV-2 S glycoprotein variant of claim 3, comprising at least one additional amino acid residue substitution selected from: P7D, V11I, A18P, N24E, R27K, Y35W, V37F, K48R, S53D, L60Y, F62W, I72V, R78D, Q84A, K87V, D98N, L111I, L125N, Q168D, Y178H, L188D, V194R, and any combination thereof.

12. A SARS-CoV-2 S glycoprotein variant, wherein the S glycoprotein variant comprises a RBD comprising a mutation of at least one amino acid residue in an ACE2 RBM relative to a wild-type RBD comprising the amino acid sequence of SEQ ID NO: 1, wherein the amino acid residue is L122 of SEQ ID NO: 1, and optionally F160 of SEQ ID NO: 1, and wherein the mutation is a substitution with a different amino acid residue.

13. The SARS-CoV-2 S glycoprotein variant of claim 12, wherein the mutation of L122 of SEQ ID NO: 1 is a substitution of leucine with lysine (L122K), phenylalanine (L122F), tyrosine (L122Y), or serine (L122S).

14. The SARS-CoV-2 S glycoprotein variant of claim 12, wherein the S glycoprotein variant comprises a mutation of F160 of SEQ ID NO: 1, wherein the mutation is a substitution with a different amino acid residue, optionally wherein the different amino acid residue is less hydrophobic, found at the same position in a genetic background of at least one species of SARS-CoV, or both.

15. A nucleic acid comprising a nucleotide sequence encoding the SARS-CoV-2 S glycoprotein variant of claim 1.

16. An expression vector comprising the nucleic acid of claim 15.

17. A cell transformed with an expression vector of claim 16.

18. A method for producing an SARS-CoV-2 S glycoprotein variant, the method comprising maintaining the cell of claim 17 under conditions permitting expression of the S glycoprotein variant.

19. A composition comprising:
(a) the SARS-CoV-2 S glycoprotein variant of claim 1, and
(b) a pharmaceutically acceptable carrier, adjuvant, or package insert comprising instructions for administration of the composition to a subject for inducing an immune response against the S glycoprotein variant.

20. A method of inducing an immune response in a subject or preventing infection of SARS-CoV-2 in a subject comprising, administering to the subject the SARS-CoV-2 S glycoprotein variant of claim 1.

* * * * *

SEQUENCE LISTING

<160> NUMBER OF SEQ ID NOS: 123

<210> SEQ ID NO 1
<211> LENGTH: 202
<212> TYPE: PRT
<213> ORGANISM: Artificial Sequence
<220> FEATURE:
<223> OTHER INFORMATION: Synthetic

<400> SEQUENCE: 1

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn
            195                 200

<210> SEQ ID NO 2
<211> LENGTH: 201
<212> TYPE: PRT
<213> ORGANISM: Artificial Sequence
<220> FEATURE:
<223> OTHER INFORMATION: Synthetic

<400> SEQUENCE: 2

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala

```
                   130                 135                 140
Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 3
<211> LENGTH: 202
<212> TYPE: PRT
<213> ORGANISM: Artificial Sequence
<220> FEATURE:
<223> OTHER INFORMATION: Synthetic

<400> SEQUENCE: 3

Asn Ile Thr Asn Leu Cys Pro Phe Gly Glu Val Phe Gln Ala Thr Arg
1               5                   10                  15

Phe Ala Ser Val Tyr Ala Trp Asn Arg Lys Arg Ile Ser Asn Cys Val
                20                  25                  30

Ala Asp Tyr Ser Val Leu Tyr Asn Ser Ala Ser Phe Ser Thr Phe Lys
            35                  40                  45

Cys Tyr Gly Val Ser Pro Thr Lys Leu Asn Asp Leu Cys Phe Thr Asn
50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn
        195                 200

<210> SEQ ID NO 4
<211> LENGTH: 201
<212> TYPE: PRT
<213> ORGANISM: Artificial Sequence
<220> FEATURE:
<223> OTHER INFORMATION: Synthetic

<400> SEQUENCE: 4

Ile Thr Asn Leu Cys Pro Phe Gly Glu Val Phe Gln Ala Thr Arg Phe
1               5                   10                  15

Ala Ser Val Tyr Ala Trp Asn Arg Lys Arg Ile Ser Asn Cys Val Ala
                20                  25                  30
```

```
Asp Tyr Ser Val Leu Tyr Asn Ser Ala Ser Phe Ser Thr Phe Lys Cys
            35                  40                  45

Tyr Gly Val Ser Pro Thr Lys Leu Asn Asp Leu Cys Phe Thr Asn Val
 50                  55                  60

Tyr Ala Asp Ser Phe Val Ile Arg Gly Asp Glu Val Arg Gln Ile Ala
 65                  70                  75                  80

Pro Gly Gln Thr Gly Lys Ile Ala Asp Tyr Asn Tyr Lys Leu Pro Asp
                 85                  90                  95

Asp Phe Thr Gly Cys Val Ile Ala Trp Asn Ser Asn Asn Leu Asp Ser
                100                 105                 110

Lys Val Gly Gly Asn Tyr Asn Tyr Leu Tyr Arg Leu Phe Arg Lys Ser
                115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn
                195                 200

<210> SEQ ID NO 5
<211> LENGTH: 240
<212> TYPE: PRT
<213> ORGANISM: Artificial Sequence
<220> FEATURE:
<223> OTHER INFORMATION: Synthetic

<400> SEQUENCE: 5

Ile Thr Asn Leu Cys Pro Phe Gly Glu Val Phe Asn Ala Thr Lys Phe
 1               5                  10                  15

Pro Ser Val Tyr Ala Trp Glu Arg Lys Lys Ile Ser Asn Cys Val Ala
                 20                  25                  30

Asp Tyr Ser Val Leu Tyr Asn Ser Thr Phe Phe Ser Thr Phe Lys Cys
            35                  40                  45

Tyr Gly Val Ser Ala Thr Lys Leu Asn Asp Leu Cys Phe Ser Asn Val
 50                  55                  60

Tyr Ala Asp Ser Phe Val Val Lys Gly Asp Asp Val Arg Gln Ile Ala
 65                  70                  75                  80

Pro Gly Gln Thr Gly Val Ile Ala Asp Tyr Asn Tyr Lys Leu Pro Asp
                 85                  90                  95

Asp Phe Met Gly Cys Val Leu Ala Trp Asn Thr Arg Asn Ile Asp Ala
                100                 105                 110

Thr Ser Thr Gly Asn Tyr Asn Tyr Lys Tyr Arg Tyr Leu Arg His Gly
                115                 120                 125

Lys Leu Arg Pro Phe Glu Arg Asp Ile Ser Asn Val Pro Phe Ser Pro
    130                 135                 140

Asp Gly Lys Pro Cys Thr Pro Pro Ala Leu Asn Cys Tyr Trp Pro Leu
145                 150                 155                 160

Asn Asp Tyr Gly Phe Tyr Thr Thr Thr Gly Ile Gly Tyr Gln Pro Tyr
                165                 170                 175

Arg Val Val Val Leu Ser Phe Glu Leu Leu Asn Ala Pro Ala Thr Val
                180                 185                 190
```

```
Cys Gly Pro Lys Leu Ser Thr Asp Leu Ile Lys Asn Gln Cys Val Asn
            195                 200                 205
Phe Asn Phe Asn Gly Leu Thr Gly Thr Gly Gly Ser Leu Glu Val Leu
210                 215                 220
Phe Gln Gly Pro Gly Ser His His His His His His His His
225                 230                 235                 240

<210> SEQ ID NO 6
<211> LENGTH: 201
<212> TYPE: PRT
<213> ORGANISM: Artificial Sequence
<220> FEATURE:
<223> OTHER INFORMATION: Synthetic

<400> SEQUENCE: 6

Ile Thr Asn Leu Cys Pro Phe Gly Glu Val Phe Asn Ala Thr Arg Phe
1               5                   10                  15
Ala Ser Val Tyr Ala Trp Asn Arg Lys Arg Ile Ser Asn Cys Val Ala
            20                  25                  30
Asp Tyr Ser Val Ala Tyr Asn Ser Ala Ser Phe Ser Thr Phe Lys Cys
        35                  40                  45
Tyr Gly Val Ser Pro Thr Lys Leu Asn Asp Leu Cys Phe Thr Asn Val
50                  55                  60
Tyr Ala Asp Ser Phe Val Ile Arg Gly Asp Glu Val Arg Gln Ile Ala
65                  70                  75                  80
Pro Gly Gln Thr Gly Lys Ile Ala Asp Tyr Asn Tyr Lys Leu Pro Asp
            85                  90                  95
Asp Phe Thr Gly Cys Val Ile Ala Trp Asn Ser Asn Asn Leu Asp Ser
        100                 105                 110
Lys Val Gly Gly Asn Tyr Asn Tyr Lys Tyr Arg Tyr Leu Arg Lys Ser
            115                 120                 125
Asn Leu Lys Pro Phe Glu Arg Asp Ile Ser Thr Glu Ile Tyr Gln Ala
130                 135                 140
Gly Ser Thr Pro Cys Asn Gly Val Glu Gly Phe Asn Cys Tyr Trp Pro
145                 150                 155                 160
Leu Gln Ser Tyr Gly Phe Gln Pro Thr Asn Gly Val Gly Tyr Gln Pro
            165                 170                 175
Tyr Arg Val Val Val Leu Ser Phe Glu Ala Ala His Ala Pro Ala Thr
        180                 185                 190
Val Cys Gly Pro Lys Lys Ser Thr Asn
            195                 200

<210> SEQ ID NO 7
<211> LENGTH: 201
<212> TYPE: PRT
<213> ORGANISM: Artificial Sequence
<220> FEATURE:
<223> OTHER INFORMATION: Synthetic

<400> SEQUENCE: 7

Ile Thr Asn Leu Cys Pro Phe Gly Glu Val Phe Asn Ala Thr Arg Phe
1               5                   10                  15
Ala Ser Val Tyr Ala Trp Asn Arg Lys Arg Ile Ser Asn Cys Val Ala
            20                  25                  30
Asp Tyr Ser Val Ala Tyr Asn Ser Ala Ser Phe Ser Thr Phe Lys Cys
        35                  40                  45
Tyr Gly Val Ser Pro Thr Lys Leu Asn Asp Leu Cys Phe Thr Asn Val
50                  55                  60
```

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Ala Ala His Ala Pro Ala Thr
            180                 185                 190

Val Cys Gly Pro Lys Lys Ser Thr Asn
        195                 200

<210> SEQ ID NO 8
<211> LENGTH: 201
<212> TYPE: PRT
<213> ORGANISM: Artificial Sequence
<220> FEATURE:
<223> OTHER INFORMATION: Synthetic

<400> SEQUENCE: 8

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Tyr Leu Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 9

<211> LENGTH: 201
<212> TYPE: PRT
<213> ORGANISM: Artificial Sequence
<220> FEATURE:
<223> OTHER INFORMATION: Synthetic

<400> SEQUENCE: 9

```
Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200
```

<210> SEQ ID NO 10
<211> LENGTH: 201
<212> TYPE: PRT
<213> ORGANISM: Artificial Sequence
<220> FEATURE:
<223> OTHER INFORMATION: Synthetic

<400> SEQUENCE: 10

```
Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Ala Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
```

```
            115                 120                 125

Asn Leu Lys Pro Phe Glu Arg Asp Ile Ser Thr Glu Ile Tyr Gln Ala
            130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Ala Ala His Ala Pro Ala Thr
                180                 185                 190

Val Cys Gly Pro Lys Lys Ser Thr Asn
            195                 200

<210> SEQ ID NO 11
<211> LENGTH: 201
<212> TYPE: PRT
<213> ORGANISM: Artificial Sequence
<220> FEATURE:
<223> OTHER INFORMATION: Synthetic

<400> SEQUENCE: 11

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn
            195                 200

<210> SEQ ID NO 12
<211> LENGTH: 201
<212> TYPE: PRT
<213> ORGANISM: Artificial Sequence
<220> FEATURE:
<223> OTHER INFORMATION: Synthetic

<400> SEQUENCE: 12

Ile Thr Asn Leu Cys Pro Phe Gly Glu Val Phe Asn Ala Thr Arg Phe
1               5                   10                  15
```

```
Ala Ser Val Tyr Ala Trp Asn Arg Lys Arg Ile Ser Asn Cys Val Ala
             20                  25                  30

Asp Tyr Ser Val Met Tyr Asn Ser Ala Ser Phe Ser Thr Phe Lys Cys
         35                  40                  45

Tyr Gly Val Ser Pro Thr Lys Leu Asn Asp Leu Cys Phe Thr Asn Val
     50                  55                  60

Tyr Ala Asp Ser Phe Val Ile Arg Gly Asp Glu Val Arg Gln Ile Ala
 65                  70                  75                  80

Pro Gly Gln Thr Gly Lys Ile Ala Asp Tyr Asn Tyr Lys Leu Pro Asp
                 85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
            195                 200

<210> SEQ ID NO 13
<211> LENGTH: 201
<212> TYPE: PRT
<213> ORGANISM: Artificial Sequence
<220> FEATURE:
<223> OTHER INFORMATION: Synthetic

<400> SEQUENCE: 13

Ile Thr Asn Leu Cys Pro Phe Gly Glu Val Phe Asn Ala Thr Arg Phe
  1               5                  10                  15

Ala Ser Val Tyr Ala Trp Asn Arg Lys Arg Ile Ser Asn Cys Val Ala
             20                  25                  30

Asp Tyr Ser Val Met Tyr Asn Ser Ala Ser Phe Ser Thr Phe Lys Cys
         35                  40                  45

Tyr Gly Val Ser Pro Thr Lys Leu Asn Asp Leu Cys Phe Thr Asn Val
     50                  55                  60

Tyr Ala Asp Ser Phe Val Ile Arg Gly Asp Glu Val Arg Gln Ile Ala
 65                  70                  75                  80

Pro Gly Gln Thr Gly Lys Ile Ala Asp Tyr Asn Tyr Lys Leu Pro Asp
                 85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175
```

```
Tyr Arg Val Val Val Leu Ser Phe Glu Leu Met His Ala Pro Ala Thr
            180                 185                 190

Val Cys Gly Pro Lys Lys Ser Thr Asn
        195                 200

<210> SEQ ID NO 14
<211> LENGTH: 201
<212> TYPE: PRT
<213> ORGANISM: Artificial Sequence
<220> FEATURE:
<223> OTHER INFORMATION: Synthetic

<400> SEQUENCE: 14

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Met Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Met His Ala Pro Ala Thr
            180                 185                 190

Val Cys Gly Pro Lys Lys Ser Thr Asn
        195                 200

<210> SEQ ID NO 15
<211> LENGTH: 201
<212> TYPE: PRT
<213> ORGANISM: Artificial Sequence
<220> FEATURE:
<223> OTHER INFORMATION: Synthetic

<400> SEQUENCE: 15

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80
```

Pro Gly Gln Thr Gly Lys Ile Ala Asp Tyr Asn Tyr Lys Leu Pro Asp
            85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
            115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Arg Phe Pro
145                 150                 155                 160

Leu Gln Ser Tyr Gly Phe Gln Pro Thr Asn Gly Val Gly Tyr Gln Pro
            165                 170                 175

Tyr Arg Val Val Val Leu Ser Phe Glu Leu Leu His Ala Pro Ala Thr
            180                 185                 190

Val Cys Gly Pro Lys Lys Ser Thr Asn
            195                 200

<210> SEQ ID NO 16
<211> LENGTH: 201
<212> TYPE: PRT
<213> ORGANISM: Artificial Sequence
<220> FEATURE:
<223> OTHER INFORMATION: Synthetic

<400> SEQUENCE: 16

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
            35                  40                  45

Tyr Gly Val Ser Pro Thr Lys Leu Asn Asp Leu Cys Phe Thr Asn Val
        50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
            85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
            115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Met Pro
145                 150                 155                 160

Leu Gln Ser Tyr Gly Phe Gln Pro Thr Asn Gly Val Gly Tyr Gln Pro
            165                 170                 175

Tyr Arg Val Val Val Leu Ser Phe Glu Leu Leu His Ala Pro Ala Thr
            180                 185                 190

Val Cys Gly Pro Lys Lys Ser Thr Asn
            195                 200

<210> SEQ ID NO 17
<211> LENGTH: 201
<212> TYPE: PRT
<213> ORGANISM: Artificial Sequence
<220> FEATURE:
<223> OTHER INFORMATION: Synthetic

<400> SEQUENCE: 17

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Arg Met Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 18
<211> LENGTH: 201
<212> TYPE: PRT
<213> ORGANISM: Artificial Sequence
<220> FEATURE:
<223> OTHER INFORMATION: Synthetic

<400> SEQUENCE: 18

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Met Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala

```
                130                 135                 140
Gly Ser Thr Pro Cys Asn Gly Val Glu Gly Phe Asn Cys Arg Met Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Met His Ala Pro Ala Thr
            180                 185                 190

Val Cys Gly Pro Lys Lys Ser Thr Asn
        195                 200

<210> SEQ ID NO 19
<211> LENGTH: 201
<212> TYPE: PRT
<213> ORGANISM: Artificial Sequence
<220> FEATURE:
<223> OTHER INFORMATION: Synthetic

<400> SEQUENCE: 19

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Tyr Leu Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 20
<211> LENGTH: 201
<212> TYPE: PRT
<213> ORGANISM: Artificial Sequence
<220> FEATURE:
<223> OTHER INFORMATION: Synthetic

<400> SEQUENCE: 20

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30
```

```
Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
                100                 105                 110

Lys Val Gly Gly Asn Tyr Asn Tyr Lys Tyr Arg Tyr Leu Arg Lys Ser
            115                 120                 125

Asn Leu Lys Pro Phe Glu Arg Asp Ile Ser Thr Glu Ile Tyr Gln Ala
        130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 21
<211> LENGTH: 201
<212> TYPE: PRT
<213> ORGANISM: Artificial Sequence
<220> FEATURE:
<223> OTHER INFORMATION: Synthetic

<400> SEQUENCE: 21

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
                100                 105                 110

Lys Val Gly Gly Asn Tyr Asn Tyr Leu Tyr Arg Ser Leu Arg Lys Ser
            115                 120                 125

Asn Leu Lys Pro Phe Glu Arg Asp Ile Ser Thr Glu Ile Tyr Gln Ala
        130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190
```

Val Cys Gly Pro Lys Lys Ser Thr Asn
        195                 200

<210> SEQ ID NO 22
<211> LENGTH: 201
<212> TYPE: PRT
<213> ORGANISM: Artificial Sequence
<220> FEATURE:
<223> OTHER INFORMATION: Synthetic

<400> SEQUENCE: 22

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Ser Leu Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 23
<211> LENGTH: 201
<212> TYPE: PRT
<213> ORGANISM: Artificial Sequence
<220> FEATURE:
<223> OTHER INFORMATION: Synthetic

<400> SEQUENCE: 23

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

```
Asp Phe Thr Gly Cys Val Ile Ala Trp Asn Ser Asn Asn Leu Asp Ser
            100                 105                 110

Lys Val Gly Gly Asn Tyr Asn Tyr Ala Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn
        195                 200

<210> SEQ ID NO 24
<211> LENGTH: 201
<212> TYPE: PRT
<213> ORGANISM: Artificial Sequence
<220> FEATURE:
<223> OTHER INFORMATION: Synthetic

<400> SEQUENCE: 24

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Val Arg Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn
        195                 200

<210> SEQ ID NO 25
<211> LENGTH: 201
<212> TYPE: PRT
<213> ORGANISM: Artificial Sequence
<220> FEATURE:
<223> OTHER INFORMATION: Synthetic
```

<400> SEQUENCE: 25

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Asn Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 26
<211> LENGTH: 201
<212> TYPE: PRT
<213> ORGANISM: Artificial Sequence
<220> FEATURE:
<223> OTHER INFORMATION: Synthetic

<400> SEQUENCE: 26

Ile Thr Asn Leu Cys Pro Phe Gly Glu Val Phe Asn Ala Thr Arg Phe
1               5                   10                  15

Ala Ser Val Tyr Ala Trp Glu Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro

```
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn
                195                 200

<210> SEQ ID NO 27
<211> LENGTH: 201
<212> TYPE: PRT
<213> ORGANISM: Artificial Sequence
<220> FEATURE:
<223> OTHER INFORMATION: Synthetic

<400> SEQUENCE: 27

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
                20                  25                  30

Asp Trp Ser Val Leu Tyr Asn Ser Ala Ser Phe Ser Thr Phe Lys Cys
            35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn
                195                 200

<210> SEQ ID NO 28
<211> LENGTH: 201
<212> TYPE: PRT
<213> ORGANISM: Artificial Sequence
<220> FEATURE:
<223> OTHER INFORMATION: Synthetic

<400> SEQUENCE: 28

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
                20                  25                  30

Asp Tyr Ser Phe Leu Tyr Asn Ser Ala Ser Phe Ser Thr Phe Lys Cys
            35                  40                  45
```

Tyr Gly Val Ser Pro Thr Lys Leu Asn Asp Leu Cys Phe Thr Asn Val
 50                  55                  60

Tyr Ala Asp Ser Phe Val Ile Arg Gly Asp Glu Val Arg Gln Ile Ala
 65                  70                  75                  80

Pro Gly Gln Thr Gly Lys Ile Ala Asp Tyr Asn Tyr Lys Leu Pro Asp
                 85                  90                  95

Asp Phe Thr Gly Cys Val Ile Ala Trp Asn Ser Asn Asn Leu Asp Ser
                100                 105                 110

Lys Val Gly Gly Asn Tyr Asn Tyr Lys Tyr Arg Leu Phe Arg Lys Ser
                115                 120                 125

Asn Leu Lys Pro Phe Glu Arg Asp Ile Ser Thr Glu Ile Tyr Gln Ala
130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn
                195                 200

<210> SEQ ID NO 29
<211> LENGTH: 201
<212> TYPE: PRT
<213> ORGANISM: Artificial Sequence
<220> FEATURE:
<223> OTHER INFORMATION: Synthetic

<400> SEQUENCE: 29

Ile Thr Asn Leu Cys Pro Phe Gly Glu Ala Phe Asn Ala Thr Arg Phe
 1               5                  10                  15

Ala Ser Val Tyr Ala Trp Asn Arg Lys Arg Ile Ser Asn Cys Val Ala
                 20                  25                  30

Asp Tyr Ser Val Leu Tyr Asn Ser Ala Ser Phe Ser Thr Phe Lys Cys
             35                  40                  45

Tyr Gly Val Ser Pro Thr Lys Leu Asn Asp Leu Cys Phe Thr Asn Val
 50                  55                  60

Tyr Ala Asp Ser Phe Val Ile Arg Gly Asp Glu Val Arg Gln Ile Ala
 65                  70                  75                  80

Pro Gly Gln Thr Gly Lys Ile Ala Asp Tyr Asn Tyr Lys Leu Pro Asp
                 85                  90                  95

Asp Phe Thr Gly Cys Val Ile Ala Trp Asn Ser Asn Asn Leu Asp Ser
                100                 105                 110

Lys Val Gly Gly Asn Tyr Asn Tyr Lys Tyr Arg Leu Phe Arg Lys Ser
                115                 120                 125

Asn Leu Lys Pro Phe Glu Arg Asp Ile Ser Thr Glu Ile Tyr Gln Ala
130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn
                195                 200

```
<210> SEQ ID NO 30
<211> LENGTH: 201
<212> TYPE: PRT
<213> ORGANISM: Artificial Sequence
<220> FEATURE:
<223> OTHER INFORMATION: Synthetic

<400> SEQUENCE: 30

Ile Thr Asn Leu Cys Pro Phe Gly Glu Val Phe Asn Ala Thr Arg Phe
1               5                   10                  15

Pro Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 31
<211> LENGTH: 201
<212> TYPE: PRT
<213> ORGANISM: Artificial Sequence
<220> FEATURE:
<223> OTHER INFORMATION: Synthetic

<400> SEQUENCE: 31

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Val Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110
```

```
Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 32
<211> LENGTH: 201
<212> TYPE: PRT
<213> ORGANISM: Artificial Sequence
<220> FEATURE:
<223> OTHER INFORMATION: Synthetic

<400> SEQUENCE: 32

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Asp His Ala Pro Ala Thr
            180                 185                 190

Val Cys Gly Pro Lys Lys Ser Thr Asn
        195                 200

<210> SEQ ID NO 33
<211> LENGTH: 201
<212> TYPE: PRT
<213> ORGANISM: Artificial Sequence
<220> FEATURE:
<223> OTHER INFORMATION: Synthetic

<400> SEQUENCE: 33

Ile Thr Asn Leu Cys Pro Phe Gly Glu Val Phe Asn Ala Thr Arg Phe
```

```
            1               5                  10                 15
Ala Ser Val Tyr Ala Trp Asn Arg Lys Arg Ile Ser Asn Cys Val Ala
                20                  25                 30

Asp Tyr Ser Val Leu Tyr Asn Ser Ala Ser Phe Ser Thr Phe Lys Cys
            35                  40                 45

Tyr Gly Val Ser Pro Thr Lys Leu Asn Asp Leu Cys Phe Thr Asn Val
        50                  55                 60

Tyr Ala Asp Ser Phe Val Ile Arg Gly Asp Glu Val Arg Gln Ile Ala
65                  70                  75                 80

Pro Gly Gln Thr Gly Lys Ile Ala Asp Tyr Asn Tyr Lys Leu Pro Asp
                85                  90                 95

Asp Phe Thr Gly Cys Val Ile Ala Trp Asn Ser Asn Asn Leu Asp Ser
                100                 105                110

Lys Val Gly Gly Asn Tyr Asn Tyr Lys Tyr Arg Leu Phe Arg Lys Ser
                115                 120                125

Asn Leu Lys Pro Phe Glu Arg Asp Ile Ser Thr Glu Ile Tyr Gln Ala
        130                 135                 140

Gly Ser Thr Pro Cys Asn Gly Val Glu Gly Phe Asn Cys Tyr Phe Pro
145                 150                 155                160

Leu Gln Ser Tyr Gly Phe Gln Pro Thr Asn Gly Val Gly Tyr Gln Pro
                165                 170                175

Tyr Arg Val Val Val Leu Ser Phe Glu Leu Leu His Ala Pro Ala Thr
                180                 185                190

Arg Cys Gly Pro Lys Lys Ser Thr Asn
        195                 200
```

<210> SEQ ID NO 34
<211> LENGTH: 201
<212> TYPE: PRT
<213> ORGANISM: Artificial Sequence
<220> FEATURE:
<223> OTHER INFORMATION: Synthetic

<400> SEQUENCE: 34

```
Ile Thr Asn Leu Cys Asp Phe Gly Glu Val Phe Asn Ala Thr Arg Phe
1               5                   10                 15

Ala Ser Val Tyr Ala Trp Asn Arg Lys Arg Ile Ser Asn Cys Val Ala
                20                  25                 30

Asp Tyr Ser Val Leu Tyr Asn Ser Ala Ser Phe Ser Thr Phe Lys Cys
            35                  40                 45

Tyr Gly Val Ser Pro Thr Lys Leu Asn Asp Leu Cys Phe Thr Asn Val
        50                  55                 60

Tyr Ala Asp Ser Phe Val Ile Arg Gly Asp Glu Val Arg Gln Ile Ala
65                  70                  75                 80

Pro Gly Gln Thr Gly Lys Ile Ala Asp Tyr Asn Tyr Lys Leu Pro Asp
                85                  90                 95

Asp Phe Thr Gly Cys Val Ile Ala Trp Asn Ser Asn Asn Leu Asp Ser
                100                 105                110

Lys Val Gly Gly Asn Tyr Asn Tyr Lys Tyr Arg Leu Phe Arg Lys Ser
                115                 120                125

Asn Leu Lys Pro Phe Glu Arg Asp Ile Ser Thr Glu Ile Tyr Gln Ala
        130                 135                 140

Gly Ser Thr Pro Cys Asn Gly Val Glu Gly Phe Asn Cys Tyr Phe Pro
145                 150                 155                160

Leu Gln Ser Tyr Gly Phe Gln Pro Thr Asn Gly Val Gly Tyr Gln Pro
```

```
                          165                 170                 175

Tyr Arg Val Val Val Leu Ser Phe Glu Leu Leu His Ala Pro Ala Thr
            180                 185                 190

Val Cys Gly Pro Lys Lys Ser Thr Asn
            195                 200

<210> SEQ ID NO 35
<211> LENGTH: 201
<212> TYPE: PRT
<213> ORGANISM: Artificial Sequence
<220> FEATURE:
<223> OTHER INFORMATION: Synthetic

<400> SEQUENCE: 35

Ile Thr Asn Leu Cys Pro Phe Gly Glu Val Phe Asn Ala Thr Arg Phe
1               5                   10                  15

Ala Ser Val Tyr Ala Trp Asn Arg Lys Lys Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
            195                 200

<210> SEQ ID NO 36
<211> LENGTH: 201
<212> TYPE: PRT
<213> ORGANISM: Artificial Sequence
<220> FEATURE:
<223> OTHER INFORMATION: Synthetic

<400> SEQUENCE: 36

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Asp Pro Thr Lys Leu Asn Asp Leu Cys Phe Thr Asn Val
    50                  55                  60
```

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn
            195                 200

<210> SEQ ID NO 37
<211> LENGTH: 201
<212> TYPE: PRT
<213> ORGANISM: Artificial Sequence
<220> FEATURE:
<223> OTHER INFORMATION: Synthetic

<400> SEQUENCE: 37

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Tyr Cys Phe Thr Asn Val
50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn
            195                 200

<210> SEQ ID NO 38
<211> LENGTH: 201

<212> TYPE: PRT
<213> ORGANISM: Artificial Sequence
<220> FEATURE:
<223> OTHER INFORMATION: Synthetic

<400> SEQUENCE: 38

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Trp Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 39
<211> LENGTH: 201
<212> TYPE: PRT
<213> ORGANISM: Artificial Sequence
<220> FEATURE:
<223> OTHER INFORMATION: Synthetic

<400> SEQUENCE: 39

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Asp Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

```
Asn Leu Lys Pro Phe Glu Arg Asp Ile Ser Thr Glu Ile Tyr Gln Ala
        130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
            195                 200
```

<210> SEQ ID NO 40
<211> LENGTH: 201
<212> TYPE: PRT
<213> ORGANISM: Artificial Sequence
<220> FEATURE:
<223> OTHER INFORMATION: Synthetic

<400> SEQUENCE: 40

```
Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Ala Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
            195                 200
```

<210> SEQ ID NO 41
<211> LENGTH: 201
<212> TYPE: PRT
<213> ORGANISM: Artificial Sequence
<220> FEATURE:
<223> OTHER INFORMATION: Synthetic

<400> SEQUENCE: 41

```
Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30
```

```
            20                  25                  30
Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asn Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 42
<211> LENGTH: 201
<212> TYPE: PRT
<213> ORGANISM: Artificial Sequence
<220> FEATURE:
<223> OTHER INFORMATION: Synthetic

<400> SEQUENCE: 42

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Ile Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
```

Val Cys Gly Pro Lys Lys Ser Thr Asn
            195                 200

<210> SEQ ID NO 43
<211> LENGTH: 201
<212> TYPE: PRT
<213> ORGANISM: Artificial Sequence
<220> FEATURE:
<223> OTHER INFORMATION: Synthetic

<400> SEQUENCE: 43

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

His Arg Val Val Val Leu Ser Phe Glu Leu Leu His Ala Pro Ala Thr
            180                 185                 190

Val Cys Gly Pro Lys Lys Ser Thr Asn
            195                 200

<210> SEQ ID NO 44
<211> LENGTH: 201
<212> TYPE: PRT
<213> ORGANISM: Artificial Sequence
<220> FEATURE:
<223> OTHER INFORMATION: Synthetic

<400> SEQUENCE: 44

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Arg Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

```
Pro Gly Gln Thr Gly Lys Ile Ala Asp Tyr Asn Tyr Lys Leu Pro Asp
            85                  90                  95

Asp Phe Thr Gly Cys Val Ile Ala Trp Asn Ser Asn Asn Leu Asp Ser
        100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 45
<211> LENGTH: 201
<212> TYPE: PRT
<213> ORGANISM: Artificial Sequence
<220> FEATURE:
<223> OTHER INFORMATION: Synthetic

<400> SEQUENCE: 45

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Val Arg Gly Asp Glu Val Arg Gln Ile Ala
65                  70                  75                  80

Pro Gly Gln Thr Gly Lys Ile Ala Asp Tyr Asn Tyr Lys Leu Pro Asp
            85                  90                  95

Asp Phe Thr Gly Cys Val Ile Ala Trp Asn Ser Asn Asn Leu Asp Ser
        100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn
        195                 200

<210> SEQ ID NO 46
<211> LENGTH: 201
<212> TYPE: PRT
<213> ORGANISM: Artificial Sequence
<220> FEATURE:
```

<223> OTHER INFORMATION: Synthetic

<400> SEQUENCE: 46

```
Ile Thr Asn Leu Cys Pro Phe Gly Glu Val Phe Asn Ala Thr Arg Phe
1               5                   10                  15
Ala Ser Val Tyr Ala Trp Asn Arg Lys Arg Ile Ser Asn Cys Val Ala
            20                  25                  30
Asp Tyr Ser Val Leu Tyr Asn Ser Ala Ser Phe Ser Thr Phe Lys Cys
        35                  40                  45
Tyr Gly Val Ser Pro Thr Lys Leu Asn Asp Leu Cys Phe Thr Asn Val
    50                  55                  60
Tyr Ala Asp Ser Phe Val Ile Arg Gly Asp Glu Val Arg Gln Ile Ala
65                  70                  75                  80
Pro Gly Gln Thr Gly Lys Ile Ala Asp Tyr Asn Tyr Lys Leu Pro Asp
                85                  90                  95
Asp Phe Thr Gly Cys Val Ile Ala Trp Asn Ser Asn Asn Leu Asp Ser
            100                 105                 110
Lys Val Gly Gly Asn Tyr Asn Tyr Lys Tyr Arg Leu Phe Arg Lys Ser
        115                 120                 125
Asn Leu Lys Pro Phe Glu Arg Asp Ile Ser Thr Glu Ile Tyr Gln Ala
    130                 135                 140
Gly Ser Thr Pro Cys Asn Gly Val Glu Gly Phe Asn Cys Tyr Phe Pro
145                 150                 155                 160
Leu Asp Ser Tyr Gly Phe Gln Pro Thr Asn Gly Val Gly Tyr Gln Pro
                165                 170                 175
Tyr Arg Val Val Val Leu Ser Phe Glu Leu Leu His Ala Pro Ala Thr
            180                 185                 190
Val Cys Gly Pro Lys Lys Ser Thr Asn
        195                 200
```

<210> SEQ ID NO 47
<211> LENGTH: 201
<212> TYPE: PRT
<213> ORGANISM: Artificial Sequence
<220> FEATURE:
<223> OTHER INFORMATION: Synthetic

<400> SEQUENCE: 47

```
Ile Thr Asn Leu Cys Pro Phe Gly Glu Val Phe Asn Ala Thr Arg Phe
1               5                   10                  15
Ala Ser Val Tyr Ala Trp Asn Arg Lys Arg Ile Ser Asn Cys Val Ala
            20                  25                  30
Asp Tyr Ser Val Leu Tyr Asn Ser Ala Ser Phe Ser Thr Phe Lys Cys
        35                  40                  45
Tyr Gly Val Ser Pro Thr Lys Leu Asn Asp Leu Cys Phe Thr Asn Val
    50                  55                  60
Tyr Ala Asp Ser Phe Val Ile Arg Gly Asp Glu Val Arg Gln Ile Ala
65                  70                  75                  80
Pro Gly Gln Thr Gly Lys Ile Ala Asp Tyr Asn Tyr Lys Leu Pro Asp
                85                  90                  95
Asp Phe Thr Gly Cys Val Ile Ala Trp Asn Ser Asn Asn Leu Asp Ser
            100                 105                 110
Lys Val Gly Gly Asn Tyr Asn Tyr Lys Tyr Arg Asn Phe Arg Lys Ser
        115                 120                 125
Asn Leu Lys Pro Phe Glu Arg Asp Ile Ser Thr Glu Ile Tyr Gln Ala
    130                 135                 140
```

```
Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
            165                 170                 175

Tyr Arg Val Val Val Leu Ser Phe Glu Leu Leu His Ala Pro Ala Thr
        180                 185                 190

Val Cys Gly Pro Lys Lys Ser Thr Asn
        195                 200

<210> SEQ ID NO 48
<211> LENGTH: 208
<212> TYPE: PRT
<213> ORGANISM: Artificial Sequence
<220> FEATURE:
<223> OTHER INFORMATION: Synthetic

<400> SEQUENCE: 48

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
            165                 170                 175

Tyr Arg Val Val Val Leu Ser Phe Glu Leu Leu His Ala Pro Ala Thr
        180                 185                 190

Val Cys Gly Pro Lys Lys Ser Thr Asn His His His His His His Cys
        195                 200                 205

<210> SEQ ID NO 49
<211> LENGTH: 225
<212> TYPE: PRT
<213> ORGANISM: Artificial Sequence
<220> FEATURE:
<223> OTHER INFORMATION: Synthetic

<400> SEQUENCE: 49

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
```

```
            35                  40                  45
Tyr Gly Val Ser Pro Thr Lys Leu Asn Asp Leu Cys Phe Thr Asn Val
 50                  55                  60

Tyr Ala Asp Ser Phe Val Ile Arg Gly Asp Glu Val Arg Gln Ile Ala
 65                  70                  75                  80

Pro Gly Gln Thr Gly Lys Ile Ala Asp Tyr Asn Tyr Lys Leu Pro Asp
                 85                  90                  95

Asp Phe Thr Gly Cys Val Ile Ala Trp Asn Ser Asn Asn Leu Asp Ser
                100                 105                 110

Lys Val Gly Gly Asn Tyr Asn Tyr Leu Tyr Arg Leu Phe Arg Lys Ser
                115                 120                 125

Asn Leu Lys Pro Phe Glu Arg Asp Ile Ser Thr Glu Ile Tyr Gln Ala
130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn Gly Gly Asp Gly Gly Asp Gly
                195                 200                 205

Gly Asp Gly Gly Ala His Ile Val Met Val Asp Ala Tyr Lys Pro Thr
210                 215                 220

Lys
225

<210> SEQ ID NO 50
<211> LENGTH: 225
<212> TYPE: PRT
<213> ORGANISM: Artificial Sequence
<220> FEATURE:
<223> OTHER INFORMATION: Synthetic

<400> SEQUENCE: 50

Ile Thr Asn Leu Cys Pro Phe Gly Glu Val Phe Asn Ala Thr Arg Phe
 1               5                  10                  15

Ala Ser Val Tyr Ala Trp Asn Arg Lys Arg Ile Ser Asn Cys Val Ala
                 20                  25                  30

Asp Tyr Ser Val Leu Tyr Asn Ser Ala Ser Phe Ser Thr Phe Lys Cys
                 35                  40                  45

Tyr Gly Val Ser Pro Thr Lys Leu Asn Asp Leu Cys Phe Thr Asn Val
 50                  55                  60

Tyr Ala Asp Ser Phe Val Ile Arg Gly Asp Glu Val Arg Gln Ile Ala
 65                  70                  75                  80

Pro Gly Gln Thr Gly Lys Ile Ala Asp Tyr Asn Tyr Lys Leu Pro Asp
                 85                  90                  95

Asp Phe Thr Gly Cys Val Ile Ala Trp Asn Ser Asn Asn Leu Asp Ser
                100                 105                 110

Lys Val Gly Gly Asn Tyr Asn Tyr Lys Tyr Arg Leu Phe Arg Lys Ser
                115                 120                 125

Asn Leu Lys Pro Phe Glu Arg Asp Ile Ser Thr Glu Ile Tyr Gln Ala
130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
```

```
                165                 170                 175
Tyr Arg Val Val Val Leu Ser Phe Glu Leu Leu His Ala Pro Ala Thr
            180                 185                 190

Val Cys Gly Pro Lys Lys Ser Thr Asn Gly Gly Asp Gly Gly Asp Gly
        195                 200                 205

Gly Asp Gly Gly Ala His Ile Val Met Val Asp Ala Tyr Lys Pro Thr
    210                 215                 220

Lys
225

<210> SEQ ID NO 51
<211> LENGTH: 207
<212> TYPE: PRT
<213> ORGANISM: Artificial Sequence
<220> FEATURE:
<223> OTHER INFORMATION: Synthetic

<400> SEQUENCE: 51

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn Leu Val Lys Asn Lys Cys
        195                 200                 205

<210> SEQ ID NO 52
<211> LENGTH: 207
<212> TYPE: PRT
<213> ORGANISM: Artificial Sequence
<220> FEATURE:
<223> OTHER INFORMATION: Synthetic

<400> SEQUENCE: 52

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30
```

```
Asp Tyr Ser Val Leu Tyr Asn Ser Ala Ser Phe Ser Thr Phe Lys Cys
            35                  40                  45

Tyr Gly Val Ser Pro Thr Lys Leu Asn Asp Leu Cys Phe Thr Asn Val
        50                  55                  60

Tyr Ala Asp Ser Phe Val Ile Arg Gly Asp Glu Val Arg Gln Ile Ala
 65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
               100                 105                 110

Lys Val Gly Gly Asn Tyr Asn Tyr Lys Tyr Arg Leu Phe Arg Lys Ser
           115                 120                 125

Asn Leu Lys Pro Phe Glu Arg Asp Ile Ser Thr Glu Ile Tyr Gln Ala
130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
               165                 170                 175

Tyr Arg Val Val Val Leu Ser Phe Glu Leu Leu His Ala Pro Ala Thr
           180                 185                 190

Val Cys Gly Pro Lys Lys Ser Thr Asn Leu Val Lys Asn Lys Cys
       195                 200                 205

<210> SEQ ID NO 53
<211> LENGTH: 259
<212> TYPE: PRT
<213> ORGANISM: Artificial Sequence
<220> FEATURE:
<223> OTHER INFORMATION: Synthetic

<400> SEQUENCE: 53

Ile Thr Asn Leu Cys Pro Phe Gly Glu Val Phe Asn Ala Thr Arg Phe
 1               5                  10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
            35                  40                  45

Tyr Gly Val Ser Pro Thr Lys Leu Asn Asp Leu Cys Phe Thr Asn Val
        50                  55                  60

Tyr Ala Asp Ser Phe Val Ile Arg Gly Asp Glu Val Arg Gln Ile Ala
 65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
               100                 105                 110

Lys Val Gly Gly Asn Tyr Asn Tyr Leu Tyr Arg Leu Phe Arg Lys Ser
           115                 120                 125

Asn Leu Lys Pro Phe Glu Arg Asp Ile Ser Thr Glu Ile Tyr Gln Ala
130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
               165                 170                 175

Tyr Arg Val Val Val Leu Ser Phe Glu Leu Leu His Ala Pro Ala Thr
           180                 185                 190
```

Val Cys Gly Pro Lys Lys Ser Thr Asn Leu Val Lys Asn Lys Ser Val
            195                 200                 205

Asn Phe Asn Phe Asn Gly Leu Thr Gly Thr Gly Val Leu Thr Glu Ser
        210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
                245                 250                 255

Thr Pro Cys

<210> SEQ ID NO 54
<211> LENGTH: 262
<212> TYPE: PRT
<213> ORGANISM: Artificial Sequence
<220> FEATURE:
<223> OTHER INFORMATION: Synthetic

<400> SEQUENCE: 54

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn Leu Val Lys Asn Lys Ser Val
        195                 200                 205

Asn Phe Asn Phe Asn Gly Leu Thr Gly Thr Gly Val Leu Thr Glu Ser
    210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
                245                 250                 255

Thr Pro Cys Pro Pro Cys
            260

<210> SEQ ID NO 55
<211> LENGTH: 259
<212> TYPE: PRT

<213> ORGANISM: Artificial Sequence
<220> FEATURE:
<223> OTHER INFORMATION: Synthetic

<400> SEQUENCE: 55

```
Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn Leu Val Lys Asn Lys Ser Val
        195                 200                 205

Asn Phe Asn Phe Asn Gly Leu Thr Gly Thr Gly Val Leu Thr Glu Ser
    210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
                245                 250                 255

Thr Pro Cys
```

<210> SEQ ID NO 56
<211> LENGTH: 262
<212> TYPE: PRT
<213> ORGANISM: Artificial Sequence
<220> FEATURE:
<223> OTHER INFORMATION: Synthetic

<400> SEQUENCE: 56

```
Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
```

```
                65                  70                  75                  80
Pro Gly Gln Thr Gly Lys Ile Ala Asp Tyr Asn Tyr Lys Leu Pro Asp
                    85                  90                  95

Asp Phe Thr Gly Cys Val Ile Ala Trp Asn Ser Asn Leu Asp Ser
                100                 105                 110

Lys Val Gly Gly Asn Tyr Asn Tyr Lys Tyr Arg Leu Phe Arg Lys Ser
                115                 120                 125

Asn Leu Lys Pro Phe Glu Arg Asp Ile Ser Thr Glu Ile Tyr Gln Ala
            130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn Leu Val Lys Asn Lys Ser Val
                195                 200                 205

Asn Phe Asn Phe Asn Gly Leu Thr Gly Thr Gly Val Leu Thr Glu Ser
            210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
                245                 250                 255

Thr Pro Cys Pro Pro Cys
            260

<210> SEQ ID NO 57
<211> LENGTH: 260
<212> TYPE: PRT
<213> ORGANISM: Artificial Sequence
<220> FEATURE:
<223> OTHER INFORMATION: Synthetic

<400> SEQUENCE: 57

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
                20                  25                  30

Asp Tyr Ser Val Leu Tyr Asn Ser Ala Ser Phe Ser Thr Phe Lys Cys
            35                  40                  45

Tyr Gly Val Ser Pro Thr Lys Leu Asn Asp Leu Cys Phe Thr Asn Val
        50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                    85                  90                  95

Asp Phe Thr Gly Cys Val Ile Ala Trp Asn Ser Asn Asn Leu Asp Ser
                100                 105                 110

Lys Val Gly Gly Asn Tyr Asn Tyr Leu Tyr Arg Leu Phe Arg Lys Ser
                115                 120                 125

Asn Leu Lys Pro Phe Glu Arg Asp Ile Ser Thr Glu Ile Tyr Gln Ala
            130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
```

```
            165                 170                 175
Tyr Arg Val Val Val Leu Ser Phe Glu Leu Leu His Ala Pro Ala Thr
            180                 185                 190

Val Cys Gly Pro Lys Lys Ser Thr Asn Leu Val Lys Asn Lys Cys Val
        195                 200                 205

Asn Phe Asn Phe Asn Gly Leu Thr Gly Thr Gly Val Leu Thr Glu Ser
    210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
                245                 250                 255

Thr Pro Cys Ser
            260

<210> SEQ ID NO 58
<211> LENGTH: 260
<212> TYPE: PRT
<213> ORGANISM: Artificial Sequence
<220> FEATURE:
<223> OTHER INFORMATION: Synthetic

<400> SEQUENCE: 58

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Lys Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Trp Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn Leu Val Lys Asn Lys Cys Val
        195                 200                 205

Asn Phe Asn Phe Asn Gly Leu Thr Gly Thr Gly Val Leu Thr Glu Ser
    210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
                245                 250                 255

Thr Pro Cys Ser
```

<210> SEQ ID NO 59
<211> LENGTH: 1272
<212> TYPE: PRT
<213> ORGANISM: Artificial Sequence
<220> FEATURE:
<223> OTHER INFORMATION: Synthetic

<400> SEQUENCE: 59

```
Phe Val Phe Leu Val Leu Leu Pro Leu Val Ser Ser Gln Cys Val Asn
1               5                   10                  15

Leu Thr Thr Arg Thr Gln Leu Pro Pro Ala Tyr Thr Asn Ser Phe Thr
            20                  25                  30

Arg Gly Val Tyr Tyr Pro Asp Lys Val Phe Arg Ser Ser Val Leu His
        35                  40                  45

Ser Thr Gln Asp Leu Phe Leu Pro Phe Phe Ser Asn Val Thr Trp Phe
    50                  55                  60

His Ala Ile His Val Ser Gly Thr Asn Gly Thr Lys Arg Phe Asp Asn
65                  70                  75                  80

Pro Val Leu Pro Phe Asn Asp Gly Val Tyr Phe Ala Ser Thr Glu Lys
                85                  90                  95

Ser Asn Ile Ile Arg Gly Trp Ile Phe Gly Thr Thr Leu Asp Ser Lys
            100                 105                 110

Thr Gln Ser Leu Leu Ile Val Asn Asn Ala Thr Asn Val Val Ile Lys
        115                 120                 125

Val Cys Glu Phe Gln Phe Cys Asn Asp Pro Phe Leu Gly Val Tyr Tyr
    130                 135                 140

His Lys Asn Asn Lys Ser Trp Met Glu Ser Glu Phe Arg Val Tyr Ser
145                 150                 155                 160

Ser Ala Asn Asn Cys Thr Phe Glu Tyr Val Ser Gln Pro Phe Leu Met
                165                 170                 175

Asp Leu Glu Gly Lys Gln Gly Asn Phe Lys Asn Leu Arg Glu Phe Val
            180                 185                 190

Phe Lys Asn Ile Asp Gly Tyr Phe Lys Ile Tyr Ser Lys His Thr Pro
        195                 200                 205

Ile Asn Leu Val Arg Asp Leu Pro Gln Gly Phe Ser Ala Leu Glu Pro
    210                 215                 220

Leu Val Asp Leu Pro Ile Gly Ile Asn Ile Thr Arg Phe Gln Thr Leu
225                 230                 235                 240

Leu Ala Leu His Arg Ser Tyr Leu Thr Pro Gly Asp Ser Ser Ser Gly
                245                 250                 255

Trp Thr Ala Gly Ala Ala Ala Tyr Tyr Val Gly Tyr Leu Gln Pro Arg
            260                 265                 270

Thr Phe Leu Leu Lys Tyr Asn Glu Asn Gly Thr Ile Thr Asp Ala Val
        275                 280                 285

Asp Cys Ala Leu Asp Pro Leu Ser Glu Thr Lys Cys Thr Leu Lys Ser
    290                 295                 300

Phe Thr Val Glu Lys Gly Ile Tyr Gln Thr Ser Asn Phe Arg Val Gln
305                 310                 315                 320

Pro Thr Glu Ser Ile Val Arg Phe Pro Asn Ile Thr Asn Leu Cys Pro
                325                 330                 335

Phe Gly Glu Val Phe Asn Ala Thr Arg Phe Ala Ser Val Tyr Ala Trp
            340                 345                 350

Asn Arg Lys Arg Ile Ser Asn Cys Val Ala Asp Tyr Ser Val Leu Tyr
```

-continued

```
                355                 360                 365
Asn Ser Ala Ser Phe Ser Thr Phe Lys Cys Tyr Gly Val Ser Pro Thr
370                 375                 380
Lys Leu Asn Asp Leu Cys Phe Thr Asn Val Tyr Ala Asp Ser Phe Val
385                 390                 395                 400
Ile Arg Gly Asp Glu Val Arg Gln Ile Ala Pro Gly Gln Thr Gly Lys
                405                 410                 415
Ile Ala Asp Tyr Asn Tyr Lys Leu Pro Asp Asp Phe Thr Gly Cys Val
                420                 425                 430
Ile Ala Trp Asn Ser Asn Asn Leu Asp Ser Lys Val Gly Gly Asn Tyr
                435                 440                 445
Asn Tyr Leu Tyr Arg Leu Phe Arg Lys Ser Asn Leu Lys Pro Phe Glu
            450                 455                 460
Arg Asp Ile Ser Thr Glu Ile Tyr Gln Ala Gly Ser Thr Pro Cys Asn
465                 470                 475                 480
Gly Val Glu Gly Phe Asn Cys Tyr Phe Pro Leu Gln Ser Tyr Gly Phe
                485                 490                 495
Gln Pro Thr Asn Gly Val Gly Tyr Gln Pro Tyr Arg Val Val Val Leu
            500                 505                 510
Ser Phe Glu Leu Leu His Ala Pro Ala Thr Val Cys Gly Pro Lys Lys
            515                 520                 525
Ser Thr Asn Leu Val Lys Asn Lys Cys Val Asn Phe Asn Phe Asn Gly
            530                 535                 540
Leu Thr Gly Thr Gly Val Leu Thr Glu Ser Asn Lys Lys Phe Leu Pro
545                 550                 555                 560
Phe Gln Gln Phe Gly Arg Asp Ile Ala Asp Thr Thr Asp Ala Val Arg
                565                 570                 575
Asp Pro Gln Thr Leu Glu Ile Leu Asp Ile Thr Pro Cys Ser Phe Gly
            580                 585                 590
Gly Val Ser Val Ile Thr Pro Gly Thr Asn Thr Ser Asn Gln Val Ala
            595                 600                 605
Val Leu Tyr Gln Asp Val Asn Cys Thr Glu Val Pro Val Ala Ile His
        610                 615                 620
Ala Asp Gln Leu Thr Pro Thr Trp Arg Val Tyr Ser Thr Gly Ser Asn
625                 630                 635                 640
Val Phe Gln Thr Arg Ala Gly Cys Leu Ile Gly Ala Glu His Val Asn
                645                 650                 655
Asn Ser Tyr Glu Cys Asp Ile Pro Ile Gly Ala Gly Ile Cys Ala Ser
            660                 665                 670
Tyr Gln Thr Gln Thr Asn Ser Pro Ser Gly Ala Gly Ser Val Ala Ser
            675                 680                 685
Gln Ser Ile Ile Ala Tyr Thr Met Ser Leu Gly Ala Glu Asn Ser Val
            690                 695                 700
Ala Tyr Ser Asn Asn Ser Ile Ala Ile Pro Thr Asn Phe Thr Ile Ser
705                 710                 715                 720
Val Thr Thr Glu Ile Leu Pro Val Ser Met Thr Lys Thr Ser Val Asp
                725                 730                 735
Cys Thr Met Tyr Ile Cys Gly Asp Ser Thr Glu Cys Ser Asn Leu Leu
            740                 745                 750
Leu Gln Tyr Gly Ser Phe Cys Thr Gln Leu Asn Arg Ala Leu Thr Gly
            755                 760                 765
Ile Ala Val Glu Gln Asp Lys Asn Thr Gln Glu Val Phe Ala Gln Val
            770                 775                 780
```

```
Lys Gln Ile Tyr Lys Thr Pro Pro Ile Lys Asp Phe Gly Gly Phe Asn
785                 790                 795                 800

Phe Ser Gln Ile Leu Pro Asp Pro Ser Lys Pro Ser Lys Arg Ser Phe
            805                 810                 815

Ile Glu Asp Leu Leu Phe Asn Lys Val Thr Leu Ala Asp Ala Gly Phe
            820                 825                 830

Ile Lys Gln Tyr Gly Asp Cys Leu Gly Asp Ile Ala Ala Arg Asp Leu
            835                 840                 845

Ile Cys Ala Gln Lys Phe Asn Gly Leu Thr Val Leu Pro Pro Leu Leu
850                 855                 860

Thr Asp Glu Met Ile Ala Gln Tyr Thr Ser Ala Leu Leu Ala Gly Thr
865                 870                 875                 880

Ile Thr Ser Gly Trp Thr Phe Gly Ala Gly Ala Ala Leu Gln Ile Pro
                885                 890                 895

Phe Ala Met Gln Met Ala Tyr Arg Phe Asn Gly Ile Gly Val Thr Gln
            900                 905                 910

Asn Val Leu Tyr Glu Asn Gln Lys Leu Ile Ala Asn Gln Phe Asn Ser
            915                 920                 925

Ala Ile Gly Lys Ile Gln Asp Ser Leu Ser Ser Thr Ala Ser Ala Leu
930                 935                 940

Gly Lys Leu Gln Asp Val Val Asn Gln Asn Ala Gln Ala Leu Asn Thr
945                 950                 955                 960

Leu Val Lys Gln Leu Ser Ser Asn Phe Gly Ala Ile Ser Ser Val Leu
            965                 970                 975

Asn Asp Ile Leu Ser Arg Leu Asp Pro Pro Glu Ala Glu Val Gln Ile
            980                 985                 990

Asp Arg Leu Ile Thr Gly Arg Leu Gln Ser Leu Gln Thr Tyr Val Thr
            995                 1000                1005

Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg
    1025                1030                1035

Val Asp Phe Cys Gly Lys Gly Tyr His Leu Met Ser Phe Pro Gln
    1040                1045                1050

Ser Ala Pro His Gly Val Val Phe Leu His Val Thr Tyr Val Pro
    1055                1060                1065

Ala Gln Glu Lys Asn Phe Thr Thr Ala Pro Ala Ile Cys His Asp
    1070                1075                1080

Gly Lys Ala His Phe Pro Arg Glu Gly Val Phe Val Ser Asn Gly
    1085                1090                1095

Thr His Trp Phe Val Thr Gln Arg Asn Phe Tyr Glu Pro Gln Ile
    1100                1105                1110

Ile Thr Thr Asp Asn Thr Phe Val Ser Gly Asn Cys Asp Val Val
    1115                1120                1125

Ile Gly Ile Val Asn Asn Thr Val Tyr Asp Pro Leu Gln Pro Glu
    1130                1135                1140

Leu Asp Ser Phe Lys Glu Glu Leu Asp Lys Tyr Phe Lys Asn His
    1145                1150                1155

Thr Ser Pro Asp Val Asp Leu Gly Asp Ile Ser Gly Ile Asn Ala
    1160                1165                1170

Ser Val Val Asn Ile Gln Lys Glu Ile Asp Arg Leu Asn Glu Val
    1175                1180                1185
```

-continued

```
Ala Lys Asn Leu Asn Glu Ser Leu Ile Asp Leu Gln Glu Leu Gly
    1190                1195                1200

Lys Tyr Glu Gln Tyr Ile Lys Trp Pro Trp Tyr Ile Trp Leu Gly
    1205                1210                1215

Phe Ile Ala Gly Leu Ile Ala Ile Val Met Val Thr Ile Met Leu
    1220                1225                1230

Cys Cys Met Thr Ser Cys Cys Ser Cys Leu Lys Gly Cys Cys Ser
    1235                1240                1245

Cys Gly Ser Cys Cys Lys Phe Asp Glu Asp Asp Ser Glu Pro Val
    1250                1255                1260

Leu Lys Gly Val Lys Leu His Tyr Thr
    1265                1270

<210> SEQ ID NO 60
<211> LENGTH: 12
<212> TYPE: PRT
<213> ORGANISM: Artificial Sequence
<220> FEATURE:
<223> OTHER INFORMATION: Synthetic

<400> SEQUENCE: 60

Phe Val Phe Leu Val Leu Leu Pro Leu Val Ser Ser
1               5                   10

<210> SEQ ID NO 61
<211> LENGTH: 1260
<212> TYPE: PRT
<213> ORGANISM: Artificial Sequence
<220> FEATURE:
<223> OTHER INFORMATION: Synthetic

<400> SEQUENCE: 61

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205
```

```
Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620
```

```
Thr Gly Ser Asn Val Phe Gln Thr Arg Ala Gly Cys Leu Ile Gly Ala
625                 630                 635                 640

Glu His Val Asn Ser Tyr Glu Cys Asp Ile Pro Ile Gly Ala Gly
                645                 650                 655

Ile Cys Ala Ser Tyr Gln Thr Gln Thr Asn Ser Pro Ser Gly Ala Gly
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln
        1010                1015                1020

Ser Lys Arg Val Asp Phe Cys Gly Lys Gly Tyr His Leu Met Ser
        1025                1030                1035

Phe Pro Gln Ser Ala Pro His Gly Val Val Phe Leu His Val Thr
```

```
                1040              1045              1050
Tyr Val Pro Ala Gln Glu Lys Asn Phe Thr Thr Ala Pro Ala Ile
    1055              1060              1065

Cys His Asp Gly Lys Ala His Phe Pro Arg Glu Gly Val Phe Val
    1070              1075              1080

Ser Asn Gly Thr His Trp Phe Val Thr Gln Arg Asn Phe Tyr Glu
    1085              1090              1095

Pro Gln Ile Ile Thr Thr Asp Asn Thr Phe Val Ser Gly Asn Cys
    1100              1105              1110

Asp Val Val Ile Gly Ile Val Asn Asn Thr Val Tyr Asp Pro Leu
    1115              1120              1125

Gln Pro Glu Leu Asp Ser Phe Lys Glu Glu Leu Asp Lys Tyr Phe
    1130              1135              1140

Lys Asn His Thr Ser Pro Asp Val Asp Leu Gly Asp Ile Ser Gly
    1145              1150              1155

Ile Asn Ala Ser Val Val Asn Ile Gln Lys Glu Ile Asp Arg Leu
    1160              1165              1170

Asn Glu Val Ala Lys Asn Leu Asn Glu Ser Leu Ile Asp Leu Gln
    1175              1180              1185

Glu Leu Gly Lys Tyr Glu Gln Tyr Ile Lys Trp Pro Trp Tyr Ile
    1190              1195              1200

Trp Leu Gly Phe Ile Ala Gly Leu Ile Ala Ile Val Met Val Thr
    1205              1210              1215

Ile Met Leu Cys Cys Met Thr Ser Cys Cys Ser Cys Leu Lys Gly
    1220              1225              1230

Cys Cys Ser Cys Gly Ser Cys Cys Lys Phe Asp Glu Asp Asp Ser
    1235              1240              1245

Glu Pro Val Leu Lys Gly Val Lys Leu His Tyr Thr
    1250              1255              1260
```

<210> SEQ ID NO 62
<211> LENGTH: 606
<212> TYPE: DNA
<213> ORGANISM: Artificial Sequence
<220> FEATURE:
<223> OTHER INFORMATION: Synthetic

<400> SEQUENCE: 62

```
aacatcacca acttgtgccc attcggtgag gttttcaacg ctactagatt cgcttccgtt   60
tacgcctgga acagaaagag aatctccaac tgcgttgctg actactccgt cttgtacaac  120
tctgcttcat tctccacctt caagtgctac ggtgtttccc aactaagtt gaacgacctg   180
tgtttcacta acgtctacgc cgactccttc gttattagag gtgacgaggt tagacagatc  240
gctccaggtc aaactggtaa gatcgctgac tacaactaca gctgccaga cgacttcacc   300
ggttgtgtta ttgcttggaa ctccaacaac ctggactcca ggttggtgg taactacaat   360
tacctgtacc gtctgttcag aaagtccaac ctgaagccat cgagagaga catctccact   420
gagatctacc aagctggttc cactccatgt aacggtgttg agggtttcaa ctgttacttc  480
ccattgcagt cctacggttt ccagccaact aatggtgttg gttaccagcc atacagagtc  540
gtcgttttgt ccttcgagtt gttgcatgct ccagctactg tttgcggtcc aaagaagtcc  600
actaac                                                             606
```

<210> SEQ ID NO 63
<211> LENGTH: 603

<212> TYPE: DNA
<213> ORGANISM: Artificial Sequence
<220> FEATURE:
<223> OTHER INFORMATION: Synthetic

<400> SEQUENCE: 63

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gtttccccaa ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
tgtgttattg cttggaactc aacaacctg gactccaagg ttggtggtaa ctacaattac      360
ctgtaccgtc tgttcagaaa gtccaacctg aagccattcg agagacat ctccactgag       420
atctaccaag ctggttccac tccatgtaac ggtgttgagg gtttcaactg ttacttccca     480
ttgcagtcct acggtttcca gccaactaat ggtgttggtt accagccata cagagtcgtc     540
gttttgtcct tcgagttgtt gcatgctcca gctactgttt gcggtccaaa gaagtccact     600
aac                                                                    603
```

<210> SEQ ID NO 64
<211> LENGTH: 606
<212> TYPE: DNA
<213> ORGANISM: Artificial Sequence
<220> FEATURE:
<223> OTHER INFORMATION: Synthetic

<400> SEQUENCE: 64

```
aacatcacca acttgtgccc attcggtgag gttttccagg ctactagatt cgcttctgtt      60
tacgcctgga acagaaagag aatctccaac tgcgttgctg actactccgt cttgtacaac     120
tctgcttcat tctccacctt caagtgctac ggtgtttccc aactaagtt gaacgacctg      180
tgtttcacca acgtttacgc cgactccttc gttattagag gtgacgaggt tagacagatc     240
gctccaggtc aaactggtaa gatcgctgac tacaactaca agctgccaga cgacttcacc     300
ggttgtgtta ttgcttggaa ctccaacaac ctggactcca aggttggtgg taactacaat     360
tacctgtacc gtctgttcag aaagtccaac ctgaagccat tcgagagaga catctccact     420
gagatctacc aagctggttc cactccatgt aacggtgttg agggtttcaa ctgctacttc     480
ccattgcagt cttacggttt ccagccaact aacggtgtcg ttaccaacc atacagagtt     540
gtcgttttgt ccttcgagtt gttgcacgct ccagctactg tttgtggtcc aaagaagtcc     600
actaac                                                                606
```

<210> SEQ ID NO 65
<211> LENGTH: 603
<212> TYPE: DNA
<213> ORGANISM: Artificial Sequence
<220> FEATURE:
<223> OTHER INFORMATION: Synthetic

<400> SEQUENCE: 65

```
atcaccaact tgtgtccatt cggtgaggtt ttccaggcta ctagattcgc ttctgtttac      60
gcctggaaca gaaagagaat ctccaactgc gttgctgact actccgtctt gtacaactct     120
gcttcattct ccaccttcaa gtgctacggt gtttccccaa ctaagttgaa cgacctgtgt     180
ttcaccaacg tttacgccga ctccttcgtt attagaggtg acgaggttag acagatcgct     240
```

```
ccaggtcaaa ctggtaagat cgctgactac aactacaagc tgccagacga cttcaccggt    300
tgtgttattg cttggaactc caacaacctg gactccaagg ttggtggtaa ctacaattac    360
ctgtaccgtc tgttcagaaa gtccaacctg aagccattcg agagagacat ctccactgag    420
atctaccaag ctggttccac tccatgtaac ggtgttgagg gtttcaactg ctacttccca    480
ttgcagtctt acggtttcca gccaactaac ggtgtcggtt accaaccata cagagttgtc    540
gttttgtcct tcgagttgtt gcacgctcca gctactgttt gtggtccaaa gaagtccact    600
aac                                                                  603
```

<210> SEQ ID NO 66
<211> LENGTH: 720
<212> TYPE: DNA
<213> ORGANISM: Artificial Sequence
<220> FEATURE:
<223> OTHER INFORMATION: Synthetic

<400> SEQUENCE: 66

```
atcaccaact tgtgtccatt cggtgaggtt ttcaacgcca ctaagttccc atctgtttac     60
gcctgggaga gaaagaagat ctccaactgc gttgctgact actccgtctt gtacaactcc    120
acattcttca gcaccttcaa gtgctacggt gtttccgcta ctaagttgaa cgacctgtgt    180
ttctccaacg tttacgccga ctccttcgtt gttaagggtg acgacgttag acagattgct    240
ccaggtcaga ctggtgttat cgctgactac aactacaagc tgccagacga cttcatgggt    300
tgtgttttgg cttggaacac cagaaacatc gacgctactt ccaccggtaa ttacaattac    360
aagtaccgtt acctgaggca cggtaagctt agaccattcg agagagacat ctctaacgtc    420
ccattctctc cagacggtaa gccttgtact cctcctgctt tgaactgtta ctggccattg    480
aacgactacg gttctacac tactaccggt atcggttacc agccatacag agttgttgtc    540
ttgtccttcg agttgttgaa cgctccagct actgtttgcg gtccaaagtt gtccaccgac    600
ctgattaaga accagtgcgt caactttaac ttcaacggtc tgactggtac tggtggttcc    660
ttggaggttt tgtttcaagg tccaggttct catcaccacc accatcacca tcatcaccac    720
```

<210> SEQ ID NO 67
<211> LENGTH: 603
<212> TYPE: DNA
<213> ORGANISM: Artificial Sequence
<220> FEATURE:
<223> OTHER INFORMATION: Synthetic

<400> SEQUENCE: 67

```
atcaccaact tgtgtccatt cggtgaggtt ttcaacgcta ctagattcgc ttccgtttac     60
gcctggaaca gaaagagaat ctccaactgc gttgctgact actccgtcgc ttacaactct    120
gcttcattct ccaccttcaa gtgctacggt gtttccccaa ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
aaataccgtt atttgagaaa gtccaacctg aagccattcg agagagacat ctccactgag    420
atctaccaag ctggttccac tccatgtaac ggtgttgagg gtttcaactg ttactggcca    480
ttgcagtcct acggtttcca gccaactaat ggtgttggtt accagccata cagagtcgtc    540
gttttgtcct tcgaggctgc tcatgctcca gctactgttt gcggtccaaa gaagtccact    600
aac                                                                  603
```

<210> SEQ ID NO 68
<211> LENGTH: 603
<212> TYPE: DNA
<213> ORGANISM: Artificial Sequence
<220> FEATURE:
<223> OTHER INFORMATION: Synthetic

<400> SEQUENCE: 68

```
atcaccaact tgtgtccatt cggtgaggtt ttcaacgcta ctagattcgc ttccgtttac      60
gcctggaaca gaaagagaat ctccaactgc gttgctgact actccgtcgc ttacaactct     120
gcttcattct ccaccttcaa gtgctacggt gtttccccaa ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
tgtgttattg cttggaactc caacaacctg gactccaagg ttggtggtaa ctacaattac     360
aaataccgtt tgtttagaaa gtccaacctg aagccattcg agagagacat ctccactgag     420
atctaccaag ctggttccac tccatgtaac ggtgttgagg gtttcaactg ttactggcca     480
ttgcagtcct acggtttcca gccaactaat ggtgttggtt accagccata cagagtcgtc     540
gttttgtcct tcgaggctgc tcatgctcca gctactgttt gcggtccaaa gaagtccact     600
aac                                                                  603
```

<210> SEQ ID NO 69
<211> LENGTH: 603
<212> TYPE: DNA
<213> ORGANISM: Artificial Sequence
<220> FEATURE:
<223> OTHER INFORMATION: Synthetic

<400> SEQUENCE: 69

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gtttccccaa ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
tgtgttattg cttggaactc caacaacctg gactccaagg ttggtggtaa ctacaattac     360
aaataccgtt atttgagaaa gtccaacctg aagccattcg agagagacat ctccactgag     420
atctaccaag ctggttccac tccatgtaac ggtgttgagg gtttcaactg ttactggcca     480
ttgcagtcct acggtttcca gccaactaat ggtgttggtt accagccata cagagtcgtc     540
gttttgtcct tcgagttgtt gcatgctcca gctactgttt gcggtccaaa gaagtccact     600
aac                                                                  603
```

<210> SEQ ID NO 70
<211> LENGTH: 603
<212> TYPE: DNA
<213> ORGANISM: Artificial Sequence
<220> FEATURE:
<223> OTHER INFORMATION: Synthetic

<400> SEQUENCE: 70

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
```

| | |
|---|---|
| gcttcattct ccaccttcaa gtgctacggt gtttccccaa ctaagttgaa cgacctgtgt | 180 |
| ttcactaacg tctacgccga ctccttcgtt attagaggtg acgaggttag acagatcgct | 240 |
| ccaggtcaaa ctggtaagat cgctgactac aactacaagc tgccagacga cttcaccggt | 300 |
| tgtgttattg cttggaactc caacaacctg gactccaagg ttggtggtaa ctacaattac | 360 |
| aaataccgtt tgtttagaaa gtccaacctg aagccattcg agagagacat ctccactgag | 420 |
| atctaccaag ctggttccac tccatgtaac ggtgttgagg gtttcaactg ttactggcca | 480 |
| ttgcagtcct acggtttcca gccaactaat ggtgttggtt accagccata cagagtcgtc | 540 |
| gttttgtcct tcgagttgtt gcatgctcca gctactgttt gcggtccaaa gaagtccact | 600 |
| aac | 603 |

<210> SEQ ID NO 71
<211> LENGTH: 603
<212> TYPE: DNA
<213> ORGANISM: Artificial Sequence
<220> FEATURE:
<223> OTHER INFORMATION: Synthetic

<400> SEQUENCE: 71

| | |
|---|---|
| atcaccaact tgtgtccatt cggtgaggtt ttcaacgcta ctagattcgc ttccgtttac | 60 |
| gcctggaaca gaaagagaat ctccaactgc gttgctgact actccgtcgc ttacaactct | 120 |
| gcttcattct ccaccttcaa gtgctacggt gtttccccaa ctaagttgaa cgacctgtgt | 180 |
| ttcactaacg tctacgccga ctccttcgtt attagaggtg acgaggttag acagatcgct | 240 |
| ccaggtcaaa ctggtaagat cgctgactac aactacaagc tgccagacga cttcaccggt | 300 |
| tgtgttattg cttggaactc caacaacctg gactccaagg ttggtggtaa ctacaattac | 360 |
| ttgtaccgtt tgtttagaaa gtccaacctg aagccattcg agagagacat ctccactgag | 420 |
| atctaccaag ctggttccac tccatgtaac ggtgttgagg gtttcaactg ttactttcca | 480 |
| ttgcagtcct acggtttcca gccaactaat ggtgttggtt accagccata cagagtcgtc | 540 |
| gttttgtcct tcgaggctgc tcatgctcca gctactgttt gcggtccaaa gaagtccact | 600 |
| aac | 603 |

<210> SEQ ID NO 72
<211> LENGTH: 603
<212> TYPE: DNA
<213> ORGANISM: Artificial Sequence
<220> FEATURE:
<223> OTHER INFORMATION: Synthetic

<400> SEQUENCE: 72

| | |
|---|---|
| atcaccaact tgtgtccatt cggtgaggtt ttcaacgcta ctagattcgc ttccgtttac | 60 |
| gcctggaaca gaaagagaat ctccaactgc gttgctgact actccgtctt gtacaactct | 120 |
| gcttcattct ccaccttcaa gtgctacggt gtttccccaa ctaagttgaa cgacctgtgt | 180 |
| ttcactaacg tctacgccga ctccttcgtt attagaggtg acgaggttag acagatcgct | 240 |
| ccaggtcaaa ctggtaagat cgctgactac aactacaagc tgccagacga cttcaccggt | 300 |
| tgtgttattg cttggaactc caacaacctg gactccaagg ttggtggtaa ctacaattac | 360 |
| aaataccgtc tgttcagaaa gtccaacctg aagccattcg agagagacat ctccactgag | 420 |
| atctaccaag ctggttccac tccatgtaac ggtgttgagg gtttcaactg ttacttccca | 480 |
| ttgcagtcct acggtttcca gccaactaat ggtgttggtt accagccata cagagtcgtc | 540 |
| gttttgtcct tcgagttgtt gcatgctcca gctactgttt gcggtccaaa gaagtccact | 600 |

```
aac                                                                603

<210> SEQ ID NO 73
<211> LENGTH: 603
<212> TYPE: DNA
<213> ORGANISM: Artificial Sequence
<220> FEATURE:
<223> OTHER INFORMATION: Synthetic

<400> SEQUENCE: 73
atcaccaact tgtgtccatt cggtgaggtt ttcaacgcta ctagattcgc ttccgtttac    60
gcctggaaca gaaagagaat ctccaactgc gttgctgact actccgtcat gtacaactct   120
gcttcattct ccaccttcaa gtgctacggt gttccccaa ctaagttgaa cgacctgtgt    180
ttcactaacg tctacgccga ctccttcgtt attagaggtg acgaggttag acagatcgct   240
ccaggtcaaa ctggtaagat cgctgactac aactacaagc tgccagacga cttcaccggt   300
tgtgttattg cttggaactc caacaacctg gactccaagg ttggtggtaa ctacaattac   360
ctgtaccgtc tgttcagaaa gtccaacctg aagccattcg agagagacat ctccactgag   420
atctaccaag ctggttccac tccatgtaac ggtgttgagg gtttcaactg ttacttccca   480
ttgcagtcct acggtttcca gccaactaat ggtgttggtt accagccata cagagtcgtc   540
gttttgtcct tcgagttgtt gcatgctcca gctactgttt gcggtccaaa gaagtccact   600
aac                                                                603

<210> SEQ ID NO 74
<211> LENGTH: 603
<212> TYPE: DNA
<213> ORGANISM: Artificial Sequence
<220> FEATURE:
<223> OTHER INFORMATION: Synthetic

<400> SEQUENCE: 74
atcaccaact tgtgtccatt cggtgaggtt ttcaacgcta ctagattcgc ttccgtttac    60
gcctggaaca gaaagagaat ctccaactgc gttgctgact actccgtcat gtacaactct   120
gcttcattct ccaccttcaa gtgctacggt gttccccaa ctaagttgaa cgacctgtgt    180
ttcactaacg tctacgccga ctccttcgtt attagaggtg acgaggttag acagatcgct   240
ccaggtcaaa ctggtaagat cgctgactac aactacaagc tgccagacga cttcaccggt   300
tgtgttattg cttggaactc caacaacctg gactccaagg ttggtggtaa ctacaattac   360
ctgtaccgtc tgttcagaaa gtccaacctg aagccattcg agagagacat ctccactgag   420
atctaccaag ctggttccac tccatgtaac ggtgttgagg gtttcaactg ttacttccca   480
ttgcagtcct acggtttcca gccaactaat ggtgttggtt accagccata cagagtcgtc   540
gttttgtcct tcgagttgat gcatgctcca gctactgttt gcggtccaaa gaagtccact   600
aac                                                                603

<210> SEQ ID NO 75
<211> LENGTH: 603
<212> TYPE: DNA
<213> ORGANISM: Artificial Sequence
<220> FEATURE:
<223> OTHER INFORMATION: Synthetic

<400> SEQUENCE: 75
atcaccaact tgtgtccatt cggtgaggtt ttcaacgcta ctagattcgc ttccgtttac    60
```

```
gcctggaaca gaaagagaat ctccaactgc gttgctgact actccgtcat gtacaactct    120
gcttcattct ccaccttcaa gtgctacggt gttccccaa ctaagttgaa cgacctgtgt     180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
aaataccgtc tgttcagaaa gtccaacctg aagccattcg agagagacat ctccactgag    420
atctaccaag ctggttccac tccatgtaac ggtgttgagg gtttcaactg ttacttccca    480
ttgcagtcct acggtttcca gccaactaat ggtgttggtt accagccata cagagtcgtc    540
gttttgtcct tcgagttgat gcatgctcca gctactgttt gcggtccaaa gaagtccact    600
aac                                                                  603

<210> SEQ ID NO 76
<211> LENGTH: 603
<212> TYPE: DNA
<213> ORGANISM: Artificial Sequence
<220> FEATURE:
<223> OTHER INFORMATION: Synthetic

<400> SEQUENCE: 76
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gttccccaa ctaagttgaa cgacctgtgt     180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
ctgtaccgtc tgttcagaaa gtccaacctg aagccattcg agagagacat ctccactgag    420
atctaccaag ctggttccac tccatgtaac ggtgttgagg gtttcaactg tagattccca    480
ttgcagtcct acggtttcca gccaactaat ggtgttggtt accagccata cagagtcgtc    540
gttttgtcct tcgagttgtt gcatgctcca gctactgttt gcggtccaaa gaagtccact    600
aac                                                                  603

<210> SEQ ID NO 77
<211> LENGTH: 603
<212> TYPE: DNA
<213> ORGANISM: Artificial Sequence
<220> FEATURE:
<223> OTHER INFORMATION: Synthetic

<400> SEQUENCE: 77
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gttccccaa ctaagttgaa cgacctgtgt     180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
ctgtaccgtc tgttcagaaa gtccaacctg aagccattcg agagagacat ctccactgag    420
atctaccaag ctggttccac tccatgtaac ggtgttgagg gtttcaactg ttacatgcca    480
ttgcagtcct acggtttcca gccaactaat ggtgttggtt accagccata cagagtcgtc    540
```

```
gttttgtcct tcgagttgtt gcatgctcca gctactgttt gcggtccaaa gaagtccact    600
aac                                                                  603
```

<210> SEQ ID NO 78
<211> LENGTH: 603
<212> TYPE: DNA
<213> ORGANISM: Artificial Sequence
<220> FEATURE:
<223> OTHER INFORMATION: Synthetic

<400> SEQUENCE: 78

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gttttcccaa ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
ctgtaccgtc tgttcagaaa gtccaacctg aagccattcg agagagacat ctccactgag    420
atctaccaag ctggttccac tccatgtaac ggtgttgagg gtttcaactg tagaatgcca    480
ttgcagtcct acggtttcca gccaactaat ggtgttggtt accagccata cagagtcgtc    540
gttttgtcct tcgagttgtt gcatgctcca gctactgttt gcggtccaaa gaagtccact    600
aac                                                                  603
```

<210> SEQ ID NO 79
<211> LENGTH: 603
<212> TYPE: DNA
<213> ORGANISM: Artificial Sequence
<220> FEATURE:
<223> OTHER INFORMATION: Synthetic

<400> SEQUENCE: 79

```
atcaccaact tgtgtccatt cggtgaggtt ttcaacgcta ctagattcgc ttccgtttac     60
gcctggaaca gaaagagaat ctccaactgc gttgctgact actccgtcat gtacaactct    120
gcttcattct ccaccttcaa gtgctacggt gttttcccaa ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
aaataccgtc tgttcagaaa gtccaacctg aagccattcg agagagacat ctccactgag    420
atctaccaag ctggttccac tccatgtaac ggtgttgagg gtttcaactg tagaatgcca    480
ttgcagtcct acggtttcca gccaactaat ggtgttggtt accagccata cagagtcgtc    540
gttttgtcct tcgagttgat gcatgctcca gctactgttt gcggtccaaa gaagtccact    600
aac                                                                  603
```

<210> SEQ ID NO 80
<211> LENGTH: 603
<212> TYPE: DNA
<213> ORGANISM: Artificial Sequence
<220> FEATURE:
<223> OTHER INFORMATION: Synthetic

<400> SEQUENCE: 80

```
atcaccaact tgtgtccatt cggtgaggtt ttcaacgcta ctagattcgc ttccgtttac    60
gcctggaaca gaaagagaat ctccaactgc gttgctgact actccgtctt gtacaactct   120
gcttcattct ccaccttcaa gtgctacggt gttttcccca ctaagttgaa cgacctgtgt   180
ttcactaacg tctacgccga ctccttcgtt attagaggtg acgaggttag acagatcgct   240
ccaggtcaaa ctggtaagat cgctgactac aactacaagc tgccagacga cttcaccggt   300
tgtgttattg cttggaactc caacaacctg gactccaagg ttggtggtaa ctacaattac   360
ctgtaccgtt acctgagaaa gtccaacctg aagccattcg agagagacat ctccactgag   420
atctaccaag ctggttccac tccatgtaac ggtgttgagg gtttcaactg ttacttccca   480
ttgcagtcct acggtttcca gccaactaat ggtgttggtt accagccata cagagtcgtc   540
gttttgtcct tcgagttgtt gcatgctcca gctactgttt gcggtccaaa gaagtccact   600
aac                                                                 603
```

<210> SEQ ID NO 81
<211> LENGTH: 603
<212> TYPE: DNA
<213> ORGANISM: Artificial Sequence
<220> FEATURE:
<223> OTHER INFORMATION: Synthetic

<400> SEQUENCE: 81

```
atcaccaact tgtgtccatt cggtgaggtt ttcaacgcta ctagattcgc ttccgtttac    60
gcctggaaca gaaagagaat ctccaactgc gttgctgact actccgtctt gtacaactct   120
gcttcattct ccaccttcaa gtgctacggt gttttcccca ctaagttgaa cgacctgtgt   180
ttcactaacg tctacgccga ctccttcgtt attagaggtg acgaggttag acagatcgct   240
ccaggtcaaa ctggtaagat cgctgactac aactacaagc tgccagacga cttcaccggt   300
tgtgttattg cttggaactc caacaacctg gactccaagg ttggtggtaa ttacaattac   360
aagtaccgtt acctgaggaa gtccaacctg aagccattcg agagagacat ctccactgag   420
atctaccaag ctggttccac tccatgtaac ggtgttgagg gtttcaactg ttacttccca   480
ttgcagtcct acggtttcca gccaactaat ggtgttggtt accagccata cagagtcgtc   540
gttttgtcct tcgagttgtt gcatgctcca gctactgttt gcggtccaaa gaagtccact   600
aac                                                                 603
```

<210> SEQ ID NO 82
<211> LENGTH: 603
<212> TYPE: DNA
<213> ORGANISM: Artificial Sequence
<220> FEATURE:
<223> OTHER INFORMATION: Synthetic

<400> SEQUENCE: 82

```
atcaccaact tgtgtccatt cggtgaggtt ttcaacgcta ctagattcgc ttccgtttac    60
gcctggaaca gaaagagaat ctccaactgc gttgctgact actccgtctt gtacaactct   120
gcttcattct ccaccttcaa gtgctacggt gttttcccca ctaagttgaa cgacctgtgt   180
ttcactaacg tctacgccga ctccttcgtt attagaggtg acgaggttag acagatcgct   240
ccaggtcaaa ctggtaagat cgctgactac aactacaagc tgccagacga cttcaccggt   300
tgtgttattg cttggaactc caacaacctg gactccaagg ttggtggtaa ctacaattac   360
ctgtacagat ccctgagaaa gtccaacctg aagccattcg agagagacat ctccactgag   420
atctaccaag ctggttccac tccatgtaac ggtgttgagg gtttcaactg ttacttccca   480
```

```
ttgcagtcct acggtttcca gccaactaat ggtgttggtt accagccata cagagtcgtc    540
gttttgtcct tcgagttgtt gcatgctcca gctactgttt gcggtccaaa gaagtccact    600
aac                                                                  603
```

<210> SEQ ID NO 83
<211> LENGTH: 603
<212> TYPE: DNA
<213> ORGANISM: Artificial Sequence
<220> FEATURE:
<223> OTHER INFORMATION: Synthetic

<400> SEQUENCE: 83

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gtttccccaa ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
gcctacaggc tgttcagaaa gtccaacttg aagccattcg agagagacat ctccaccgag    420
atctaccaag ctggttctac tccatgtaac ggtgtcgagg gtttcaactg ttacttccca    480
ttgcagtcct acggtttcca gccaactaac ggtgttggtt accagccata cagagttgtc    540
gttttgtcct tcgagttgtt gcacgctcca gctactgttt gtggtccaaa gaagtccact    600
aac                                                                  603
```

<210> SEQ ID NO 84
<211> LENGTH: 603
<212> TYPE: DNA
<213> ORGANISM: Artificial Sequence
<220> FEATURE:
<223> OTHER INFORMATION: Synthetic

<400> SEQUENCE: 84

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gtttccccaa ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ttacaattac    360
aagtacaggc tgttccgtaa gtccaacctg aagccattcg agagagacat ctccactgag    420
atctaccaag ctggttccac tccatgtaac ggtgttgagg gtttcaactg cgtcagacca    480
ttgcaatctt acggtttcca gccaactaac ggtgtcggtt accaaccata cagagttgtc    540
gttttgtcct tcgagttgtt gcacgctcca gctactgttt gtggtccaaa gaagtccact    600
aac                                                                  603
```

<210> SEQ ID NO 85
<211> LENGTH: 603
<212> TYPE: DNA
<213> ORGANISM: Artificial Sequence
<220> FEATURE:
<223> OTHER INFORMATION: Synthetic

<400> SEQUENCE: 85

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gtttccccaa ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
tgtgttattg cttggaactc caacaacctg gactccaagg ttggtggtaa ttacaattac     360
aagtacaggc tgttccgtaa gtccaacctg aagccattcg agagagacat ctccactgag     420
atctaccaag ctggttccac tccatgtaac ggtgttgagg gtttcaactg ttacaaccca     480
ttgcagtcct acggtttcca gccaactaat ggtgttggtt accagccata cagagtcgtc     540
gttttgtcct tcgagttgtt gcatgctcca gctactgttt gcggtccaaa gaagtccact     600
aac                                                                  603
```

<210> SEQ ID NO 86
<211> LENGTH: 603
<212> TYPE: DNA
<213> ORGANISM: Artificial Sequence
<220> FEATURE:
<223> OTHER INFORMATION: Synthetic

<400> SEQUENCE: 86

```
atcaccaact tgtgtccatt cggtgaggtt ttcaacgcta ctagattcgc ttccgtttac      60
gcctgggaaa gaaagagaat ctccaactgc gttgctgact actccgtctt gtacaactct     120
gcttcattct ccaccttcaa gtgctacggt gtttccccaa ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
tgtgttattg cttggaactc caacaacctg gactccaagg ttggtggtaa ctacaattac     360
aaataccgtc tgttcagaaa gtccaacctg aagccattcg agagagacat ctccactgag     420
atctaccaag ctggttccac tccatgtaac ggtgttgagg gtttcaactg ttacttccca     480
ttgcagtcct acggtttcca gccaactaat ggtgttggtt accagccata cagagtcgtc     540
gttttgtcct tcgagttgtt gcatgctcca gctactgttt gcggtccaaa gaagtccact     600
aac                                                                  603
```

<210> SEQ ID NO 87
<211> LENGTH: 603
<212> TYPE: DNA
<213> ORGANISM: Artificial Sequence
<220> FEATURE:
<223> OTHER INFORMATION: Synthetic

<400> SEQUENCE: 87

```
atcaccaact tgtgtccatt cggtgaggtt ttcaacgcta ctagattcgc ttccgtttac      60
gcctggaaca gaaagagaat ctccaactgc gttgctgact ggtccgtctt gtacaactct     120
gcttcattct ccaccttcaa gtgctacggt gtttccccaa ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
tgtgttattg cttggaactc caacaacctg gactccaagg ttggtggtaa ctacaattac     360
aaataccgtc tgttcagaaa gtccaacctg aagccattcg agagagacat ctccactgag     420
```

```
atctaccaag ctggttccac tccatgtaac ggtgttgagg gtttcaactg ttacttccca        480
ttgcagtcct acggtttcca gccaactaat ggtgttggtt accagccata cagagtcgtc        540
gttttgtcct tcgagttgtt gcatgctcca gctactgttt gcggtccaaa gaagtccact        600
aac                                                                      603
```

<210> SEQ ID NO 88
<211> LENGTH: 603
<212> TYPE: DNA
<213> ORGANISM: Artificial Sequence
<220> FEATURE:
<223> OTHER INFORMATION: Synthetic

<400> SEQUENCE: 88

```
atcaccaact tgtgtccatt cggtgaggtt tcaacgcta ctagattcgc ttccgtttac          60
gcctggaaca gaaagagaat ctccaactgc gttgctgact actccttttt gtacaactct        120
gcttcattct ccaccttcaa gtgctacggt gttccccaa ctaagttgaa cgacctgtgt         180
ttcactaacg tctacgccga ctccttcgtt attagaggtg acgaggttag acagatcgct        240
ccaggtcaaa ctggtaagat cgctgactac aactacaagc tgccagacga cttcaccggt        300
tgtgttattg cttggaactc caacaacctg gactccaagg ttggtggtaa ctacaattac        360
aaataccgtc tgttcagaaa gtccaacctg aagccattcg agagagacat ctccactgag        420
atctaccaag ctggttccac tccatgtaac ggtgttgagg gtttcaactg ttacttccca        480
ttgcagtcct acggtttcca gccaactaat ggtgttggtt accagccata cagagtcgtc        540
gttttgtcct tcgagttgtt gcatgctcca gctactgttt gcggtccaaa gaagtccact        600
aac                                                                      603
```

<210> SEQ ID NO 89
<211> LENGTH: 603
<212> TYPE: DNA
<213> ORGANISM: Artificial Sequence
<220> FEATURE:
<223> OTHER INFORMATION: Synthetic

<400> SEQUENCE: 89

```
atcaccaact tgtgtccatt cggtgagatt tcaacgcta ctagattcgc ttccgtttac          60
gcctggaaca gaaagagaat ctccaactgc gttgctgact actccgtctt gtacaactct        120
gcttcattct ccaccttcaa gtgctacggt gttccccaa ctaagttgaa cgacctgtgt         180
ttcactaacg tctacgccga ctccttcgtt attagaggtg acgaggttag acagatcgct        240
ccaggtcaaa ctggtaagat cgctgactac aactacaagc tgccagacga cttcaccggt        300
tgtgttattg cttggaactc caacaacctg gactccaagg ttggtggtaa ctacaattac        360
aaataccgtc tgttcagaaa gtccaacctg aagccattcg agagagacat ctccactgag        420
atctaccaag ctggttccac tccatgtaac ggtgttgagg gtttcaactg ttacttccca        480
ttgcagtcct acggtttcca gccaactaat ggtgttggtt accagccata cagagtcgtc        540
gttttgtcct tcgagttgtt gcatgctcca gctactgttt gcggtccaaa gaagtccact        600
aac                                                                      603
```

<210> SEQ ID NO 90
<211> LENGTH: 603
<212> TYPE: DNA
<213> ORGANISM: Artificial Sequence
<220> FEATURE:

<223> OTHER INFORMATION: Synthetic

<400> SEQUENCE: 90

```
atcaccaact tgtgtccatt cggtgaggtt ttcaacgcta ctagattccc atccgtttac      60
gcctggaaca gaaagagaat ctccaactgc gttgctgact actccgtctt gtacaactct     120
gcttcattct ccaccttcaa gtgctacggt gttttcccca ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
tgtgttattg cttggaactc caacaacctg gactccaagg ttggtggtaa ctacaattac     360
aaataccgtc tgttcagaaa gtccaacctg aagccattcg agagagacat ctccactgag     420
atctaccaag ctggttccac tccatgtaac ggtgttgagg gtttcaactg ttacttccca     480
ttgcagtcct acggtttcca gccaactaat ggtgttggtt accagccata cagagtcgtc     540
gttttgtcct tcgagttgtt gcatgctcca gctactgttt gcggtccaaa gaagtccact     600
aac                                                                    603
```

<210> SEQ ID NO 91
<211> LENGTH: 603
<212> TYPE: DNA
<213> ORGANISM: Artificial Sequence
<220> FEATURE:
<223> OTHER INFORMATION: Synthetic

<400> SEQUENCE: 91

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gttttcccca ctaagttgaa cgacctgtgt     180
ttcactaacg tctacgccga ctccttcgtt attagaggtg acgaggttag acagatcgct     240
ccaggtcaaa ctggtgttat cgctgactac aactacaagc tgccagacga cttcaccggt     300
tgtgttattg cttggaactc caacaacctg gactccaagg ttggtggtaa ctacaattac     360
aaataccgtc tgttcagaaa gtccaacctg aagccattcg agagagacat ctccactgag     420
atctaccaag ctggttccac tccatgtaac ggtgttgagg gtttcaactg ttacttccca     480
ttgcagtcct acggtttcca gccaactaat ggtgttggtt accagccata cagagtcgtc     540
gttttgtcct tcgagttgtt gcatgctcca gctactgttt gcggtccaaa gaagtccact     600
aac                                                                    603
```

<210> SEQ ID NO 92
<211> LENGTH: 603
<212> TYPE: DNA
<213> ORGANISM: Artificial Sequence
<220> FEATURE:
<223> OTHER INFORMATION: Synthetic

<400> SEQUENCE: 92

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gttttcccca ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
tgtgttattg cttggaactc caacaacctg gactccaagg ttggtggtaa ctacaattac     360
```

```
aaataccgtc tgttcagaaa gtccaacctg aagccattcg agagagacat ctccactgag    420
atctaccaag ctggttccac tccatgtaac ggtgttgagg gtttcaactg ttacttccca    480
ttgcagtcct acggtttcca gccaactaat ggtgttggtt accagccata cagagtcgtc    540
gttttgtcct tcgagttgga tcatgctcca gctactgttt gcggtccaaa gaagtccact    600
aac                                                                 603
```

<210> SEQ ID NO 93
<211> LENGTH: 603
<212> TYPE: DNA
<213> ORGANISM: Artificial Sequence
<220> FEATURE:
<223> OTHER INFORMATION: Synthetic

<400> SEQUENCE: 93

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gtttccccaa ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
aaataccgtc tgttcagaaa gtccaacctg aagccattcg agagagacat ctccactgag    420
atctaccaag ctggttccac tccatgtaac ggtgttgagg gtttcaactg ttacttccca    480
ttgcagtcct acggtttcca gccaactaat ggtgttggtt accagccata cagagtcgtc    540
gttttgtcct tcgagttgtt gcatgctcca gctactagat gcggtccaaa gaagtccact    600
aac                                                                 603
```

<210> SEQ ID NO 94
<211> LENGTH: 603
<212> TYPE: DNA
<213> ORGANISM: Artificial Sequence
<220> FEATURE:
<223> OTHER INFORMATION: Synthetic

<400> SEQUENCE: 94

```
atcaccaact tgtgtgattt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gtttccccaa ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
aaataccgtc tgttcagaaa gtccaacctg aagccattcg agagagacat ctccactgag    420
atctaccaag ctggttccac tccatgtaac ggtgttgagg gtttcaactg ttacttccca    480
ttgcagtcct acggtttcca gccaactaat ggtgttggtt accagccata cagagtcgtc    540
gttttgtcct tcgagttgtt gcatgctcca gctactgttt gcggtccaaa gaagtccact    600
aac                                                                 603
```

<210> SEQ ID NO 95
<211> LENGTH: 603
<212> TYPE: DNA

<213> ORGANISM: Artificial Sequence
<220> FEATURE:
<223> OTHER INFORMATION: Synthetic

<400> SEQUENCE: 95

| | | | | | |
|---|---|---|---|---|---|
| atcaccaact | tgtgtccatt | cggtgaggtt | ttcaacgcta | ctagattcgc | ttccgtttac | 60 |
| gcctggaaca | gaaagaaaat | ctccaactgc | gttgctgact | actccgtctt | gtacaactct | 120 |
| gcttcattct | ccaccttcaa | gtgctacggt | gttttcccca | ctaagttgaa | cgacctgtgt | 180 |
| ttcactaacg | tctacgccga | ctccttcgtt | attagaggtg | acgaggttag | acagatcgct | 240 |
| ccaggtcaaa | ctggtaagat | cgctgactac | aactacaagc | tgccagacga | cttcaccggt | 300 |
| tgtgttattg | cttggaactc | caacaacctg | gactccaagg | ttggtggtaa | ctacaattac | 360 |
| aaataccgtc | tgttcagaaa | gtccaacctg | aagccattcg | agagagacat | ctccactgag | 420 |
| atctaccaag | ctggttccac | tccatgtaac | ggtgttgagg | gtttcaactg | ttacttccca | 480 |
| ttgcagtcct | acggtttcca | gccaactaat | ggtgttggtt | accagccata | cagagtcgtc | 540 |
| gttttgtcct | tcgagttgtt | gcatgctcca | gctactgttt | gcggtccaaa | gaagtccact | 600 |
| aac | | | | | | 603 |

<210> SEQ ID NO 96
<211> LENGTH: 603
<212> TYPE: DNA
<213> ORGANISM: Artificial Sequence
<220> FEATURE:
<223> OTHER INFORMATION: Synthetic

<400> SEQUENCE: 96

| | | | | | |
|---|---|---|---|---|---|
| atcaccaact | tgtgtccatt | cggtgaggtt | ttcaacgcta | ctagattcgc | ttccgtttac | 60 |
| gcctggaaca | gaaagagaat | ctccaactgc | gttgctgact | actccgtctt | gtacaactct | 120 |
| gcttcattct | ccaccttcaa | gtgctacggt | gttgatccaa | ctaagttgaa | cgacctgtgt | 180 |
| ttcactaacg | tctacgccga | ctccttcgtt | attagaggtg | acgaggttag | acagatcgct | 240 |
| ccaggtcaaa | ctggtaagat | cgctgactac | aactacaagc | tgccagacga | cttcaccggt | 300 |
| tgtgttattg | cttggaactc | caacaacctg | gactccaagg | ttggtggtaa | ctacaattac | 360 |
| aaataccgtc | tgttcagaaa | gtccaacctg | aagccattcg | agagagacat | ctccactgag | 420 |
| atctaccaag | ctggttccac | tccatgtaac | ggtgttgagg | gtttcaactg | ttacttccca | 480 |
| ttgcagtcct | acggtttcca | gccaactaat | ggtgttggtt | accagccata | cagagtcgtc | 540 |
| gttttgtcct | tcgagttgtt | gcatgctcca | gctactgttt | gcggtccaaa | gaagtccact | 600 |
| aac | | | | | | 603 |

<210> SEQ ID NO 97
<211> LENGTH: 603
<212> TYPE: DNA
<213> ORGANISM: Artificial Sequence
<220> FEATURE:
<223> OTHER INFORMATION: Synthetic

<400> SEQUENCE: 97

| | | | | | |
|---|---|---|---|---|---|
| atcaccaact | tgtgtccatt | cggtgaggtt | ttcaacgcta | ctagattcgc | ttccgtttac | 60 |
| gcctggaaca | gaaagagaat | ctccaactgc | gttgctgact | actccgtctt | gtacaactct | 120 |
| gcttcattct | ccaccttcaa | gtgctacggt | gttttcccca | ctaagttgaa | cgactattgt | 180 |
| ttcactaacg | tctacgccga | ctccttcgtt | attagaggtg | acgaggttag | acagatcgct | 240 |
| ccaggtcaaa | ctggtaagat | cgctgactac | aactacaagc | tgccagacga | cttcaccggt | 300 |

```
tgtgttattg cttggaactc caacaacctg gactccaagg ttggtggtaa ctacaattac    360
aaataccgtc tgttcagaaa gtccaacctg aagccattcg agagagacat ctccactgag    420
atctaccaag ctggttccac tccatgtaac ggtgttgagg gtttcaactg ttacttccca    480
ttgcagtcct acggtttcca gccaactaat ggtgttggtt accagccata cagagtcgtc    540
gttttgtcct tcgagttgtt gcatgctcca gctactgttt gcggtccaaa gaagtccact    600
aac                                                                  603
```

\<210\> SEQ ID NO 98
\<211\> LENGTH: 603
\<212\> TYPE: DNA
\<213\> ORGANISM: Artificial Sequence
\<220\> FEATURE:
\<223\> OTHER INFORMATION: Synthetic

\<400\> SEQUENCE: 98

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gttttccccaa ctaagttgaa cgacctgtgt   180
tggactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
aaataccgtc tgttcagaaa gtccaacctg aagccattcg agagagacat ctccactgag    420
atctaccaag ctggttccac tccatgtaac ggtgttgagg gtttcaactg ttacttccca    480
ttgcagtcct acggtttcca gccaactaat ggtgttggtt accagccata cagagtcgtc    540
gttttgtcct tcgagttgtt gcatgctcca gctactgttt gcggtccaaa gaagtccact    600
aac                                                                  603
```

\<210\> SEQ ID NO 99
\<211\> LENGTH: 603
\<212\> TYPE: DNA
\<213\> ORGANISM: Artificial Sequence
\<220\> FEATURE:
\<223\> OTHER INFORMATION: Synthetic

\<400\> SEQUENCE: 99

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gttttccccaa ctaagttgaa cgacctgtgt   180
ttcactaacg tctacgccga ctccttcgtt attagaggtg acgaggttga tcagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
aaataccgtc tgttcagaaa gtccaacctg aagccattcg agagagacat ctccactgag    420
atctaccaag ctggttccac tccatgtaac ggtgttgagg gtttcaactg ttacttccca    480
ttgcagtcct acggtttcca gccaactaat ggtgttggtt accagccata cagagtcgtc    540
gttttgtcct tcgagttgtt gcatgctcca gctactgttt gcggtccaaa gaagtccact    600
aac                                                                  603
```

\<210\> SEQ ID NO 100

<211> LENGTH: 603
<212> TYPE: DNA
<213> ORGANISM: Artificial Sequence
<220> FEATURE:
<223> OTHER INFORMATION: Synthetic

<400> SEQUENCE: 100

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gttccccaa ctaagttgaa cgacctgtgt      180
ttcactaacg tctacgccga ctccttcgtt attagaggtg acgaggttag acagatcgct     240
ccaggtgcta ctggtaagat cgctgactac aactacaagc tgccagacga cttcaccggt     300
tgtgttattg cttggaactc caacaacctg gactccaagg ttggtggtaa ctacaattac     360
aaataccgtc tgttcagaaa gtccaacctg aagccattcg agagagacat ctccactgag     420
atctaccaag ctggttccac tccatgtaac ggtgttgagg gtttcaactg ttacttccca     480
ttgcagtcct acggtttcca gccaactaat ggtgttggtt accagccata cagagtcgtc     540
gttttgtcct tcgagttgtt gcatgctcca gctactgttt gcggtccaaa gaagtccact     600
aac                                                                   603
```

<210> SEQ ID NO 101
<211> LENGTH: 603
<212> TYPE: DNA
<213> ORGANISM: Artificial Sequence
<220> FEATURE:
<223> OTHER INFORMATION: Synthetic

<400> SEQUENCE: 101

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gttccccaa ctaagttgaa cgacctgtgt      180
ttcactaacg tctacgccga ctccttcgtt attagaggtg acgaggttag acagatcgct     240
ccaggtcaaa ctggtaagat cgctgactac aactacaagc tgccagacaa tttcaccggt     300
tgtgttattg cttggaactc caacaacctg gactccaagg ttggtggtaa ctacaattac     360
aaataccgtc tgttcagaaa gtccaacctg aagccattcg agagagacat ctccactgag     420
atctaccaag ctggttccac tccatgtaac ggtgttgagg gtttcaactg ttacttccca     480
ttgcagtcct acggtttcca gccaactaat ggtgttggtt accagccata cagagtcgtc     540
gttttgtcct tcgagttgtt gcatgctcca gctactgttt gcggtccaaa gaagtccact     600
aac                                                                   603
```

<210> SEQ ID NO 102
<211> LENGTH: 603
<212> TYPE: DNA
<213> ORGANISM: Artificial Sequence
<220> FEATURE:
<223> OTHER INFORMATION: Synthetic

<400> SEQUENCE: 102

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gttccccaa ctaagttgaa cgacctgtgt      180
ttcactaacg tctacgccga ctccttcgtt attagaggtg acgaggttag acagatcgct     240
```

```
ccaggtcaaa ctggtaagat cgctgactac aactacaagc tgccagacga cttcaccggt    300
tgtgttattg cttggaactc caacaacatt gactccaagg ttggtggtaa ctacaattac    360
aaataccgtc tgttcagaaa gtccaacctg aagccattcg agagagacat ctccactgag    420
atctaccaag ctggttccac tccatgtaac ggtgttgagg gtttcaactg ttacttccca    480
ttgcagtcct acggtttcca gccaactaat ggtgttggtt accagccata cagagtcgtc    540
gttttgtcct tcgagttgtt gcatgctcca gctactgttt gcggtccaaa gaagtccact    600
aac                                                                  603
```

<210> SEQ ID NO 103
<211> LENGTH: 603
<212> TYPE: DNA
<213> ORGANISM: Artificial Sequence
<220> FEATURE:
<223> OTHER INFORMATION: Synthetic

<400> SEQUENCE: 103

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gttttcccaa ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
aaataccgtc tgttcagaaa gtccaacctg aagccattcg agagagacat ctccactgag    420
atctaccaag ctggttccac tccatgtaac ggtgttgagg gtttcaactg ttacttccca    480
ttgcagtcct acggtttcca gccaactaat ggtgttggtt accagccaca tagagtcgtc    540
gttttgtcct tcgagttgtt gcatgctcca gctactgttt gcggtccaaa gaagtccact    600
aac                                                                  603
```

<210> SEQ ID NO 104
<211> LENGTH: 603
<212> TYPE: DNA
<213> ORGANISM: Artificial Sequence
<220> FEATURE:
<223> OTHER INFORMATION: Synthetic

<400> SEQUENCE: 104

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcag atgctacggt gttttcccaa ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
aaataccgtc tgttcagaaa gtccaacctg aagccattcg agagagacat ctccactgag    420
atctaccaag ctggttccac tccatgtaac ggtgttgagg gtttcaactg ttacttccca    480
ttgcagtcct acggtttcca gccaactaat ggtgttggtt accagccata cagagtcgtc    540
gttttgtcct tcgagttgtt gcatgctcca gctactgttt gcggtccaaa gaagtccact    600
aac                                                                  603
```

<210> SEQ ID NO 105
<211> LENGTH: 603
<212> TYPE: DNA
<213> ORGANISM: Artificial Sequence
<220> FEATURE:
<223> OTHER INFORMATION: Synthetic

<400> SEQUENCE: 105

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gtttccccaa ctaagttgaa cgacctgtgt     180
ttcactaacg tctacgccga ctccttcgtt gttagaggtg acgaggttag acagatcgct     240
ccaggtcaaa ctggtaagat cgctgactac aactacaagc tgccagacga cttcaccggt     300
tgtgttattg cttggaactc caacaacctg gactccaagg ttggtggtaa ctacaattac     360
aaataccgtc tgttcagaaa gtccaacctg aagccattcg agagagacat ctccactgag     420
atctaccaag ctggttccac tccatgtaac ggtgttgagg gtttcaactg ttacttccca     480
ttgcagtcct acggtttcca gccaactaat ggtgttggtt accagccata cagagtcgtc     540
gttttgtcct tcgagttgtt gcatgctcca gctactgttt gcggtccaaa gaagtccact     600
aac                                                                   603
```

<210> SEQ ID NO 106
<211> LENGTH: 603
<212> TYPE: DNA
<213> ORGANISM: Artificial Sequence
<220> FEATURE:
<223> OTHER INFORMATION: Synthetic

<400> SEQUENCE: 106

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gtttccccaa ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
tgtgttattg cttggaactc caacaacctg gactccaagg ttggtggtaa ctacaattac     360
aaataccgtc tgttcagaaa gtccaacctg aagccattcg agagagacat ctccactgag     420
atctaccaag ctggttccac tccatgtaac ggtgttgagg gtttcaactg ttacttccca     480
ttgcagtcct acggtttcga tccaactaat ggtgttggtt accagccata cagagtcgtc     540
gttttgtcct tcgagttgtt gcatgctcca gctactgttt gcggtccaaa gaagtccact     600
aac                                                                   603
```

<210> SEQ ID NO 107
<211> LENGTH: 603
<212> TYPE: DNA
<213> ORGANISM: Artificial Sequence
<220> FEATURE:
<223> OTHER INFORMATION: Synthetic

<400> SEQUENCE: 107

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gtttccccaa ctaagttgaa cgacctgtgt     180
```

```
ttcactaacg tctacgccga ctccttcgtt attagaggtg acgaggttag acagatcgct      240
ccaggtcaaa ctggtaagat cgctgactac aactacaagc tgccagacga cttcaccggt      300
tgtgttattg cttggaactc caacaacctg gactccaagg ttggtggtaa ctacaattac      360
aaataccgta atttcagaaa gtccaacctg aagccattcg agagagacat ctccactgag      420
atctaccaag ctggttccac tccatgtaac ggtgttgagg gtttcaactg ttacttccca      480
ttgcagtcct acggtttcca gccaactaat ggtgttggtt accagccata cagagtcgtc      540
gttttgtcct tcgagttgtt gcatgctcca gctactgttt gcggtccaaa gaagtccact      600
aac                                                                    603

<210> SEQ ID NO 108
<211> LENGTH: 624
<212> TYPE: DNA
<213> ORGANISM: Artificial Sequence
<220> FEATURE:
<223> OTHER INFORMATION: Synthetic

<400> SEQUENCE: 108
atcaccaact tgtgtccatt cggtgaggtt ttcaacgcta ctagattcgc ttccgtttac       60
gcctggaaca gaaagagaat ctccaactgc gttgctgact actccgtctt gtacaactct      120
gcttcattct ccaccttcaa gtgctacggt gttttcccca ctaagttgaa cgacctgtgt      180
ttcactaacg tctacgccga ctccttcgtt attagaggtg acgaggttag acagatcgct      240
ccaggtcaaa ctggtaagat cgctgactac aactacaagc tgccagacga cttcaccggt      300
tgtgttattg cttggaactc caacaacctg gactccaagg ttggtggtaa ctacaattac      360
ctgtaccgtc tgttcagaaa gtccaacctg aagccattcg agagagacat ctccactgag      420
atctaccaag ctggttccac tccatgtaac ggtgttgagg gtttcaactg ttacttccca      480
ttgcagtcct acggtttcca gccaactaat ggtgttggtt accagccata cagagtcgtc      540
gttttgtcct tcgagttgtt gcatgctcca gctactgttt gcggtccaaa gaagtccact      600
aaccatcatc atcatcatca ttgt                                             624

<210> SEQ ID NO 109
<211> LENGTH: 675
<212> TYPE: DNA
<213> ORGANISM: Artificial Sequence
<220> FEATURE:
<223> OTHER INFORMATION: Synthetic

<400> SEQUENCE: 109
atcaccaact tgtgtccatt cggtgaggtt ttcaacgcta ctagattcgc ttccgtttac       60
gcctggaaca gaaagagaat ctccaactgc gttgctgact actccgtctt gtacaactct      120
gcttcattct ccaccttcaa gtgctacggt gttttcccca ctaagttgaa cgacctgtgt      180
ttcactaacg tctacgccga ctccttcgtt attagaggtg acgaggttag acagatcgct      240
ccaggtcaaa ctggtaagat cgctgactac aactacaagc tgccagacga cttcaccggt      300
tgtgttattg cttggaactc caacaacctg gactccaagg ttggtggtaa ctacaattac      360
ctgtaccgtc tgttcagaaa gtccaacctg aagccattcg agagagacat ctccactgag      420
atctaccaag ctggttccac tccatgtaac ggtgttgagg gtttcaactg ttacttccca      480
ttgcagtcct acggtttcca gccaactaat ggtgttggtt accagccata cagagtcgtc      540
gttttgtcct tcgagttgtt gcatgctcca gctactgttt gcggtccaaa gaaatctacc      600
```

```
aatggtggtg atggtggcga cggcggagat ggtggtgctc atatagttat ggttgacgcc    660
tacaagccta ctaag                                                     675
```

<210> SEQ ID NO 110
<211> LENGTH: 675
<212> TYPE: DNA
<213> ORGANISM: Artificial Sequence
<220> FEATURE:
<223> OTHER INFORMATION: Synthetic

<400> SEQUENCE: 110

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gttttcccca ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ttacaattac    360
aagtacaggc tgttccgtaa gtccaacctg aagccattcg agagagacat ctccactgag    420
atctaccaag ctggttccac tccatgtaac ggtgttgagg tttcaactg ttactggcca     480 ttgcagtctt acggtttcca gccaactaac ggtgtcggtt accaaccata cagagttgtc    540
gttttgtcct tcgagttgtt gcacgctcca gctactgttt gtggtccaaa gaatccacc     600 aatggtggtg atggtggcga cggcggagat ggtggtgctc atatagttat ggttgacgcc    660
tacaagccta ctaag                                                     675
```

<210> SEQ ID NO 111
<211> LENGTH: 621
<212> TYPE: DNA
<213> ORGANISM: Artificial Sequence
<220> FEATURE:
<223> OTHER INFORMATION: Synthetic

<400> SEQUENCE: 111

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gttttcccca ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
ctgtaccgtc tgttcagaaa gtccaacctg aagccattcg agagagacat ctccactgag    420
atctaccaag ctggttccac tccatgtaac ggtgttgagg tttcaactg ttacttccca     480 ttgcagtcct acggtttcca gccaactaat ggtgttggtt accagccata cagagtcgtc    540
gttttgtcct tcgagttgtt gcatgctcca gctactgttt gcggtccaaa gaagtccact    600
aacttggtca agaacaaatg t                                              621
```

<210> SEQ ID NO 112
<211> LENGTH: 621
<212> TYPE: DNA
<213> ORGANISM: Artificial Sequence
<220> FEATURE:
<223> OTHER INFORMATION: Synthetic

<400> SEQUENCE: 112

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gtttccccaa ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
tgtgttattg cttggaactc caacaacctg gactccaagg ttggtggtaa ctacaattac     360
aaataccgtt tgtttagaaa gtccaacctg aagccattcg agagagacat ctccactgag     420
atctaccaag ctggttccac tccatgtaac ggtgttgagg gtttcaactg ttactggcca     480
ttgcagtcct acggtttcca gccaactaat ggtgttggtt accagccata cagagtcgtc     540
gttttgtcct tcgagttgtt gcatgctcca gctactgttt gcggtccaaa gaagtccact     600
aacttggtca agaacaaatg t                                                621
```

<210> SEQ ID NO 113
<211> LENGTH: 777
<212> TYPE: DNA
<213> ORGANISM: Artificial Sequence
<220> FEATURE:
<223> OTHER INFORMATION: Synthetic

<400> SEQUENCE: 113

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gtttccccaa ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
tgtgttattg cttggaactc caacaacctg gactccaagg ttggtggtaa ctacaattac     360
ctgtaccgtc tgttcagaaa gtccaacctg aagccattcg agagagacat ctccactgag     420
atctaccaag ctggttccac tccatgtaac ggtgttgagg gtttcaactg ttacttccca     480
ttgcagtcct acggtttcca gccaactaat ggtgttggtt accagccata cagagtcgtc     540
gttttgtcct tcgagttgtt gcatgctcca gctactgttt gcggtccaaa gaagtccact     600
aacttggtca agaacaaatc tgtcaacttt aacttcaacg gcctgaccgg tactggtgtt     660
ttgactgaat ccaacaagaa gttcctgcca ttccagcagt tcggtagaga cattgctgac     720
actactgacg ccgttagaga tccacagact ttggagatct tggacatcac cccatgt       777
```

<210> SEQ ID NO 114
<211> LENGTH: 786
<212> TYPE: DNA
<213> ORGANISM: Artificial Sequence
<220> FEATURE:
<223> OTHER INFORMATION: Synthetic

<400> SEQUENCE: 114

```
atcaccaact tgtgtccatt cggtgaggtt ttcaacgcta ctagattcgc ttccgtttac      60
gcctggaaca gaaagagaat ctccaactgc gttgctgact actccgtctt gtacaactct     120
gcttcattct ccaccttcaa gtgctacggt gtttccccaa ctaagttgaa cgacctgtgt     180
ttcactaacg tctacgccga ctccttcgtt attagaggtg acgaggttag acagatcgct     240
ccaggtcaaa ctggtaagat cgctgactac aactacaagc tgccagacga cttcaccggt     300
```

```
tgtgttattg cttggaactc caacaacctg gactccaagg ttggtggtaa ctacaattac    360
ctgtaccgtc tgttcagaaa gtccaacctg aagccattcg agagagacat ctccactgag    420
atctaccaag ctggttccac tccatgtaac ggtgttgagg gtttcaactg ttacttccca    480
ttgcagtcct acggtttcca gccaactaat ggtgttggtt accagccata cagagtcgtc    540
gttttgtcct tcgagttgtt gcatgctcca gctactgttt gcggtccaaa gaagtccact    600
aacttggtca agaacaaatc tgtcaacttt aacttcaacg gcctgaccgg tactggtgtt    660
ttgactgaat ccaacaagaa gttcctgcca ttccagcagt tcggtagaga cattgctgac    720
actactgacg ccgttagaga tccacagact ttggagatct tggacatcac cccatgtcca    780
ccatgt                                                               786
```

<210> SEQ ID NO 115
<211> LENGTH: 777
<212> TYPE: DNA
<213> ORGANISM: Artificial Sequence
<220> FEATURE:
<223> OTHER INFORMATION: Synthetic

<400> SEQUENCE: 115

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gtttccccaa ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
aaataccgtt tgtttagaaa gtccaacctg aagccattcg agagagacat ctccactgag    420
atctaccaag ctggttccac tccatgtaac ggtgttgagg gtttcaactg ttactggcca    480
ttgcagtcct acggtttcca gccaactaat ggtgttggtt accagccata cagagtcgtc    540
gttttgtcct tcgagttgtt gcatgctcca gctactgttt gcggtccaaa gaagtccact    600
aacttggtca agaacaaatc tgtcaacttt aacttcaacg gcctgaccgg tactggtgtt    660
ttgactgaat ccaacaagaa gttcctgcca ttccagcagt tcggtagaga cattgctgac    720
actactgacg ccgttagaga tccacagact ttggagatct tggacatcac cccatgt      777
```

<210> SEQ ID NO 116
<211> LENGTH: 786
<212> TYPE: DNA
<213> ORGANISM: Artificial Sequence
<220> FEATURE:
<223> OTHER INFORMATION: Synthetic

<400> SEQUENCE: 116

```
atcaccaact tgtgtccatt cggtgaggtt ttcaacgcta ctagattcgc ttccgtttac     60
gcctggaaca gaaagagaat ctccaactgc gttgctgact actccgtctt gtacaactct    120
gcttcattct ccaccttcaa gtgctacggt gtttccccaa ctaagttgaa cgacctgtgt    180
ttcactaacg tctacgccga ctccttcgtt attagaggtg acgaggttag acagatcgct    240
ccaggtcaaa ctggtaagat cgctgactac aactacaagc tgccagacga cttcaccggt    300
tgtgttattg cttggaactc caacaacctg gactccaagg ttggtggtaa ctacaattac    360
aaataccgtt tgtttagaaa gtccaacctg aagccattcg agagagacat ctccactgag    420
atctaccaag ctggttccac tccatgtaac ggtgttgagg gtttcaactg ttactggcca    480
```

| | |
|---|---|
| ttgcagtcct acggtttcca gccaactaat ggtgttggtt accagccata cagagtcgtc | 540 |
| gttttgtcct tcgagttgtt gcatgctcca gctactgttt gcggtccaaa gaagtccact | 600 |
| aacttggtca agaacaaatc tgtcaacttt aacttcaacg gcctgaccgg tactggtgtt | 660 |
| ttgactgaat ccaacaagaa gttcctgcca ttccagcagt tcggtagaga cattgctgac | 720 |
| actactgacg ccgttagaga tccacagact ttggagatct tggacatcac cccatgtcca | 780 |
| ccatgt | 786 |

<210> SEQ ID NO 117
<211> LENGTH: 780
<212> TYPE: DNA
<213> ORGANISM: Artificial Sequence
<220> FEATURE:
<223> OTHER INFORMATION: Synthetic

<400> SEQUENCE: 117

| | |
|---|---|
| atcaccaact tgtgtccatt cggtgaggtt ttcaacgcta ctagattcgc ttccgtttac | 60 |
| gcctggaaca gaaagagaat ctccaactgc gttgctgact actccgtctt gtacaactct | 120 |
| gcttcattct ccaccttcaa gtgctacggt gttttcccaa ctaagttgaa cgacctgtgt | 180 |
| ttcactaacg tctacgccga ctccttcgtt attagaggtg acgaggttag acagatcgct | 240 |
| ccaggtcaaa ctggtaagat cgctgactac aactacaagc tgccagacga cttcaccggt | 300 |
| tgtgttattg cttggaactc caacaacctg gactccaagg ttggtggtaa ctacaattac | 360 |
| ctgtaccgtc tgttcagaaa gtccaacctg aagccattcg agagagacat ctccactgag | 420 |
| atctaccaag ctggttccac tccatgtaac ggtgttgagg gtttcaactg ttacttccca | 480 |
| ttgcagtcct acggtttcca gccaactaat ggtgttggtt accagccata cagagtcgtc | 540 |
| gttttgtcct tcgagttgtt gcatgctcca gctactgttt gcggtccaaa gaagtccact | 600 |
| aacctggtca agaacaagtg cgtcaacttt aacttcaacg gtctgaccgg tactggtgtt | 660 |
| ttgactgagt ccaacaagaa gttcctgcca ttccagcaat tcggtagaga cattgctgac | 720 |
| actactgacg ccgttagaga tccacagact ttggagatct tggacatcac cccatgttct | 780 |

<210> SEQ ID NO 118
<211> LENGTH: 780
<212> TYPE: DNA
<213> ORGANISM: Artificial Sequence
<220> FEATURE:
<223> OTHER INFORMATION: Synthetic

<400> SEQUENCE: 118

| | |
|---|---|
| atcaccaact tgtgtccatt cggtgaggtt ttcaacgcta ctagattcgc ttccgtttac | 60 |
| gcctggaaca gaaagagaat ctccaactgc gttgctgact actccgtctt gtacaactct | 120 |
| gcttcattct ccaccttcaa gtgctacggt gttttcccaa ctaagttgaa cgacctgtgt | 180 |
| ttcactaacg tctacgccga ctccttcgtt attagaggtg acgaggttag acagatcgct | 240 |
| ccaggtcaaa ctggtaagat cgctgactac aactacaagc tgccagacga cttcaccggt | 300 |
| tgtgttattg cttggaactc caacaacctg gactccaagg ttggtggtaa ctacaattac | 360 |
| ctgtaccgtc tgttcagaaa gtccaacctg aagccattcg agagagacat ctccactgag | 420 |
| atctaccaag ctggttccac tccatgtaac ggtgttgagg gtttcaactg ttacttccca | 480 |
| ttgcagtcct acggtttcca gccaactaat ggtgttggtt accagccata cagagtcgtc | 540 |
| gttttgtcct tcgagttgtt gcatgctcca gctactgttt gcggtccaaa gaagtccact | 600 |

```
aacctggtca agaacaagtg cgtcaacttt aacttcaacg gtctgaccgg tactggtgtt      660
ttgactgagt ccaacaagaa gttcctgcca ttccagcaat tcggtagaga cattgctgac      720
actactgacg ccgttagaga tccacagact ttggagatct tggacatcac cccatgttct      780

<210> SEQ ID NO 119
<211> LENGTH: 9
<212> TYPE: PRT
<213> ORGANISM: Artificial Sequence
<220> FEATURE:
<223> OTHER INFORMATION: Synthetic

<400> SEQUENCE: 119

Tyr Lys Tyr Arg Tyr Leu Cys Tyr Trp
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic

<400> SEQUENCE: 120

Tyr Lys Tyr Arg Ser Leu Cys Tyr Trp
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic

<400> SEQUENCE: 121

Tyr Leu Tyr Arg Leu Phe Cys Tyr Phe
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic

<400> SEQUENCE: 122

Tyr Lys Tyr Arg Tyr Leu Cys Tyr Trp
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic

<400> SEQUENCE: 123

Tyr Lys Tyr Arg Leu Phe Cys Tyr Trp
1               5
```